(12) United States Patent
Ullman et al.

(10) Patent No.: US 11,692,032 B2
(45) Date of Patent: *Jul. 4, 2023

(54) ANTI-LAG3 ANTIBODIES AND USES THEREOF

(71) Applicant: Regeneron Pharmaceuticals, Inc., Tarrytown, NY (US)

(72) Inventors: Erica Ullman, Yorktown Heights, NY (US); Aynur Hermann, Jersey City, NJ (US); Ella Ioffe, Bronx, NY (US); Elena Burova, Mount Kisco, NY (US); Gavin Thurston, Briarcliff Manor, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 393 days.

This patent is subject to a terminal disclaimer.

(21) Appl. No.: 16/433,263

(22) Filed: Jun. 6, 2019

(65) Prior Publication Data

US 2019/0284277 A1 Sep. 19, 2019

Related U.S. Application Data

(63) Continuation of application No. 15/289,032, filed on Oct. 7, 2016, now Pat. No. 10,358,495.

(60) Provisional application No. 62/365,006, filed on Jul. 21, 2016, provisional application No. 62/359,921, filed on Jul. 8, 2016, provisional application No. 62/315,119, filed on Mar. 30, 2016, provisional application No. 62/257,791, filed on Nov. 20, 2015, provisional application No. 62/239,524, filed on Oct. 9, 2015.

(51) Int. Cl.
| | |
|---|---|
| *C07K 16/28* | (2006.01) |
| *C12N 15/79* | (2006.01) |
| *C12N 15/63* | (2006.01) |
| *A61K 39/395* | (2006.01) |
| *A61K 45/06* | (2006.01) |
| *A61K 39/00* | (2006.01) |

(52) U.S. Cl.
CPC ...... *C07K 16/2803* (2013.01); *A61K 39/3955* (2013.01); *A61K 45/06* (2013.01); *C07K 16/2818* (2013.01); *A61K 2039/505* (2013.01); *A61K 2039/507* (2013.01); *C07K 2317/21* (2013.01); *C07K 2317/34* (2013.01); *C07K 2317/52* (2013.01); *C07K 2317/56* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,976,877 A | 11/1999 | Hercend et al. |
| 6,143,273 A | 11/2000 | Faure et al. |
| 6,197,524 B1 | 3/2001 | Romagnani |
| 6,524,802 B1 | 2/2003 | Lee et al. |
| 6,596,541 B2 | 7/2003 | Murphy et al. |
| 8,246,995 B2 | 8/2012 | Dai et al. |
| 8,257,740 B1 | 9/2012 | Sung et al. |
| 8,502,018 B2 | 10/2013 | Pardoll et al. |
| 8,551,481 B2 | 10/2013 | Pardoll et al. |
| 9,321,832 B2 | 4/2016 | Tomlinson et al. |
| 10,358,495 B2 | 7/2019 | Ullman et al. |
| 10,905,784 B2 * | 2/2021 | Kelly ............... A61K 51/1039 |
| 2004/0101920 A1 | 5/2004 | Radziejewski et al. |
| 2010/0331527 A1 | 12/2010 | Davis et al. |
| 2011/0070238 A1 | 3/2011 | Triebel et al. |
| 2011/0150892 A1 | 6/2011 | Thudium et al. |
| 2011/0195454 A1 | 8/2011 | McWhirter |
| 2013/0022759 A1 | 1/2013 | Okumura et al. |
| 2013/0095114 A1 | 4/2013 | Pardoll et al. |
| 2014/0088295 A1 | 3/2014 | Smith et al. |
| 2014/0093511 A1 | 4/2014 | Lonberg et al. |
| 2014/0127226 A1 | 5/2014 | Pardoll et al. |
| 2014/0243504 A1 | 8/2014 | Davis et al. |
| 2014/0286935 A1 | 9/2014 | Hamblin et al. |
| 2015/0203579 A1 | 7/2015 | Papadopoulos et al. |
| 2016/0310570 A1 | 10/2016 | Triebel et al. |

(Continued)

FOREIGN PATENT DOCUMENTS

| | | |
|---|---|---|
| EP | 0510079 B1 | 5/1999 |
| EP | 0977856 B1 | 8/2004 |

(Continued)

OTHER PUBLICATIONS

Tian et al. (2015) "The Upregulation of LAG-3 on T Cells Defines a Subpopulation with Functional Exhaustion and Correlates with Disease Progression in HIV-Infected Subjects," J. Immunol. 194:3873-3882.

Triebel (2003) "LAG-3: a regulator of T-cell and DC responses and its use in therapeutic vaccination," Trends in Immunology 24(12): 619-622.

Triebel et al. (2006) "A soluble lymphocyte activation gene-3 (sLAG-3) protein as a prognostic factor in human breast cancer expressing estrogen or progesterone receptors," Cancer Letters 235:147-153.

(Continued)

*Primary Examiner* — Ilia I Ouspenski
(74) *Attorney, Agent, or Firm* — FisherBroyles, LLP; Cara L. Crowley-Weber; Aparna G. Patankar

(57) ABSTRACT

The present invention provides antibodies that bind to the T cell co-inhibitor lymphocyte activation gene 3 (LAG3) protein, and methods of use. In various embodiments of the invention, the antibodies are fully human antibodies that specifically bind to LAG3. In some embodiments, the antibodies of the invention are useful for inhibiting or neutralizing LAG3 activity, thus providing a means of treating a disease or disorder such as cancer or viral infection.

28 Claims, 22 Drawing Sheets

Specification includes a Sequence Listing.

(56) References Cited

U.S. PATENT DOCUMENTS

| | | | | |
|---|---|---|---|---|
| 2018/0201991 | A1* | 7/2018 | Zhang | G16B 20/20 |
| 2019/0087538 | A1* | 3/2019 | Lim | C12Q 1/6806 |
| 2021/0138096 | A1* | 5/2021 | Kelly | A61K 51/1039 |

FOREIGN PATENT DOCUMENTS

| | | |
|---|---|---|
| EP | 0758383 B1 | 1/2007 |
| EP | 1897548 B1 | 8/2013 |
| EP | 2320940 B1 | 3/2015 |
| EP | 2142210 B1 | 8/2016 |
| WO | 1995/30750 A2 | 11/1995 |
| WO | 1997/03695 A1 | 2/1997 |
| WO | 1998/58059 A1 | 12/1998 |
| WO | 2004/078928 A2 | 9/2004 |
| WO | 2005/103081 A2 | 11/2005 |
| WO | 2008/132601 A1 | 11/2008 |
| WO | 2010/019570 A2 | 2/2010 |
| WO | 2013/022782 A1 | 2/2013 |
| WO | 2014/008218 A1 | 1/2014 |
| WO | 2014/140180 A1 | 9/2014 |
| WO | 2015/042246 A1 | 3/2015 |
| WO | 2015/048312 A1 | 4/2015 |
| WO | 2015/138920 A1 | 9/2015 |
| WO | 2016028672 | 2/2016 |
| WO | 2016/172010 A1 | 10/2016 |
| WO | 2016/200782 | 12/2016 |
| WO | 2017/015560 A2 | 1/2017 |
| WO | 2017/016497 | 2/2017 |
| WO | 2017/062888 A1 | 4/2017 |
| WO | 2017/087589 | 5/2017 |
| WO | 2017/087901 A2 | 5/2017 |
| WO | 2017/106129 A1 | 6/2017 |
| WO | 2017/149143 | 9/2017 |
| WO | 2017/198741 | 11/2017 |
| WO | 2017/219995 | 12/2017 |
| WO | 2017/220569 | 12/2017 |

OTHER PUBLICATIONS

Turnis et al. (2012) "Combinatorial immunotherapy PD-1 may not be LAG-ing behind any more," OncoImmunology 1(7):1172-1174.
Turnis et al. (2015) "Inhibitory receptors as targets for cancer immunotherapy," Eur. J. Immunol. 45:1892-1905.
Tutt et al. (1991) "Trispecific F(ab')3 derivatives that use cooperative signaling via the TCR/CD3 complex and CD2 to activate and rediret resting cytotoxic T cells," J. Immunol. 147:60-69.
Vajdos et al. (2002) "Comprehensive Functional Maps of the Antigen-binding Site of an Anti-ErbB2 Antibody Obtained with Shotgun Scanning Mutagenesis," J. Mol. Biol. 320:415-428.
Wang-Gillam et al. (2013) "A phase I study of IMP321 and gemcitabine as the front-line therapy in patients with advanced pancreatic adenocarcinoma," Invest New Drugs 31:707-713.
Williams et al. (2015) "LAG-3 and 4-1BB identify dysfunctional antigenspecific T cells in the tumor microenvironment and combinatorial LAG-3/4-1BB targeting gives synergistic tumor control," Journal for ImmunoTherapy of Cancer; 3 (Suppl 2):p. 328.
Wong, et al. (1998) "Structural Requirements for a Specificity Switch and for Maintenance of Affinity Using Mutational Analysis of a Phage-Displayed Anti-Arsonate Antibody of Fab Heavy Chain First Complementarity-Determining Region," The Journal of Immunology, 160:5990-5997.
Woo et al. (2010) "Differential subcellular localization of the regulatory T-cell protein LAG-3 and the coreceptor CD4," Eur J Immunol; 40(6): 1768-1777.
Woo et al. (2012) "Immune Inhibitory Molecules LAG-3 and PD-1 Synergistically Regulate T-cell Function to Promote Tumoral Immune Escape," Cancer Res. 72:917-927.
Wolchok et al. (2009) "Guidelines for the Evaluation of Immune Therapy Activity in Solid Tumors: Immune-Related Response Criteria," Clin. Cancer Res. 15:7412-7420.
Workman et al. (2002) "Cutting Edge: Molecular Analysis of the Negative Regulatory Function of Lymphocyte Activation Gene-31," J. Immunol. 169:5392-5395.

Workman et al. (2009) "LAG-3 Regulates Plasmacytoid Dendritic Cell Homeostasis1," J. Immunol. 182(4):1885-1891.
Wu et al. (1987) "Receptor-mediated in vitro gene transformation by a soluble DNA carrier system," J. Biol. Chem. 262:4429-4432.
Xiao and Freeman (2015) "The Microsatellite Instable Subset of Colorectal Cancer Is a Particularly Good Candidate for Checkpoint Blockade Immunotherapy," Cancer Discovery 5:16-18.
Xu et al. (2014) "LSECtin Expressed on Melanoma Cells Promotes Tumor Progression by Inhibiting Antitumor T-cell Responses," Cancer Res. 74(13):3418-3428.
Yan et al. (2015) "Targeting C-type lectin receptors for cancer immunity," Frontiers in Immunology 6:408.
"NCT01968109on Sep. 3, 2015," ClinicalTrials.gov Archive, Sep. 3, 2015, pp. 1-6, XP055328270, retrieved from the Internet: URL:https://clinicaltrials.gov/archive/NCT01968109/2015_09_03.
International Search Report and Written Opinion, received for PCT/US2016/056156, dated Mar. 10, 2017, 23 pages.
Abaza and Atassi (1992) "Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin" Journal of Protein Chemistry 11(5):433-444.
Colman, et al. (1994) "Effects of amino acid sequence changes on antibody-antigen interactions", Research in Immunology 145(1):33-36.
Edwards, et al. (2003) "The Remarkable Flexibility of the Human Antibody Repertoire; Isolation of Over One Thousand Different Antibodies to a Single Protein, BLyS" J. Mol. Biol. 334:103-118.
Ferrara, et al. (2015) "Recombinant renewable polyclonal antibodies" mAbs 7(1):32-41.
Lederman et al. (1991) "A Single Amino Acid Substitution in a Common African Allele of the CD4 Molecule Ablates Bidning of the Monoclonal Antibody, OKT4" Molecular Immunology 28:1171-1181.
Lerner (1982) "Tapping the immunological repertoire to produce antibodies of predetermined specificity" Nature 299:592-596.
Huard et al. (1997) "Characterization of the major histocompatibility complex class II binding site on LAG-3 protein," PNAS 94:5744-5749.
Invitation to Pay Additional Fees and, Where Applicable, Protest Fee, received for PCT/US2016/056156, dated Jan. 10, 2017, 10pgs.
Jackson, et al. (1995) "In Vitro Antibody Maturation Improvement of a High Affinity, Neutralizing Antibody Against IL-1 beta," The Journal of Immunology 154:3310-3319.
Jing et al. (2015) "Combined immune checkpoint protein blockade and low dose whole body irradiation as Immunotherapy for myeloma," J. for Immuno. Therapy of Cancer 3:2 pp. 1-15.
Junghans et al. (1990) "Anti-Tac-H, a Humanized Antibody to the Interleukin 2 Receptor with New Features for Immunotherapy in Malignant and Immune Disorders," Cancer Research 50:1495-1502.
Juno et al. (2015) "Elevated expression of LAG-3, but not PD-1, is associated with impaired iNKT cytokine production during chronic HIV-1 infection and treatment," Retrovirology 12:17.
Kazane, et al. (2013) "Self-Assembled Antibody Multimers through Peptide Nucleic Acid Conjugation," Journal of the American Chemical Society, 135(1):340-346.
Klein, et al. (2012) "Progress in overcoming the chain association issue in bispecific heterodimeric IgG antibodies," mAbs 4(6):653-663.
Kouo et al. (2015) "Galectin-3 shapes antitumor immune responses by suppressing CD8+ T cells via LAG-3 and inhibiting expansion of plasmacytoid dendritic cells," Cancer Immunol. Res. Published Online First Feb. 17, 2015, 42 pages.
Kufer et al. (2004) "A revival of bispecific antibodies," Trends in Biotech. 22(5):238-244.
Langer (1990) "New methods of drug delivery," Science 249:1527-1533.
Legat et al. (2013) "Inhibitory receptor expression depends more dominantly on differentiation and activation than 'exhaustion' of human CD8 T cells," Frontiers in Immunol., Tumor Immunity 4:455.

(56) References Cited

OTHER PUBLICATIONS

Li et al. (2007) "Metalloproteases regulate T-cell proliferation and effector function via LAG-3," The EMBO Journal 26(2) 494-504.
Liang et al. (2008) "Regulatory T Cells Inhibit Dendritic Cells by Lymphocyte Activation Gene-3 Engagement of MHC Class II 1," J. Immunol. 180:5916-5926.
Llosa et al. (2014) "The Vigorous Immune Microenvironment of Microsatellite Instable Colon Cancer Is Balanced by Multiple Counter-Inhibitory Checkpoints," Cancer Discov. 5(1):43-51.
Lloyd (1999) "The Art, Science and Technology of Pharmaceutical Compounding," 8 pages.
Macon-Lemaitre and Triebel (2005) "The negative regulatory function of the lymphocyte-activation gene-3 co-receptor (CD223) on human T cells," Immunology 115:170-178.
Martin et al. (1989) "Modeling antibody hypervariable loops: A combined algorithm," PNAS 86:9268-9272.
Mao et al. (2016) "Pathological a-synuclein transmission initiated by binding lymphocyte-activation gene 3," Science 353:6307.
Matsuzaki et al. (2010) "Tumor-infiltrating NY-ESO-1-specific CD8+ T cells are negatively regulated by LAG-3 and PD-1 in human ovarian cancer," PNAS 107(17):7875-7880.
Miyazaki et al. (1996) "Independent Modes of Natural Killing Distinguished in Mice Lacking Lag3," Science 272:405-408.
Needleman and Wunsch (1970) "A general method applicable to the search for similarities in the amino acid sequence of two proteins," J. Mol. Biol. 48:443-453.
Nguyen and Ohashi (2015) "Clinical blockade of PD1 and LAG3—potential mechanisms of action," Immunology 15:45-56.
Nishino et al. (2013) "Developing a Common Language for Tumor Response to Immunotherapy: Immune-Related Response Criteria Using Unidimensional Measurements," Clin. Cancer Res. 19:3936-3943.
Norde et al. (2012) "Coinhibitory molecules in hematologic malignancies: targets for therapeutic intervention," Blood 120(4):728-736.
Okamura et al. (2009) "CD4+ CD25− LAG3+ regulatory T cells controlled by the transcription factor Egr-2," PNAS 106(33):13974-13979.
Okamura et al. (2012) "Roles of LAG3 and EGR2 in regulatory T cells," Ann. Rheum. Dis. 71: i96-i100. doi:10.1136/annrheumdis-2011-200588.
Okamura et al. (2015) "TGF-b3-expressing CD4+ CD25− LAG3+ regulatory T cells control humoral immune responses," Nature Communications 6:6329.
Okazaki (2010) "PD-1 and LAG-3 inhibitory co-receptors act synergistically to prevent autoimmunity in mice," J. Exp. Med. 208(2):395-407.
Padlan et al. (1995) "Identification of specificity-determining residues in antibodies," The FASEB Journal 9:133-139.
Pardol (2012) "Regulating the Regulators for Cancer Immunotherapy: LAG-3 Finally Catches Up," LAG-3 Presentation.
Pardoll (2012) "The blockade of immune checkpoints in cancer immunotherapy," Nature Reviews Cancer 12:252-264.
Pearson (1994) "Using the FASTA Program to Search Protein and DNA Sequence Databases," Methods in Molecular Biology 24:307-331.
Perez-Garcia (2014) "Orchestrating immune check-point blockade for cancer immunotherapy in combinations," Current Opinion in Immunology, Tumour Immunology 27:89-97.
Poirier, et al. (2011) "Antibody-mediated depletion of lymphocyte-activation gene-3 (LAG-3+)-activated T lymphocytes prevents delayed-type hypersensitivity in non-human primates," British Society for Immunology, Clinical and Experimental Immunology 164: 265-274.
Powell et al. (1998) "Compendium of excipients for parenteral formulations," J. Pharm. Sci. Technol. 52:238-311.
Reddy et al. (2000) "Elimination of Fc Receptor-Dependent Effector Functions of a Modified IgG4 Monoclonal Antibody to Human CD4," J. Immunol. 164:1925-1933.
Reineke (2004) "Antibody Epitope Mapping Using Arrays of Synthetic Peptides," Methods Mol. Biol. 248:443-463.
Roncarolo et al. (2014) "Tr1 Cells and the Counter-Regulation of Immunity: Natural Mechanisms and Therapeutic Applications," Curr. Top. Microbiol. Immunol. 380: 39-68.
Rouhani et al. (2015) "Roles of lymphatic endothelial cells expressing peripheral tissue antigens in CD4 T-cell tolerance induction," Nature Communications 6:6771.
Rudikoff, et al. (1982) "Single amino acid substitution altering antigen-binding specificity," Proc. Natl. Acad. Sci. 79:1979-1983.
Sega et al. (2014) "Role of Lymphocyte Activation Gene-3 (Lag-3) in Conventional and Regulatory T Cell Function in Allogeneic Transplantation," PLoS One 9(1):e86551.
Shield et al. (2002) "Lack of Fucose on Human IgG1 N-Linked Oligosaccharide Improves Binding to Human Fc RIII and Antibody-dependent Cellular Toxicity," J. of Biol. Chem. 277(30):26733-26740.
Shin and Ribas (2015) "The evolution of checkpoint blockade as a cancer therapy: what's here, what's next?" Current Opinion in Immunology, Tumour Immunology 33:23-35.
Sierro et al. (2011) "The CD4-like molecule LAG-3, biology and therapeutic applications," Expert Opin. Ther. Targets 15(1):91-101.
Sittig et al. (2013) "Clonal expansion of renal cell carcinoma-infiltrating T lymphocytes," Landes Bioscience, OncoImmunology 2:9, e26014-1-10.
Smith and Waterman (1981) "Identification of common molecular subsequences," J. Mol. Biol. 147:195-197.
Sun et al. (2014) "Expression regulation of co-inhibitory molecules on human natural killer cells in response to cytokine stimulations," Cytokine 65:33-41.
Taube et al. (2015) "Differential expression of immune-regulatory genes associated with PD-L1 display in melanoma: Implications for PD-L1 pathway blockade," Clin Cancer Res Published Online First May 5, 2015.
Thaventhiran et al. (2012) "T Cell Co-inhibitory Receptors: Functions and Signalling Mechanisms," J. Clin. Cell Immunol. S12:004. doi:10.4172/2155-9899.S12-004.
Brown, et al. (1996) "Tolerance to Single, but Not Multiple, Amino Acid Replacements in Antibody V, CDR2", The Journal of Immunology, 156: 3285-3291.
LAG3 protein [Homo sapiens] AAH52589, GenBank: AAH52589.1 dated Oct. 7, 2003.
Anderson et al. (2016) "Lag-3, Tim-3, and TIGIT: Co-inhibitory Receptors with Specialized Functions in Immune Regulation," Immunity 44:989-1004.
Al-Lazikani et al. (1997) "Standard Conformations for the Canonical Structures of Immunoglobulins," J. Mol. Biol. 273:927-948.
Altschul et al. (1990) "Basic Local Alignment Search Tool," J. Mol. Biol. 215:403-410.
Altschul et al. (1997) "Gapped BLAST and PSI-BLAST: a new generation of protein database search programs," Nucleic Acids Research, 25(17):3389-3402.
Andreae et al. (2002) "Maturation and Activation of Dendritic Cells Induced by Lymphocyte Activation Gene-3 (CD223)," J. Immunol. 168:3874-3880.
Andreae et al. (2003) "MHC class II signal transduction in human dendritic cells induced by a natural ligand, the LAG-3 protein (CD223)," Blood 102(6):2130-2137.
Arruebo et al. (2009) "Antibody-conjugated nanoparticles for biomedical applications," J. of Nanomaterials, vol. 2009, Article ID 439389, 24 pgs, doi:10.1155/2009/439389.
Bae et al. (2014) "Trafficking of LAG-3 to the Surface on Activated T Cells via Its Cytoplasmic Domain and Protein Kinase C Signaling," J. Immunol. 2014; 193:3101-3112.
Barber et al. (2006) "Restoring function in exhausted CD8 T cells during chronic viral infection," Nature 439:682-687.
Blackburn et al. (2009) "Coregulation of CD8+ T cell exhaustion by multiple inhibitory receptors during chronic viral infection," Nature Immunology 10(1):29-37.
Brignone et al. (2007) "IMP321 (sLAG-3) safety and T cell response potentiation using an influenza vaccine as a model antigen: A single-blind phase I study," Vaccine 25:4641-4650.

(56) References Cited

OTHER PUBLICATIONS

Brignone et al. (2007) "IMP321 (sLAG-3), an immunopotentiator for T cell responses against a HBsAg antigen in healthy adults: a single blind randomised controlled phase I study," Journal of Immune Based Therapies and Vaccines 5:1-15.
Brignone et al. (2007) "A Soluble Form of Lymphocyte Activation Gene-3 (IMP321) Induces Activation of a Large Range of Human Effector Cytotoxic Cells," J. Immunol 179:4202-4211.
Brignone et al. (2009) "A Phase I Pharmacokinetic and Biological Correlative Study of IMP321, a Novel MHC Class II Agonist, in Patients with Advanced Renal Cell Carcinoma," Clin. Cancer Res. 15(19):6225-6231.
Brignone et al. (2010) "First-line chemoimmunotherapy in metastatic breast carcinoma: combination of paclitaxel and IMP321 (LAG-3Ig) enhances immune responses and antitumor activity," J. of Translational Medicine 8:71.
Buisson and Triebel (2005) "LAG-3 (CD223) reduces macrophage and dendritic cell differentiation from monocyte precursors," Immunology 114:369-374.
Camisaschi et al. (2010) "LAG-3 Expression Defines a Subset of CD4+CD25highFoxp3+ Regulatory T Cells That Are Expanded at Tumor Sites," J. Immunol. 184:6545-6551.
Camisaschi et al. (2014) "Alternative Activation of Human Plasmacytoid DCs In Vitro and in Melanoma Lesions: Involvement of LAG-3," J. of Investigative Dermatology 134:1893-1902.
Casati et al. (2006) "Soluble Human LAG-3 Molecule Amplifies the In vitro Generation of Type 1 Tumor-Specific Immunity," Cancer Res. 66(8):4450-4460.
Casati et al. (2008) "Human Lymphocyte Activation Gene-3 Molecules Expressed by Activated T Cells Deliver Costimulation Signal for Dendritic Cell Activation1," J. Immunol. 180:3782-3788.
Chen and Flies (2013) "Molecular mechanisms of T cell co-stimulation and co-inhibition," Nature Rev. Immunol. 13:227-242.
Chen and Chen (2014) "The effect of immune microenvironment on the progression and prognosis of colorectal cancer," Med. Oncol. 31:82.
Chen et al. (2015) "LAG-3 Negatively Regulates the Function of Intrahepatic HCV-specific CD8+ T Cells," doi: 10.1111/jgh.13017.
Cheson et al. (2014) "Recommendations for Initial Evaluation, Staging, and Response Assessment of Hodgkin and Non-Hodgkin Lymphoma: The Lugano Classification," J. Clin. Oncol. 32(27):3059-3068.
Chun et al. (2004) "The effect of soluble LAG-3 (CD223) treatment in fetal thymic organ culture," Biotechnology Letters 26: 1371-1377.
Crawford et al. (2014) Molecular and Transcriptional Basis of CD4+ T Cell Dysfunction during Chronic Infection, Immunity 40:289-302.
Creelan (2015) "Update on Immune Checkpoint Inhibitors in Lung Cancer," Cancer Control, J. of Moffitt Cancer Center 21(1):80-89.
Demeure et al. (2001) "T Lymphocytes infiltrating various tumour types express the MHC class II ligand lymphocyte activation gene-3 (LAG-3): role of LAG-3/MHC class II interactions in cell—cell contacts," Eur. J. of Cancer 37:1709-1718.
Domizio et al. (2014) "Plasmacytoid Dendritic Cells in Melanoma: Can We Revert Bad into Good?" J. of Investigative Dermatology 134, 1797-1800.
Ehring (1999) "Hydrogen Exchange/Electrospray Ionization Mass Spectrometry Studies of Structural Features of Proteins and Protein/Protein Interactions," Analytical Biochem. 267:252-259.
Eisenhauer et al. (2009) "New response evaluation criteria in solid tumours: Revised RECIST guideline (version 1.1)," Eur. J. Cancer 45:228-247.
Engen and Smith (2001) "The Basics of Ion Chromatography," Anal. Chem. 73:256A-265A.

Ferris et al. (2014) "Too Much of a Good Thing? Tim-3 and TCR Signaling in T Cell Exhaustion," J. Immunol. 193:1525-1530.
Flies et al (2011) "Blockade of the B7-H1/PD-1 Pathway for Cancer Immunotherapy," Yale J. Biol. Med. 84(4):409-421.
Fougeray et al. (2006) "A soluble LAG-3 protein as an immunopotentiator for therapeutic vaccines: Preclinical evaluation of IMP321," Vaccine 24:5426-5433.
Gagliani et al. (2013) "Coexpression of CD49b and LAG-3 identifies human and mouse T regulatory type 1 cells," Nature Medicine 19(6):739-746.
Gautron, et al. (2014) "Enhanced suppressor function of TIM-3+ FoxP3+ regulatory T cells," Eur. J. Immunol. 44:2703-2711.
Goldberg and Drake (2011) "LAG-3 in Cancer Immunotherapy," LAG-3 Biology Review, 269-278.
Goldrath et al. (1999) "Selecting and maintaining a diverse T-cell repertoire," Nature 402:255-262.
Gonnet et al. (1992) "Exhaustive Matching of the Entire Protein Sequence Database," Science 256:1443-1445.
Gros et al. (2014) "PD-1 identifies the patient-specific CD8+ tumor-reactive repertoire infiltrating human tumors," J. of Clinical Investigation 125(5):2246-2259.
Grosso et al. (2007) "LAG-3 regulates CD8+ T cell accumulation and effector function in murine self and tumor-tolerance systems," J. of Clinical Investigation 117(11):3383-3392.
Grosso (2009) "Functionally Distinct LAG-3 and PD-1 Subsets on Activated and Chronically Stimulated CD8 T Cells1," J. Immunol. 182:6659-6669.
Hemon et al. (2011) "MHC Class II Engagement by Its Ligand LAG-3 (CD223) Contributes to Melanoma Resistance to Apoptosis," J. Immunol. 186:5173-5183.
Hochleitner et al. (2000) "Characterization of a discontinuous epitope of the human immunodeficiency virus (HIV) core protein p24 by epitope excision and differential chemical modification followed by mass spectrometric peptide mapping analysism" Protein Sci. 9:487-496.
Huang et al. (2004) "Role of LAG-3 in Regulatory T Cells," Immunity 21:503-513.
Huang et al. (2015) "LAG3 and PD1 co-inhibitory molecules collaborate to limit CD8+ T cell signaling and dampen antitumor immunity in a murine ovarian cancer model," Oncotarget, 6(29):27359-27377.
Huard et al. (1994) "Cellular expression and tissue distribution of the human LAG-3-encoded protein, an MHC class II ligand," Immunogenetics 39: 213-217.
Huard, et al. (1995) "CD4/major histocompatibility complex class II interaction analyzed with CD4- and lymphocyte activation gene-3 (LAG-3)-Ig fusion proteins," Eur. J. Immunol. 25:2718-2721.
Huard et al. (1996) "T cell major histocompatibility complex class II molecules down-regulate CD4+ T cell clone responses following LAG-3 binding," Eur. J. Immunol. 26:1180-1186.
International Search Report and Written Opinion, PCT/US2018/017525, dated Apr. 17, 2018, 14 pages.
U.S. Department of Health and Human Services, Public Health Service National Institutes of Health, NIH Publication No. 91-3242, Kabat, E. A., Wu, T. T., Perry, H. M., Gottesman, K.S., and Foeller, C., "Sequences of Proteins of Immunological Interest." 5th Edition in: Tabulation and Analysis of Amino Acid and Nucleic Acid Sequences of Percursors, V-Regions, C-Regions, J-Chain, T-Cell Receptors for Antigen, T-Cell Surface Antigens, β2-Microglobulins, Major Histocompatibility Antigens, Thy-1, Complement, C-Reactive Protein, Thymopoietin, Integris, Post-gamma, (1991).
Schumacher, et al. (2016) "Current Status: Site-Specific Antibody Drug Conjugates", J. Clin. Immunol. 36(Suppl1): S100-S107.
Foote et al. (1992) "Antibody Framework Residues Affecting the Conformation of the Hypervariable Loops," J. Mol. Biol. 224: 487-499.

\* cited by examiner

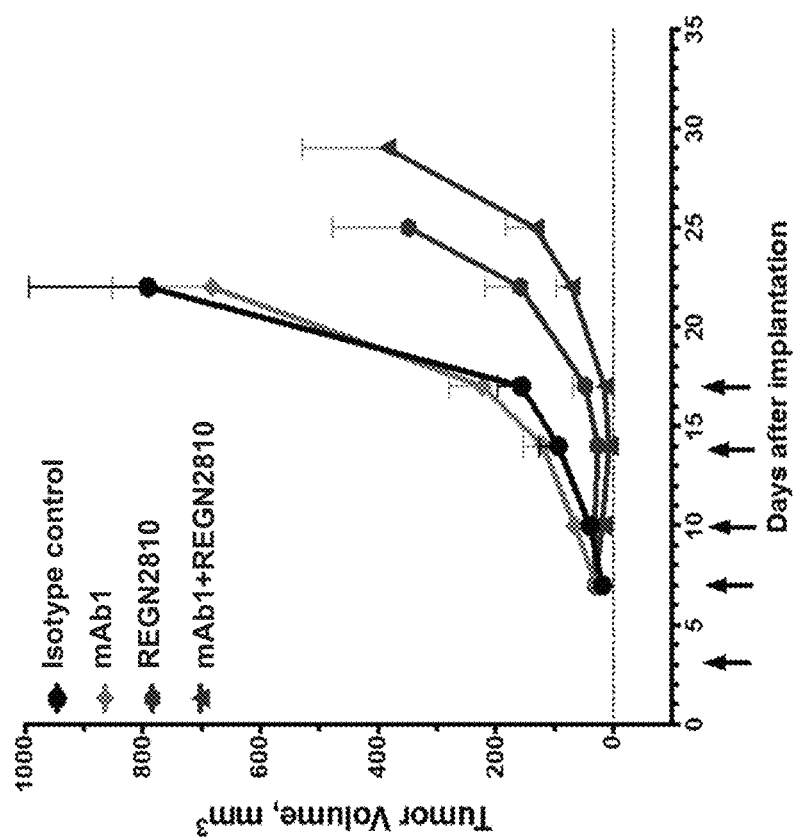

ANTI-LAG3 ANTIBODIES AND USES THEREOF

CROSS-REFERENCE TO RELATED APPLICATIONS

This application is a continuation of U.S. patent application Ser. No. 15/289,032, filed Oct. 7, 2016, which claims the benefit under 35 U.S.C. § 119(e) of U.S. Provisional Application Nos. 62/239,524, filed Oct. 9, 2015; 62/257,791, filed Nov. 20, 2015; 62/315,119, filed Mar. 30, 2016; 62/359,921, filed Jul. 8, 2016; and 62/365,006, filed Jul. 21, 2016, the disclosures of each herein incorporated by reference in their entireties.

SEQUENCE LISTING

An official copy of the sequence listing is submitted concurrently with the specification electronically via EFS-Web as an ASCII formatted sequence listing with a file name of 2016_10_07_10176US01_SEQ_LIST_ST25.txt, a creation date of Oct. 7, 2016, and a size of about 240 kilobytes. The sequence listing contained in this ASCII formatted document is part of the specification and is herein incorporated by reference in its entirety.

FIELD OF THE INVENTION

The present invention is related to antibodies and antigen-binding fragments of antibodies that specifically bind to the immunomodulatory receptor lymphocyte activation gene-3 (LAG3), and therapeutic and diagnostic methods of using those antibodies.

BACKGROUND OF THE INVENTION

T cell co-stimulatory and co-inhibitory molecules (collectively named co-signaling molecules) play a crucial role in regulating T cell activation, subset differentiation, effector function and survival (Chen et al 2013, Nature Rev. Immunol. 13: 227-242). Following recognition of cognate peptide-MHC complexes on antigen-presenting cells by the T cell receptor, co-signaling receptors co-localize with T cell receptors at the immune synapse, where they synergize with TCR signaling to promote or inhibit T cell activation and function (Flies et al 2011, Yale J. Biol. Med. 84: 409-421). The ultimate immune response is regulated by a balance between co-stimulatory and co-inhibitory signals ("immune checkpoints") (Pardoll 2012, Nature Reviews Cancer 12: 252-264). Lymphocyte activation gene-3 (LAG3) functions as one such 'immune checkpoint' in mediating peripheral T cell tolerance.

LAG3 (also called CD223) is a 503 amino acid transmembrane protein receptor expressed on activated CD4 and CD8 T cells, γδ T cells, natural killer T cells, B-cells, natural killer cells, plasmacytoid dendritic cells and regulatory T cells. LAG3 is a member of the immunoglobulin (Ig) superfamily. The primary function of LAG3 is to attenuate the immune response. LAG3 binding to MHC class II molecules results in delivery of a negative signal to LAG3-expressing cells and down-regulates antigen-dependent CD4 and CD8 T cell responses. LAG3 negatively regulates the ability of T cells to proliferate, produce cytokines and lyse target cells, termed as 'exhaustion' of T cells. LAG3 is also reported to play a role in enhancing T regulatory (Treg) cell function (Pardoll 2012, Nature Reviews Cancer 12: 252-264).

Since LAG3 plays an important role in tumor immunity and infectious immunity, it is an ideal target for immunotherapy. Blocking LAG3 with antagonists, including monoclonal antibodies, has been studied in treatments of cancer and chronic viral infections (Turnis et al 2015, Eur. J. Immunol. 45: 1892-1905).

Monoclonal antibodies to LAG3 are known in the art and have been described, for example, in US Patent/Publication Nos. 5976877, 6143273, 6197524, 8551481, 20110070238, 20110150892, 20130095114, 20140093511, 20140127226, 20140286935, and in WO95/30750, WO97/03695, WO98/58059, WO2004/078928, WO2008/132601, WO2010/019570, WO2014/008218, EP0510079B1, EP0758383B1, EP0843557B1, EP0977856B1, EP1897548B2, EP2142210A1, and EP2320940B1.

When developing an immunotherapy for treating human beings, there is a need for antibodies exhibiting properties such as low immunogenicity, suitable binding kinetics parameters, cross-reactivity to the monkey target, suitable in vitro activity and/or suitable in vivo activity.

BRIEF SUMMARY OF THE INVENTION

The present invention provides antibodies and antigen-binding fragments thereof that bind LAG3. The antibodies of the present invention are useful, inter alia, for targeting immune cells expressing LAG3, and for modulating LAG3 activity. In certain embodiments, the antibodies of the invention are useful for inhibiting or neutralizing LAG3 activity and/or for stimulating T cell activation, e.g., under circumstances where T cell-mediated killing is beneficial or desirable. In certain embodiments, the antibodies are useful for inhibiting regulatory T cell function and/or for reversing the anergic state of exhausted T cells. The anti-LAG3 antibodies of the invention, or antigen-binding portions thereof, may be included as part of a multi-specific antigen-binding molecule, for example, to modulate the immune response and/or to target the antibodies to a specific cell type, such as a tumor cell, or a virally infected cell. The antibodies are useful in treating a disease or disorder such as cancer and viral infection.

The antibodies of the invention can be full-length (for example, an IgG1 or IgG4 antibody) or may comprise only an antigen-binding portion (for example, a Fab, F(ab')$_2$ or scFv fragment), and may be modified to affect functionality, e.g., to eliminate residual effector functions (Reddy et al., 2000, J. Immunol. 164:1925-1933). In certain embodiments, the antibodies may be bispecific.

In a first aspect, the present invention provides isolated recombinant monoclonal antibodies or antigen-binding fragments thereof that bind specifically to LAG3. In certain embodiments, the antibodies are fully human.

Exemplary anti-LAG3 antibodies of the present invention are listed in Tables 1-3 herein. Table 1 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of the exemplary anti-LAG3 antibodies. Table 2 sets forth the nucleic acid sequence identifiers of the HCVRs, LCVRs, HCDR1, HCDR2 HCDR3, LCDR1, LCDR2 and LCDR3 of the exemplary anti-LAG3 antibodies. Table 3 sets forth the amino acid sequence identifiers of heavy chain and light chain sequences of exemplary anti-LAG3 antibodies.

The present invention provides antibodies, or antigen-binding fragments thereof, comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

The present invention also provides antibodies, or antigen-binding fragments thereof, comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

The present invention also provides antibodies, or antigen-binding fragments thereof, comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present invention provides antibodies, or antigen-binding fragments thereof, comprising an HCVR/LCVR amino acid sequence pair contained within any of the exemplary anti-LAG3 antibodies listed in Table 1. In certain embodiments, the HCVR/LCVR amino acid sequence pair is selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330, 338/346, 354/362, 370/378, 386/394, 402/410, 418/426, 434/442, 450/522, 458/522, 466/522, 474/522, 482/522, 490/522, 498/530, 506/530, 514/530, 538/546, and 554/562. In certain embodiments, the HCVR/LCVR amino acid sequence pair is selected from one of SEQ ID NOs: 386/394 (e.g., H4sH15479P), 418/426 (e.g., H4sH15482P) or 538/546 (e.g., H4sH14813N). In certain embodiments, the present invention provides anti-LAG3 antibodies or antigen-binding fragments thereof comprising a HCVR and a LCVR, said HCVR comprising an amino acid sequence listed in Table 1 having no more than five amino acid substitutions, and said LCVR comprising an amino acid sequence listed in Table 1 having no more than five amino acid substitutions. For example, the present invention provides anti-LAG3 antibodies or antigen-binding fragments thereof comprising a HCVR and a LCVR, said HCVR comprising an amino acid sequence of SEQ ID NO: 418 having no more than five amino acid substitutions, and said LCVR comprising an amino acid sequence of SEQ ID NO: 426 having no more than five amino acid substitutions. In another exemplary embodiment, the present invention provides anti-LAG3 antibodies or antigen-binding fragments thereof comprising a HCVR and a LCVR, said HCVR comprising an amino acid sequence of SEQ ID NO: 418 having at least one amino acid substitution, and said LCVR comprising an amino acid sequence of SEQ ID NO: 426 having one amino acid substitution.

The present invention also provides antibodies, or antigen-binding fragments thereof, comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

The present invention also provides antibodies, or antigen-binding fragments thereof, comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present invention provides antibodies, or antigen-binding fragments thereof, comprising an HCDR3/LCDR3 amino acid sequence pair contained within any of the exemplary anti-LAG3 antibodies listed in Table 1. In certain embodiments, the HCDR3/LCDR3 amino acid sequence pair is selected from the group consisting of SEQ ID NOs: 392/400 (e.g., H4sH15479P), 424/432 (e.g., H4sH15482P) and 544/552 (e.g., H4sH14813N).

The present invention also provides antibodies, or antigen-binding fragments thereof, comprising a HCVR and a LCVR, said HCVR comprising HCDR1 comprising an amino acid sequence differing from an amino acid sequence listed in Table 1 by 1 amino acid, HCDR2 comprising an amino acid sequence differing from an amino acid sequence listed in Table 1 by 1 amino acid, and HCDR3 comprising an amino acid sequence differing from an amino acid sequence listed in Table 1 by 1 amino acid. In certain embodiments, the present invention provides antibodies, or antigen-binding fragments thereof, comprising a HCVR and a LCVR, said LCVR comprising LCDR1 comprising an amino acid sequence differing from an amino acid sequence listed in Table 1 by 1 amino acid, LCDR2 comprising an amino acid sequence differing from an amino acid sequence listed in Table 1 by 1 amino acid, and LCDR3 comprising an amino acid sequence differing from an amino acid sequence listed in Table 1 by 1 amino acid. For example, the present invention provides anti-LAG3 antibodies, or antigen-binding fragments thereof, comprising a HCVR and a LCVR, said HCVR comprising HCDR1 comprising an amino acid sequence of SEQ ID NO: 420 or an amino acid sequence differing from SEQ ID NO: 420 by 1 amino acid, HCDR2 comprising an amino acid sequence of SEQ ID NO: 422 or an amino acid sequence differing from SEQ ID NO: 422 by 1 amino acid, and HCDR3 comprising an amino acid sequence of SEQ ID NO: 424 or an amino acid sequence differing from SEQ ID NO: 424 by 1 amino acid. In another exemplary embodiment, the present invention provides antibodies, or antigen-binding fragments thereof, comprising a HCVR and a LCVR, said LCVR comprising LCDR1 comprising an amino acid sequence of SEQ ID NO: 428 or an amino acid sequence differing from SEQ ID NO: 428 by 1 amino acid, LCDR2 comprising an amino acid sequence of SEQ ID NO: 430 or an amino acid sequence differing from SEQ ID NO: 430 by 1 amino acid, and LCDR3 comprising an amino acid sequence of SEQ ID NO: 432 or an amino acid sequence differing from SEQ ID NO: 432 by 1 amino acid.

The present invention provides antibodies, or antigen-binding fragments thereof, comprising a heavy chain comprising an amino acid sequence selected from any of the HC amino acid sequences listed in Table 3, or a substantially similar sequence thereof having at least 90%, at least 95%, at least 98% or at least 99% sequence identity thereto.

The present invention also provides antibodies, or antigen-binding fragments thereof, comprising a light chain comprising an amino acid sequence selected from any of the LC amino acid sequences listed in Table 3, or a substantially similar sequence thereof having at least 90%, at least 95%, at least 98% or at least 99% sequence identity thereto.

The present invention also provides antibodies, or antigen-binding fragments thereof, comprising a HC and a LC amino acid sequence pair (HC/LC) comprising any of the HC amino acid sequences listed in Table 3 paired with any of the LC amino acid sequences listed in Table 3. According to certain embodiments, the present invention provides antibodies, or antigen-binding fragments thereof, comprising an HC/LC amino acid sequence pair contained within any of the exemplary anti-LAG3 antibodies listed in Table 3. In certain embodiments, the HC/LC amino acid sequence pair is selected from the group consisting of SEQ ID NOs: 577/578, 579/578, and 580/581.

The present invention also provides antibodies, or antigen-binding fragments thereof, comprising a set of six CDRs (i.e., HCDR1-HCDR2-HCDR3-LCDR1-LCDR2-LCDR3) contained within any of the exemplary anti-LAG3 antibodies listed in Table 1. In certain embodiments, the HCDR1-HCDR2-HCDR3-LCDR1-LCDR2-LCDR3 amino acid sequence set is selected from the group consisting of SEQ ID NOs: 388-390-392-396-398-400 (e.g., H4sH15479P), 420-422-424-428-430-432 (e.g., H4sH15482P) and 540-542-544-548-550-552 (e.g., H4sH14813N).

In a related embodiment, the present invention provides antibodies, or antigen-binding fragments thereof, comprising a set of six CDRs (i.e., HCDR1-HCDR2-HCDR3-LCDR1-LCDR2-LCDR3) contained within an HCVR/LCVR amino acid sequence pair as defined by any of the exemplary anti-LAG3 antibodies listed in Table 1. For example, the present invention includes antibodies, or antigen-binding fragments thereof, comprising the HCDR1-HCDR2-HCDR3-LCDR1-LCDR2-LCDR3 amino acid sequences set contained within an HCVR/LCVR amino acid sequence pair selected from the group consisting of SEQ ID NOs: 386/394 (e.g., H4sH15479P), 418/426 (e.g., H4sH15482P) and 538/546 (e.g., H4sH14813N). Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

The present invention includes anti-LAG3 antibodies having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

The present invention includes anti-LAG3 antibodies comprising a Fc domain, wherein the Fc domain comprises IgG1 or IgG4 isotype as described elsewhere herein. In certain embodiments, the Fc domain comprises an amino acid sequence selected from the group consisting of SEQ ID NOs: 569, 570, 571, 572 and 573.

The present invention also provides for antibodies and antigen-binding fragments thereof that compete for specific binding to LAG3 with an antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

The present invention also provides isolated antibodies and antigen-binding fragments thereof that block LAG3 binding to MHC class II. In some embodiments, the antibody or antigen-binding fragment thereof that blocks LAG3 binding may bind to the same epitope on LAG3 as MHC class II or may bind to a different epitope on LAG3 as MHC class II.

The present invention also provides antibodies and antigen-binding fragments thereof that bind specifically to LAG3 from human or other species. In certain embodiments, the antibodies may bind to human LAG3 and/or to monkey LAG3.

The present invention also provides antibodies and antigen-binding fragments thereof that cross-compete for binding to LAG3 with a reference antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

The present invention also provides antibodies and antigen-binding fragments thereof that bind to the same epitope as a reference antibody or antigen-binding fragment thereof comprising the CDRs of a HCVR and the CDRs of a LCVR, wherein the HCVR and LCVR each has an amino acid sequence selected from the HCVR and LCVR sequences listed in Table 1. In certain embodiments, the present invention provides antibodies and antigen-binding fragments thereof that bind to the same epitope as a reference antibody or antigen-binding fragment thereof comprising the CDRs of a HCVR and the CDRs of a LCVR, wherein the HCVR/LCVR amino acid sequence pair has SEQ ID NOs: 418/426.

The present invention also includes anti-LAG3 antibodies that interact with one or more amino acids contained within the extracellular domain of human LAG3 (SEQ ID NO: 588). In certain embodiments, the present invention provides anti-LAG3 antibodies and antigen-binding fragments thereof that interact with an amino acid sequence selected from the group consisting of (a) amino acids 28 to 69 of SEQ ID NO: 588; (b) amino acids 28 to 71 of SEQ ID NO: 588; (c) amino acids 31 to 52 of SEQ ID NO: 588; and (d) amino acids 32 to 69 of SEQ ID NO: 588. In certain embodiments, the present invention provides anti-LAG3 antibodies and antigen-binding fragments thereof that interact with one or more amino acids contained within SEQ ID NO: 589, for example, the present invention provides anti-LAG3 antibodies and antigen-binding fragments thereof that interact with at least 5 amino acids, at least 10 amino acids, or at least 20 amino acids contained within SEQ ID NO: 589. In certain embodiments, the present invention provides anti-LAG3 antibodies and antigen-binding fragments thereof that interact with the amino acid sequence of SEQ ID NO: 589 (corresponding to amino acids 28 to 71 of SEQ ID NO: 588).

In one embodiment, the invention provides a recombinant human monoclonal antibody or antigen-binding fragment that has one or more of the following characteristics: (a) binds specifically to human LAG3 and/or cynomolgus LAG3; (b) blocks the binding of LAG3 to MHC class II; (c) blocks LAG3-induced T cell down regulation and rescues T cell signaling; and (d) suppresses tumor growth and increases survival in a subject with cancer.

In some embodiments, the antibody or antigen binding fragment thereof may bind specifically to LAG3 in an agonist manner, i.e., it may enhance or stimulate LAG3 binding and/or activity; in other embodiments, the antibody may bind specifically to LAG3 in an antagonist manner, i.e., it may block LAG3 from binding to its ligand.

In certain embodiments, the antibodies or antigen-binding fragments of the present invention are bispecific comprising a first binding specificity to LAG3 and a second binding specificity for a second target epitope. The second target epitope may be another epitope on LAG3 or on a different protein. In certain embodiments, the second target epitope may be on a different cell including a different T cell, a B-cell, a tumor cell or a virally infected cell.

In a second aspect, the present invention provides nucleic acid molecules encoding anti-LAG3 antibodies or portions thereof. For example, the present invention provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto.

The present invention also provides nucleic acid molecules encoding any of the LCVR amino acid sequences listed in Table 1; in certain embodiments the nucleic acid molecule comprises a polynucleotide sequence selected from any of the LCVR nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 2, or a substantially similar sequence thereof having at least 90%, at least 95%, at least 98% or at least 99% sequence identity thereto.

The present invention also provides nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by any of the exemplary anti-LAG3 antibodies listed in Table 1.

The present invention also provides nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by any of the exemplary anti-LAG3 antibodies listed in Table 1.

The present invention also provides nucleic acid molecules encoding both an HCVR and an LCVR, wherein the HCVR comprises an amino acid sequence of any of the HCVR amino acid sequences listed in Table 1, and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from any of the LCVR nucleic acid sequences listed in Table 2, or a substantially similar sequence thereof having at least 90%, at least 95%, at least 98% or at least 99% sequence identity thereto. In certain embodiments according to this aspect of the invention, the nucleic acid molecule encodes an HCVR and LCVR, wherein the HCVR and LCVR are both derived from the same anti-LAG3 antibody listed in Table 1.

The present invention provides nucleic acid molecules encoding any of the heavy chain amino acid sequences listed in Table 3. The present invention also provides nucleic acid molecules encoding any of the light chain amino acid sequences listed in Table 3.

The present invention also provides nucleic acid molecules encoding both heavy chain (HC) and a light chain (LC), wherein the HC comprises an amino acid sequence of any of the HC amino acid sequences listed in Table 3, and wherein the LC comprises an amino acid sequence of any of the LC amino acid sequences listed in Table 3.

In a related aspect, the present invention provides recombinant expression vectors capable of expressing a polypeptide comprising a heavy or light chain variable region of an anti-LAG3 antibody. For example, the present invention includes recombinant expression vectors comprising any of the nucleic acid molecules mentioned above, i.e., nucleic acid molecules encoding any of the HCVR, LCVR, and/or CDR sequences as set forth in Table 1. The present invention also provides recombinant expression vectors capable of expressing a polypeptide comprising a heavy or light chain of an anti-LAG3 antibody. For example, the present invention includes recombinant expression vectors comprising any of the nucleic acid molecules mentioned above, i.e., nucleic acid molecules encoding any of the heavy chain or light chain sequences as set forth in Table 3. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced.

In a third aspect, the present invention provides a pharmaceutical composition comprising a recombinant human antibody or fragment thereof which specifically binds LAG3 and a pharmaceutically acceptable carrier. In a related aspect, the invention features a composition which is a combination of an anti-LAG3 antibody and a second therapeutic agent. In one embodiment, the second therapeutic agent is any agent that is advantageously combined with an anti-LAG3 antibody. Exemplary agents that may be advantageously combined with an anti-LAG3 antibody include, without limitation, other agents that bind and/or modulate LAG3 signaling (including other antibodies or antigen-binding fragments thereof, etc.) and/or agents which do not directly bind LAG3 but nonetheless modulate immune cell activation. Additional combination therapies and co-formulations involving the anti-LAG3 antibodies of the present invention are disclosed elsewhere herein.

In a fourth aspect, the invention provides methods to modulate the immune response in a subject, the method comprising administering a therapeutically effective amount of an anti-LAG3 antibody or antigen-binding fragment thereof of the invention to the subject in need thereof. In certain embodiments, the invention provides methods to enhance the immune response in a subject, the methods comprising administering to the subject an effective amount of an antibody or fragment thereof of the invention that binds LAG3. In one embodiment, the invention provides a method to stimulate or enhance T cell activation in a subject. In certain embodiments, the invention provides methods to rescue T cell activity comprising contacting the T cell with an effective amount of an antibody of the invention such that T cell activity is rescued. In one embodiment, the invention provides methods to inhibit a T regulatory (Treg) cell in a subject, the methods comprising administering a therapeutically effective amount of an antibody or antigen-binding fragment thereof of the invention to the subject in need thereof. In certain embodiments, the subject in need thereof may suffer from a disease or disorder such as cancer or viral infection. In certain embodiments, the present invention provides methods to rescue LAG3-mediated inhibition of T cell activity comprising contacting the T cell with an effective amount of an antibody of the present invention.

In a fifth aspect, the invention provides therapeutic methods for treating a disease or disorder such as cancer or viral infection in a subject using an anti-LAG3 antibody or antigen-binding portion of an antibody of the invention, wherein the therapeutic methods comprise administering a therapeutically effective amount of a pharmaceutical composition comprising an antibody or fragment of an antibody of the invention to the subject in need thereof. The disorder treated is any disease or condition which is improved, ameliorated, inhibited or prevented by stimulation or inhibition of LAG3 activity or signaling. In certain embodiments, the antibody or antigen-binding fragment thereof the invention is administered in combination with a second therapeutic agent to the subject in need thereof. The second therapeutic agent may be selected from the group consisting of an antibody to another T cell co-inhibitor, an antibody to a tumor cell antigen, an antibody to a T cell receptor, an antibody to an epitope on a virally infected cell, a cytotoxic agent, an anti-cancer drug, an anti-viral drug, an anti-inflammatory drug (e.g., corticosteroids), chemotherapeutic agent, radiation therapy, an immunosuppressant and any other drug or therapy known in the art. In certain embodiments, the second therapeutic agent may be an agent that helps to counteract or reduce any possible side effect(s) associated with an antibody or antigen-binding fragment thereof of the invention, if such side effect(s) should occur.

In certain embodiments, the present invention provides methods for suppressing tumor growth. For example, the present invention provides to suppress tumor growth due to a primary tumor or a metastatic tumor in a subject. In certain embodiments, the present invention provides methods to enhance survival (e.g., progression-free survival or overall survival) of a subject with cancer. Examples of cancer include, but are not limited to, primary and/or recurrent cancer, including blood cancer (e.g., a hematologic malignancy such as lymphoma, myeloma or leukemia), brain cancer (e.g., glioblastoma multiforme), lung cancer (e.g., non-small cell lung cancer), squamous cell carcinoma of head and neck, hepatic cell carcinoma, renal cell carcinoma, melanoma, mesothelioma, ovarian cancer, bladder cancer, breast cancer, bone cancer, colorectal cancer, prostate cancer, and colon cancer. In certain embodiments, the present invention provides methods for inhibiting or suppressing growth of established tumors. The methods comprise administering to a subject in need thereof a pharmaceutical composition comprising a therapeutically effective amount of an anti-LAG3 antibody of the present invention. In certain embodiments, the antibody is administered in combination with a second therapeutic agent selected from the group consisting of a programmed death-1 (PD-1) inhibitor (e.g., an anti-PD-1 antibody such as nivolumab or REGN2810), a programmed death-ligand 1 (PD-L1) inhibitor (e.g., an anti-PD-L1 antibody), a vascular endothelial growth factor (VEGF) antagonist (e.g., aflibercept, bevacizumab), an angiopoietin-2 (Ang2) inhibitor (e.g., an anti-Ang2 antibody such as nesvacumab), a cytotoxic T-lymphocyte antigen 4

(CTLA-4) inhibitor (e.g., ipilimumab), CD20×CD3 bispecific antibody, a cytotoxin, a chemotherapeutic agent, and radiation therapy. Additional examples of additional therapies/therapeutic agents that can be used in combination with an anti-LAG3 antibody of the invention for use in treating cancer are described elsewhere herein.

The antibody or fragment thereof may be administered subcutaneously, intravenously, intradermally, intraperitoneally, orally, intramuscularly, or intracranially. The antibody or fragment thereof may be administered at a dose of about 0.1 mg/kg of body weight to about 100 mg/kg of body weight of the subject.

The present invention also includes use of an anti-LAG3 antibody or antigen-binding fragment thereof of the invention in the manufacture of a medicament for the treatment of a disease or disorder that would benefit from the blockade of LAG3 binding and/or signaling such as cancer.

Other embodiments will become apparent from a review of the ensuing detailed description.

BRIEF DESCRIPTION OF THE FIGURES

FIG. 2A. Average tumor volumes (mm$^3$±SEM) in each treatment group were measured at multiple time points after tumor implantation. Treatment was started on day 14 when average tumor volume reached 50 mm$^3$. Treatment days are indicated by arrows. All antibodies were administered intraperitoneally (i.p.) at 10 mg/kg. FIG. 2B. Individual tumor volumes within each treatment group were measured at day 35 post-implantation. Statistical significance was determined by one-way ANOVA with Dunnett's multiple comparison post-test (*p<0.05). FIGS. 2A-2B. Treatment groups: isotype controls rat IgG2a+mouse IgG1 control antibody: (•); anti-mouse PD-1 antibody+mouse IgG1 control (▲); anti-mouse LAG3 antibody+rat IgG2a control (■); anti-mouse PD-1 antibody+ anti-mouse LAG3 antibody (▼).

FIG. 3A. Average tumor volumes (mm$^3$±SEM) in each treatment group were measured at multiple time points after tumor implantation. Treatment was started on day 8, when average tumor volume reached 45 mm$^3$. Treatment days are indicated by arrows. FIG. 3B. Individual tumor volumes in each treatment group were measured on day 23 post-implantation. Statistical significance was determined by one-way ANOVA with Dunnett's multiple comparison post-test (****p<0.0001). FIGS. 3A-3B. Treatment groups: isotype controls rat IgG2a+ mouse IgG1 (•), anti-mouse PD-1 antibody+mIgG1 control (▲), anti-mouse LAG3 antibody+rat IgG2a control (■), and anti-mouse PD-1+anti-mouse LAG3 antibody (▼).

FIG. 5A. Average tumor volumes (mm$^3$±SEM) in each treatment group at multiple time-points post-tumor implantation. Treatment days are indicated by arrows. FIG. 5B. Individual tumor volumes in each group were monitored for 24 days. The number of tumor-free mice in each group at day 24 is shown. FIGS. 5A-5B. Treatment groups: mAb1 (anti-hLAG3) at 25 mg/kg (■); REGN2810 (anti-hPD-1) at 10 mg/kg (▲), and human isotype control antibody at 25 mg/kg (•).

FIGS. 6A-6C summarizes the in vivo efficacy of anti-human LAG3 antibody ("mAb1") alone and in combination with anti-human PD-1 antibody (REGN2810) against MC38 tumors (described in Example 13). FIG. 6A. Average tumor volumes (mm$^3$±SEM) in each treatment group at multiple time points post tumor implantation. Treatment days are indicated by arrows. FIG. 6B. Individual tumor volumes in each treatment group were measured on day 22 post-implantation. Statistical significance was determined by one-way ANOVA with Tukey's multiple comparison post-test (*p<0.05; p<0.01) FIGS. 6A-6B. Treatment groups: mAb1 (anti-hLAG3) at 25 mg/kg (♦); REGN2810 (anti-hPD-1) at 10 mg/kg (■); combination of mAb1 (anti-hLAG3) at 25 mg/kg and REGN2810 (anti-hPD-1) at 10 mg/kg (▲); human isotype control at 25 mg/kg (•). FIG. 6C. Percent tumor-free survival in treated mice. Statistical significance was determined by log-rank (Mantel-Cox) test (**p<0.0001). Treatment groups: mAb1 (anti-hLAG3) at 25 mg/kg (♦); REGN2810 (anti-hPD-1) at 10 mg/kg (▼); combination of mAb1 (anti-hLAG3) at 25 mg/kg and REGN2810 (anti-hPD-1) at 10 mg/kg (▲); human isotype control at 25 mg/kg (•).

FIG. 7A. Average tumor volumes (mm$^3$±SEM) in each treatment group at multiple time points post tumor implantation. Treatment days are indicated by arrows. FIG. 7B. Individual tumor volumes in each treatment group were measured on day 22 post-implantation. Statistical significance was determined by one-way ANOVA with Tukey's multiple comparison post-test (*p<0.05) FIG. 7C. Percent tumor-free survival in treated mice. Statistical significance was determined by log-rank (Mantel-Cox) test (*p<0.0197). Treatment groups: mAb1 (anti-hLAG3) at 25 mg/kg (♦); REGN2810 (anti-hPD-1) at 10 mg/kg (●); REGN2810 (anti-hPD-1) at 1 mg/kg (▲); combination of mAb1 (anti-hLAG3) at 25 mg/kg and REGN2810 (anti-hPD-1) at 10 mg/kg (■); combination of mAb1 (anti-hLAG3) at 25 mg/kg and REGN2810 (anti-hPD-1) at 1 mg/kg (▼); and human isotype control at 25 mg/kg (•).

FIG. 8A. Average tumor volumes (mm$^3$±SEM) in each treatment group at multiple time points post tumor implantation. Treatment days are indicated by arrows. Statistical significance was determined by two-way ANOVA with Dunnett's multiple comparison test (*p<0.05). FIG. 8B. Individual tumor volumes in each treatment group as measured on day 23 post-implantation. Statistical significance was determined by one-way ANOVA with Dunnett's multiple comparison test (p<0.01). FIG. 8C. Percent tumor-free survival in treated mice. Statistical significance was determined by log-rank (Mantel-Cox) test, with Bonferroni adjustment for multiple comparisons (*p<0.001, **p<0.01). Treatment groups: mAb1 (anti-hLAG3) at 25 mg/kg (♦); mAb1 (anti-hLAG3) at 5 mg/kg (●); REGN2810 (anti-hPD-1) at 10 mg/kg (▲); combination of mAb1 (anti-hLAG3) at 25 mg/kg and REGN2810 (anti-hPD-1) at 10 mg/kg (■); combination of mAb1 (anti-hLAG3) at 5 mg/kg and REGN2810 (anti-hPD-1) at 10 mg/kg (▼); and human isotype control at 25 mg/kg (•).

DETAILED DESCRIPTION

Figure 1:
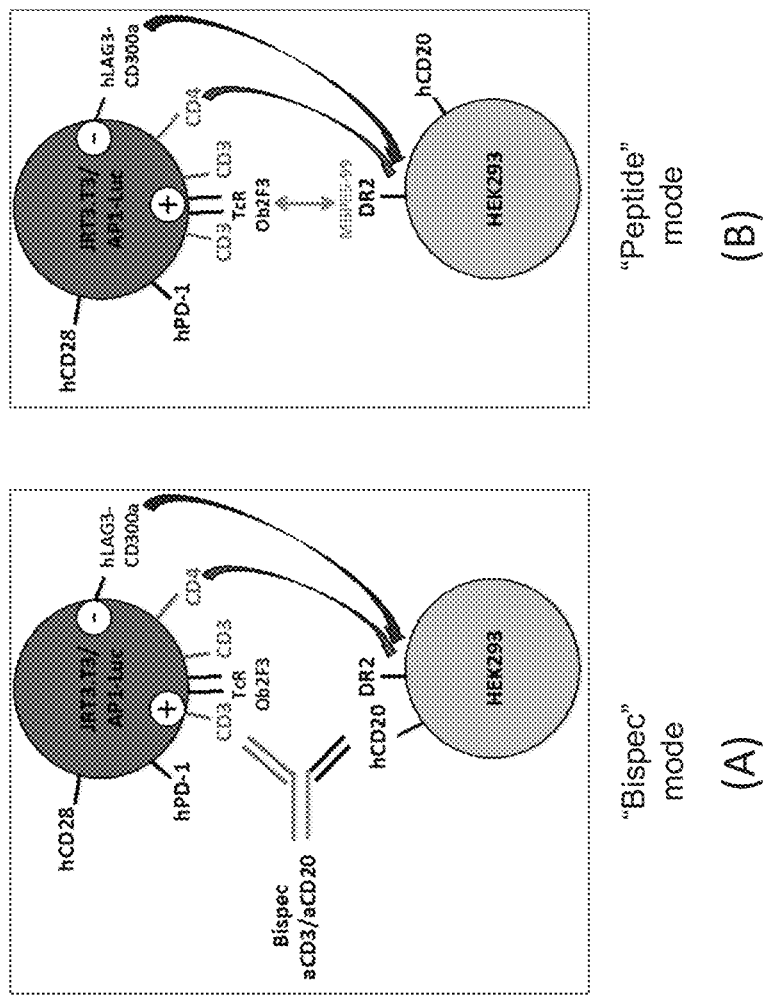
FIG. 1 is a schematic of the luciferase-based LAG3 bioassay described in Example 8 herein. Panel (A): "Bispec" mode: Inactive Jurkat derived T cells are activated by T-cell receptor (TCR) clustering through the CD3×CD20 bispecific antibody. Panel (B): "Peptide" mode: In this mode, inactive Jurkat derived T cells are activated by specific MHC/peptide complex (Ob2F3 TCR heterodimer with the MHCII protein, HLA-DR2AB, in complex with the MBP85-99 peptide). LAG3 binding to DR2 attenuates response in activated Jurkat derived T cells. Blocking LAG3 antibody rescues the response in activated Jurkat derived T cells.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are now described. All publications mentioned herein are incorporated herein by reference in their entirety.

The term "LAG3" refers to the lymphocyte activation gene-3 protein, an immune checkpoint receptor or T cell co-inhibitor, also known as CD223. The amino acid sequence of full-length LAG3 is provided in GenBank as accession number NP_002277.4 and is also referred to herein as SEQ ID NO: 582. The term "LAG3" also includes protein variants of LAG3 having the amino acid sequence of SEQ ID NOs: 574, 575 or 576. The term "LAG3" includes recombinant LAG3 or a fragment thereof. The term also encompasses LAG3 or a fragment thereof coupled to, for example, histidine tag, mouse or human Fc, or a signal sequence such as ROR1. For example, the term includes sequences exemplified by SEQ ID NO: 575, comprising a mouse Fc (mIgG2a) at the C-terminal, coupled to amino acid residues 29-450 of full-length LAG3. Protein variants as exemplified by SEQ ID NO: 574 comprise a histidine tag at the C-terminal, coupled to amino acid residues 29-450 of full length LAG3. Unless specified as being from a non-human species, the term "LAG3" means human LAG3.

LAG3 is a member of the immunoglobulin (Ig) superfamily. LAG3 is a 503-amino acid type-1 transmembrane protein with four extracellular Ig-like domains D1 to D4 and is expressed on activated T cells, natural killer cells, B cells, plasmacytoid dendritic cells, and regulatory T cells. The LAG3 receptor binds to MHC class II molecules present on antigen presenting cells (APCs).

As used herein, the term "T cell co-inhibitor" refers to a ligand and/or receptor which modulates the immune response via T cell activation or suppression. The term "T cell co-inhibitor", also known as T cell co-signaling molecule, includes, but is not limited to, programmed death-1 (PD-1), cytotoxic T-lymphocyte antigen-4 (CTLA-4), B and T lymphocyte attenuator (BTLA), CD-28, 2B4, LY108, T cell immunoglobulin and mucin 3 (TIM3), T cell immunoreceptor with immunoglobulin and ITIM (TIGIT; also known as VSIG9), leucocyte associated immunoglobulin-like receptor 1 (LAIR1; also known as CD305), inducible T cell costimulator (ICOS; also known as CD278), V-domain Ig suppressor of T cell activation (VISTA) and CD160.

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments of the invention, the FRs of the antibody (or antigen binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The fully human anti-LAG3 monoclonal antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes fully human anti-LAG3 monoclonal antibodies comprising variants of any of the HCVR, LCVR, and/or CDR amino acid sequences disclosed herein having one or more conservative substitutions. For example, the present invention includes anti-LAG3 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "human antibody", as used herein, is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences. The term includes antibodies recombinantly produced in a non-human mammal, or in cells of a non-human mammal. The term is not intended to include antibodies isolated from or generated in a human subject.

The term "recombinant", as used herein, refers to antibodies or antigen-binding fragments thereof of the invention created, expressed, isolated or obtained by technologies or methods known in the art as recombinant DNA technology which include, e.g., DNA splicing and transgenic expression. The term refers to antibodies expressed in a non-human mammal (including transgenic non-human mammals, e.g., transgenic mice), or a cell (e.g., CHO cells) expression system or isolated from a recombinant combinatorial human antibody library.

The term "multi-specific antigen-binding molecules", as used herein refers to bispecific, tri-specific or multi-specific antigen-binding molecules, and antigen-binding fragments thereof. Multi-specific antigen-binding molecules may be specific for different epitopes of one target polypeptide or may contain antigen-binding domains specific for epitopes of more than one target polypeptide. A multi-specific antigen-binding molecule can be a single multifunctional polypeptide, or it can be a multimeric complex of two or more polypeptides that are covalently or non-covalently associated with one another. The term "multi-specific antigen-binding molecules" includes antibodies of the present invention that may be linked to or co-expressed with another functional molecule, e.g., another peptide or protein. For example, an antibody or fragment thereof can be functionally linked (e.g., by chemical coupling, genetic fusion, non-covalent association or otherwise) to one or more other molecular entities, such as a protein or fragment thereof to produce a bi-specific or a multi-specific antigen-binding molecule with a second binding specificity. According to the present invention, the term "multi-specific antigen-binding molecules" also includes bi-specific, tri-specific or multi-specific antibodies or antigen-binding fragments thereof. In certain embodiments, an antibody of the present invention is functionally linked to another antibody or antigen-binding fragment thereof to produce a bispecific antibody with a second binding specificity. Bispecific and multi-specific antibodies of the present invention are described elsewhere herein.

The term "specifically binds," or "binds specifically to", or the like, means that an antibody or antigen-binding fragment thereof forms a complex with an antigen that is relatively stable under physiologic conditions. Specific binding can be characterized by an equilibrium dissociation constant of at least about $1 \times 10^{-8}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been identified by surface plasmon resonance, e.g., BIACORE™, which bind specifically to LAG3. Moreover, multi-specific antibodies that bind to one domain in LAG3 and one or more additional antigens or a bi-specific that binds to two different regions of LAG3 are nonetheless considered antibodies that "specifically bind", as used herein.

The term "high affinity" antibody refers to those mAbs having a binding affinity to LAG3, expressed as $K_D$, of at least $10^{-8}$ M; preferably $10^{-9}$ M; more preferably $10^{-10}$M, even more preferably $10^{-11}$ M, even more preferably $10^{-12}$ M, as measured by surface plasmon resonance, e.g., BIACORE™ or solution-affinity ELISA.

By the term "slow off rate", "Koff" or "kd" is meant an antibody that dissociates from LAG3, with a rate constant of $1\times10^{-3}$ $s^{-1}$ or less, preferably $1\times10^{-4}$ $s^{-1}$ or less, as determined by surface plasmon resonance, e.g., BIACORE™.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to bind to LAG3.

In specific embodiments, antibody or antibody fragments of the invention may be conjugated to a moiety such a ligand or a therapeutic moiety ("immunoconjugate"), such as a cytotoxin, a second anti-LAG3 antibody, an antibody to a tumor-specific antigen, an anti-cancer drug, or any other therapeutic moiety useful for treating a disease or condition including cancer or viral infection including chronic viral infection.

An "isolated antibody", as used herein, is intended to refer to an antibody that is substantially free of other antibodies (Abs) having different antigenic specificities (e.g., an isolated antibody that specifically binds LAG3, or a fragment thereof, is substantially free of Abs that specifically bind antigens other than LAG3.

A "blocking antibody" or a "neutralizing antibody", as used herein (or an "antibody that neutralizes LAG3 activity" or "antagonist antibody"), is intended to refer to an antibody whose binding to LAG3 results in inhibition of at least one biological activity of LAG3. For example, an antibody of the invention may prevent or block LAG3 binding to MHC class II.

An "activating antibody" or an "enhancing antibody", as used herein (or an "agonist antibody"), is intended to refer to an antibody whose binding to LAG3 results in increasing or stimulating at least one biological activity of LAG3. For example, an antibody of the invention may increase LAG3 binding to MHC class II.

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "cross-competes", as used herein, means an antibody or antigen-binding fragment thereof binds to an antigen and inhibits or blocks the binding of another antibody or antigen-binding fragment thereof. The term also includes competition between two antibodies in both orientations, i.e., a first antibody that binds and blocks binding of second antibody and vice-versa. In certain embodiments, the first antibody and second antibody may bind to the same epitope. Alternatively, the first and second antibodies may bind to different, but overlapping epitopes such that binding of one inhibits or blocks the binding of the second antibody, e.g., via steric hindrance. Cross-competition between antibodies may be measured by methods known in the art, for example, by a real-time, label-free bio-layer interferometry assay. Cross-competition between two antibodies may be expressed as the binding of the second antibody that is less than the background signal due to self-self binding (wherein first and second antibodies is the same antibody). Cross-competition between 2 antibodies may be expressed, for example, as % binding of the second antibody that is less than the baseline self-self background binding (wherein first and second antibodies is the same antibody).

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

Sequence identity can be calculated using an algorithm, for example, the Needleman Wunsch algorithm (Needleman and Wunsch 1970, J. Mol. Biol. 48: 443-453) for global alignment, or the Smith Waterman algorithm (Smith and Waterman 1981, J. Mol. Biol. 147: 195-197) for local alignment. Another preferred algorithm is described by Dufresne et al in Nature Biotechnology in 2002 (vol. 20, pp. 1269-71) and is used in the software GenePAST (GQ Life Sciences, Inc. Boston, Mass.).

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215: 403-410 and (1997) Nucleic Acids Res. 25:3389-3402, each of which is herein incorporated by reference.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

As used herein, the term "subject" refers to an animal, preferably a mammal, in need of amelioration, prevention and/or treatment of a disease or disorder such as viral infection, or cancer. The term includes human subjects who have or are at risk of having cancer, metastatic cancer or viral infection.

As used herein, "anti-cancer drug" means any agent useful to treat or ameliorate or inhibit cancer including, but not limited to, cytotoxins and agents such as antimetabolites, alkylating agents, anthracyclines, antibiotics, antimitotic agents, procarbazine, hydroxyurea, asparaginase, corticosteroids, cyclophosphamide, mytotane (O,P'-(DDD)), biologics (e.g., antibodies and interferons) and radioactive agents. As used herein, "a cytotoxin or cytotoxic agent", also refers to a chemotherapeutic agent and means any agent that is detrimental to cells. Examples include Taxol® (paclitaxel), temozolamide, cytochalasin B, gramicidin D, ethidium bromide, emetine, cisplatin, mitomycin, etoposide, tenoposide, vincristine, vinbiastine, coichicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

As used herein, the term "anti-viral drug" refers to any drug or therapy used to treat, prevent, or ameliorate a viral infection in a host subject. The term "anti-viral drug" includes, but is not limited to zidovudine, lamivudine, abacavir, ribavirin, lopinavir, efavirenz, cobicistat, tenofovir, rilpivirine, analgesics and corticosteroids. In the context of the present invention, the viral infections include long-term or chronic infections caused by viruses including, but not limited to, human immunodeficiency virus (HIV), hepatitis B virus (HBV), hepatitis C virus (HCV), human papilloma virus (HPV), lymphocytic choriomeningitis virus (LCMV), and simian immunodeficiency virus (SIV).

As used herein, the term "to enhance immune response", refers to an increase in activity of an immune cell such as T cell or NK cell against a tumor cell or a virally infected cell. In the context of the present invention, the term includes blocking of LAG3-mediated inhibition of T cell activity, or rescue or reversal of exhausted state of T cells. It also includes inhibition of regulatory T cell activity. The enhanced immune response, as used in the context of the present invention, results in increased killing of tumor cells and/or inhibition of tumor growth.

The antibodies and antigen-binding fragments of the present invention specifically bind to LAG3 and enhance T cell activation. The anti-LAG3 antibodies may bind to LAG3 with high affinity or with low affinity. In certain embodiments, the antibodies of the present invention may be blocking antibodies wherein the antibodies may bind to LAG3 and inhibit LAG3 signaling. In some embodiments, the antibodies of the invention block the binding of LAG3 to MHC class II and/or stimulate or enhance T cell activation. In some embodiments, the antibodies bind to LAG3 and reverse the anergic state of exhausted T cells. In certain embodiments, the antibodies bind to LAG3 and inhibit regulatory T cell activity. In some embodiments, the antibodies may be useful for stimulating or enhancing the immune response and/or for treating a subject suffering from cancer, or a viral infection. The antibodies when administered to a subject in need thereof may reduce chronic infection by a virus such as HIV, LCMV or HBV in the subject. They may be used to inhibit the growth of tumor cells in a subject. They may be used alone or as adjunct therapy with other therapeutic moieties or modalities known in the art for treating cancer, or viral infection.

In certain embodiments, the anti-LAG3 antibodies may be multi-specific antigen-binding molecules, wherein they comprise a first binding specificity to LAG3 and a second binding specificity to an antigen selected from the group consisting of another T cell co-inhibitor, and a different epitope of LAG3.

An immunogen comprising any one of the following can be used to generate antibodies to LAG3. In certain embodiments, the antibodies of the invention are obtained from mice immunized with a full length, native LAG3 (See NCBI accession number NP_002277.4) (SEQ ID NO: 582), or with a recombinant LAG3 peptide. Alternatively, LAG3 or a fragment thereof may be produced using standard biochemical techniques and modified (SEQ ID NOs: 574-576) and used as immunogen.

In certain embodiments, the immunogen is one or more extracellular domains of LAG3. In one embodiment of the invention, the immunogen is a fragment of LAG3 that ranges from about amino acid residues 29-450 of SEQ ID NO: 582.

In some embodiments, the immunogen may be a recombinant LAG3 peptide expressed in E. coli or in any other eukaryotic or mammalian cells such as Chinese hamster ovary (CHO) cells.

In certain embodiments, antibodies that bind specifically to LAG3 may be prepared using fragments of the above-noted regions, or peptides that extend beyond the designated regions by about 5 to about 20 amino acid residues from either, or both, the N or C terminal ends of the regions described herein. In certain embodiments, any combination of the above-noted regions or fragments thereof may be used in the preparation of LAG3 specific antibodies.

The peptides may be modified to include addition or substitution of certain residues for tagging or for purposes of conjugation to carrier molecules, such as, KLH. For example, a cysteine may be added at either the N terminal or C terminal end of a peptide, or a linker sequence may be added to prepare the peptide for conjugation to, for example, KLH for immunization.

Certain anti-LAG3 antibodies of the present invention are able to bind to and neutralize the activity of LAG3, as determined by in vitro or in vivo assays. The ability of the antibodies of the invention to bind to and neutralize the activity of LAG3 may be measured using any standard method known to those skilled in the art, including binding assays, or activity assays, as described herein.

Non-limiting, exemplary in vitro assays for measuring binding activity are illustrated in Examples herein. In Example 3, the binding affinities and kinetic constants of human anti-LAG3 antibodies for human LAG3 were determined by surface plasmon resonance and the measurements were conducted on a Biacore 4000 or T200 instrument. In Example 4, blocking assays were used to determine cross-competition between anti-LAG3 antibodies. Examples 5 and 6 describe the binding of the antibodies to cells overexpressing LAG3. In Example 7, binding assays were used to determine the ability of the anti-LAG3 antibodies to block MHC class II-binding ability of LAG3 in vitro. In Example 8, a luciferase assay was used to determine the ability of anti-LAG3 antibodies to antagonize LAG3 signaling in T cells. In Example 9, a fluorescence assay was used to determine the ability of anti-LAG3 antibodies to bind to activated monkey CD4+ and CD8+ T cells.

In certain embodiments, the antibodies of the present invention are able to enhance or stimulate T cell activity in vitro, in a subject with cancer or in a subject infected with a virus such as LCMV. In certain embodiments, the antibodies of the present invention are used in combination with a second therapeutic agent, such as an antibody to a second T cell co-inhibitor, to enhance the immune response and inhibit tumor growth in a subject.

The antibodies specific for LAG3 may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface. In one embodiment, the label may be a radionuclide, a fluorescent dye or a MRI-detectable label. In certain embodiments, such labeled antibodies may be used in diagnostic assays including imaging assays.

EXEMPLARY EMBODIMENTS OF THE INVENTION

In certain embodiments, the present invention provides an isolated antibody or antigen-binding fragment thereof that binds specifically to human lymphocyte activation gene 3 (LAG3) protein, wherein the antibody or antigen-binding fragment thereof has a property selected from the group consisting of: (a) binds monomeric human LAG3 with a binding dissociation equilibrium constant ($K_D$) of less than about 10 nM as measured in a surface plasmon resonance assay at 25° C.; (b) binds monomeric human LAG3 with a $K_D$ less than about 8 nM as measured in a surface plasmon resonance assay at 37° C.; (c) binds dimeric human LAG3 with a $K_D$ less than about 1.1 nM as measured in a surface plasmon resonance assay at 25° C.; (d) binds dimeric human LAG3 with a $K_D$ less than about 1 nM as measured in a surface plasmon resonance assay at 37° C.; (e) binds to a hLAG3-expressing cell with an $EC_{50}$ less than about 8 nM as measured in a flow cytometry assay; (f) binds to a mfLAG3-expressing cell with a $EC_{50}$ less than about 2.3 nM as measured in a flow cytometry assay; (g) blocks binding of hLAG3 to human MHC class II with $IC_{50}$ less than about 32 nM as determined by a cell adherence assay; (h) blocks binding of hLAG3 to mouse MHC class II with $IC_{50}$ less than about 30 nM as determined by a cell adherence assay; (i) blocks binding of hLAG3 to MHC class II by more than 90% as determined by a cell adherence assay; (j) rescues LAG3-mediated inhibition of T cell activity with $EC_{50}$ less than about 9 nM as determined in a luciferase reporter assay; and (k) binds to activated CD4+ and CD8+ T cells with $EC_{50}$ less than about 1.2 nM, as determined in a fluorescence assay.

In certain embodiments, the isolated antibody or antigen-binding fragment thereof of the invention comprises three heavy chain complementarity determining regions (CDRs) (HCDR1, HCDR2 and HCDR3) contained within any one of the heavy chain variable region (HCVR) sequences listed in Table 1; and three light chain CDRs (LCDR1, LCDR2 and LCDR3) contained within any one of the light chain variable region (LCVR) sequences listed in Table 1. In certain embodiments, the isolated antibody or antigen-binding fragment thereof comprises a HCVR having an amino acid sequence selected from the group consisting of HCVR sequences listed in Table 1. In certain embodiments, the isolated antibody or antigen-binding fragment thereof comprises a LCVR having an amino acid sequence selected from the group consisting of LCVR sequences listed in Table 1.

In certain embodiments, the isolated antibody or antigen-binding fragment thereof comprises: (a) a HCDR1 domain having an amino acid sequence selected from the group consisting of SEQ ID NOs: 4, 20, 36, 52, 68, 84, 100, 116, 132, 148, 164, 180, 196, 212, 228, 244, 260, 276, 292, 308, 324, 340, 356, 372, 388, 404, 420, 436, 452, 460, 468, 476, 484, 492, 500, 508, 516, 540, and 556; (b) a HCDR2 domain having an amino acid sequence selected from the group consisting of SEQ ID NOs: 6, 22, 38, 54, 70, 86, 102, 118, 134, 150, 166, 182, 198, 214, 230, 246, 262, 278, 294, 310, 326, 342, 358, 374, 390, 406, 422, 438, 454, 462, 470, 478, 486, 494, 502, 510, 518, 542, and 558; (c) a HCDR3 domain having an amino acid sequence selected from the group consisting of SEQ ID NOs: 8, 24, 40, 56, 72, 88, 104, 120, 136, 152, 168, 184, 200, 216, 232, 248, 264, 280, 296, 312, 328, 344, 360, 376, 392, 408, 424, 440, 456, 464, 472, 480, 488, 496, 504, 512, 520, 544, and 560; (d) a LCDR1 domain having an amino acid sequence selected from the group consisting of SEQ ID NOs: 12, 28, 44, 60, 76, 92, 108, 124, 140, 156, 172, 188, 204, 220, 236, 252, 268, 284, 300, 316, 332, 348, 364, 380, 396, 412, 428, 444, 524, 532, 548, and 564; (e) a LCDR2 domain having an amino acid sequence selected from the group consisting of SEQ ID NOs: 14, 30, 46, 62, 78, 94, 110, 126, 142, 158, 174, 190, 206, 222, 238, 254, 270, 286, 302, 318, 334, 350, 366, 382, 398, 414, 430, 446, 526, 534, 550, and 566; and (f) a LCDR3 domain having an amino acid sequence selected from the group consisting of SEQ ID NOs: 16, 32, 48, 64, 80, 96, 112, 128, 144, 160, 176, 192, 208, 224, 240, 256, 272, 288, 304, 320, 336, 352, 368, 384, 400, 416, 432, 448, 528, 536, 552, and 568.

In certain embodiments, the isolated antibody or antigen-binding fragment thereof of the present invention comprises a HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330, 338/346, 354/362, 370/378, 386/394, 402/410, 418/426, 434/442, 450/522, 458/522, 466/522, 474/522, 482/522, 490/522, 498/530, 506/530, 514/530, 538/546, and 554/562.

In certain embodiments, the isolated antibody or antigen-binding fragment of claim 7, wherein the antibody or antigen-binding fragment thereof comprises an HCVR/LCVR amino acid sequence pair selected from the group consisting of SEQ ID NOs: 386/394, 418/426, and 538/546.

In certain embodiments, the present invention provides an isolated antibody or antigen-binding fragment thereof that blocks LAG3 binding to MHC class II comprising three CDRs of a HCVR, wherein the HCVR has an amino acid sequence selected from the group consisting of SEQ ID NOs: 2, 18, 34, 50, 66, 82, 98, 114, 130, 146, 162, 178, 194, 210, 226, 242, 258, 274, 290, 306, 322, 338, 354, 370, 386, 402, 418, 434, 450, 458, 466, 474, 482, 490, 498, 506, 514, 538, and 554; and three CDRs of a LCVR, wherein the LCVR has an amino acid sequence selected from the group consisting of SEQ ID NOs: 10, 26, 42, 58, 74, 90, 106, 122, 138, 154, 170, 186, 202, 218, 234, 250, 266, 282, 298, 314, 330, 346, 362, 378, 394, 410, 426, 442, 522, 530, 546, and 562.

In certain embodiments, the isolated antibody or antigen-binding fragment comprises a HCVR/LCVR amino acid sequence pair selected from the group consisting of SEQ ID NOs: 386/394, 418/426, and 538/546.

In certain embodiments, the present invention provides an antibody or antigen-binding fragment thereof that competes for binding to an antibody or antigen-binding fragment thereof comprising a HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330, 338/346, 354/362, 370/378, 386/394, 402/410, 418/426, 434/442, 450/522, 458/522, 466/522, 474/522, 482/522, 490/522, 498/530, 506/530, 514/530, 538/546, and 554/562.

In certain embodiments, the present invention provides an antibody or antigen-binding fragment thereof that binds to the same epitope as an antibody or antigen-binding fragment thereof comprising a HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330, 338/346, 354/362, 370/378, 386/394, 402/410, 418/426, 434/442, 450/522, 458/522, 466/522, 474/522, 482/522, 490/522, 498/530, 506/530, 514/530, 538/546, and 554/562.

In certain embodiments, the present invention provides an antibody or antigen-binding fragment hereof that is a human, humanized or a chimeric antibody. Said antibody or antigen-binding fragment thereof can for instance be an IgG1 or an IgG4 antibody, such as e.g., a human IgG1 or an IgG4 antibody. The constant regions of those antibodies might correspond to wild-type constant regions, or to constant regions into which mutations have been introduced.

In certain embodiments, the present invention provides an isolated antibody comprising a heavy chain and a light chain, wherein the heavy chain comprises an amino acid sequence selected from the group consisting of SEQ ID NOs: 577, 579, and 580. In certain embodiments, the present invention provides an isolated antibody comprising a heavy chain and a light chain, wherein the light chain comprises an amino acid sequence selected from the group consisting of SEQ ID NOs: 578, and 581. In certain embodiments, the present invention provides an isolated antibody or antigen-binding fragment thereof comprising a heavy chain/light chain amino acid sequence pair selected from the group consisting of SEQ ID NOs: 577/578, 579/578, and 580/581.

In one aspect, the present invention provides a multi-specific antigen-binding molecule comprising a first antigen-binding specificity that binds specifically to LAG3 and a second antigen-binding specificity that specifically binds to a second target epitope.

In one aspect, the present invention provides a pharmaceutical composition comprising an anti-LAG3 antibody or antigen-binding fragment thereof of any of the above embodiments and a pharmaceutically acceptable carrier or diluent.

In one aspect, the present invention provides isolated polynucleotide molecules and vectors comprising polynucleotide sequences of the antibodies or antigen-binding fragment thereof disclosed herein. In certain embodiments, comprising the present invention provides an isolated polynucleotide molecule and/or a vector comprising a polynucleotide sequence that encodes a HCVR of an antibody as set forth herein. In certain embodiments, the present invention provides an isolated polynucleotide molecule and/or a vector comprising a polynucleotide sequence that encodes a LCVR of an antibody as set forth herein.

In one aspect, the present invention provides methods of enhancing an immune response in a subject, the method comprising administering a pharmaceutical composition comprising an isolated anti-LAG3 antibody or antigen-binding fragment thereof as disclosed herein. In certain embodiments, the present invention provides methods of inhibiting a T-regulatory (Treg) cell in a subject comprising administering a pharmaceutical composition comprising an isolated anti-LAG3 antibody or antigen-binding fragment thereof as disclosed herein. In certain embodiments, the present invention provides methods of enhancing T cell activation in a subject, the method comprising administering a pharmaceutical composition comprising an isolated anti-LAG3 antibody or antigen-binding fragment thereof as disclosed herein. In certain embodiments, the subject has a disease or disorder selected from the group consisting of blood cancer, brain cancer, renal cell carcinoma (e.g., clear cell renal carcinoma), ovarian cancer, bladder cancer, prostate cancer, breast cancer (e.g., triple negative breast cancer), hepatic cell carcinoma, bone cancer, colon cancer, non-small-cell lung cancer, squamous cell carcinoma of head and neck, colorectal cancer, mesothelioma, lymphoma (e.g., B cell lymphoma, diffuse large B cell lymphoma) and melanoma. In certain embodiments, the subject has a chronic viral infection caused by a virus selected from the group consisting of human immunodeficiency virus (HIV), hepatitis C virus (HCV), hepatitis B virus (HBV), human papilloma virus (HPV), lymphocytic choriomeningitis virus (LCMV) and simian immunodeficiency virus (SIV). In certain embodiments, the anti-LAG3 antibody is administered to the subject in combination with a second therapeutic agent selected from the group consisting of a PD-1 inhibitor, a CTLA inhibitor, an antibody to a tumor specific antigen, an antibody to a virally-infected-cell antigen, a PD-L1 inhibitor, a CD20 inhibitor, a bispecific antibody against CD20 and CD3, a dietary supplement such as an antioxidant, a VEGF antagonist, a chemotherapeutic agent, a cytotoxic agent, radiation, a NSAID, a corticosteroid, and any other therapy useful for ameliorating at least one symptom associated with the disease or disorder.

In one aspect, the present invention provides methods of inhibiting growth of a tumor or a tumor cell in a subject comprising administering to the subject in need thereof a therapeutically effective amount of an anti-LAG3 antibody or antigen-binding fragment thereof as disclosed herein. In certain embodiments, the tumor is primary or recurrent. In certain embodiments, the tumor is an established tumor. In certain embodiments, the subject has metastatic disease and/or has been treated with prior therapy. In certain embodiments, the tumor is present in a subject with a disease or disorder selected from the group consisting of blood cancer, brain cancer, renal cell cancer, ovarian cancer, bladder cancer, prostate cancer, breast cancer, hepatic cell carcinoma, bone cancer, colon cancer, non-small-cell lung cancer, squamous cell carcinoma of head and neck, colorectal cancer, mesothelioma, lymphoma, and melanoma. In certain embodiments, the anti-LAG3 antibody or antigen-binding fragment thereof is administered as one or more doses wherein each dose is administered 1 to 4 weeks after the immediately preceding dose. In certain embodiments, the anti-LAG3 antibody or antigen-binding fragment thereof is administered at a dose of about 0.1 mg/kg of body weight to about 100 mg/kg of body weight of the subject. In certain embodiments, the anti-LAG3 antibody is administered to the subject in combination with a second therapeutic agent selected from the group consisting of a PD-1 inhibitor, a CTLA inhibitor, an antibody to a tumor specific antigen, a PD-L1 inhibitor, a CD20 inhibitor, a bispecific antibody against CD20 and CD3, a dietary supplement such as an antioxidant, a VEGF antagonist, a chemotherapeutic agent, a cytotoxic agent, radiation, a NSAID, a corticosteroid, and any other therapy useful for ameliorating at least one symptom associated with the disease or disorder. In one embodiment, the second therapeutic agent is a PD-1 inhibitor wherein the PD-1 inhibitor is an antibody or antigen-binding fragment thereof that specifically binds to PD-1. In one embodiment, the PD-1 inhibitor is REGN2810. In certain embodiments, the anti-LAG3 antibody or antigen-binding fragment thereof is administered subcutaneously, intravenously, intradermally, intraperitoneally, orally, intramuscularly or intracranially.

In one aspect, the present invention provides methods of rescuing LAG3-mediated inhibition of T cell activity comprising contacting the T cell with an anti-LAG3 antibody or antigen-binding fragment thereof as disclosed herein. In on embodiment, the T cell is contacted by an anti-LAG3 antibody of the present invention in combination with an anti-PD-1 antibody (e.g., REGN2810).

Antigen-Binding Fragments of Antibodies

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to specifically bind to LAG3. An antibody fragment may include a Fab fragment, a F(ab')$_2$ fragment, a Fv fragment, a dAb fragment, a fragment containing a CDR, or an isolated CDR. In certain embodiments, the term "antigen-binding fragment" refers to a polypeptide fragment of a multi-specific antigen-binding molecule. In such embodiments, the term "antigen-binding fragment" includes, e.g., a MHC class II molecule which binds specifically to LAG3. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or heterodimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present invention using routine techniques available in the art.

Preparation of Human Antibodies

Methods for generating human antibodies in transgenic mice are known in the art. Any such known methods can be used in the context of the present invention to make human antibodies that specifically bind to LAG3.

Using VELOCIMMUNE® technology (see, for example, U.S. Pat. No. 6,596,541, Regeneron Pharmaceuticals, VELOCIMMUNE®) or any other known method for generating monoclonal antibodies, high affinity chimeric antibodies to LAG3 are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

Bioequivalents

The anti-LAG3 antibodies and antibody fragments of the present invention encompass proteins having amino acid sequences that vary from those of the described antibodies, but that retain the ability to bind LAG3. Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences of the present invention encompass sequences that comprise one or more additions, deletions, or substitutions of nucleotides when compared to the disclosed sequence, but that encode an antibody or antibody fragment that is essentially bioequivalent to an antibody or antibody fragment of the invention.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple doses. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, or potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes, which modify the glycosylation characteristics of the antibodies, e.g., mutations that eliminate or remove glycosylation.

Anti-LAG3 Antibodies Comprising Fc Variants

According to certain embodiments of the present invention, anti-LAG3 antibodies are provided comprising an Fc domain comprising one or more mutations which enhance or diminish antibody binding to the FcRn receptor, e.g., at acidic pH as compared to neutral pH. For example, the present invention includes anti-LAG3 antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification.

For example, the present invention includes anti-LAG3 antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); 257I and 311I (e.g., P257I and Q311I); 257I and 434H (e.g., P257I and N434H); 376V and 434H (e.g., D376V and N434H); 307A, 380A and 434A (e.g., T307A, E380A and N434A); and 433K and 434F (e.g., H433K and N434F). In one embodiment, the present invention includes anti-LAG3 antibodies comprising an Fc domain comprising a S108P mutation in the hinge region of IgG4 to promote dimer stabilization. All possible combinations of the foregoing Fc domain mutations, and other mutations within the antibody variable domains disclosed herein, are contemplated within the scope of the present invention.

The present invention also includes anti-LAG3 antibodies comprising a chimeric heavy chain constant ($C_H$) region, wherein the chimeric $C_H$ region comprises segments derived from the $C_H$ regions of more than one immunoglobulin isotype. For example, the antibodies of the invention may comprise a chimeric $C_H$ region comprising part or all of a $C_H2$ domain derived from a human IgG1, human IgG2 or human IgG4 molecule, combined with part or all of a $C_H3$ domain derived from a human IgG1, human IgG2 or human IgG4 molecule. According to certain embodiments, the antibodies of the invention comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric $C_H$ region as described herein may, in certain embodiments, exhibit modified Fc effector functions without adversely affecting the therapeutic or pharmacokinetic properties of the antibody. (See, e.g., US Patent Publication No. 20140243504, the disclosure of which is hereby incorporated by reference in its entirety). In certain embodiments, the Fc region comprises a sequence selected from the group consisting of SEQ ID NOs: 569, 570, 571, 572 and 573.

Biological Characteristics of the Antibodies

In general, the antibodies of the present invention function by binding to LAG3. The present invention includes anti-LAG3 antibodies and antigen-binding fragments thereof that bind soluble monomeric or dimeric LAG3 molecules with high affinity. For example, the present invention includes antibodies and antigen-binding fragments of antibodies that bind monomeric LAG3 (e.g., at 25° C. or at 37° C.) with a $K_D$ of less than about 10 nM as measured by surface plasmon resonance, e.g., using the assay format as defined in Example 3 herein. In certain embodiments, the antibodies or antigen-binding fragments thereof bind monomeric LAG3 with a $K_D$ of less than about 5 nM, less than about 2 nM, less than about 1 nM, less than about 0.5 nM less than about 0.1 nM, less than about 0.05 nM or less than about 0.04 nM, as measured by surface plasmon resonance, e.g., using the assay format as defined in Example 3 herein, or a substantially similar assay.

The present invention also includes antibodies and antigen-binding fragments thereof that bind dimeric LAG3 (e.g., at 25° C. or at 37° C.) with a $K_D$ of less than about 1.1 nM as measured by surface plasmon resonance, e.g., using the assay format as defined in Example 3 herein. In certain embodiments, the antibodies or antigen-binding fragments thereof bind dimeric LAG3 with a $K_D$ of less than about 0.5 nM, less than about 0.25 nM, less than about 0.1 nM, less than about 0.05 nM, or less than about 0.01M, as measured by surface plasmon resonance, e.g., using the assay format as defined in Example 3 herein, or a substantially similar assay.

The present invention also includes antibodies and antigen-binding fragments thereof that bind LAG3 with a dissociative half-life (t½) of greater than about 1.6 minutes as measured by surface plasmon resonance at 25° C. or 37° C., e.g., using an assay format as defined in Example 3 herein, or a substantially similar assay. In certain embodiments, the antibodies or antigen-binding fragments of the present invention bind LAG3 with a t½ of greater than about 5 minutes, greater than about 10 minutes, greater than about 30 minutes, greater than about 50 minutes, greater than about 60 minutes, greater than about 70 minutes, greater than about 80 minutes, greater than about 90 minutes, greater than about 100 minutes, greater than about 200 minutes, greater than about 300 minutes, greater than about 400 minutes, greater than about 500 minutes, greater than about 600 minutes, greater than about 700 minutes, greater than about 800 minutes, greater than about 900 minutes, greater than about 1000 minutes, or greater than about 1100 minutes, as measured by surface plasmon resonance at 25° C. or 37° C., e.g., using an assay format as defined in Example 3 herein (e.g., mAb-capture or antigen-capture format), or a substantially similar assay.

The present invention also includes antibodies or antigen-binding fragments thereof that bind to a human LAG3-expressing cell with an $EC_{50}$ less than about 8 nM as measured by a flow cytometry assay as defined in Example 5 herein, or a substantially similar assay. In certain embodiments, the antibodies or antigen-binding fragments thereof bind to a hLAG3-expressing cell with an $EC_{50}$ less than about 5 nM, less than about 2 nM, less than about 1 nM, or less than about 0.5 nM, as measured by a flow cytometry assay, e.g., using the assay format in Example 5 herein, or a substantially similar assay.

The present invention also includes antibodies or antigen-binding fragments thereof that bind to a cynomolgus monkey LAG3-expressing cell with an $EC_{50}$ less than about 2.5 nM as measured by a flow cytometry assay as defined in Example 5 herein, or a substantially similar assay. In certain embodiments, the antibodies or antigen-binding fragments thereof bind to a mfLAG3-expressing cell with an $EC_{50}$ less than about 2 nM, or less than about 1 nM, as measured by a flow cytometry assay, e.g., using the assay format as defined in Example 5 herein, or a substantially similar assay.

The present invention also includes antibodies or antigen-binding fragments thereof that block LAG3 binding to MHC class II (human HLA-DR2) with an $IC_{50}$ of less than about 32 nM as determined using a cell adherence assay, e.g., as shown in Example 7, or a substantially similar assay. In certain embodiments, the antibodies or antigen-binding fragments thereof block LAG3 binding to human MHC class II with an $IC_{50}$ less than about 25 nM, less than about 20 nM, less than about 10 nM, or less than about 5 nM, as measured by a cell adherence assay, e.g., using the assay format as defined in Example 7 herein, or a substantially similar assay.

The present invention also includes antibodies or antigen-binding fragments thereof that block LAG3 binding to MHC class II (mouse HLA-DR2) with an $IC_{50}$ of less than about 30 nM as determined using a cell adherence assay, e.g., as shown in Example 7, or a substantially similar assay. In certain embodiments, the antibodies or antigen-binding fragments thereof block mouse LAG3 binding to human MHC class II with an $IC_{50}$ less than about 25 nM, less than about 20 nM, less than about 10 nM, or less than about 5 nM, as measured by a cell adherence assay, e.g., using the assay format as defined in Example 7 herein, or a substantially similar assay.

The present invention also includes antibodies or antigen-binding fragment thereof that block binding of LAG3 to human or mouse MHC class II by more than 90% as measured by a cell adherence assay as defined in Example 7 herein, or a substantially similar assay.

The present invention also includes antibodies or antigen-binding fragments thereof that block LAG-induced T cell down-regulation with an $EC_{50}$ less than 9 nM as measured by a T cell/APC luciferase reporter assay as defined in Example 8 herein, or a substantially similar assay. In certain embodiments, the antibodies or antigen-binding fragments thereof block LAG3-induced T cell down-regulation with an $EC_{50}$ less than about 5 nM, less than about 1 nM, less than about 0.5 nM, or less than about 0.1 nM, as measured by a T cell/APC luciferase reporter assay, e.g., using the assay format as defined in Example 8 herein, or a substantially similar assay.

The present invention also includes antibodies or antigen-binding fragments thereof that bind to cynomolgus activated CD4+ and CD8+ T cells with an $EC_{50}$ less than about 1.2 nM as measured by a fluorescence assay as defined in Example 9 herein, or a substantially similar assay. In certain embodiments, the antibodies or antigen-binding fragments thereof bind to cynomolgus activated CD4+ and CD8+ T cells with an $EC_{50}$ less than about 1.1 nM, less than about 1 nM, less than about 0.5 nM, less than about 0.2 nM, or less than about 0.1 nM, as measured by a fluorescence assay, e.g., using the assay format as defined in Example 9 herein, or a substantially similar assay.

In certain embodiments, the antibodies of the present invention may function by blocking or inhibiting the MHC class II-binding activity associated with LAG3 by binding to any other region or fragment of the full length protein, the amino acid sequence of which is shown in SEQ ID NO: 582.

In certain embodiments, the antibodies of the present invention are useful in inhibiting the growth of a tumor or delaying the progression of cancer when administered prophylactically to a subject in need thereof and may increase survival of the subject. For example, the administration of an antibody of the present invention may lead to shrinking of a primary tumor and may prevent metastasis or development of secondary tumors. In certain embodiments, the antibodies of the present invention are useful in inhibiting the growth of a tumor when administered therapeutically to a subject in need thereof and may increase survival of the subject. For example, the administration of a therapeutically effective amount of an antibody of the invention to a subject may lead to shrinking and disappearance of an established tumor in the subject.

In one embodiment, the invention provides an isolated recombinant monoclonal antibody or antigen-binding fragment thereof that binds to LAG3, wherein the antibody or fragment thereof exhibits one or more of the following characteristics: (i) comprises a HCVR having an amino acid sequence selected from the group consisting of SEQ ID NO: 2, 18, 34, 50, 66, 82, 98, 114, 130, 146, 162, 178, 194, 210, 226, 242, 258, 274, 290, 306, 322, 338, 354, 370, 386, 402, 418, 434, 450, 458, 466, 474, 482, 490, 498, 506, 514, 538, and 554, or a substantially similar sequence thereof having at least 90%, at least 95%, at least 98% or at least 99% sequence identity; (ii) comprises a LCVR having an amino acid sequence selected from the group consisting of SEQ ID NO: 10, 26, 42, 58, 74, 90, 106, 122, 138, 154, 170, 186, 202, 218, 234, 250, 266, 282, 298, 314, 330, 346, 362, 378, 394, 410, 426, 442, 522, 530, 546, and 562, or a substantially similar sequence thereof having at least 90%, at least 95%, at least 98% or at least 99% sequence identity; (iii) comprises a HCDR3 domain having an amino acid sequence selected from the group consisting of SEQ ID NO: 8, 24, 40, 56, 72, 88, 104, 120, 136, 152, 168, 184, 200, 216, 232, 248, 264, 280, 296, 312, 328, 344, 360, 376, 392, 408, 424, 440, 456, 464, 472, 480, 488, 496, 504, 512, 520, 544, and 560, or a substantially similar sequence thereof having at least 90%, at least 95%, at least 98% or at least 99% sequence identity; and a LCDR3 domain having an amino acid sequence selected from the group consisting of SEQ ID NO: 16, 32, 48, 64, 80, 96, 112, 128, 144, 160, 176, 192, 208, 224, 240, 256, 272, 288, 304, 320, 336, 352, 368, 384, 400, 416, 432, 448, 528, 536, 552, and 568, or a substantially similar sequence thereof having at least 90%, at least 95%, at least 98% or at least 99% sequence identity; (iv) comprises a HCDR1 domain having an amino acid sequence selected from the group consisting of SEQ ID NO: 4, 20, 36, 52, 68, 84, 100, 116, 132, 148, 164, 180, 196, 212, 228, 244, 260, 276, 292, 308, 324, 340, 356, 372, 388, 404, 420, 436, 452, 460, 468, 476, 484, 492, 500, 508, 516, 540, and 556, or a substantially similar sequence thereof having at least 90%, at least 95%, at least 98% or at least 99% sequence identity; a HCDR2 domain having an amino acid sequence selected from the group consisting of SEQ ID NO: 6, 22, 38, 54, 70, 86, 102, 118, 134, 150, 166, 182, 198, 214, 230, 246, 262, 278, 294, 310, 326, 342, 358, 374, 390, 406, 422, 438, 454, 462, 470, 478, 486, 494, 502, 510, 518, 542, and 558, or a substantially similar sequence thereof having at least 90%, at least 95%, at least 98% or at least 99% sequence identity; a LCDR1 domain having an amino acid sequence selected from the group consisting of SEQ ID NO: 12, 28, 44, 60, 76, 92, 108, 124, 140, 156, 172, 188, 204, 220, 236, 252, 268, 284, 300, 316, 332, 348, 364, 380, 396, 412, 428, 444, 524, 532, 548, and 564, or a substantially similar sequence thereof having at least 90%, at least 95%, at least 98% or at least 99% sequence identity; and a LCDR2 domain having an amino acid sequence selected from the group consisting of SEQ ID NO: 14, 30, 46, 62, 78, 94, 110, 126, 142, 158, 174, 190, 206, 222, 238, 254, 270, 286, 302, 318, 334, 350, 366, 382, 398, 414, 430, 446, 526, 534, 550, and 566, or a substantially similar sequence thereof having at least 90%, at least 95%, at least 98% or at least 99% sequence identity; (v) binds monomeric human LAG3 with a binding dissociation equilibrium constant ($K_D$) of less than about 10 nM as measured in a surface plasmon resonance assay at 25° C.; (vi) binds monomeric human LAG3 with a $K_D$ less than about 8 nM as measured in a surface plasmon resonance assay at 37° C.; (vii) binds dimeric human LAG3 with a $K_D$ less than about 1.1 nM as measured in a surface plasmon resonance assay at 25° C.; (viii) binds dimeric human LAG3 with a $K_D$ less than about 1 nM as measured in a surface plasmon resonance assay at 37° C.; (ix) binds to a hLAG3-expressing cell with an $EC_{50}$ less than about 8 nM as measured in a flow cytometry assay; (x) binds to a mfLAG3-expressing cell with a $EC_{50}$ less than about 2.3 nM as measured in a flow cytometry assay; (xi) blocks binding of hLAG3 to human MHC class II with $IC_{50}$ less than about 32 nM as determined by a cell adherence assay; (xii) blocks binding of hLAG3 to mouse MHC class II with $IC_{50}$ less than about 30 nM as determined by a cell adherence assay; (xiii) blocks binding of hLAG3 to MHC class II by more than 90% as determined by a cell adherence assay; (xiv) rescues LAG3-mediated inhibition of T cell activity with $EC_{50}$ less than about 9 nM as determined in a luciferase reporter assay; (xv) binds to activated CD4+ and CD8+ T cells with $EC_{50}$ less than about 1.2 nM, as determined in a fluorescence assay; (xvi) suppresses tumor growth and increases survival in a subject with cancer, and (xvii) is fully human.

The antibodies of the present invention may possess one or more of the aforementioned biological characteristics, or any combinations thereof. Other biological characteristics of the antibodies of the present invention will be evident to a person of ordinary skill in the art from a review of the present disclosure including the working Examples herein.

Species Selectivity and Species Cross-Reactivity

According to certain embodiments of the invention, the anti-LAG3 antibodies bind to human LAG3 but not to LAG3 from other species. Alternatively, the anti-LAG3 antibodies of the invention, in certain embodiments, bind to human LAG3 and to LAG3 from one or more non-human species. For example, the anti-LAG3 antibodies of the invention may bind to human LAG3 and may bind or not bind, as the case may be, to one or more of mouse, rat, guinea pig, hamster, gerbil, pig, cat, dog, rabbit, goat, sheep, cow, horse, camel, cynomolgus, marmoset, rhesus or chimpanzee LAG3. In certain embodiments, the anti-LAG3 antibodies of the invention may bind to human and cynomolgus LAG3 with the same affinities or with different affinities, but do not bind to rat and mouse LAG3.

Epitope Mapping and Related Technologies

The present invention includes anti-LAG3 antibodies which interact with one or more amino acids found within one or more domains of the LAG3 molecule including, e.g., extracellular D1 to D4 domains, a transmembrane domain, and an intracellular domain. The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids located within any of the aforementioned domains of the LAG3 molecule (e.g. a linear epitope in a domain). Alternatively, the epitope may consist of a plurality of non-contiguous amino acids (or amino acid sequences) located within either or both of the aforementioned domains of the LAG3 molecule (e.g. a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, N.Y.). Other methods include alanine scanning mutational analysis, peptide blot analysis (Reineke (2004) Methods Mol. Biol. 248: 443-63), peptide cleavage analysis crystallographic studies and NMR analysis. In addition, methods such as epitope excision, epitope extraction and chemical modification of antigens can be employed (Tomer (2000) Prot. Sci. 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) Analytical Biochemistry 267: 252-259; Engen and Smith (2001) Anal. Chem. 73: 256A-265A.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the invention into groups of antibodies binding different epitopes.

In certain embodiments, the anti-LAG3 antibodies or antigen-binding fragments thereof bind an epitope within any one or more of the regions exemplified in LAG3, either in natural form, as exemplified in SEQ ID NO: 582, or recombinantly produced, as exemplified in SEQ ID NOS: 574-576, or to a fragment thereof. In some embodiments, the antibodies of the invention bind to an extracellular region comprising one or more amino acids selected from the group consisting of amino acid residues 29-450 of LAG3. In some embodiments, the antibodies of the invention bind to an extracellular region comprising one or more amino acids selected from the group consisting of amino acid residues 1-533 of cynomolgus LAG3, as exemplified by SEQ ID NO: 576.

In certain embodiments, the present invention includes anti-LAG3 antibodies and antigen-binding fragments thereof that interact with one or more epitopes found within the extracellular region of LAG3 (SEQ ID NO: 588). The epitope(s) may consist of one or more contiguous sequences of 3 or more (e.g., 3, 4, 5, 6, 7, 8, 9, 10, 11, 12, 13, 14, 15, 16, 17, 18, 19, 20 or more) amino acids located within the extracellular region of LAG3. Alternatively, the epitope may consist of a plurality of non-contiguous amino acids (or amino acid sequences) located within the extracellular region of LAG3. As shown in Example 18 herein, the epitope of LAG3 with which the exemplary antibody of the invention H4sH15482P interacts is defined by the amino acid sequence LRRAGVTWQHQPDSGPPAAAPGH-PLAPGPHPAAPSSWGPRPRRY (SEQ ID NO: 589), which corresponds to amino acids 28 to 71 of SEQ ID NO: 588. Accordingly, the present invention includes anti-LAG3 antibodies that interact with one or more amino acids contained within the region consisting of amino acids 28 to 71 of SEQ ID NO: 588 (i.e., the sequence LRRAGVTWQHQPDSGP-PAAAPGHPLAPGPHPAAPSSWGPRPRRY [SEQ ID NO: 589]).

The present invention includes anti-LAG3 antibodies that bind to the same epitope, or a portion of the epitope, as any of the specific exemplary antibodies described herein in Table 1, or an antibody having the CDR sequences of any of the exemplary antibodies described in Table 1. Likewise, the present invention also includes anti-LAG3 antibodies that compete for binding to LAG3 or a LAG3 fragment with any of the specific exemplary antibodies described herein in Table 1, or an antibody having the CDR sequences of any of the exemplary antibodies described in Table 1. For example, the present invention includes anti-LAG3 antibodies that cross-compete for binding to LAG3 with one or more antibodies as defined in Example 4 herein (e.g., H4sH15482P, H4sH15479P, H4sH14813N, H4H14813N, H4H15479P, H4H15482P, H4H15483P, H4sH15498P, H4H15498P, H4H17828P2, H4H17819P, and H4H17823P).

One can easily determine whether an antibody binds to the same epitope as, or competes for binding with, a reference anti-LAG3 antibody by using routine methods known in the art. For example, to determine if a test antibody binds to the same epitope as a reference anti-LAG3 antibody of the invention, the reference antibody is allowed to bind to a LAG3 protein or peptide under saturating conditions. Next, the ability of a test antibody to bind to the LAG3 molecule is assessed. If the test antibody is able to bind to LAG3 following saturation binding with the reference anti-LAG3 antibody, it can be concluded that the test antibody binds to a different epitope than the reference anti-LAG3 antibody. On the other hand, if the test antibody is not able to bind to the LAG3 protein following saturation binding with the reference anti-LAG3 antibody, then the test antibody may bind to the same epitope as the epitope bound by the reference anti-LAG3 antibody of the invention.

To determine if an antibody competes for binding with a reference anti-LAG3 antibody, the above-described binding methodology is performed in two orientations: In a first orientation, the reference antibody is allowed to bind to a LAG3 protein under saturating conditions followed by assessment of binding of the test antibody to the LAG3 molecule. In a second orientation, the test antibody is allowed to bind to a LAG3 molecule under saturating conditions followed by assessment of binding of the reference antibody to the LAG3 molecule. If, in both orientations, only the first (saturating) antibody is capable of binding to the LAG3 molecule, then it is concluded that the test antibody and the reference antibody compete for binding to LAG3. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Immunoconjugates

The invention encompasses a human anti-LAG3 monoclonal antibody conjugated to a therapeutic moiety ("immunoconjugate"), such as a cytotoxin or a chemotherapeutic agent to treat cancer. As used herein, the term "immunoconjugate" refers to an antibody which is chemically or biologically linked to a cytotoxin, a radioactive agent, a cytokine, an interferon, a target or reporter moiety, an enzyme, a toxin, a peptide or protein or a therapeutic agent. The antibody may be linked to the cytotoxin, radioactive agent, cytokine, interferon, target or reporter moiety, enzyme, toxin, peptide or therapeutic agent at any location along the molecule so long as it is able to bind its target. Examples of immunoconjugates include antibody drug conjugates and antibody-toxin fusion proteins. In one embodiment, the agent may be a second different antibody to LAG3. In certain embodiments, the antibody may be conjugated to an agent specific for a tumor cell or a virally infected cell. The type of therapeutic moiety that may be conjugated to the anti-LAG3 antibody and will take into account the condition to be treated and the desired therapeutic effect to be achieved. Examples of suitable agents for forming immunoconjugates are known in the art; see for example, WO 05/103081.

Multi-Specific Antibodies

The antibodies of the present invention may be monospecific, bi-specific, or multi-specific. Multi-specific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244.

In one aspect, the present invention includes multi-specific antigen-binding molecules or antigen-binding fragments thereof wherein one specificity of an immunoglobulin is specific for the extracellular domain of LAG3, or a fragment thereof, and the other specificity of the immunoglobulin is specific for binding outside the extracellular domain of LAG3, or a second therapeutic target, or is conjugated to a therapeutic moiety.

Any of the multi-specific antigen-binding molecules of the invention, or variants thereof, may be constructed using standard molecular biological techniques (e.g., recombinant DNA and protein expression technology), as will be known to a person of ordinary skill in the art.

In some embodiments, LAG3-specific antibodies are generated in a bi-specific format (a "bi-specific") in which variable regions binding to distinct domains of LAG3 are linked together to confer dual-domain specificity within a single binding molecule. Appropriately designed bi-specifics may enhance overall LAG3 inhibitory efficacy through increasing both specificity and binding avidity. Variable regions with specificity for individual domains, (e.g., segments of the N-terminal domain), or that can bind to different regions within one domain, are paired on a structural scaffold that allows each region to bind simultaneously to the separate epitopes, or to different regions within one domain. In one example for a bi-specific, heavy chain variable regions ($V_H$) from a binder with specificity for one domain are recombined with light chain variable regions ($V_L$) from a series of binders with specificity for a second domain to identify non-cognate $V_L$ partners that can be paired with an original $V_H$ without disrupting the original specificity for that $V_H$. In this way, a single $V_L$ segment (e.g., $V_L1$) can be combined with two different $V_H$ domains (e.g., $V_H1$ and $V_H2$) to generate a bi-specific comprised of two binding "arms" ($V_H1$-$V_L1$ and $V_H2$-$V_L1$). Use of a single $V_L$ segment reduces the complexity of the system and thereby simplifies and increases efficiency in cloning, expression, and purification processes used to generate the bi-specific (See, for example, U.S. Ser. No. 13/022,759 and US2010/0331527).

Alternatively, antibodies that bind more than one domains and a second target, such as, but not limited to, for example, a second different anti-LAG3 antibody, may be prepared in a bi-specific format using techniques described herein, or other techniques known to those skilled in the art. Antibody variable regions binding to distinct regions may be linked together with variable regions that bind to relevant sites on, for example, the extracellular domain of LAG3, to confer dual-antigen specificity within a single binding molecule. Appropriately designed bi-specifics of this nature serve a dual function. Variable regions with specificity for the extracellular domain are combined with a variable region with specificity for outside the extracellular domain and are paired on a structural scaffold that allows each variable region to bind to the separate antigens.

An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Other exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

Therapeutic Administration and Formulations

The invention provides therapeutic compositions comprising the anti-LAG3 antibodies or antigen-binding fragments thereof of the present invention. Therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody may vary depending upon the age and the size of a subject to be administered, target disease, conditions, route of administration, and the like. When an antibody of the present invention is used for treating a disease or disorder in an adult patient, or for preventing such a disease, it is advantageous to administer the antibody of the present invention normally at a single dose of about 0.1 to about 60 mg/kg body weight, more preferably about 5 to about 60, about 20 to about 50, about 10 to about 50, about 1 to about 10, or about 0.8 to about 11 mg/kg body weight. Depending on the severity of the condition, the frequency and the duration of the treatment can be adjusted. In certain embodiments, the antibody or antigen-binding fragment thereof of the invention can be administered as an initial dose of at least about 0.1 mg to about 800 mg, about 1 to about 500 mg, about 5 to about 300 mg, or about 10 to about 200 mg, to about 100 mg, or to about 50 mg. In certain embodiments, the initial dose may be followed by administration of a second or a plurality of subsequent doses of the antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The pharmaceutical composition can be also delivered in a vesicle, in particular a liposome (see, for example, Langer (1990) Science 249: 1527-1533).

The use of nanoparticles to deliver the antibodies of the present invention is also contemplated herein. Antibody-conjugated nanoparticles may be used both for therapeutic and diagnostic applications. Antibody-conjugated nanoparticles and methods of preparation and use are described in detail by Arruebo, M., et al. 2009 ("Antibody-conjugated nanoparticles for biomedical applications" in J. Nanomat. Volume 2009, Article ID 439389, 24 pages, doi: 10.1155/2009/439389), incorporated herein by reference. Nanoparticles may be developed and conjugated to antibodies contained in pharmaceutical compositions to target tumor cells or autoimmune tissue cells or virally infected cells. Nanoparticles for drug delivery have also been described in, for example, U.S. Pat. No. 8,257,740, or U.S. Pat. No. 8,246, 995, each incorporated herein in its entirety.

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracutaneous, intracranial, intraperitoneal and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present invention include, but certainly are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.) and the HUMIRA™ Pen (Abbott Labs, Abbott Park, Ill.), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the antibody contained is generally about 5 to about 500 mg per dosage form in a unit dose; especially in the form of injection, it is preferred that the antibody is contained in about 5 to about 100 mg and in about 10 to about 250 mg for the other dosage forms.

Therapeutic Uses of the Antibodies

The antibodies of the invention are useful, inter alia, for the treatment, prevention and/or amelioration of any disease or disorder associated with or mediated by LAG3 expression, signaling or activity, or treatable by blocking the interaction between LAG3 and the LAG3 ligand MHC class II or otherwise inhibiting LAG3 activity and/or signaling. For example, the present invention provides methods for treating cancer (tumor growth inhibition) and/or viral infections by administering an anti-LAG3 antibody (or pharmaceutical composition comprising an anti-LAG3 antibody) as described herein to a patient in need of such treatment, and anti-LAG3 antibodies (or pharmaceutical composition comprising an anti-LAG3 antibody) for use in the treatment of cancer (tumor growth inhibition) and/or viral infections. The antibodies of the present invention are useful for the treatment, prevention, and/or amelioration of disease or disorder or condition such as cancer or a viral infection and/or for ameliorating at least one symptom associated with such disease, disorder or condition. In the context of the methods of treatment described herein, the anti-LAG3 antibody may be administered as a monotherapy (i.e., as the only therapeutic agent) or in combination with one or more additional therapeutic agents (examples of which are described elsewhere herein).

In some embodiments of the invention, the antibodies described herein are useful for treating subjects suffering from primary or recurrent cancer, including, but not limited to, blood cancer, brain cancer (e.g., glioblastoma multiforme), renal cell carcinoma (e.g., clear cell renal cancer), ovarian cancer, bladder cancer, prostate cancer, breast cancer (e.g., triple negative breast cancer), hepatic cell carcinoma, bone cancer, colon cancer, non-small-cell lung cancer, squamous cell carcinoma of head and neck, colorectal cancer, mesothelioma, and melanoma.

As used herein, the term "blood cancer" includes a hematologic malignancy that affects blood, bone marrow, lymph or lymphatic system. As such, the term includes malignancies of cells from the lymphoid and myeloid cell lineages. The myeloid cell line normally produces granulocytes, erythrocytes, thrombocytes, macrophages, and mast cells; the lymphoid cell line produces B, T, NK and plasma cells. The term, therefore, includes malignancies of the above-mentioned cells, viz. lymphomas, myelomas, lymphoid leukemias and myelogenous leukemias. Examples include, but are not limited to, acute lymphoblastic leukemia, acute myelogenous leukemia, chronic lymphocytic leukemia, chronic myelogenous leukemia, acute monocytic leukemia, Hodgkin's lymphomas, non-Hodgkin's lymphomas (e.g., B cell lymphoma, diffuse large B cell lymphoma), and myeloma (including multiple myeloma).

The antibodies may be used to treat early stage or late-stage symptoms of cancer. In one embodiment, an antibody or fragment thereof of the invention may be used to treat advanced or metastatic cancer. The antibodies are useful in reducing or inhibiting or shrinking tumor growth of both solid tumors and blood cancers. In certain embodiments, treatment with an antibody or antigen-binding fragment thereof of the invention leads to more than 40% regression, more than 50% regression, more than 60% regression, more than 70% regression, more than 80% regression or more than 90% regression of a tumor in a subject. In certain embodiments, the antibodies may be used to prevent relapse of a tumor. In certain embodiments, the antibodies are useful in extending progression-free survival or overall survival in a subject with cancer. In some embodiments, the antibodies are useful in reducing toxicity due to chemotherapy or radiotherapy while maintaining long-term survival in a patient suffering from cancer.

In certain embodiments, the subject is a patient suffering from cancer, and who:
  has not previously received therapy with anti-PD-1/PD-L1 but are appropriate candidates to receive anti-PD-1-based therapy; and/or
  has previously received anti-PD-1/PD-L1 based therapy and had a confirmed objective response (CR or PR) or SD for at least 3 months on anti-PD-1/PD-L1 therapy but subsequently progressed on that therapy or had SD or a PR as best response with subsequent stable response for 6 months; and/or
  is not candidate for standard therapy, or for whom no available therapy is expected to convey clinical benefit and are appropriate for mAb1 monotherapy; and/or
  is suffering from anti-PD-1/PD-L1 naïve stage IIIB or IV NSCLC either without prior therapy for metastatic disease or with disease progression/recurrence after one platinum-containing regimen; and/or
  is suffering from anti-PD-1/PD-L1 experienced stage IIIB or IV NSCLC with no more than 2 prior therapies for metastatic disease; and/or
  is suffering from anti-PD-1/PD-L1 naïve advanced or metastatic ccRCC with a clear cell component who had received 1 to 2 previous regimens of anti-angiogenic therapy; and/or
  is suffering from anti-PD-1/PD-L1 experienced* advanced or metastatic ccRCC with a clear cell component who had received 1 to 2 previous regimens of anti-angiogenic therapy; and/or
  is suffering from anti-PD-1/PD-L1 naïve metastatic TNBC (estrogen, progesterone, and human epidermal growth factor receptor 2 negative) who have received 5 or fewer prior lines of therapy; and/or is suffering from anti-PD-1/PD-L1 naïve advanced or metastatic melanoma who have received no more than 2 previous regimens for metastatic disease; and/or is suffering from anti-PD-1/PD-L1 experienced advanced or metastatic melanoma who have received no more than 2 previous regimens for metastatic disease; and/or is suffering from anti-PD-1/PD-L1 naïve relapsed/refractory DLBCL who have either progressed after or are not candidates for autologous stem cell transplant; and/or is suffering from anti-PD-1/PD-L1 experience* relapsed/refractory DLBCL who have either progressed after or are not candidates for autologous stem cell transplant.

In certain embodiments, the antibodies of the invention are useful to treat subjects suffering from a chronic viral infection. In some embodiments, the antibodies of the invention are useful in decreasing viral titers in the host and/or rescuing exhausted T cells. In certain embodiments, an antibody or fragment thereof of the invention may be used to treat chronic viral infection by lymphocytic choriomeningitis virus (LCMV). In some embodiments, an antibody or antigen-binding fragment thereof the invention may be administered at a therapeutic dose to a patient with an infection by human immunodeficiency virus (HIV) or human papilloma virus (HPV) or hepatitis B/C virus (HBV/HCV). In a related embodiment, an antibody or antigen-binding fragment thereof of the invention may be used to treat an infection by simian immunodeficiency virus (SIV) in a simian subject such as cynomolgus.

In certain embodiments, a blocking antibody of the present invention may be administered in a therapeutically effective amount to a subject suffering from a cancer or a viral infection.

One or more antibodies of the present invention may be administered to relieve or prevent or decrease the severity of one or more of the symptoms or conditions of the disease or disorder.

It is also contemplated herein to use one or more antibodies of the present invention prophylactically to patients at risk for developing a disease or disorder such as cancer, and viral infection.

In a further embodiment of the invention, the present antibodies are used for the preparation of a pharmaceutical composition for treating patients suffering from cancer, or viral infection. In another embodiment of the invention, the present antibodies are used as adjunct therapy with any other agent or any other therapy known to those skilled in the art useful for treating cancer or viral infection.

Combination Therapies and Formulations

Combination therapies may include an anti-LAG3 antibody of the invention and any additional therapeutic agent that may be advantageously combined with an antibody of the invention, or with a biologically active fragment of an antibody of the invention.

The antibodies of the present invention may be combined synergistically with one or more anti-cancer drugs or therapy used to treat or inhibit cancer, including, for example, blood cancer, brain cancer (e.g., glioblastoma multiforme), renal cell carcinoma, ovarian cancer, bladder cancer, prostate cancer, breast cancer, hepatic cell carcinoma, bone cancer, colon cancer, non-small-cell lung cancer, squamous cell carcinoma of head and neck, colorectal cancer, mesothelioma, and melanoma. It is contemplated herein to use anti-LAG3 antibodies of the invention in combination with immunostimulatory and/or immunosupportive therapies to inhibit tumor growth, and/or enhance survival of cancer patients. The immunostimulatory therapies include direct immunostimulatory therapies to augment immune cell activity by either "releasing the brake" on suppressed immune cells or "stepping on the gas" to activate an immune response. Examples include targeting other checkpoint receptors, vaccination and adjuvants. The immunosupportive modalities may increase antigenicity of the tumor by promoting immunogenic cell death, inflammation or have other indirect effects that promote an anti-tumor immune response. Examples include radiation, chemotherapy, anti-angiogenic agents, and surgery.

In various embodiments, one or more antibodies of the present invention may be used in combination with a PD-1 inhibitor (e.g., an anti-PD-1 antibody such as nivolumab, pembrolizumab, pidilizumab, BGB-A317 or REGN2810), a PD-L1 inhibitor (e.g., an anti-PD-L1 antibody such as avelumab, atezolizumab, durvalumab, MDX-1105, or REGN3504), a CTLA-4 inhibitor (e.g., ipilimumab), a TIM3 inhibitor, a BTLA inhibitor, a TIGIT inhibitor, a CD47 inhibitor, a GITR inhibitor, an antagonist of another T cell co-inhibitor or ligand (e.g., an antibody to CD-28, 2B4, LY108, LAIR1, ICOS, CD160 or VISTA), an indoleamine-2,3-dioxygenase (IDO) inhibitor, a vascular endothelial growth factor (VEGF) antagonist [e.g., a "VEGF-Trap" such as aflibercept or other VEGF-inhibiting fusion protein as set forth in U.S. Pat. No. 7,087,411, or an anti-VEGF antibody or antigen binding fragment thereof (e.g., bevacizumab, or ranibizumab) or a small molecule kinase inhibitor of VEGF receptor (e.g., sunitinib, sorafenib, or pazopanib)], an Ang2 inhibitor (e.g., nesvacumab), a transforming growth factor beta (TGFβ) inhibitor, an epidermal growth factor receptor (EGFR) inhibitor (e.g., erlotinib, cetuximab), a CD20 inhibitor (e.g., an anti-CD20 antibody such as rituximab), an antibody to a tumor-specific antigen [e.g., CA9, CA125, melanoma-associated antigen 3 (MAGE3), carcinoembryonic antigen (CEA), vimentin, tumor-M2-PK, prostate-specific antigen (PSA), mucin-1, MART-1, and CA19-9], a vaccine (e.g., Bacillus Calmette-Guerin, a cancer vaccine), an adjuvant to increase antigen presentation (e.g., granulocyte-macrophage colony-stimulating factor), a bispecific antibody (e.g., CD3×CD20 bispecific antibody, or PSMA× CD3 bispecific antibody), a cytotoxin, a chemotherapeutic agent (e.g., dacarbazine, temozolomide, cyclophosphamide, docetaxel, doxorubicin, daunorubicin, cisplatin, carboplatin, gemcitabine, methotrexate, mitoxantrone, oxaliplatin, paclitaxel, and vincristine), cyclophosphamide, radiotherapy, an IL-6R inhibitor (e.g., sarilumab), an IL-4R inhibitor (e.g., dupilumab), an IL-10 inhibitor, a cytokine such as IL-2, IL-7, IL-21, and IL-15, an antibody-drug conjugate (ADC) (e.g., anti-CD19-DM4 ADC, and anti-DS6-DM4 ADC), an anti-inflammatory drug (e.g., corticosteroids, and non-steroidal anti-inflammatory drugs), a dietary supplement such as anti-oxidants or any other therapy care to treat cancer. In certain embodiments, the anti-LAG3 antibodies of the present invention may be used in combination with cancer vaccines including dendritic cell vaccines, oncolytic viruses, tumor cell vaccines, etc. to augment the anti-tumor response. Examples of cancer vaccines that can be used in combination with anti-LAG3 antibodies of the present invention include MAGE3 vaccine for melanoma and bladder cancer, MUC1 vaccine for breast cancer, EGFRv3 (e.g., Rindopepimut) for brain cancer (including glioblastoma multiforme), or ALVAC-CEA (for CEA+ cancers).

In certain embodiments, the anti-LAG3 antibodies of the invention may be administered in combination with radiation therapy in methods to generate long-term durable anti-tumor responses and/or enhance survival of patients with cancer. In some embodiments, the anti-LAG3 antibodies of the invention may be administered prior to, concomitantly or after administering radiation therapy to a cancer patient. For example, radiation therapy may be administered in one or more doses to tumor lesions followed by administration of one or more doses of anti-LAG3 antibodies of the invention. In some embodiments, radiation therapy may be administered locally to a tumor lesion to enhance the local immunogenicity of a patient's tumor (adjuvinating radiation) and/or to kill tumor cells (ablative radiation) followed by systemic administration of an anti-LAG3 antibody of the invention. For example, intracranial radiation may be administered to a patient with brain cancer (e.g., glioblastoma multiforme) in combination with systemic administration of an anti-LAG3 antibody of the invention. In certain embodiments, the anti-LAG3 antibodies of the invention may be administered in combination with radiation therapy and a chemotherapeutic agent (e.g., temozolomide) or a VEGF antagonist (e.g., aflibercept).

In certain embodiments, the anti-LAG3 antibodies of the invention may be administered in combination with one or more anti-viral drugs to treat chronic viral infection caused by LCMV, HIV, HPV, HBV or HCV. Examples of anti-viral drugs include, but are not limited to, zidovudine, lamivudine, abacavir, ribavirin, lopinavir, efavirenz, cobicistat, tenofovir, rilpivirine and corticosteroids.

The additional therapeutically active agent(s)/component(s) may be administered prior to, concurrent with, or after the administration of the anti-LAG3 antibody of the present invention. For purposes of the present disclosure, such administration regimens are considered the administration of an anti-LAG3 antibody "in combination with" a second therapeutically active component.

The additional therapeutically active component(s) may be administered to a subject prior to administration of an anti-LAG3 antibody of the present invention. For example, a first component may be deemed to be administered "prior to" a second component if the first component is administered 1 week before, 72 hours before, 60 hours before, 48 hours before, 36 hours before, 24 hours before, 12 hours before, 6 hours before, 5 hours before, 4 hours before, 3 hours before, 2 hours before, 1 hour before, 30 minutes before, 15 minutes before, 10 minutes before, 5 minutes before, or less than 1 minute before administration of the second component. In other embodiments, the additional therapeutically active component(s) may be administered to a subject after administration of an anti-LAG3 antibody of the present invention. For example, a first component may be deemed to be administered "after" a second component if the first component is administered 1 minute after, 5 minutes after, 10 minutes after, 15 minutes after, 30 minutes after, 1 hour after, 2 hours after, 3 hours after, 4 hours after, 5 hours after, 6 hours after, 12 hours after, 24 hours after, 36 hours after, 48 hours after, 60 hours after, 72 hours after administration of the second component. In yet other embodiments, the additional therapeutically active component(s) may be administered to a subject concurrent with administration of an anti-LAG3 antibody of the present invention. "Concurrent" administration, for purposes of the present invention, includes, e.g., administration of an anti-LAG3 antibody and an additional therapeutically active component to a subject in a single dosage form (e.g., co-formulated), or in separate dosage forms administered to the subject within about 30 minutes or less of each other. If administered in separate dosage forms, each dosage form may be administered via the same route (e.g., both the anti-LAG3 antibody and the additional therapeutically active component may be administered intravenously, subcutaneously, etc.); alternatively, each dosage form may be administered via a different route (e.g., the anti-LAG3 antibody may be administered intravenously, and the additional therapeutically active component may be administered subcutaneously). In any event, administering the components in a single dosage from, in separate dosage forms by the same route, or in separate dosage forms by different routes are all considered "concurrent administration," for purposes of the present disclosure. For purposes of the present disclosure, administration of an anti-LAG3 antibody "prior to", "concurrent with," or "after" (as those terms are defined herein above) administration of an additional therapeutically active component is considered administration of an anti-LAG3 antibody "in combination with" an additional therapeutically active component).

The present invention includes pharmaceutical compositions in which an anti-LAG3 antibody of the present invention is co-formulated with one or more of the additional therapeutically active component(s) as described elsewhere herein using a variety of dosage combinations.

In exemplary embodiments in which an anti-LAG3 antibody of the invention is administered in combination with a PD-1 inhibitor (e.g., an anti-PD-1 antibody as disclosed in US 2015/0203579, herein incorporated by reference in its entirety), including administration of co-formulations comprising an anti-LAG3 antibody and a PD-1 inhibitor, the individual components may be administered to a subject and/or co-formulated using a variety of dosage combinations. Thus, the present invention includes a combination of (i) an anti-LAG3 antibody of the invention, and (ii) a PD-1 inhibitor (e.g., an anti-PD-1 antibody as disclosed in US 2015/0203579, herein incorporated by reference in its entirety), for simultaneous, separate and/or sequential use in the treatment of cancer or viral infections. For example, the anti-LAG3 antibody and the PD-1 inhibitor (e.g., an anti-PD-1 antibody) each may be administered to a subject and/or contained in a co-formulation in an amount selected from the group consisting of 0.01 mg, 0.02 mg, 0.03 mg, 0.04 mg, 0.05 mg, 0.1 mg, 0.2 mg, 0.3 mg, 0.4 mg, 0.5 mg, 0.6 mg, 0.7 mg, 0.8 mg, 0.9 mg, 1.0 mg, 1.5 mg, 2.0 mg, 2.5 mg, 3.0 mg, 3.5 mg, 4.0 mg, 4.5 mg, 5.0 mg, 6.0 mg, 7.0 mg, 8.0 mg, 9.0 mg, and 10.0 mg. The combinations/co-formulations may be administered to a subject according to any of the administration regimens disclosed elsewhere herein, including, e.g., twice a week, once every week, once every 2 weeks, once every 3 weeks, once every month, once every 2 months, once every 3 months, once every 4 months, once every 5 months, once every 6 months, etc. The anti-LAG3 antibody of the invention might, for instance, be administered at a dose of about 0.8 to about 11, about 1 to about 10, about 3 to about 10, about 1, about 3 or about 10 mg/kg, simultaneously with an PD-1 inhibitor (e.g. an anti-PD-1 antibody as disclosed in US 2015/0203579) at a dose of about 3 to 5, or about 3.0 mg/kg. The simultaneous administration might for instance occur every 14 days, 21 days or 28 days.

In exemplary embodiments in which an anti-LAG3 antibody of the invention is administered in combination with a VEGF antagonist (e.g., a VEGF trap such as aflibercept), including administration of co-formulations comprising an anti-LAG3 antibody and a VEGF antagonist, the individual components may be administered to a subject and/or co-formulated using a variety of dosage combinations. For example, the anti-LAG3 antibody may be administered to a subject and/or contained in a co-formulation in an amount selected from the group consisting of 0.01 mg, 0.02 mg, 0.03 mg, 0.04 mg, 0.05 mg, 0.1 mg, 0.2 mg, 0.3 mg, 0.4 mg, 0.5 mg, 0.6 mg, 0.7 mg, 0.8 mg, 0.9 mg, 1.0 mg, 1.5 mg, 2.0 mg, 2.5 mg, 3.0 mg, 3.5 mg, 4.0 mg, 4.5 mg, 5.0 mg, 6.0 mg, 7.0 mg, 8.0 mg, 9.0 mg, and 10.0 mg; and the VEGF antagonist (e.g., a VEGF trap such as aflibercept) may be administered to the subject and/or contained in a co-formulation in an amount selected from the group consisting of 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg and 3.0 mg. The combinations/co-formulations may be administered to a subject according to any of the administration regimens disclosed elsewhere herein, including, e.g., twice a week, once every week, once every 2 weeks, once every 3 weeks, once every month, once every 2 months, once every 3 months, once every 4 months, once every 5 months, once every 6 months, etc.

Administrative Regimens

According to certain embodiments of the present invention, multiple doses of an anti-LAG3 antibody (or a pharmaceutical composition comprising a combination of an anti-LAG3 antibody and any of the additional therapeutically active agents mentioned herein) may be administered to a subject over a defined time course. The methods according to this aspect of the invention comprise sequentially administering to a subject multiple doses of an anti-LAG3 antibody of the invention. As used herein, "sequentially administering" means that each dose of anti-LAG3 antibody is administered to the subject at a different point in time, e.g., on different days separated by a predetermined interval (e.g., hours, days, weeks or months). The present invention includes methods which comprise sequentially administering to the patient a single initial dose of an anti-LAG3 antibody, followed by one or more secondary doses of the anti-LAG3 antibody, and optionally followed by one or more tertiary doses of the anti-LAG3 antibody. The anti-LAG3 antibody may be administered at a dose between 0.1 mg/kg to 100 mg/kg body weight of the subject.

The terms "initial dose," "secondary doses," and "tertiary doses," refer to the temporal sequence of administration of the anti-LAG3 antibody of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-LAG3 antibody, but generally may differ from one another in terms of frequency of administration. In certain embodiments, however, the amount of anti-LAG3 antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain embodiments, the amount of anti-LAG3 antibody contained in the initial, secondary and/or tertiary doses may be sub-optimal or sub-therapeutic. As used herein, the terms "sub-therapeutic" or "sub-optimal" refer to an antibody dose administered at too low a level to produce a therapeutic effect or below the level necessary to treat a disease such as cancer.

In certain exemplary embodiments of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of anti-LAG3 antibody which is administered to a patient prior to the administration of the very next dose in the sequence with no intervening doses.

The methods according to this aspect of the invention may comprise administering to a patient any number of secondary and/or tertiary doses of an anti-LAG3 antibody. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments of the invention, the frequency at which the secondary and/or tertiary doses are administered to a patient can vary over the course of the treatment regimen. The frequency of administration may also be adjusted during the course of treatment by a physician depending on the needs of the individual patient following clinical examination.

Diagnostic Uses of the Antibodies

The anti-LAG3 antibodies of the present invention may be used to detect and/or measure LAG3 in a sample, e.g., for diagnostic purposes. Some embodiments contemplate the use of one or more antibodies of the present invention in assays to detect a disease or disorder such as cancer, autoimmune disease or viral infection. Exemplary diagnostic assays for LAG3 may comprise, e.g., contacting a sample, obtained from a subject (e.g., a patient), with an anti-LAG3 antibody of the invention, wherein the anti-LAG3 antibody is labeled with a detectable label or reporter molecule or used as a capture ligand to selectively isolate LAG3 from subject samples. Alternatively, an unlabeled anti-LAG3 antibody can be used in diagnostic applications in combination with a secondary antibody which is itself detectably labeled. The detectable label or reporter molecule can be a radioisotope, such as $^3$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure LAG3 in a sample include enzyme-linked immunosorbent assay (ELISA), radioimmunoassay (RIA), and fluorescence-activated cell sorting (FACS).

Samples that can be used in LAG3 diagnostic assays according to the present invention include any tissue or fluid sample obtainable from a subject, which contains detectable quantities of either LAG3 protein, or fragments thereof, under normal or pathological conditions. Generally, levels of LAG3 in a particular sample obtained from a healthy patient (e.g., a patient not afflicted with cancer or an autoimmune disease) will be measured to initially establish a baseline, or standard, level of LAG3. This baseline level of LAG3 can then be compared against the levels of LAG3 measured in samples obtained from individuals suspected of having a cancer-related condition, or symptoms associated with such condition.

The antibodies specific for LAG3 may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface.

Aspects of the invention relate to use of the disclosed antibodies as markers for predicting prognosis of cancer or a viral infection in patients. Antibodies of the present invention may be used in diagnostic assays to evaluate prognosis of cancer in a patient and to predict survival.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, room temperature is about 25° C., and pressure is at or near atmospheric.

Example 1: Generation of Human Antibodies to LAG3

Human antibodies to LAG3 were generated using a fragment of LAG3 that ranges from about amino acids 29-450 of GenBank Accession NP_002277.4 (SEQ ID NO: 582) coupled to a mouse Fc region. The immunogen was administered directly, with an adjuvant to stimulate the immune response, to a VELOCIMMUNE® mouse (i.e., an engineered mouse comprising DNA encoding human Immunoglobulin heavy and kappa light chain variable regions), as described in U.S. Pat. No. 8,502,018 B2, or to a humanized Universal Light Chain (ULC) VelocImmune® mouse, as described in WO 2013022782. The antibody immune response was monitored by a LAG3-specific immunoassay. When a desired immune response was achieved splenocytes were harvested and fused with mouse myeloma cells to preserve their viability and form hybridoma cell lines. The hybridoma cell lines were screened and selected to identify cell lines that produce LAG3-specific antibodies. Using this technique, and the immunogen described above, several anti-LAG3 chimeric antibodies (i.e., antibodies possessing human variable domains and mouse constant domains) were obtained; exemplary antibodies generated in this manner from the VELOCIMMUNE® mice were designated as H1M14985N, H1M14987N, H2M14811N, H2M14885N, H2M14926N, H2M14927N, H2M14931N, H2M18336N, H2M18337N and H4H14813N.

Anti-LAG3 antibodies were also isolated directly from antigen-positive B cells (from either of the immunized mice) without fusion to myeloma cells, as described in U.S. Pat. No. 7,582,298, herein specifically incorporated by reference in its entirety. Using this method, several fully human anti-LAG3 antibodies (i.e., antibodies possessing human variable domains and human constant domains) were obtained; exemplary antibodies generated in this manner were designated as follows: H4H15477P, H4H15483P, H4H15484P, H4H15491P, H4H17823P, H4H17826P2, H4H17828P2, H4sH15460P, H4sH15462P, H4sH15463P, H4sH15464P, H4sH15466P, H4sH15467P, H4sH15470P, H4sH15475P, H4sH15479P, H4sH15480P, H4sH15482P, H4sH15488P, H4sH15496P2, H4sH15498P2, H4sH15505P2, H4sH15518P2, H4sH15523P2, H4sH15530P2, H4sH15555P2, H4sH15558P2, H4sH15567P2, and H4H17819P.

Exemplary antibodies H4sH15496P2, H4sH15498P2, H4sH15505P2, H4sH15518P2, H4sH15523P2, H4sH15530P2, H4sH15555P2, H4sH15558P2, and H4sH15567P2 were generated from B-cells from the ULC Velocimmune® mice.

The biological properties of the exemplary antibodies generated in accordance with the methods of this Example are described in detail in the Examples set forth below.

Example 2: Heavy and Light Chain Variable Region Amino Acid and Nucleotide Sequences Table 1 sets forth the amino acid sequence identifiers of the heavy and light chain variable regions and CDRs of selected anti-LAG3 antibodies of the invention. The corresponding nucleic acid sequence identifiers are set forth in Table 2.

TABLE 1

Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1M14985N | 2 | 4 | 6 | 8 | 10 | 12 | 14 | 16 |
| H1M14987N | 18 | 20 | 22 | 24 | 26 | 28 | 30 | 32 |
| H2M14811N | 34 | 36 | 38 | 40 | 42 | 44 | 46 | 48 |
| H2M14885N | 50 | 52 | 54 | 56 | 58 | 60 | 62 | 64 |
| H2M14926N | 66 | 68 | 70 | 72 | 74 | 76 | 78 | 80 |
| H2M14927N | 82 | 84 | 86 | 88 | 90 | 92 | 94 | 96 |
| H2M14931N | 98 | 100 | 102 | 104 | 106 | 108 | 110 | 112 |
| H2M18336N | 114 | 116 | 118 | 120 | 122 | 124 | 126 | 128 |
| H2M18337N | 130 | 132 | 134 | 136 | 138 | 140 | 142 | 144 |
| H4H15477P | 146 | 148 | 150 | 152 | 154 | 156 | 158 | 160 |

TABLE 1-continued

Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H4H15483P | 162 | 164 | 166 | 168 | 170 | 172 | 174 | 176 |
| H4H15484P | 178 | 180 | 182 | 184 | 186 | 188 | 190 | 192 |
| H4H15491P | 194 | 196 | 198 | 200 | 202 | 204 | 206 | 208 |
| H4H17823P | 210 | 212 | 214 | 216 | 218 | 220 | 222 | 224 |
| H4H17826P2 | 226 | 228 | 230 | 232 | 234 | 236 | 238 | 240 |
| H4H17828P2 | 242 | 244 | 246 | 248 | 250 | 252 | 254 | 256 |
| H4sH15460P | 258 | 260 | 262 | 264 | 266 | 268 | 270 | 272 |
| H4sH15462P | 274 | 276 | 278 | 280 | 282 | 284 | 286 | 288 |
| H4sH15463P | 290 | 292 | 294 | 296 | 298 | 300 | 302 | 304 |
| H4sH15464P | 306 | 308 | 310 | 312 | 314 | 316 | 318 | 320 |
| H4sH15466P | 322 | 324 | 326 | 328 | 330 | 332 | 334 | 336 |
| H4sH15467P | 338 | 340 | 342 | 344 | 346 | 348 | 350 | 352 |
| H4sH15470P | 354 | 356 | 358 | 360 | 362 | 364 | 366 | 368 |
| H4sH15475P | 370 | 372 | 374 | 376 | 378 | 380 | 382 | 384 |
| H4sH15479P | 386 | 388 | 390 | 392 | 394 | 396 | 398 | 400 |
| H4sH15480P | 402 | 404 | 406 | 408 | 410 | 412 | 414 | 416 |
| H4sH15482P | 418 | 420 | 422 | 424 | 426 | 428 | 430 | 432 |
| H4sH15488P | 434 | 436 | 438 | 440 | 442 | 444 | 446 | 448 |
| H4sH15496P2 | 450 | 452 | 454 | 456 | 522 | 524 | 526 | 528 |
| H4sH15498P2 | 458 | 460 | 462 | 464 | 522 | 524 | 526 | 528 |
| H4sH15505P2 | 466 | 468 | 470 | 472 | 522 | 524 | 526 | 528 |
| H4sH15518P2 | 474 | 476 | 478 | 480 | 522 | 524 | 526 | 528 |
| H4sH15523P2 | 482 | 484 | 486 | 488 | 522 | 524 | 526 | 528 |
| H4sH15530P2 | 490 | 492 | 494 | 496 | 522 | 524 | 526 | 528 |
| H4sH15555P2 | 498 | 500 | 502 | 504 | 530 | 532 | 534 | 536 |
| H4sH15558P2 | 506 | 508 | 510 | 512 | 530 | 532 | 534 | 536 |
| H4sH15567P2 | 514 | 516 | 518 | 520 | 530 | 532 | 534 | 536 |
| H4H14813N | 538 | 540 | 542 | 544 | 546 | 548 | 550 | 552 |
| H4H17819P | 554 | 556 | 558 | 560 | 562 | 564 | 566 | 568 |

TABLE 2

Nucleic Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1M14985N | 1 | 3 | 5 | 7 | 9 | 11 | 13 | 15 |
| H1M14987N | 17 | 19 | 21 | 23 | 25 | 27 | 29 | 31 |
| H2M14811N | 33 | 35 | 37 | 39 | 41 | 43 | 45 | 47 |
| H2M14885N | 49 | 51 | 53 | 55 | 57 | 59 | 61 | 63 |
| H2M14926N | 65 | 67 | 69 | 71 | 73 | 75 | 77 | 79 |
| H2M14927N | 81 | 83 | 85 | 87 | 89 | 91 | 93 | 95 |
| H2M14931N | 97 | 99 | 101 | 103 | 105 | 107 | 109 | 111 |
| H2M18336N | 113 | 115 | 117 | 119 | 121 | 123 | 125 | 127 |
| H2M18337N | 129 | 131 | 133 | 135 | 137 | 139 | 141 | 143 |
| H4H15477P | 145 | 147 | 149 | 151 | 153 | 155 | 157 | 159 |
| H4H15483P | 161 | 163 | 165 | 167 | 169 | 171 | 173 | 175 |
| H4H15484P | 177 | 179 | 181 | 183 | 185 | 187 | 189 | 191 |
| H4H15491P | 193 | 195 | 197 | 199 | 201 | 203 | 205 | 207 |
| H4H17823P | 209 | 211 | 213 | 215 | 217 | 219 | 221 | 223 |
| H4H17826P2 | 225 | 227 | 229 | 231 | 233 | 235 | 237 | 239 |
| H4H17828P2 | 241 | 243 | 245 | 247 | 249 | 251 | 253 | 255 |
| H4sH15460P | 257 | 259 | 261 | 263 | 265 | 267 | 269 | 271 |
| H4sH15462P | 273 | 275 | 277 | 279 | 281 | 283 | 285 | 287 |
| H4sH15463P | 289 | 291 | 293 | 295 | 297 | 299 | 301 | 303 |
| H4sH15464P | 305 | 307 | 309 | 311 | 313 | 315 | 317 | 319 |
| H4sH15466P | 321 | 323 | 325 | 327 | 329 | 331 | 333 | 335 |
| H4sH15467P | 337 | 339 | 341 | 343 | 345 | 347 | 349 | 351 |
| H4sH15470P | 353 | 355 | 357 | 359 | 361 | 363 | 365 | 367 |
| H4sH15475P | 369 | 371 | 373 | 375 | 377 | 379 | 381 | 383 |
| H4sH15479P | 385 | 387 | 389 | 391 | 393 | 395 | 397 | 399 |
| H4sH15480P | 401 | 403 | 405 | 407 | 409 | 411 | 413 | 415 |
| H4sH15482P | 417 | 419 | 421 | 423 | 425 | 427 | 429 | 431 |
| H4sH15488P | 433 | 435 | 437 | 439 | 441 | 443 | 445 | 447 |
| H4sH15496P2 | 449 | 451 | 453 | 455 | 521 | 523 | 525 | 527 |
| H4sH15498P2 | 457 | 459 | 461 | 463 | 521 | 523 | 525 | 527 |
| H4sH15505P2 | 465 | 467 | 469 | 471 | 521 | 523 | 525 | 527 |
| H4sH15518P2 | 473 | 475 | 477 | 479 | 521 | 523 | 525 | 527 |

TABLE 2-continued

| | Nucleic Acid Sequence Identifiers | | | | | | | |
|---|---|---|---|---|---|---|---|---|
| Antibody | SEQ ID NOs: | | | | | | | |
| Designation | HCVR | HCDR1 | HCDR2 | HCDR3 | LCVR | LCDR1 | LCDR2 | LCDR3 |
| H4sH15523P2 | 481 | 483 | 485 | 487 | 521 | 523 | 525 | 527 |
| H4sH15530P2 | 489 | 491 | 493 | 495 | 521 | 523 | 525 | 527 |
| H4sH15555P2 | 497 | 499 | 501 | 503 | 529 | 531 | 533 | 535 |
| H4sH15558P2 | 505 | 507 | 509 | 511 | 529 | 531 | 533 | 535 |
| H4sH15567P2 | 513 | 515 | 517 | 519 | 529 | 531 | 533 | 535 |
| H4H14813N | 537 | 539 | 541 | 543 | 545 | 547 | 549 | 551 |
| H4H17819P | 553 | 555 | 557 | 559 | 561 | 563 | 565 | 567 |

Antibodies are typically referred to herein according to the following nomenclature: Fc prefix (e.g. "H1M," "H4sH," "H4H," etc.), followed by a numerical identifier (e.g. "14813," "17828," etc., as shown in Table 1), followed by a "P," "P2," or "N" suffix. Thus, according to this nomenclature, an antibody may be referred to herein as, e.g., "H4sH14813N," "H4H17819P," "H4H17828P2," etc. The H4sH and H4H prefixes on the antibody designations used herein indicate the particular Fc region isotype of the antibody. For example, an "H4sH" antibody has a human IgG4 Fc with 2 or more amino acid changes as disclosed in US20140243504 (herein incorporated in its entirety), an "H4H" antibody has a human IgG4 Fc with a serine to proline mutation in the hinge region (S108P), an "H1M" antibody has a mouse IgG1 Fc, and an "H2M" antibody has a mouse IgG2 Fc (all variable regions are fully human as denoted by the first 'H' in the antibody designation). As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Table 1—will remain the same, and the binding properties to antigen are expected to be identical or substantially similar regardless of the nature of the Fc domain.

In certain embodiments, selected antibodies with a mouse IgG1 Fc were converted to antibodies with human IgG4 Fc. In certain embodiments, the antibody comprises a human IgG4 Fc with 2 or more amino acid changes as disclosed in US20100331527 (herein incorporated in its entirety). In one embodiment, the IgG4 Fc domain comprises a serine to proline mutation in the hinge region (S108P) to promote dimer stabilization. In certain embodiments, the Fc region of the antibodies of the present invention comprises amino acid sequences of SEQ ID NOs: 569, 570, 571, 572 or 573. Table 3 sets forth the amino acid sequence identifiers of heavy chain and light chain sequences of selected anti-LAG3 antibodies with human IgG4 Fc.

TABLE 3

| Heavy Chain and Light Chain Amino Acid Sequence Identifiers | | |
|---|---|---|
| Antibody | SEQ ID NOs: | |
| Designation | Heavy Chain | Light Chain |
| H4sH15482P | 577 | 578 |
| H4H15482P | 579 | 578 |
| H4sH14813N | 580 | 581 |

Each heavy chain sequence in Table 3 comprised a variable region ($V_H$ or HCVR; comprising HCDR1, HCDR2 and HCDR3) and a constant region (comprising $C_H1$, $C_H2$ and $C_H3$ domains). Each light chain sequence in Table 3 comprised a variable region ($V_L$ or LCVR; comprising LCDR1, LCDR2 and LCDR3) and a constant region ($C_L$). SEQ ID NO: 577 comprised a HCVR comprising amino acids 1-123 and a constant region comprising amino acids 124-449. SEQ ID NO: 578 comprised a LCVR comprising amino acids 1-107 and a constant region comprising amino acids 108-214. SEQ ID NO: 579 comprised a HCVR comprising amino acids 1-123 and a constant region comprising amino acids 124-450. SEQ ID NO: 580 comprised a HCVR comprising amino acids 1-119 and a constant region comprising amino acids 120-445. SEQ ID NO: 581 comprised a LCVR comprising amino acids 1-107 and a constant region comprising amino acids 108-214.

Control Constructs Used in the Following Examples

Two control constructs (anti-LAG3 antibodies) were included in the following experiments for comparative purposes: "Comparator 1," a human monoclonal antibody against LAG3 having $V_H/V_L$ sequences of antibody "25F7" according to WO2010/019570; and "Comparator 2," a human monoclonal antibody against LAG3 having $V_H/V_L$ sequences of antibody "v3.5" according to US2014/0093511.

Example 3: Antibody Binding to LAG3 as Determined by Surface Plasmon Resonance

Binding association and dissociation rate constants ($k_a$ and $k_d$, respectively), equilibrium dissociation constants and dissociation half-lives ($K_D$ and $t_{1/2}$, respectively) for antigens binding to purified anti-LAG3 antibodies were determined using a real-time surface plasmon resonance biosensor assay on a BiaCore 4000 or BiaCore T200 instrument. The BiaCore sensor surface was derivatized with either a polyclonal rabbit anti-mouse antibody (GE, #BR-1008-38) or with a monoclonal mouse anti-human Fc antibody (GE, #BR-1008-39) to capture approximately 50-85 RUs of anti-LAG3 monoclonal antibodies, expressed with either a mouse Fc or a human Fc, respectively. The LAG3 reagents tested for binding to the anti-LAG3 antibodies included recombinant human LAG3 expressed with a C-terminal myc-myc-hexahistidine tag (hLAG3-mmh; SEQ ID: 574) and recombinant human LAG3 expressed with a C-terminal mouse IgG2a mFc tag (hLAG3-mFc; SEQ ID: 575). Different concentrations (50, 25, 12.5 and 6.25 nM) of LAG3 reagents were injected over the anti-LAG3 monoclonal antibody captured surface at a flow rate of 50 μL/min on the BiaCore T200. The binding of the LAG3 reagents to captured monoclonal antibodies was monitored for 4 minutes while their dissociation from the antibodies was monitored for 8 minutes in HBST running buffer (0.01 M HEPES pH 7.4, 0.15 M NaCl, 3 mM EDTA, 0.05% v/v Surfactant P20). Experiments were performed at 25° C. and 37° C. Kinetic association ($k_a$) and dissociation ($k_d$) rate constants were determined by processing and fitting the data to a 1:1 binding model using Scrubber 2.0c curve fitting software. Binding dissociation equilibrium constants ($K_D$) and dissociative half-lives ($t_{1/2}$) were then calculated from the kinetic rate constants as: $K_D$ (M)=$k_d/k_a$ and $t_{1/2}$ (min)=[ln 2/(60*$k_d$)].

Binding kinetics parameters for different anti-LAG3 monoclonal antibodies binding to monomeric (tagged with mmH) or dimeric (tagged with mFc) LAG3 reagents at 25° C. and 37° C. are tabulated in Tables 4-7.

TABLE 4

Binding Kinetics parameters of anti-LAG3 monoclonal antibodies binding to human LAG3-mmh at 25° C.

| | 25° C. | | | |
|---|---|---|---|---|
| Ab ID | $k_a$ (I/mol*s) | $k_d$ (1/s) | $K_D$ [M] | $t_{1/2}$ (min) |
| H4H15479P | 1.09E+06 | 5.35E−05 | 4.93E−11 | 215.9 |
| H4sH15479P | 1.23E+06 | 5.98E−05 | 4.87E−11 | 193.1 |
| H4sH14813N | 4.45E+05 | 7.89E−05 | 1.77E−10 | 146.4 |
| H4H14813N | 4.11E+05 | 8.80E−05 | 2.14E−10 | 131.2 |
| H4H15498P2 | 3.01E+05 | 7.81E−05 | 2.60E−10 | 147.9 |
| H4H17819P | 1.13E+06 | 4.43E−04 | 3.91E−10 | 26 |
| H4H17823P | 1.04E+06 | 4.47E−04 | 4.29E−10 | 25.8 |
| H4sH15498P2 | 1.57E+05 | 1.01E−04 | 6.45E−10 | 114 |
| H4H15482P | 1.99E+05 | 1.94E−04 | 9.72E−10 | 59.7 |
| H4sH15482P | 2.12E+05 | 2.60E−04 | 1.23E−09 | 44.5 |
| H4H15483P | 1.88E+05 | 3.70E−04 | 1.97E−09 | 31.2 |
| H4H17828P2 | 6.12E+05 | 1.41E−03 | 2.31E−09 | 8.2 |
| H4H15462P | 9.39E+05 | 5.40E−03 | 5.75E−09 | 2.1 |
| H4sH15462P | 1.07E+06 | 6.97E−03 | 6.51E−09 | 1.7 |
| H4H17826P2 | 4.50E+05 | 4.57E−03 | 1.02E−08 | 2.5 |
| Isotype control 1 | NB | NB | NB | NB |
| Isotype control 2 | NB | NB | NB | NB |
| Comparator 1 | 1.09E+06 | 8.70E−04 | 8.02E−10 | 13.3 |
| Comparator 2 | 1.01E+06 | 5.82E−04 | 5.77E−10 | 19.9 |

*NB indicates that under experimental conditions, LAG3 reagent did not bind to the captured anti-LAG3 monoclonal antibody Table 4 shows that at 25° C., all the anti-LAG3 antibodies of the invention bound to hLAG3-mmh with $K_D$ values ranging from 49 pM to 10 nM, while the comparators bound with $K_D$ values of 0.58 nM and 0.8 nM.

TABLE 5

Binding kinetics parameters of anti-LAG3 monoclonal antibodies binding to hLAG3-mmh at 37° C.

| | 37° C. | | | |
|---|---|---|---|---|
| Ab ID | $k_a$ (I/mol*s) | $k_d$ (1/s) | $K_D$* [M] | $t_{1/2}$ (min) |
| H4H15479P | 1.27E+06 | 4.08E−05 | 3.21E−11 | 283 |
| H4sH15479P | 1.24E+06 | 4.24E−05 | 3.41E−11 | 272.5 |
| H4H15498P2 | 3.81E+05 | 2.96E−05 | 7.83E−11 | 390.2 |
| H4sH15498P2 | 3.78E+05 | 7.08E−05 | 1.85E−10 | 163.1 |
| H4sH14813N | 5.78E+05 | 1.54E−04 | 2.66E−10 | 75.1 |
| H4H14813N | 5.35E+05 | 1.52E−04 | 2.84E−10 | 76 |
| H4H17823P | 1.76E+06 | 9.24E−04 | 5.24E−10 | 12.5 |
| H4H17819P | 1.59E+06 | 8.76E−04 | 5.52E−10 | 13.2 |
| H4H15483P | 7.74E+05 | 1.11E−03 | 1.43E−09 | 10.4 |
| H4sH15482P | 2.81E+05 | 5.12E−04 | 1.82E−09 | 22.6 |
| H4H17828P2 | 1.10E+06 | 2.07E−03 | 1.89E−09 | 5.6 |
| H4H15482P | 2.92E+05 | 5.70E−04 | 1.96E−09 | 20.2 |
| H4H17826P2 | 1.07E+06 | 2.14E−03 | 1.99E−09 | 5.4 |

TABLE 5-continued

Binding kinetics parameters of anti-LAG3 monoclonal antibodies binding to hLAG3-mmh at 37° C.

| | 37° C. | | | |
|---|---|---|---|---|
| Ab ID | $k_a$ (I/mol*s) | $k_d$ (1/s) | $K_D$* [M] | $t_{1/2}$ (min) |
| H4H15462P | 1.08E+06 | 6.26E−03 | 5.80E−09 | 1.8 |
| H4sH15462P | 1.01E+06 | 7.72E−03 | 7.66E−09 | 1.5 |
| Isotype control 1 | NB | NB | NB | NB |
| Isotype control 2 | NB | NB | NB | NB |
| Comparator 1 | 1.23E+06 | 3.74E−03 | 3.03E−09 | 3.1 |
| Comparator 2 | 1.10E+06 | 2.31E−03 | 2.10E−09 | 5 |

*NB indicates that under the experimental conditions, LAG3 reagent did not bind to the captured anti-LAG3 monoclonal antibody.

Table 5 shows that at 37° C., all the anti-LAG3 antibodies of the invention bound to hLAG3-mmh with $K_D$ values ranging from 32 pM to 7.66 nM, while the comparators bound with $K_D$ values ranging of 2.1 nM and 3.0 nM.

Data in Tables 4 and 5 indicate that all anti-LAG3 antibodies bind to monomeric hLAG3-mmh with very similar affinities at both 25° and 37° C.

TABLE 6

Binding Kinetics parameters of anti-LAG3 monoclonal antibodies binding to hLAG3 dimer (hLAG3-mFc) at 25° C.

| | 25° C. | | | |
|---|---|---|---|---|
| Ab ID | $k_a$ (I/mol*s) | $k_d$ (1/s) | $K_D$ [M] | $t_{1/2}$ (min) |
| H4H15479P | 2.30E+06 | 1.00E−05 | 4.35E−12 | ≥1155.0 |
| H4sH15479P | 3.05E+06 | 1.00E−05 | 3.28E−12 | ≥1155.0 |
| H4H15483P | 1.34E+06 | 1.00E−05 | 7.45E−12 | ≥1155.0 |
| H4H14813N | 9.58E+05 | 1.00E−05 | 1.04E−11 | ≥1155.0 |
| H4sH14813N | 1.80E+06 | 1.90E−05 | 1.06E−11 | 606.6 |
| H4H15482P | 7.58E+05 | 1.00E−05 | 1.32E−11 | ≥1155.0 |
| H4sH15482P | 7.09E+05 | 1.00E−05 | 1.41E−11 | ≥1155.0 |
| H4H15498P2 | 3.63E+05 | 1.00E−05 | 2.76E−11 | ≥1155.0 |
| H4sH15498P2 | 2.84E+05 | 1.00E−05 | 3.52E−11 | ≥1155.0 |
| H4H17819P | 1.45E+06 | 1.80E−04 | 1.24E−10 | 64.2 |
| H4H17823P | 1.26E+06 | 2.18E−04 | 1.74E−10 | 52.9 |
| H4H17828P2 | 1.88E+06 | 4.60E−04 | 2.45E−10 | 25.1 |
| H4sH15462P | 2.34E+06 | 1.90E−03 | 8.14E−10 | 6.1 |
| H4H17826P2 | 6.91E+05 | 5.64E−04 | 8.17E−10 | 20.5 |
| H4H15462P | 2.02E+06 | 2.03E−03 | 1.01E−09 | 5.7 |
| Isotype control 1 | NB* | NB | NB | NB |
| Isotype control 2 | NB | NB | NB | NB |
| Comparator 1 | 2.69E+06 | 4.50E−04 | 1.67E−10 | 25.7 |
| Comparator 2 | 3.09E+06 | 3.00E−04 | 9.68E−11 | 38.6 |

*NB indicates that under the experimental conditions, LAG3 reagent did not bind to the captured anti-LAG3 monoclonal antibody.

Table 6 shows that at 25° C., all the anti-LAG3 antibodies of the invention bound to hLAG3 dimer proteins with $K_D$ values ranging from 4.3 pM-1.0 nM, while the comparators bound with $K_D$ values of 97 pM and 0.16 nM.

TABLE 7

Binding Kinetics parameters of anti-LAG3 monoclonal antibodies binding to hLAG3 dimer (hLAG3-mFc) at 37° C.

| | 37° C. | | | |
|---|---|---|---|---|
| Ab ID | $k_a$ (I/mol*s) | $k_d$ (1/s) | $K_D$ [M] | $t_{1/2}$ (min) |
| H4H15479P | 2.50E+06 | 1.00E−05 | 3.99E−12 | ≥1155.0 |
| H4sH15479P | 2.92E+06 | 1.00E−05 | 3.42E−12 | ≥1155.0 |
| H4sH15498P2 | 5.15E+05 | 1.00E−05 | 1.94E−11 | ≥1155.0 |
| H4H15498P2 | 4.60E+05 | 1.00E−05 | 2.17E−11 | ≥1155.0 |

TABLE 7-continued

Binding Kinetics parameters of anti-LAG3 monoclonal antibodies binding to hLAG3 dimer (hLAG3-mFc) at 37° C.

| | 37° C. | | | |
|---|---|---|---|---|
| Ab ID | $k_a$ (1/mol*s) | $k_d$ (1/s) | $K_D$ [M] | $t_{1/2}$ (min) |
| H4H14813N | 4.27E+06 | 1.17E−04 | 2.74E−11 | 98.8 |
| H4sH14813N | 3.42E+06 | 1.01E−04 | 2.95E−11 | 114.4 |
| H4sH15482P | 5.19E+06 | 1.64E−04 | 3.16E−11 | 70.3 |
| H4H15482P | 1.01E+06 | 9.01E−05 | 8.91E−11 | 128.1 |
| H4H15483P | 1.38E+06 | 2.98E−04 | 2.15E−10 | 38.8 |
| H4H17826P2 | 1.98E+06 | 5.47E−04 | 2.77E−10 | 21.1 |
| H4H17819P | 1.66E+06 | 5.27E−04 | 3.17E−10 | 21.9 |
| H4H17828P2 | 1.73E+06 | 7.18E−04 | 4.15E−10 | 16.1 |
| H4H15462P | 2.16E+06 | 8.95E−04 | 4.15E−10 | 12.9 |
| H4H17823P | 1.34E+06 | 5.85E−04 | 4.37E−10 | 19.7 |
| H4sH15462P | 1.80E+06 | 1.57E−03 | 8.76E−10 | 7.3 |
| Isotype control 1 | NB | NB | NB | NB |
| Isotype control 2 | NB | NB | NB | NB |
| Comparator 1 | 3.44E+06 | 1.56E−03 | 4.54E−10 | 7.4 |
| Comparator 2 | 4.36E+06 | 1.13E−03 | 2.58E−10 | 10.3 |

*NB indicates that under the experimental conditions, LAG3 reagent did not bind to the captured anti-LAG3 monoclonal antibody Table 7 shows that at 37° C., all the anti-LAG3 antibodies of the invention bound to hLAG3 dimer proteins with $K_D$ values ranging from 4.0 pM-0.9 nM, while the comparators bound with $K_D$ values of 0.26 nM and 0.45 nM.

Data in Tables 6 and 7 indicate that all anti-LAG3 antibodies bind to hLAG3 dimer reagents with similar affinities at both 25° and 37° C.

Example 4: Octet Cross-Competition Between Anti-LAG3 Antibodies

To assess whether two antibodies compete with one another for binding to monomeric human LAG3, (hLAG3.mmh) binding competition between anti-LAG3 monoclonal antibodies was determined using a real time, label-free bio-layer interferometry assay on an Octet RED384 biosensor (Pall ForteBio Corp.). Cross competition experiment were run at 25° C. in 0.01 M HEPES pH7.4, 0.15M NaCl, 0.05% v/v Surfactant Tween-20, 0.1 mg/mL BSA (Octet HBS-P buffer) with the plate shaking at the speed of 1000 rpm. All anti-LAG3 antibody and hLAG3 solutions tested were formulated in Octet HBS-P buffer. To assess whether 2 antibodies were able to compete with one another for binding to hLAG3, approximately 0.6-0.85 nm of hLAG3.mmh was first captured on anti-His coated Octet biosensor tips from wells containing 5 μg/mL of hLAG3 for 75 seconds. The hLAG3 captured Octet biosensor tips were saturated by submerging for 5 minutes into wells containing 50 ug/ml of the first anti-LAG3 monoclonal antibody (hereby referred as mAb-1), followed by submerging in wells containing the second anti-LAG3 monoclonal antibody (hereby referred as mAb-2). Between each steps the Octet biosensor tips were washed in HBS-P buffer for 30 seconds.

The real-time binding response was monitored during the course of the experiment and the binding response at the end of every step was recorded. The response of hLAG3 binding to mAb-1 and then to the blocking mAb was corrected for background binding, compared and competitive/non-competitive behavior of different anti-Lag monoclonal antibodies was determined.

Table 8 explicitly defines the relationships of antibodies competing in both directions, independent of the order of binding.

TABLE 8

Cross-competition of anti-LAG3 antibodies for binding to monomeric hLAG3

| First mAb (mAb-1) Captured using AHC Octet Biosensors | mAb-2 Antibodies Shown to Compete with mAb-1* |
|---|---|
| H4sH15482P | H4sH15479P, H4sH14813N, H4H14813N, H4H15479P, H4H15482P, H4H15483P |
| H4sH15479P | H4sH15482P, H4sH14813N, H4H14813N, H4H15479P, H4H15482P, H4H15483P |
| H4sH14813N | H4sH15482P, H4sH15479P, H4H14813N, H4H15479P, H4H15482P, H4H15483P |
| H4H14813N | H4sH15482P, H4sH15479P, H4sH14813N, H4H15479P, H4H15482P, H4H15483P |
| H4H15479P | H4sH15482P, H4sH15479P, H4sH14813N, H4H14813N, H4H15482P, H4H15483P |
| H4H15482P | H4sH15482P, H4sH15479P, H4sH14813N, H4H14813N, H4H15479P, H4H15483P |
| H4H15483P | H4sH15482P, H4sH15479P, H4sH14813N, H4H14813N, H4H15479P, H4H15482P |
| H4sH15498P2 | H4H15498P2, H4H17828P2, H4H17819P, H4H17823P |
| H4H15498P2 | H4sH15498P2, H4H17828P2, H4H17819P, H4H17823P |
| H4H17828P2 | H4sH15498P2, H4H15498P2, H4H17819P, H4H17823P |
| H4H17819P | H4sH15498P2, H4H15498P2, H4H17828P2, H4H17823P |
| H4H17823P | H4sH15498P2, H4H15498P2, H4H17828P2, H4H17819P |
| H4sH15462P | none |
| H4H15462P | none |
| H4H17826P2 | none |

(*Self-competing mAb2s are not listed)

Example 5: Antibody Binding to Cells Overexpressing LAG3 as Determined by Flow Cytometry HEK293 cells (HEK293; ATCC, #CRL-1573) stable cell lines that express recombinant hLAG3 (NCBI Accession No. NP_002277.4) or monkey LAG3 (mfLAG3) [cynomolgus monkey sequence NCBI Accession No. XP_005570011.1 was further modified to replace the "X" at amino acid position 74 with proline based on Rhesus macaque (*Macaca mulata*) sequence NCBI Accession No. XP_001108923.1] (SEQ ID NO: 576) at the cell surface were developed and used to determine the binding specificity of anti-LAG3 monoclonal antibodies of the invention by flow cytometry analysis.

Binding of anti-LAG3 antibodies was assessed as follows: Stable HEK293 cells expressing either hLAG3 or mfLAG3 were washed 1× with D-PBS (Irvine Scientific Cat #9240), trypsinized (Specialty Media Cat #SM-2004-C) and blocked with HEK293 cell culture medium (DME+10% FBS+P/S/G+non-essential amino acids). After centrifugation cells were resuspended at 2.0×10⁶ cells/mL in staining buffer (D-PBS+2% FBS). The anti-LAG3 antibodies and isotype controls were serially diluted in staining buffer with a dose ranging from 5 pM to 100 nM including a no antibody buffer only control. The serially diluted antibodies were added to the cell suspension and incubated for 15-30 minutes on ice. The cells were centrifuged and pellets were washed with staining buffer to remove unbound antibodies. Subsequently, cells were incubated for 15-30 minutes on ice with an allophycocyanin-conjugated secondary F(ab')2 recognizing human Fc (Jackson ImmunoResearch, #109-136-170). The cells were centrifuged and pellets were washed with staining buffer to remove unbound secondary F(ab')2 and fixed overnight with a 1:1 dilution of Cytofix (BD Biosciences, #554655) and staining buffer. Following day, fixed cells were centrifuged and pellets were washed with staining buffer, resuspended and filtered. Fluorescence measurements were acquired on HyperCyt® cytometer and analyzed in ForeCyt™ (IntelliCyt; Albuquerque, N. Mex.) to determine the mean fluorescence intensities (MFI). The $EC_{50}$ values were calculated from a four-parameter logistic equation over an 11-point response curve using GraphPad Prism. $EC_{50}$ was defined as the concentration of antibody at which 50% of maximal binding signal is detected. The MFI ratio for each antibody was calculated by dividing the MFI at 100 nM by MFI at 0 nM of antibody concentration.

TABLE 9

Binding of anti-LAG3 antibodies to HEK293 wild-type (wt) cells as determined by FACS

| | FACS on HEK293 wt | |
|---|---|---|
| Ab PID# | EC50 [M] | Ratio of MFI (100 nM/0 nM) |
| hIgG4 isotype control | — | 1.5 |
| H4sH15462P | — | 0.9 |
| H4H15462P | — | 8.2 |
| H4sH15479P | — | 1.1 |
| H4H15479P | — | 1.7 |
| H4sH15482 | — | 1.2 |
| H4H15482P | — | 4.9 |
| H4sH15498P2 | — | 1 |
| H4H15498P2 | — | 1 |
| H4sH14813N | — | 1.5 |
| H4H14813N | — | 1.3 |
| H4H17828P2 | — | 1.1 |
| H4H17826P2 | — | 2.5 |
| H4H17823P | — | 2.5 |
| H4H15483P | — | 2.6 |
| H4H17819P | — | 1.1 |
| Comparator 1 | — | 1 |
| Comparator 2 | — | 1.6 |

As shown in Table 9, comparators and isotype controls did not demonstrate any measurable binding to parental wild type HEK293 cells by FACS analysis. The calculated MFI ratios ranged between 1.0 and 1.6×. A few anti-LAG3 antibodies showed higher ratios on wild type cells, suggesting a nonspecific binding, with the calculated MFI ratios ranging between 0.9 and 8.2×. Under these staining conditions no $EC_{50}$ values were determined for the anti-LAG3 antibodies as well as the comparators.

TABLE 10

Binding of anti-LAG3 antibodies to HEK293/hLag3 cells as determined by FACS

| | FACS on HEK293/hLAG3 | |
|---|---|---|
| Ab PID# | EC50 [M] | Ratio of MFI (100 nM/0 nM) |
| hIgG4 isotype control | — | 1.8 |
| H4sH15462P | 6.65E−10 | 181.6 |
| H4H15462P | 3E−10 | 62.6 |
| H4sH15479P | 9.03E−10 | 198.7 |
| H4H15479P | 7.52E−10 | 203.2 |
| H4sH15482 | 1.11E−09 | 140.8 |
| H4H15482P | 1.91E−09 | 103.7 |
| H4sH15498P2 | 7.92E−09 | 400.6 |
| H4H15498P2 | 5.76E−09 | 305 |
| H4sH14813N | 1.18E−09 | 197.2 |
| H4H14813N | 1.44E−09 | 208.5 |
| H4H17828P2 | 2.65E−09 | 355.2 |

TABLE 10-continued

Binding of anti-LAG3 antibodies to HEK293/hLag3 cells as determined by FACS

| | FACS on HEK293/hLAG3 | |
|---|---|---|
| Ab PID# | EC50 [M] | Ratio of MFI (100 nM/0 nM) |
| H4H17826P2 | 3.86E−09 | 414.2 |
| H4H17823P | 1.25E−09 | 304.9 |
| H4H15483P | 2.31E−09 | 206.3 |
| H4H17819P | 2.79E−09 | 435.8 |
| Comparator 1 | 7.52E−10 | 188.2 |
| Comparator 2 | 6.5E−10 | 150.9 |

As shown in Table 10, isotype controls did not demonstrate any measurable binding to HEK293/hLag3 cells. All 15 anti-LAG3 antibodies of the invention showed a significant binding to HEK293/hLag3 cells with $EC_{50}$ values ranging from 300 pM to 7.9 nM. The calculated MFI ratios ranged from 62-414×. The $EC_{50}$ values for comparators were 0.65 nM and 0.75 nM in the binding assay and MFI ratios were less than 200× for both the antibodies.

TABLE 11

Binding of anti-LAG3 antibodies to HEK293/mfLag3 cells as determined by FACS

| | FACS on HEK293/mfLAG3 | |
|---|---|---|
| Ab PID# | EC50 [M] | Ratio of MFI (100 nM/0 nM) |
| hIgG4 isotype control | — | 1.3 |
| H4sH15462P | — | 1 |
| H4H15462P | — | 2.9 |
| H4sH15479P | 9.02E−10 | 20.7 |
| H4H15479P | 1.35E−09 | 21.5 |
| H4sH15482 | 1.15E−09 | 10 |
| H4H15482P | 2.2E−09 | 11.9 |
| H4sH15498P2 | >10 nM | 12.1 |
| H4H15498P2 | >10 nM | 12.8 |
| H4sH14813N | 1.57E−09 | 16.7 |
| H4H14813N | 1.42E−09 | 17.1 |
| H4H17826P2 | >10 nM | 14.3 |
| H4H17823P | >10 nM | 12.4 |
| H4H15483P | >10 nM | 8.8 |
| H4H17819P | >10 nM | 12.1 |
| Comparator 1 | >10 nM | 6.7 |
| Comparator 2 | >10 nM | 8.6 |

As shown in Table 11, isotype controls did not demonstrate any measurable binding to HEK293/mfLag3 cells. A total of 13 out of 15 anti-LAG3 antibodies of the invention showed a significant binding to HEK293/mfLAG3 cells with $EC_{50}$ values ranging from 900 pM to greater than 10 nM. The calculated MFI ratios ranged from 8.8× to 21.5×. The $EC_{50}$ values for the comparators were greater than 10 nM and calculated MFI ratios were 6.7× and 8.6×.

Example 6: Antibody Binding to Cells Overexpressing LAG3 as Determined by Electrochemiluminescence Immunoassay To investigate the ability of a panel of anti-LAG3 monoclonal antibodies to bind cell-surface expressed LAG3, an in vitro binding assay utilizing human and monkey LAG3 expressing cell lines in an electrochemiluminescence based detection platform [Meso Scale Diagnostics, Rockville, Md.—(MSD)] was developed.

The HEK293 (ATCC, #CRL-1573) stable cell lines were generated by lentivirus transduction to express recombinant hLAG3 (NCBI Accession No. NP_002277.4) or monkey LAG3 (mfLAG3) [cynomolgus monkey sequence *Macaca fascicularis* Accession No. XP_005570011.1, modified to replace the "X" at amino acid position 74 with proline based on Rhesus macaque (*Macaca mulata*) sequence NCBI Accession No. XP_001108923.1) (SEQ ID NO: 576). The parental HEK293 cell line, which has no detectable expression of LAG3 by fluorescence activated cell sorting (FACS), was included in the experiment as a background binding control. Unrelated human IgG4 and hIgG4s were included as isotype control antibodies.

Experiments were carried out according to following procedure. Cells from the three cell lines described above were rinsed once in 1×PBS buffer without $Ca^{2+}/Mg^{2+}$ followed by 10-minute incubation at 37° C. with Enzyme Free Cell Dissociation Solution. The detached cells were washed one time with 1×PBS with $Ca^{2+}/Mg^{2+}$ and counted with a Cellometer™ Auto T4 cell counter (Nexcelom Bioscience). Approximately 10,000 cells per well in the cell-washing buffer were seeded into the 96-well carbon electrode plates (MULTI-ARRAY high bind plate, MSD) and incubated for 1 hour at 37° C. to allow the cells to adhere. Nonspecific binding sites were blocked by 2% BSA (w/v) in PBS for 1 hour at room temperature. To the plate-bound cells, solutions of anti-LAG3 antibodies in serial dilutions ranging from 1.7 pM to 100 nM, and the solutions without the presence of the antibody were added in duplicate, and the plates were incubated for 1 hour at room temperature. The plates were then washed to remove the unbound antibodies using an AquaMax2000 plate washer (MDS Analytical Technologies). The plate-bound antibodies were detected with a SULFO-TAG™-conjugated anti-human IgG antibody (MSD) for 1 hour at room temperature. After washes, the plates were developed with the Read Buffer (MSD) according to manufacturer's recommended procedure and the luminescent signals were recorded with a SECTOR Imager 6000 (MSD) instrument. The direct binding signals (in relative light units—RLU) were analyzed as a function of the antibody concentration and the data were fitted with a sigmoidal (four-parameter logistic) dose-response model using GraphPad Prism™ software. The potency of each antibody was determined by calculating $EC_{50}$. $EC_{50}$ for binding HEK293-hLAG3 and HEK293-mfLAG3 cells was defined as the concentration of antibody at which 50% of the maximal binding signal is detected. The ratio of signal detected with 100 nM antibody binding to the HEK293-hLAG3 or HEK293-mfLAG3 cells compared to the HEK293 parental cells was recorded as an indication of specificity of LAG3 binding. For ratios lower than 2-fold at the highest antibody concentration (100 nM), the antibody was concluded as non-specific (NS).

The binding results are summarized in Table 12.

TABLE 12

| | Antibody binding to cells overexpressing hLAG3 or mfLAG3 | | | |
|---|---|---|---|---|
| Ab ID | Potency of Cell Binding to HEK293-hLAG3 Cells EC50(M) | Potency of Cell Binding to HEK293-mfLAG3 Cells EC50(M) | Ratio of 100 nM Antibody binding HEK293-hLAG3 to HEK293 cells | Ratio of 100 nM Antibody binding HEK293-mfLAG3 to HEK293 cells |
| H4sH15462P | 8.53E−10 | NS | 6.8 | NS |
| H4sH15482P | 1.13E−08 | NS | 4.5 | NS |
| H4sH15479P | 1.34E−08 | NS | 17.8 | NS |
| H4sH15498P2 | 2.87E−09 | 2.00E−08 | 99.8 | 32.7 |
| H4sH14813N | 2.03E−08 | NS | 19.8 | NS |
| H4H14813N | 1.99E−08 | NS | 8.9 | NS |
| H4H15462P | 6.85E−09 | NS | 2.3 | NS |
| H4H15482P | 2.47E−08 | NS | 7.4 | NS |
| H4H15479P | 5.20E−08 | 7.39E−08 | 20.1 | 2.1 |
| H4H15498P2 | 2.95E−09 | 9.68E−09 | 38.8 | 13.8 |
| H4H17828P2 | 1.2E−09 | 1.31E−08 | 8.7 | 6 |
| H4H17826P2 | 3.48E−09 | 7.85E−09 | 7 | 4.7 |
| H4H17823P | 1.5E−09 | 2.78E−08 | 5.3 | 2.8 |
| H4H15483P | 1.72E−08 | NS | 6.6 | NS |
| H4H17819P | 6.9E−10 | 4.02E−08 | 22.7 | 8.3 |
| H4H isotype Control | NS | NS | NS | NS |
| H4sH isotype Control | NS | NS | NS | NS |
| Comparator 1 | 4.03E−09 | NS | 7.7 | NS |
| Comparator 2 | 6.77E−09 | NS | 8.1 | NS |

NS = Non-Specific - ratio at 100 nM ab <2

As shown in Table 12, the potency of the antibodies ranged from $EC_{50}$ values of 690 pM to 52 nM for binding to HEK293-hLAG3 cells, with all of the antibodies having specific binding of >2-fold binding to human LAG3 expressing cells compared to parental HEK293 cells with 100 nM antibody binding. Only seven of the antibodies bound specifically to HEK293-mfLAG3 cells with $EC_{50}$ values ranging from 7.9 nM to 74 nM. The comparator binding potencies on HEK293-hLag3 cells were approximately 4.0 nM and 7.0 nM. The comparators did not show specific binding to HEK293-mfLag3 cells. Irrelevant controls binding to the HEK293-hLAG3 and HEK293-mfLAG3 cells were non-specific as expected, with H4H isotype control and the H4sH isotype control binding with ratios ranging from 0.7-1.1-fold binding above the HEK293 parental cells.

Example 7: Blocking of LAG3 Binding to MHC Class II in a Cell Adherence Assay

A cell adherence assay was utilized to measure the ability of anti-LAG3 monoclonal antibodies to block either human MHCII or mouse MHCII expressing cells (RAJI and A20 cells, respectively) from adhering to hLAG3-expressing HEK293 cells attached on a microtiter plate (based on an assay described in Eur J Immunol. 1995, 25: 2718-21 by Huard, et al.).

The HEK293 (ATCC, #CRL-1573) stable cell lines were generated by lentivirus transduction to express recombinant hLAG3 (NCBI Accession No. NP_002277.4) or mouse LAG3 (mLAG3) (GenBank Accession No. NP_032505.1). The parental HEK293 cell line has no detectable expression of human LAG3 by fluorescence activated cell sorting (FACS) technology and was used to demonstrate the requirement of LAG3 for the adherence of MHCII expressing RAJI and A20 cells.

Experiments were carried out according to the following procedure: Subconfluent HEK293-hLAG3 expressing cells were washed once with 1×PBS, trypsinized, and centrifuged at 1,200 rpm for 5 minutes. Cells pellets were resuspended in 1×PBS and subsequently counted to determine cell number. The appropriate number of cells were isolated and resuspended in complete media (DME+10% FBS+penicillin/streptomycin/glutamine), such that each well would contain 100 µL of 1.2∝cells. Cells were plated into sterile Nunclon™ Delta 96-Well MicroWell™ Black Optical Bottom Plates (Thermo Scientific). The wells from the perimeter of the plate were not included in the assay design to avoid edge effects. Instead of cells, 100 µL of 1×PBS was added to the perimeter wells. Plated HEK293-hLAG3 cells were incubated overnight at 37° C., at 5% $CO_2$. After incubation these cells were treated with anti-LAG3 antibodies and isotype controls.

On the day of treatment, all antibodies were serially (1:3) diluted in RPMI media (without FBS or supplements added). The 9-point dilution ranged between 45 pM to 300 nM, with the last dilution point containing no mAb. For the testing of the H4sH antibodies in the adherence assay using RAJI cells the 9-point dilution ranged between 23 pM to 150 nM, with the last dilution point containing no mAb. A final volume of 50 µL of anti-LAG3 antibodies or isotype controls were added to HEK293-hLAG3 cells and incubated for 1 hour at 37° C., at 5% $CO_2$. While the plated HEK293-LAG3 cells were incubating with the test or control antibodies, non-adherent B-cells (RAJI or A20) were labeled with Calcein AM using the following procedure. RAJI and A20 suspension cells were harvested and centrifuged at 1,200 rpm for 5 minutes. Cell pellets were resuspended in 1×PBS and counted. Cells were washed with RPMI, and resuspended in RPMI at a concentration of $10^6$ cells per 1 ml. Cells were labeled by adding 5 µL of Calcein AM per 1 ml of cell suspension and incubated for 30 min at 37° C., at 5% $CO_2$. Labeled cells were washed 1× with RPMI, centrifuged, washed with 1×PBS and resuspended in PBS at a concentration of $5\times10^6$ cells per 1 ml. Subsequently, 10 µL of BD Pharmingen Fc Block (0.5 mg/mL) was added per 1 ml of the Calcein AM labeled cells, which were incubated at RT for 10 minutes. The Calcein AM-stained, Fc-blocked RAJI or A20 cells were resuspended in RPMI to a final concentration of $3\times10^6$ cells per 1 ml and subsequently used in the adherence assay.

At the end of the one hour LAG3 antibody treatment of HEK293-LAG3 cells, 50 µl of labeled RAJI or A20 cells were added to each well at the density of $1.5\times10^5$ cells/well. The labeled suspension cells were incubated with the HEK293 monolayer for 1 hour at 37° C., at 5% $CO_2$. Non-adherent cells were washed away by gently washing the wells 4× with RPMI, blotting plates with paper towels after each wash, followed by 2× wash with PBS. A final volume of 200 µl PBS was added to each well and the Calcein AM fluorescence was read at an excitation/emission wavelength of 485 nm/535 nm on the VICTOR™ X5 Multilabel Plate Reader. The $IC_{50}$ values were calculated using a four-parameter logistic equation over a 9-point response curve using GraphPad Prism. $IC_{50}$ was defined as the concentration of antibody at which 50% blocking of adherence of HEK cells to RAJI or A20 cells was observed.

The ability of the anti-LAG3 antibodies to block binding of LAG3 to both human and mouse MHCII was assessed using a cell based adherence assay. The assay utilized a format of florescence labeled MHCII endogenously expressing cells [human MHCII (RAJI) or mouse MHCII (A20)] binding to cells engineered to express human LAG3. The ability of LAG3 antibodies to block this interaction was evaluated and results are shown in Table 13.

TABLE 13

Anti-LAG3 antibody $IC_{50}$ values for blocking RAJI and A20 cell adherence to HEK293-hLAG3 cells

| | Adherence Assay | |
|---|---|---|
| Ab ID# | RAJI IC50 [M] | A20 IC50 [M] |
| H4sH15462P | 2.50E−09 | 3.60E−09 |
| H4H15462P | 3.20E−09 | 7.10E−09 |
| H4sH15479P | 9.60E−09 | 6.30E−09 |
| H4H15479P | 3.10E−08 | 1.10E−08 |
| H4sH15482 | 3.30E−09 | 3.80E−09 |
| H4H15482P | 1.50E−08 | 1.10E−08 |
| H4sH15498P2 | 1.60E−08 | 2.10E−08 |
| H4H15498P2 | 1.50E−08 | 3.00E−08 |
| H4sH14813N | 6.00E−09 | 1.00E−08 |
| H4H14813N | 1.70E−08 | 1.00E−08 |
| H4H17828P2 | 1.10E−08 | 1.60E−08 |
| H4H17826P2 | 2.70E−08 | 1.00E−08 |
| H4H17823P | 8.60E−09 | 9.40E−09 |
| H4H15483P | 1.90E−08 | 1.60E−08 |
| H4H17819P | 1.70E−08 | 1.60E−08 |
| Isotype control | — | — |
| Comparator 1 | 3.40E−09 | 5.10E−09 |
| Comparator 2 | 7.20E−09 | 9.60E−09 |

As shown in Table 13, isotype control did not demonstrate any measurable blocking of RAJI or A20 cell binding to HEK293-hLAG3 cells. All the LAG3 antibodies of the invention blocked 92-98% of RAJI or A20 cell adherence to HEK293-hLAG3 cells at the top antibody concentration, with IC50 values ranging from 2.5 nM to 31 nM for RAJI cell adherence and 3.6 nM to 30 nM for A20 cell adherence to HEK293-hLAG3 cells. The IC50 values for the comparators were 3.4 nM and 7.2 nM for RAJI cell adherence and 5.1 nM and 9.6 nM for A20 cell adherence to HEK293-Lag3 cells.

Example 8: Blocking of LAG3-Induced T Cell Down-Regulation in a T Cell/APC Luciferase Reporter Assay T cell activation is achieved by stimulating T cell receptors (TCR) that recognize specific peptides presented by major histocompatibility complex class I or II (MHCI or MHCII) proteins on antigen-presenting cells (APC) (Goldrath et al. 1999, *Nature* 402, 255-262). Activated TCRs in turn initiate a cascade of signaling events that can be monitored by reporter genes driven by transcription factors such as activator-protein 1 (AP-1), Nuclear Factor of Activated T cells (NFAT) or Nuclear factor kappa-light-chain-enhancer of activated B cells (NFκB). T cell response is refined via engagement of co-receptors expressed either constitutively or inducible on T cells. One such receptor is LAG3, a negative regulator of T cell activity. LAG3 interacts with its ligand, MHCII, which is expressed on target cells including APCs or cancer cells, and inhibits T cell activation by shutting down positive signals initiated by the TCR signalosome (Workman et al. 2002, *J Immunol* 169: 5392-5395).

To characterize the ability of the anti-LAG3 antibodies to antagonize LAG3-mediated signaling in T cells, a LAG3 T cell/APC reporter assay was developed to measure T cell signaling induced by interaction between APC and T cells by utilizing a mixed culture derived from two mammalian cell lines: Jurkat derived T cells (clone JRT3.T3.5, as described below) and engineered APCs in HEK293 background (as described below) (FIG. 1).

For the first component, the T cell line for LAG3 T cell/APC reporter bioassay was developed as follows: A Jurkat derived T cell clone, JRT3.T3.5 (ATCC, #TIB-153) was initially transduced with the Cignal Lenti AP-1 Luc reporter (Qiagen—Sabiosciences, #CLS-011L) as per the manufacturer's instructions. The lentivirus encodes the firefly luciferase gene under the control of a minimal CMV promoter, tandem repeats of the TPA-inducible transcriptional response element (TRE) and a puromycin resistance gene. After antibiotic selection, puromycin resistant pools of the reporter cell were further manipulated by transduction with human CD28 (NP_006130.1), Ob2F3 TCR alpha and beta subunit (Alpha AGA92550.1 Beta AAA61026.1), human LAG3 chimera (comprising the extracellular domain of human LAG3 (NP_002277.4) and trans-membrane/cytoplasmic domain of human CD300a (amino acids from 181 to 299; accession number NP 009192.2) and human PD-1 (accession number NP_005009.2). The expression of the proteins was confirmed by FACS analysis after each round of transduction. Subsequently a single clone JRT3.T3/AP1-Luc/CD28/hLAG3-CD300a chimera/hPD-1 clone 2D2 was generated and used in the T cell/APC reporter bioassay. The cell line was maintained in RPMI+10% FBS+penicillin/streptomycin/glutamine (P/S/G) supplemented with 100 ug/mL hygromycin+500 ug/mL G418+1 ug/mL puromycin, hereby referred to as selection medium. These cells are herein referred to as reporter T cells.

For the second component, the APC cell line for the LAG3 T cell/APC reporter bioassay was generated as follows: A stable HEK293 cell line (ATCC, #CRL-1573) expressing human CD20 (number NP_068769.2) was transduced with human with the MHCII subunits, HLA-DR2A (NP_061984.2) and HLA-DR2B (NP_002115). The HLA-DR2 positive cells were isolated by FACS and the resulting cell line, HEK293/CD20/HLA-DR2 was maintained in DME+10%+P/S/G+non-essential amino acids supplemented with 100 ug/mL hygromycin+500 ug/mL G418, hereby referred to as selection medium. These cells are herein referred to as APC cells.

To engage T cell and APC in order to initiate the TCR signaling, two approaches were used: (1) Bispecific mode; and (2) Peptide pulsing mode. In this bioassay, the anti-LAG3 antibodies blocked the LAG3/MHCII interaction and rescued T cell activity by disabling the inhibitory signaling delivered by the cytosolic tail of the CD300a molecule with subsequent increase in AP1-Luc signaling. T cell activation was monitored by luciferase readout.

Bispecific Mode:

In this mode, a bispecific antibody composed of one Fab arm that binds to CD3 on T cells and a second Fab binding to CD20 on HEK293 cells (CD3×CD20 bispecific antibody; e.g., as disclosed in US20140088295) was utilized. The presence of the bispecific molecule results in the formation of an immunological synapse and activation of the TCR complex due to clustering of the CD3 molecules on the engineered T-cells.

A day prior to screening, the engineered reporter T cells were cultured to $5\times10^5$ cells/mL in selection medium and tested in the bioassay the following day. The $EC_{50}$ values of anti-LAG3 antibodies were determined in the presence of a fixed concentration of CD3×CD20 bispecific antibody (100 pM). Reagents were added in the following order. The anti-Lag 3 antibodies and isotype controls were serially diluted in RPMI1640 supplemented with 10% FBS and penicillin/streptomycin/glutamine (assay medium). The 10-point dilution ranged between 15 pM to 100 nM with the final dilution point containing no mAb, buffer alone control). The serially diluted antibodies were added to corresponding wells in a 96 well white flat bottom plates containing a fixed concentration (100 pM) of the bispecific antibody. The overnight cultured reporter T cells were resuspended at $2\times10^6$/mL in assay medium, added to anti-LAG3 antibodies plus bispecific antibody containing plates and incubated for 30 minutes at 37° C./5% CO2. The final concentration of the reporter T cells was $5\times10^4$ per well.

Next, the APC cells were washed 1× with D-PBS (Irvine Scientific Cat #9240), trypsinized (Specialty Media Cat #SM-2004-C) and blocked with assay medium. After centrifugation, cells were resuspended to $4\times10^5$/mL in assay medium and added to plates containing T cell reporter cells incubated with the anti-LAG3 plus bispecific antibody. The final concentration of the APC cells was $1\times10^4$ per well. Plates were incubated for 4-6 hours at 37° C., 5% CO2. The AP1-Luc activity was detected after the addition of ONE-Glo™ (Promega, #E6051) reagent and relative light units (RLUs) were captured on a Victor luminometer. All samples were tested in duplicates.

Peptide Pulsing Mode Using MBP85-99:

TCRs recognize specific MHC/peptide complex and lead to the activation of the T cells. The Ob2F3 TCR heterodimer used in this assay has been reported to interact with the MHCII protein, HLA-DR2AB, in complex with the MBP85-99 peptide (Myelin Basic Protein NP_001020272; SEQ ID NO: 583).

A day before the screening, the engineered reporter T cells were prepared as described above for the bispecific mode. The APC cells were pulsed overnight with 0.2 µM MBP85-99 peptide (Celtek HLA-DR2 MBP85-99 in DMSO, ER-15, Lot #140411, MW 1797.1 g/mol) in corresponding antibiotic containing cell culture medium at 37° C./5% CO2. The $EC_{50}$ values of anti-LAG3 antibodies were determined in the presence of $1\times10^4$ pulsed APCs. Reagents were added in the following order: The anti-LAG3 antibodies and controls were serially diluted in assay medium. The 10-point serial dilution of anti-LAG3 antibodies ranged between 15 pM to 100 nM with the last dilution point containing no mAb. The antibodies were added to corresponding wells in a 96 well white flat bottom plate. The overnight cultured reporter T cells were resuspended to $2\times10^6$/mL in assay medium, added to plates and incubated for 30 minutes at 37 C at 5% CO$_2$. The final concentration of the reporter T cells was $5 \times 10^4$ T cells per well. Next the MBP85-99 peptide pulsed APC cells were washed 1× with D-PBS (Irvine Scientific Cat #9240), trypsinized (Specialty Media Cat #SM-2004-C) and blocked with assay medium. After centrifugation, cells were resuspended to $4 \times 10^5$/mL in assay medium and added to the anti-LAG3 plus peptide pulsed reporter T cell plates. The final concentration of the APC cells was $1 \times 10^4$ per well. Assay plates were incubated for 4-6 hours at 37° C./5% CO2. The AP1-Luc activity was detected after the addition of ONE-Glo™ (Promega, #E6051) reagent and relative light units (RLUs) were captured on a Victor luminometer. All samples were tested in duplicates.

The $EC_{50}$ values were determined from a four-parameter logistic equation over a 10-point response curve using GraphPad Prism. RLU values for each screened antibody were normalized by setting the last serial dilution containing no mAb, control to 100%, which should theoretically display the maximal AP1-Luc response elicited either with the bispecific molecule (in the bispecific mode) or by the pulsed APCs with the MBP85-99 peptide. Results are summarized in Table 14.

TABLE 14

Anti-LAG3 antibodies dependent activation of AP1-Luc signaling in LAG3 T cell/APC bioassay

| Ab ID# | $EC_{50}$ [M] Peptide mode | $EC_{50}$ [M] Bispecific mode |
|---|---|---|
| hIgG4 isotype | — | — |
| H4sH15462P | 4.86E-10 | 1.48E-10 |
| H4H15462P | 3.44E-10 | 2.24E-10 |
| H4sH15479P | 1.35E-10 | 8.72E-11 |
| H4H15479P | 2.84E-10 | 1.45E-10 |
| H4sH15482P | 8.06E-10 | 5.18E-10 |
| H4H15482P | 2.48E-09 | >100 nM |
| H4sH15498P2 | 4.61E-09 | >100 nM |
| H4H15498P2 | 5.89E-09 | 6.62E-09 |
| H4sH14813N | 8.16E-10 | 6.88E-10 |
| H4H14813N | 1.01E-09 | 1.07E-09 |
| H4H15483P | 2.54E-09 | 3.69E-09 |
| H4H17819P | 2.12E-09 | >100 nM |
| H4H17823P | 6.88E-10 | >100 nM |
| H4H17826P2 | 8.83E-09 | 2.66E-07 |
| H4H17828P2 | 4.91E-09 | >100 nM |
| Comparator 1 | 2.79E-10 | 1.57E-10 |
| Comparator 2 | 3.49E-10 | 2.38E-10 |

As shown in Table 14, all the anti-Lag3 mAbs of the invention that were tested in the T cell/APC bioassay, rescued LAG3/HLA-DR2 inhibition with $EC_{50}$ values ranging from 135 pM to 8.83 nM in the peptide mode of the assay and with $EC_{50}$ values ranging from 87 pM to more than 100 nM in the bispecific mode of the assay, while the comparators exhibited $EC_{50}$ values of 280 pM and 350 pM. Tested isotype controls did not show significant rescue activity in the bioassay. In a further experiment, the addition of an anti-PD-1 antibody (REGN 2810; described in Example 12 herein) did not enhance rescue of T-cell activation.

In a second experiment, the HEK293/CD20/HLA-DR2 cell line was transduced with human PD-L1 gene (amino acids 1-290 of accession number NP_054862.1) that had been cloned into a lentiviral (pLVX) vector system. As described above, Jurkat derived T cells expressing hLAG-3 and an AP-1-driven luciferase reporter were incubated with PD-L1 positive antigen-presenting cells expressing human MHC II/peptide complex. In this assay, anti-LAG-3 antibodies rescued T cell activity only in the presence of an anti-PD-1 antibody (REGN2810; described in Example 12 herein), not in the absence of the anti-PD-1 antibody. In summary, anti-LAG-3 antibodies rescued T cell activation by blocking LAG-3/MHC II inhibitory signaling and synergized with an anti-PD-1 antibody in this T cell assay.

Example 9: Anti-LAG3 Antibodies Display Binding to CD4+ and CD8+ Stimulated Cynomolgus T-Cells In this example, the ability of selected anti-LAG3 antibodies to bind to LAG3-expressing CD4+ and/or CD8+ cynomolgus T cells via FACS was assessed.

First, T-cells were isolated from cynomolgus whole blood (Bioreclamation, Westbury, N.Y.). Briefly, whole blood from two cynomolgus donors was diluted 1:1 in PBS and layered over 85% Ficoll-Paque solution. Following standard procedures, red blood cells were separated from mononuclear cells and T-cells were isolated using panT cells isolation kit (Miltenyi Biotech).

Isolated T-cells were activated using a T-cell Activation/Expansion kit for non-human primate (Miltenyi Biotech). The cell-bead mixture was resuspended at a concentration of $1 \times 10^6$ cells/mL in complete media. After 72 h of incubation, beads were removed and activated T-cells were expanded in complete media for 96 h.

Next, stimulated cynomolgus T-cells from each donor, as described above, were stained with LIVE/DEAD dye (Molecular Probes) to distinguish between live and dead cells via FACS. Subsequently, cells were co-incubated with PE-conjugated anti-CD8 and FITC-conjugated anti-CD4 for 15 min on ice to enable the detection of CD4 and CD8 positive and negative cell populations.

To assess the binding of anti-LAG3 antibodies to previously isolated CD4+ and CD8+ cynomolgus T-cells, anti-LAG3 antibodies and isotype controls were serially diluted in blocking buffer and plated in a 96 well V-bottom plate with final doses ranging from 100 nM to 50 pM. Next, the serially diluted antibodies were directly labeled using Zenon Alexa-Fluor 647 (Molecular Probes) and incubated with the cynomolgus CD4+/CD8+ T-cell suspension for 15-30 min on ice. Cells were centrifuged and pellets washed with staining buffer to remove unbound antibodies and fixed for 12 h with a 1:1 dilution of Cytofix (BD Biosciences) and staining buffer. Following the incubation period, fixation buffer was removed and pellets were resuspended in staining buffer, filtered, and used for fluorescence measurements.

Fluorescence measurements were acquired on the Fortessa (Becton Dickinson) and data analyzed in FlowJo to determine the mean fluorescence intensities (MFI). $EC_{50}$ values were calculated from a four-parameter logistic equation over an 11-point response curve using GraphPad Prism. The MFI ratio for each antibody was calculated by dividing the MFI at 11.1 nM by MFI at 0 nM of antibody concentration (negative control).

TABLE 15

EC$_{50}$ and MFI Ratios of Selected Anti-LAG3 Antibodies Binding to CD4+ and CD8+ Cynomolgus T-cells from Multiple Donors

| FACS binding on Stimulated T-cell population | Cynomolgus Donor 1 | | | | Cynomolgus Donor 2 | | | |
|---|---|---|---|---|---|---|---|---|
| | CD4+ | | CD8+ | | CD4+ | | CD8+ | |
| | EC$_{50}$ [M] | Ratio of MFI (11 nM/ 0 nM) | EC$_{50}$ [M] | Ratio of MFI (11 nM/ 0 nM) | EC$_{50}$ [M] | Ratio of MFI (11 nM/ 0 nM) | EC$_{50}$ [M] | Ratio of MFI (11 nM/ 0 nM) |
| H4sH15482P | 1.20E−09 | 1.3 | 4.60E−10 | 3 | 3.80E−10 | 1.3 | 4.10E−10 | 4.7 |
| H4sH14813N | 4.20E−10 | 1.3 | 8.50E−11 | 3.5 | 2.20E−10 | 1.5 | 1.10E−10 | 6.3 |
| Comparator 1 | NB | 1.1 | 9.20E−10 | 2.4 | NB | 1.2 | 7.80E−10 | 4.2 |
| hIgG4 Isotype Control | NB | 1 | NB | 1 | NB | 1 | NB | 1 |

NB: No binding

As previously shown, anti-LAG3 antibodies H4sH15482P and H4sH14813N displayed binding to engineered cynomolgus LAG3-HEK293 cell lines. In this example, H4sH15482P and H4sH14813N demonstrated binding specifically to CD4+ and CD8+ LAG3-expressing cynomolgus T-cells with EC$_{50}$'s ranging from 1.1 nM to 85 pM (Table 15). In summary, the selected anti-LAG3 antibodies described in this example binds show cross-reactivity to LAG3 expressed on cynomolgus activated CD4+ and CD8+ T-cells. In contrast, comparator 1 demonstrated binding to CD8+ cynomolgus T-cells only.

Example 10: In Vivo Efficacy of Anti-LAG3 Antibodies Against Colon26 Tumors

The in vivo efficacy of anti-mouse LAG3 antibodies alone and in combination with anti-mouse PD-1 antibodies was studied in a Colon 26 preclinical syngeneic tumor model.

BALB/c mice were purchased from Taconic Biosciences. Colon 26, a mouse adenocarcinoma cell line originated from BALB/c mouse strain, was purchased from American Type Culture Collection (ATCC). Fifty BALB/c mice were subcutaneously implanted with 1×10$^6$ Colon 26 (mouse adenocarcinoma line originated from BALB/c strain) cells on Day 0. On Day 8, forty mice with an average tumor volume of 50 mm$^3$ were selected and randomized into 4 treatment groups (N=10/group). On days 14, 17, 21, 24 and 28, mice were dosed with antibodies as follows: Group 1, rat IgG2a isotype control (clone 2A3, BioXCell, Catalog #BE0089) and mIgG1 isotype control (clone MOPC-21, BioXCell, Catalog #BE0083) antibodies; Group 2, anti-mouse PD-1 antibodies (rat IgG2a anti-mouse PD-1 antibody, clone RPMI-14, BioXCell, catalog #BE0089) and mIgG1 isotype control antibodies; Group 3, anti-mouse LAG3 antibodies (rat IgG1 anti-mouse LAG3 antibody, clone C9B7W, BioXCell, Catalog #BE0174) and rat IgG2a control antibodies; Group 4, anti-mouse PD-1 and anti-mouse LAG3 antibodies. All antibodies were administered by intraperitoneal injection at 10 mg/kg. Tumor volumes were monitored by caliper measurement twice per week for the duration of the experiment (42 days).

Figure 2A:
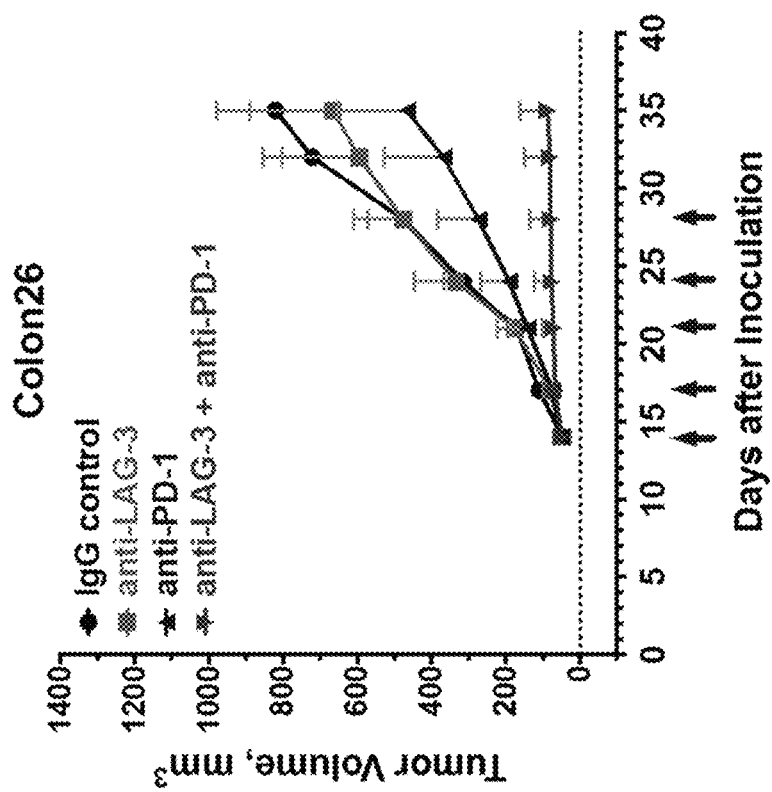
FIGS. 2A-2B summarizes the results of in vivo efficacy of anti-mouse LAG3 antibody alone and in combination with anti-mouse PD-1 antibody against established Colon 26 tumors (described in Example 10).
Figure 2B:
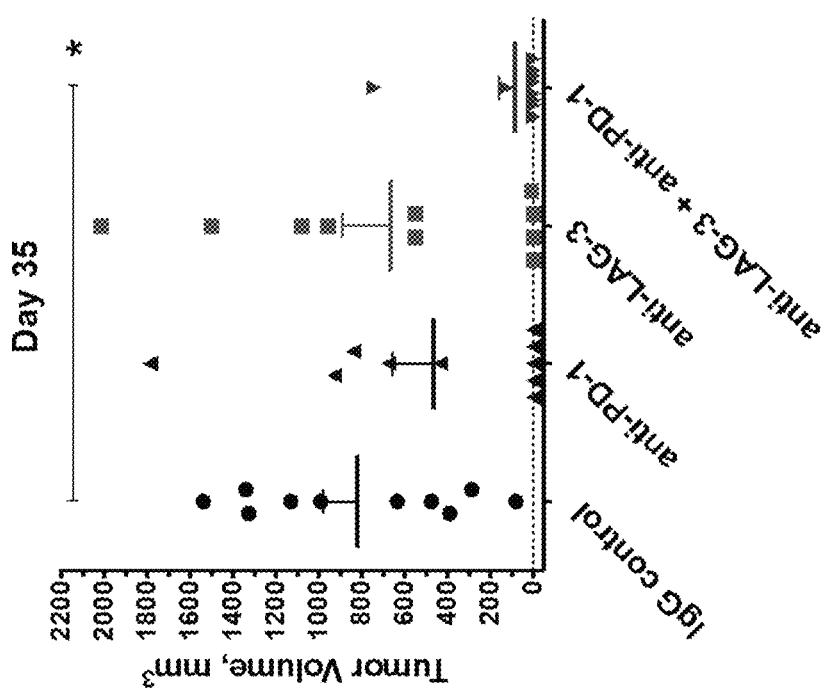
Figure 3A:
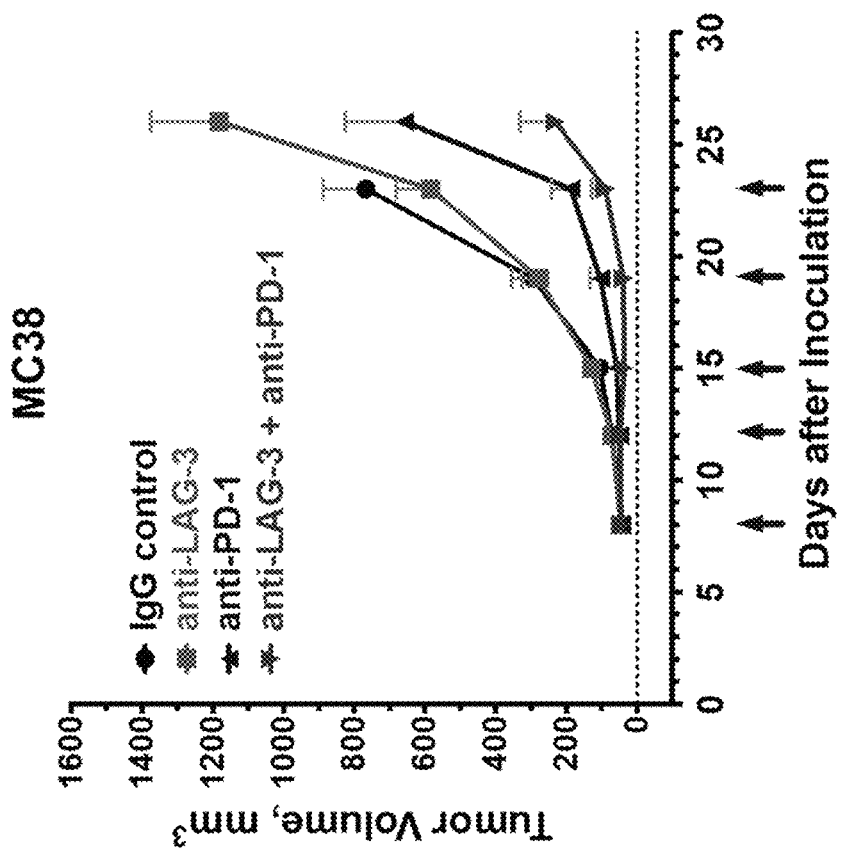
FIGS. 3A-3B summarizes the results of in vivo efficacy of anti-mouse LAG3 antibody alone and in combination with anti-mouse PD-1 antibody against established MC38 tumors (described in Example 11).
Figure 3B:
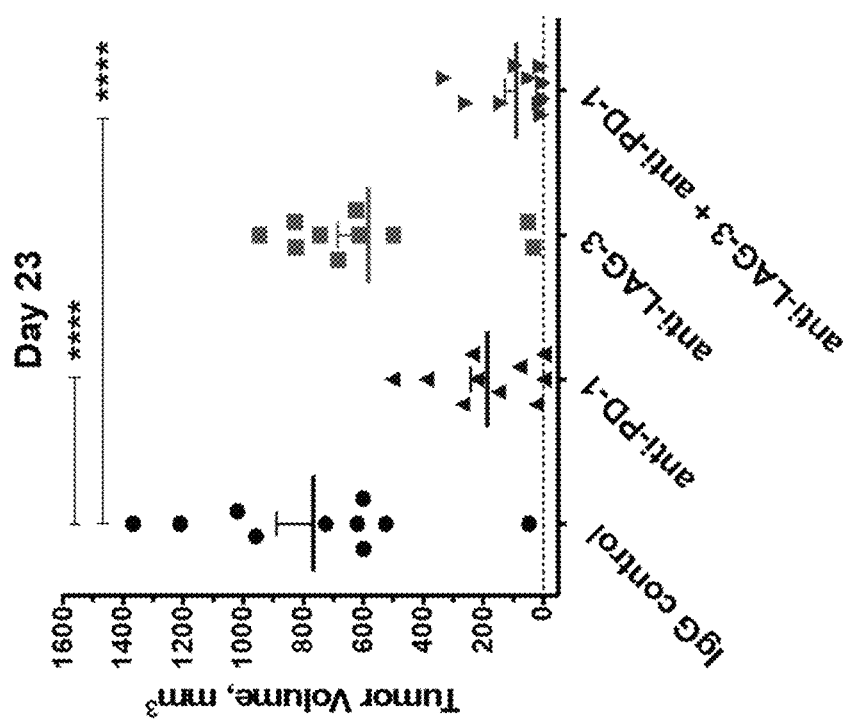

A significant reduction of tumor growth was observed in mice treated with the anti-mouse PD-1 antibody (FIGS. 2A-B), with 5 out of 10 mice becoming tumor-free by day 45 at the end of experiment. Tumor growth reduction was also observed in a subset of mice treated with the anti-mouse LAG3 antibody, with 3 out of 10 mice becoming tumor-free by day 45. In striking contrast, combination treatment with anti-LAG3 and anti-PD-1 antibodies was superior to either monotherapy, with 8 out of 10 mice becoming tumor-free at the end of experiment, suggesting a potent additive effect of anti-LAG3 and anti-PD-1 treatment. There were no tumor-free mice at the end of the experiment in the control group. By day 35, there was a statistically significant reduction of tumor volumes in mice treated with combination therapy (p<0.05, FIG. 2B) but not with either monotherapy. Despite efficient tumor clearance, no evidence of body weight loss was observed (not shown). Thus, in an established Colon 26 tumor model, a combination regimen of anti-PD-1 and anti-LAG3 antibodies was significantly more efficacious than the corresponding monotherapies.

The in vivo activity of anti-mouse PD-1 and anti-mouse LAG3 antibodies was also studied in 4T1, RENCA and A20 preclinical syngeneic tumor models. Combination treatment with both antibodies resulted in at least an additive anti-tumor effect compared to either single antibody treatment (data not shown).

Example 11: In Vivo Efficacy of Anti-Mouse LAG3 Antibodies Against MC38 Tumors

The effect of PD-1 and LAG3 dual blockade was examined against established MC38 tumors in C57BL/6 mice using anti-mouse PD-1 and anti-mouse LAG3 blocking antibodies.

C57BL/6 mice were purchased from Taconic Biosciences. MC38, a mouse adenocarcinoma cell line originated from C57BL/6 mouse strain, was obtained from the National Health Institutes depository. The anti-LAG3 and anti-PD-1 antibodies as well as controls were obtained as described in Example 10.

Fifty C57BL/6 mice were subcutaneously implanted with 3×10$^5$ MC38 cells in the flank on Day 0. On Day 8, forty mice with an average tumor volume of 45 mm$^3$ were selected and randomized into 4 treatment groups (N=10/group). On days 8, 12, 15, 19 and 23, mice were dosed with antibodies as follows: Group 1, rat IgG2a and mIgG1 isotype control antibodies; Group 2, anti-mouse PD-1 and mIgG1 antibodies; Group 3, anti-mouse LAG3 and rat IgG2a antibodies; Group 4, anti-mouse PD-1 and anti-mouse LAG3 antibodies. All antibodies were administered at 10 mg/kg by intraperitoneal injection. Tumor volumes were monitored by caliper measurement twice per week for the duration of the experiment (28 days).

Anti-PD-1 antibody therapy significantly reduced tumor growth in a subset of mice (p<0.0001; day 23) (FIGS.

3A-B), with 2 out of 10 mice becoming tumor-free at the end of experiment. Anti-LAG3 antibody monotherapy did not show any significant anti-tumor effect (0/10 mice tumor-free at the end of the experiment), whereas the combination of anti-LAG3 and anti-PD-1 antibodies was superior to anti-PD-1 therapy alone indicating a synergistic effect.

Figure 4A:
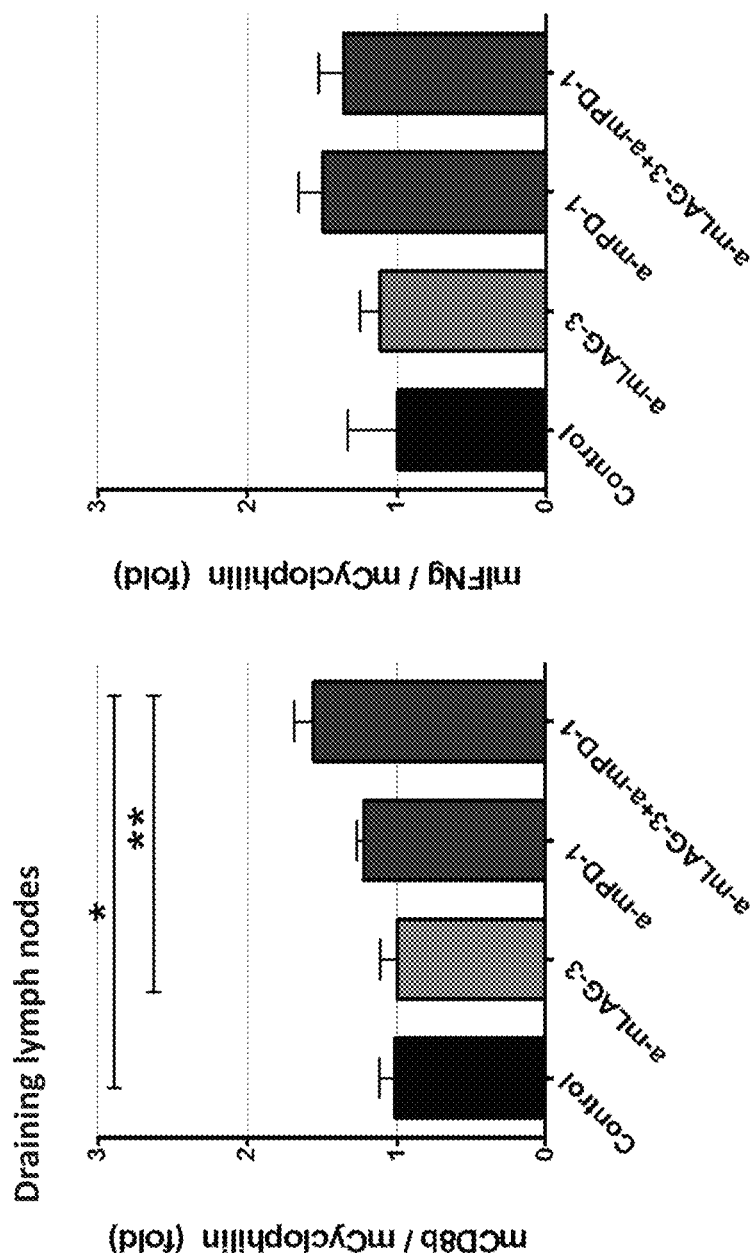
FIGS. 4A-4B shows the expression levels of murine IFNγ and CD8b genes (normalized to murine cyclophilin B expression), as examined by Taqman analysis, in draining lymph nodes (DLN) (A) and spleen (B) collected at the end of the experiment (described in Example 11) from tumor-bearing mice. *P<0.05, P<0.01, *P<0.001.
Figure 4B:
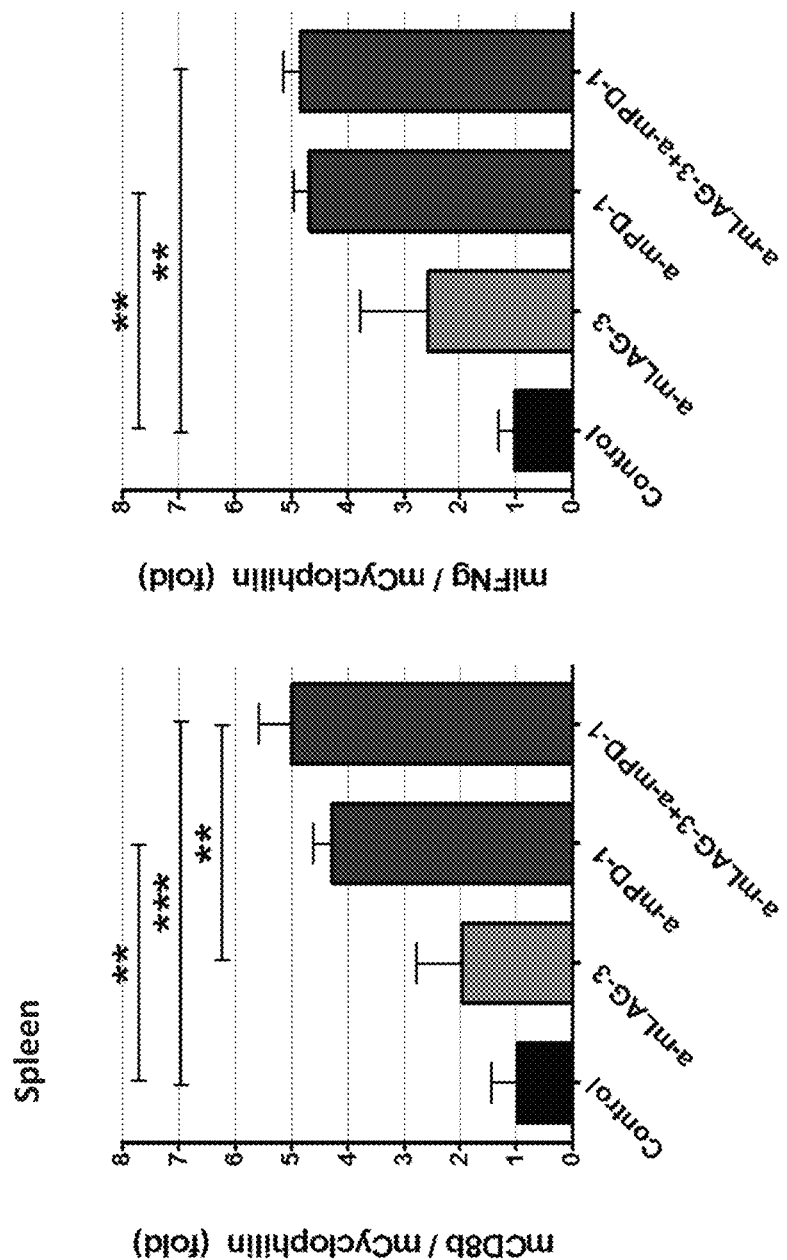

To test the immunomodulatory properties of anti-PD-1 and anti-LAG3 antibodies in combination, T-cell markers in spleens and draining lymph nodes (DLN) of the treated mice were examined (FIG. 4). Spleens and draining lymph nodes of tumor bearing mice were removed by dissection and placed into 15 mL RPMI1640 Glutamax I medium (Invitrogen). Total RNA was isolated and RT-PCR Taqman analysis was performed using a primer/probe mix specific for mouse CD8β [probe: AGCAGCTCTGCCCTCAT (SEQ ID NO: 584), forward primer: GCTCTGGCTGGTCTTCAGTATG (SEQ ID NO: 585), reverse primer: TTGCCGTATGGTTGGTTTGAAC (SEQ ID NO: 586)] and mouse IFNγ (Mm01168134_m1, Applied Biosystems). Samples were normalized to mouse cyclophilin B transcript expression levels. TaqMan analysis demonstrated CD8+ T cell expansion in both the DLN and spleens of mice in the combination treatment group, as well as increased production of T cell effector molecule IFNγ in both combination and single anti-PD-1 treated animals, indicating that PD-1 and LAG3 blockade increases proliferation and effector function of T cells.

Example 12: In Vivo Efficacy of Anti-Human LAG3 Antibodies Against MC38 Tumors

In this experiment, the efficacy of an exemplary anti-human LAG3 antibody of the invention against MC38 tumors was studied. Anti-human LAG3 mAbs do not bind to mouse LAG3. Therefore, to study the anti-tumor properties of these antibodies in vivo in mice, mice humanized to express human LAG3 protein were used. For the experiments herein, double-humanized mice that express the extracellular portion of human PD-1 and of human LAG3 and the transmembrane and intracellular portions of the mouse versions of these proteins were generated using VelociGene® technology (Valenzuela et al 2003; Nat. Biotechnol. 21: 652-659).

Double humanized LAG3/PD-1 mice were engineered using VelociGene® technology to replace the extracellular domains of mouse Pdcd1 and Lag3 genes with the corresponding regions of human PD-1 and human LAG3 genes (U.S. Patent Application Ser. No. 62/258,181, filed on Nov. 20, 2015). Humanized PD-1 and LAG3 expression was validated by examining PD-1 and LAG3 protein expression on humanized mouse T cells after anti-CD3/anti-CD28 antibody stimulation. Human PD-1 and LAG3 protein interaction with the corresponding mouse ligands was verified by testing binding of human LAG3 to mouse MHC II in a cell adhesion assay, and binding of human PD-1 to mouse PD-L1 in SPR-Biacore binding study.

The exemplary anti-LAG3 antibody used for this study is a fully human antibody that binds specifically to human LAG3 and comprises HCDR1-HCDR2-HCDR3-LCDR1-LCDR2-LCDR3 of SEQ ID NOs: 420-422-424-428-430-432 and HCVR/LCVR of SEQ ID Nos: 418/426 (also known as H4sH15482P and hereinafter "mAb1").

Anti-human PD-1 antibodies are disclosed in US Patent Application publication US20150203579, hereby incorporated by reference in its entirety. The anti-PD-1 antibody used in this Example is H4H7798N (as disclosed in US20150203579; also known as REGN2810. More specifically, H4H7798N comprises a heavy chain of SEQ ID NO: 330 and a light chain of SEQ ID NO: 331 as disclosed in US20150203579). REGN2810 (anti-hPD-1) binds with high affinity to human PD-1 and blocks PD-1 interaction with PD-L1 and PD-L2.

Mouse colon adenocarcinoma cells (MC38.Ova) were engineered to express chicken ovalbumin in order to increase tumor immunogenicity.

LAG3$^{hum/hum}$PD-1$^{hum/hum}$ mice were subcutaneously implanted with $1.5 \times 10^6$ MC38.Ova cells on day 0 and randomized into three treatment groups (N=7/group). On days 3, 6, 10, 14 and 17 mice were administered mAb1 (anti-hLAG3) (25 mg/kg), REGN2810 (anti-hPD-1) (10 mg/kg) or isotype control antibody (25 mg/kg) by intraperitoneal injection. Tumor volumes were monitored by caliper measurement twice per week for the duration of the experiment (24 days).

Figure 5A:
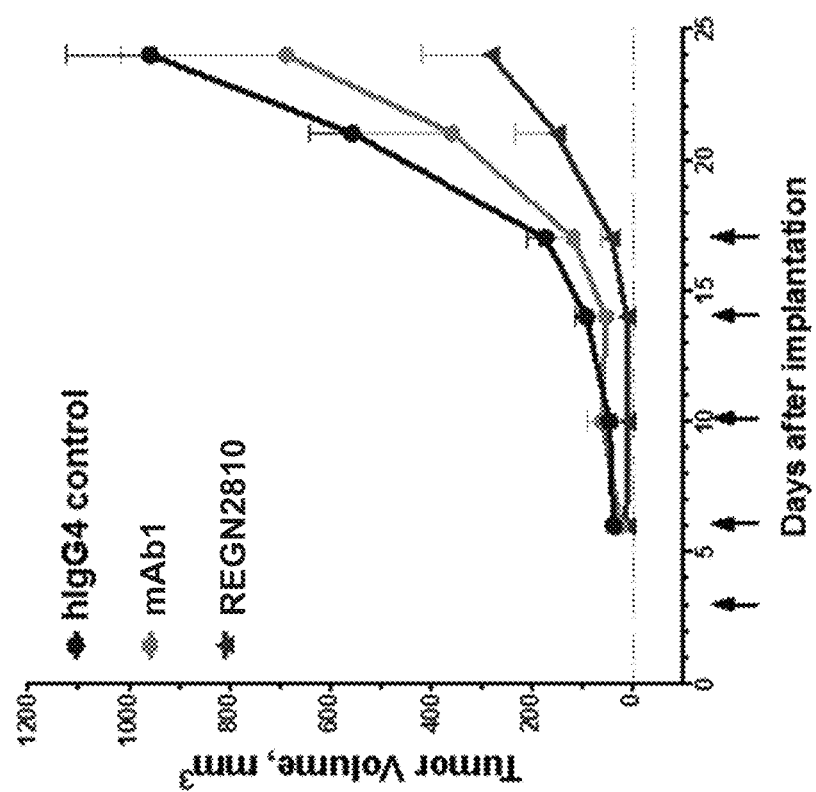
FIGS. 5A-5B summarizes the in vivo efficacy of anti-human LAG3 antibody ("mAb1") and anti-human PD-1 antibody (REGN2810) against MC38 tumors (described in Example 12).
Figure 5B:
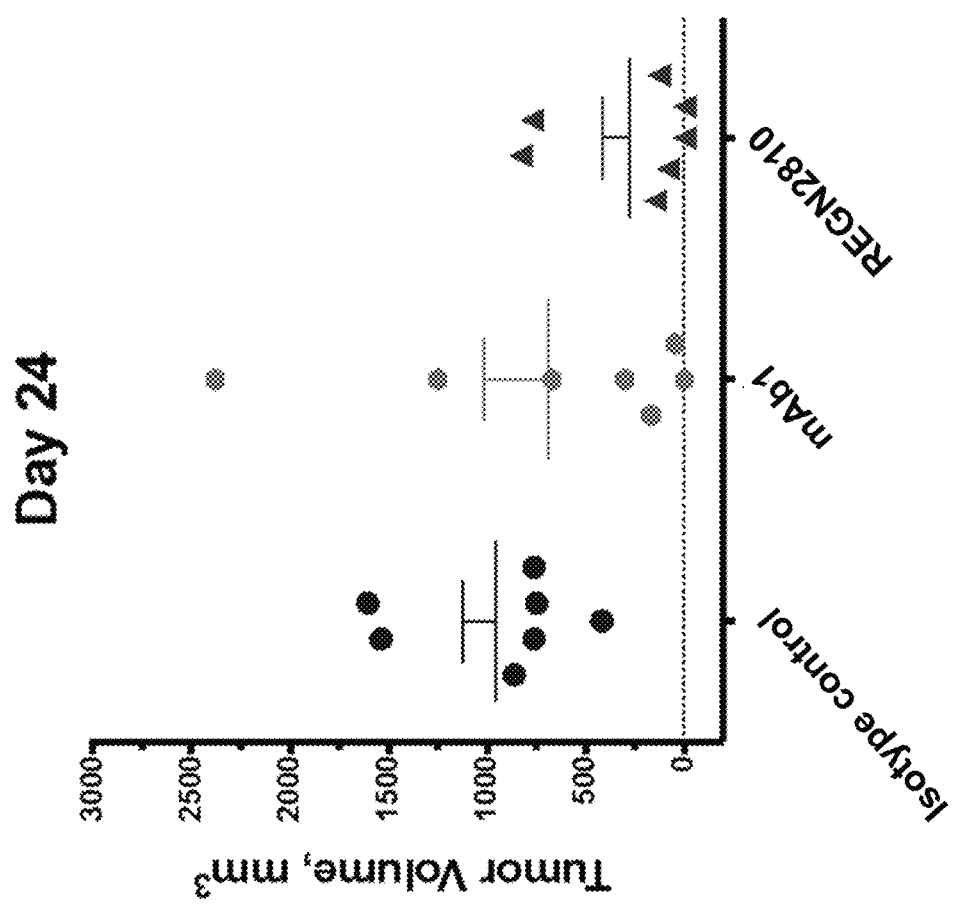

LAG3$^{hum/hum}$PD-1$^{hum/hum}$ double-humanized mice were inoculated with MC38.Ova cells on day 0 and dosed with mAb1 (anti-hLAG3) (25 mg/kg), REGN2810 (anti-hPD-1) (10 mg/kg) or isotype control (25 mg/kg) via intraperitoneal route on days 3, 6, 10, 14 and 17. REGN2810 (anti-hPD-1) showed partial tumor growth inhibition (FIG. 5), with tumor regression observed in 2 out of 7 mice, whereas none of the mice were tumor-free in isotype control group. mAb1 (anti-hLAG3) monotherapy at 25 mg/kg did not show any significant effect on tumor growth, with only 1 out of 7 mice becoming tumor-free by the end of the experiment. Mouse body weights were not affected by mAb1 (anti-hLAG3), REGN2810 (anti-hPD-1) or isotype control treatments.

Example 13: In Vivo Efficacy of a Combination of Anti-Human LAG3 and Anti-Human PD-1 Antibodies Against MC38 Tumors In this experiment, the efficacy of mAb1 (anti-hLAG3) in combination with REGN2810 (anti-hPD-1) was examined against MC38.Ova tumors in double-humanized LAG3$^{hum/hum}$PD-1$^{hum/hum}$ mice. Double-humanized mice are described in Example 12 herein.

The exemplary anti-LAG3 antibody used for this study is a fully human antibody that binds specifically to human LAG3 and comprises HCDR1-HCDR2-HCDR3-LCDR1-LCDR2-LCDR3 of SEQ ID NOs: 420-422-424-428-430-432 and HCVR/LCVR of SEQ ID Nos: 418/426 (also known as H4sH15482P and hereinafter "mAb1").

The anti-PD-1 antibody used in this Example is H4H7798N (as disclosed in US20150203579; also known as REGN2810). REGN2810 (Anti-hPD-1) binds with high affinity to human PD-1 and blocks PD-1 interaction with PD-L1 and PD-L2.

Mice were subcutaneously implanted with $1 \times 10^6$ MC38.Ova cells on day 0 and randomized into four treatment groups (N=7 in the control group, and N=12 each in mAb1 (anti-hLAG3), REGN2810 (anti-hPD-1), and mAb1 (anti-hLAG3)+REGN2810 (anti-hPD-1) combination treatment groups). On days 3, 7, 10, 14 and 17, mice were administered mAb1 (anti-hLAG3) (25 mg/kg), REGN2810 (anti-hPD-1) (10 mg/kg), combination of mAb1 (anti-hLAG3) (25 mg/kg) and REGN2810 (anti-hPD-1) (10 mg/kg), or isotype control (25 mg/kg) by intraperitoneal injection. Tumor volumes were monitored by caliper measurement twice per week for the duration of the experiment (32 days) and tumor free animals were monitored for the absence of tumor recurrence for up to 80 days.

Figure 6B:
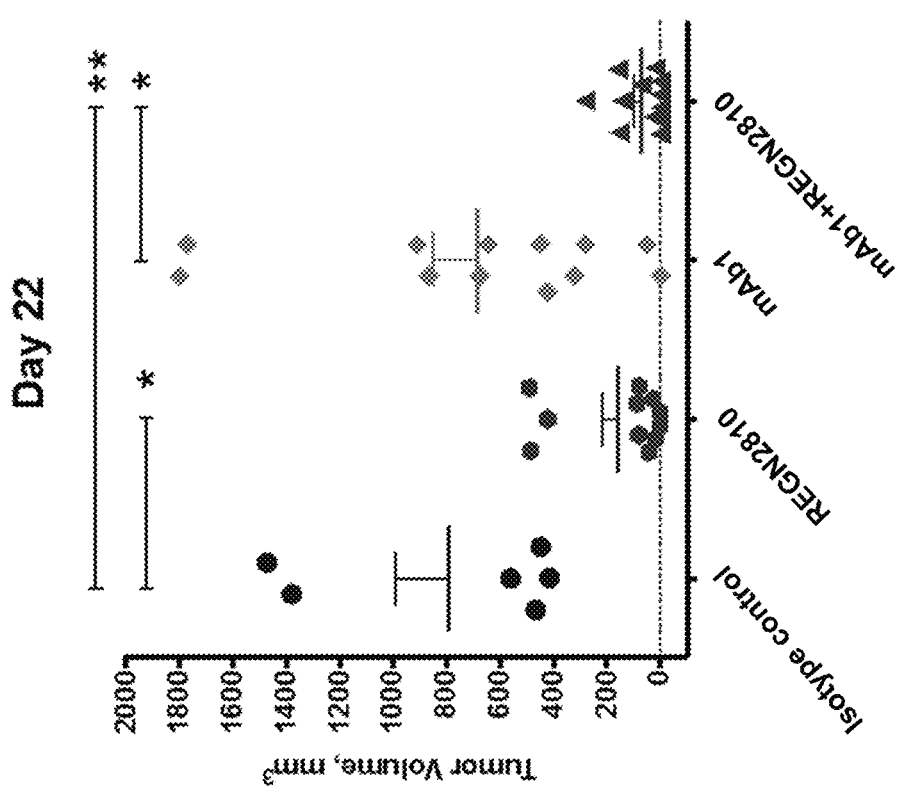
Figure 6C:
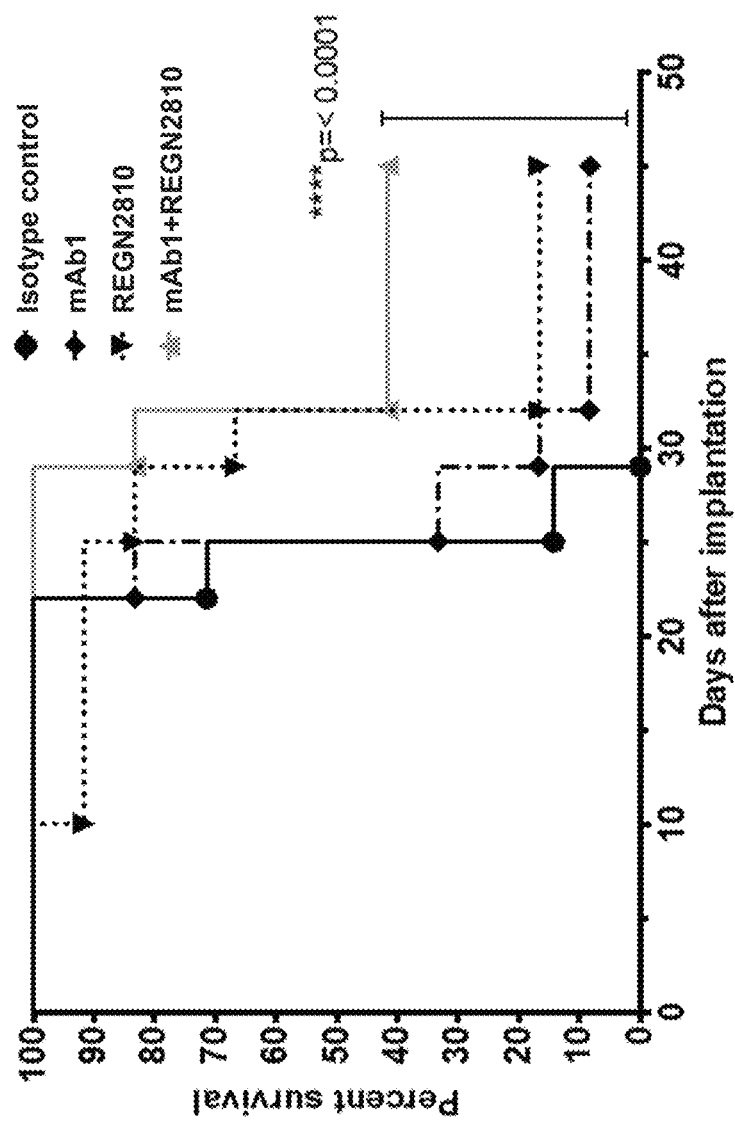

REGN2810 (anti-hPD-1) monotherapy resulted in tumor growth inhibition (FIGS. 6A-B), with tumor regression in 2 out of 12 (17%) animals, whereas mAb1 (anti-hLAG3) was not significantly efficacious, confirming the finding of the previous experiment. Tumor regression was only observed in 1 out of 12 mice treated with mAb1 (anti-hLAG3). In the isotype control group, there were no tumor-free mice on day 32. By contrast, combination of mAb1 (anti-hLAG3) and REGN2810 (anti-hPD-1) demonstrated robust inhibition of MC38.Ova tumor growth, resulting in 5 out of 12 (42%) tumor-free mice by the end of experiment. None of the tumor-free mice showed tumor recurrence for 80 days post-implantation, indicating long-lasting effects of combination immunotherapy. One-way ANOVA with Tukey's multiple comparison post-test revealed a significant difference in tumor volumes between the mAb1 (anti-hLAG3) and REGN2810 (anti-hPD-1) combination treatment groups compared to mAb1 (anti-hLAG3) monotherapy ($p<0.05$) or isotype control ($p<0.01$) on day 22 (FIG. 6B). REGN2810 (anti-hPD-1) monotherapy also showed a significant reduction of tumor growth relative to ($p<0.05$). mAb1 (anti-hLAG3) and REGN2810 (anti-hPD-1) combination treatment also resulted in a significant improvement in animal survival rate ($p<0.0001$), as analyzed by log-rank (Mantel-Cox) test (FIG. 6C). Despite improved efficacy of the combination therapy, no evidence of body weight loss was observed (data not shown). In summary, combination of mAb1 (anti-hLAG3) and REGN2810 (anti-hPD-1) resulted in improved efficacy including reduced tumor growth, improved tumor clearance and improved survival compared to REGN2810 (anti-hPD-1) or mAb1 (anti-hLAG3) monotherapies.

Example 14: Dose-Ranging Studies of a Combination of Anti-LAG3 and Anti-PD-1 Antibodies Against MC38 Tumors This Example describes a set of dose-ranging experiments measuring in vivo efficacy of a combination of anti-human PD-1 and anti-human LAG3 antibodies against MC38.Ova tumors in double-humanized LAG3$^{hum/hum}$PD-1$^{hum/hum}$ mice. Double-humanized mice are described in Example 12 herein.

The exemplary anti-LAG3 antibody used for this study is a fully human antibody that binds specifically to human LAG3 and comprises HCDR1-HCDR2-HCDR3-LCDR1-LCDR2-LCDR3 of SEQ ID NOs: 420-422-424-428-430-432 and HCVR/LCVR of SEQ ID Nos: 418/426 (also known as H4sH15482P and hereinafter "mAb1").

The anti-PD-1 antibody used in this Example is H4H7798N (as disclosed in US20150203579; also known as REGN2810). REGN2810 (Anti-hPD-1) binds with high affinity to human PD-1 and blocks PD-1 interaction with PD-L1 and PD-L2.

In a first experiment, REGN2810 (anti-hPD-1) was titrated and tested at 10 mg/kg and 1 mg/kg dose levels, both dose groups as a single agent and in combination with mAb1 (anti-hLAG3) (25 mg/kg). The results of both combination treatment groups were compared to REGN2810 (1 mg/kg or 10 mg/kg) or mAb1 (25 mg/kg) monotherapy to determine if an additive/synergistic anti-tumor effect is observed. Treatment with isotype control antibody (25 mg/kg) was also tested. LAG-3hum/humPD-1 hum/hum mice were inoculated with MC38.Ova cells on day 0 and randomized into six treatment groups (N=6 in the isotype control group and N=12 in mAb1, REGN2810, or REGN2810+mAb1 treatment groups). Mice were administered: mAb1 (25 mg/kg); REGN2810 (10 mg/kg); REGN2810 (1 mg/kg); mAb1 (25 mg/kg)+REGN2810 (10 mg/kg); mAb1 (25 mg/kg)+REGN2810 (1 mg/kg); or isotype control (25 mg/kg), via intraperitoneal injection on days 3, 7, 10, 14 and 17. Tumor volumes were monitored for 36 days, and tumor-free animals were monitored for up to 80 days.

Table 16 shows the mean tumor volumes at various time-points in the study and the number of tumor-free mice at Day 36 is shown in Table 17.

TABLE 16

Mean tumor volumes at various time-points

| Treatment Group | Tumor Volume, mm$^3$ Mean (±SEM) | | | | |
|---|---|---|---|---|---|
| | Day 7 | Day 10 | Day 14 | Day 17 | Day 22 |
| Isotype Control | 24 (±6) | 54 (±11) | 104 (±25) | 269 (±70) | 749 (±180) |
| mAb1 (anti-LAG3) (25 mg/kg) | 27 (±4) | 53 (±20) | 83 (±38) | 155 (±73) | 451 (±211) |
| R2810 (10 mg/kg) | 27 (±4) | 29 (±8) | 34 (±11) | 86 (±26) | 313 (±98) |
| R2810 (1 mg/kg) | 36 (±8) | 92 (±23) | 150 (±47) | 264 (±73) | 669 (±183) |
| R2810 (10 mg/kg) + mAb1 | 25 (±3) | 10 (±3) | 4 (±4) | 8 (±5) | 38 (±19) |
| R2810 (1 mg/kg) + mAb1 | 31 (±7) | 38 (±13) | 55 (±35) | 106 (±58) | 378 (±137) |

TABLE 17

Number of Tumor-free Mice on Day 36

| Group | Tumor-free Mice (Day 36) n/N$^a$ (%) |
|---|---|
| Isotype Control | 0/6 (0%) |
| REGN2810 (1 mg/kg) | 2/12 (16%) |
| REGN2810 (10 mg/kg) | 4/12 (33%) |
| mAb1 (25 mg/kg) | 1/12 (8%) |
| REGN2810 (1 mg/kg) + mAb1 (25 mg/kg) | 3/12 (25%) |
| REGN2810 (10 mg/kg) + mAb1 (25 mg/kg) | 6/12 (50%) |

$^a$n/N: # tumor-free mice/total mice per group

Figure 7A:
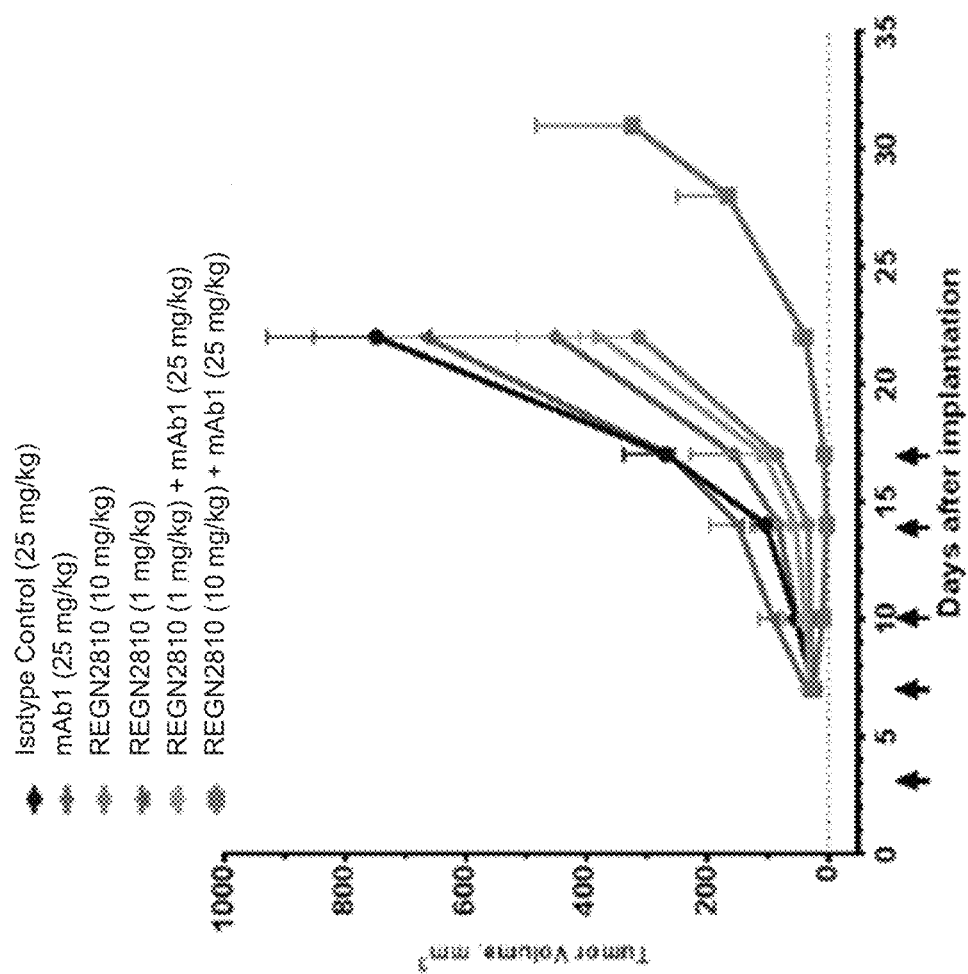
FIGS. 7A-7C summarizes the in vivo efficacy of anti-human LAG3 antibody ("mAb1") alone and in combination with anti-human PD-1 antibody (REGN2810) against MC38 tumors in a first experiment (described in Example 14).
Figure 7B:
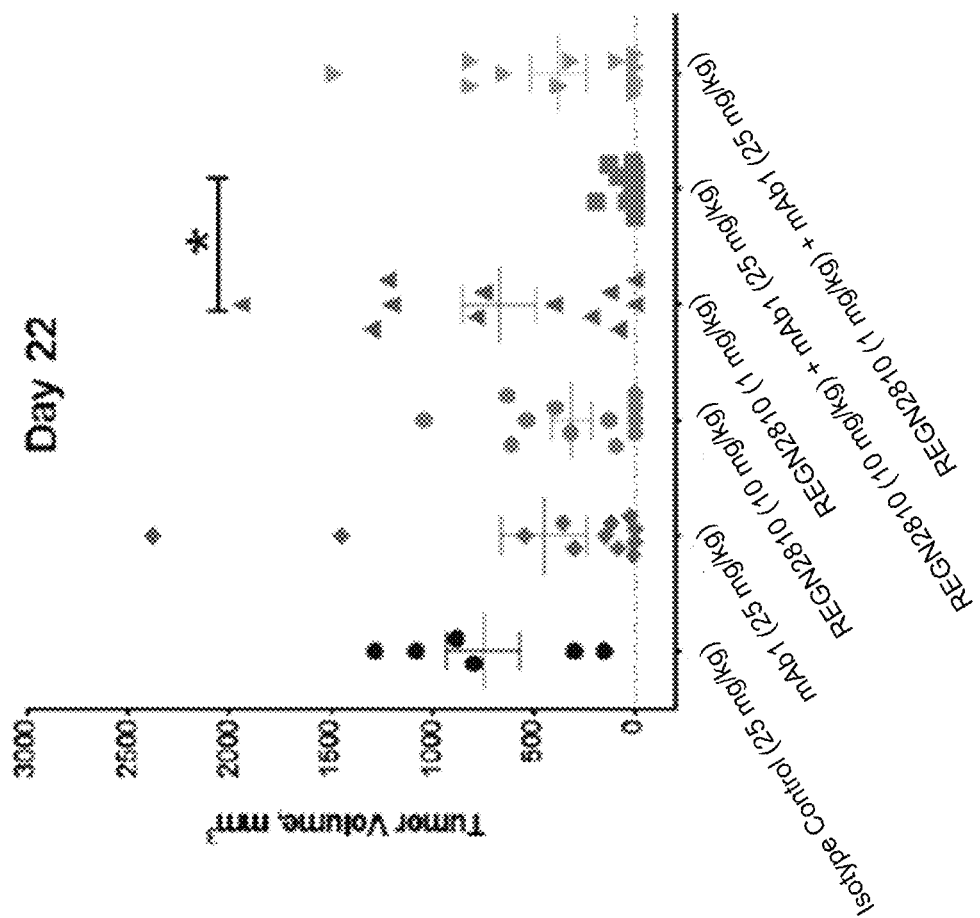

REGN2810 monotherapy at 1 mg/kg only showed minimal tumor regression over 36 days, similar to results for the isotype control treatment group (FIG. 7A-B). 2/12 (~16%) and 0/6 (0%) mice were tumor-free at Day 36 in the REGN2810 (1 mg/kg) and the isotype control groups, respectively. In contrast, mAb1 (25 mg/kg), REGN2810 (10 mg/kg) and REGN2810 (1 mg/kg)+mAb1 (25 mg/kg) treatment groups demonstrated a similar reduction in tumor growth over 22 days (FIG. 7A). On Day 36, mAb1 (25 mg/kg) treatment resulted in 1/12 (~8%) mice tumor-free, whereas 4/12 (~33%) and 3/12 (25%) mice were tumor-free in the REGN2810 (10 mg/kg) group and REGN2810 (1 mg/kg)+mAb1 (25 mg/kg) group, respectively. Overall, mAb1 (25 mg/kg)+REGN2810 (10 mg/kg) demonstrated the most robust reduction in MC38.Ova tumor growth, with 6 out of 12 (50%) mice becoming tumor-free by Day 36.

Figure 7C:
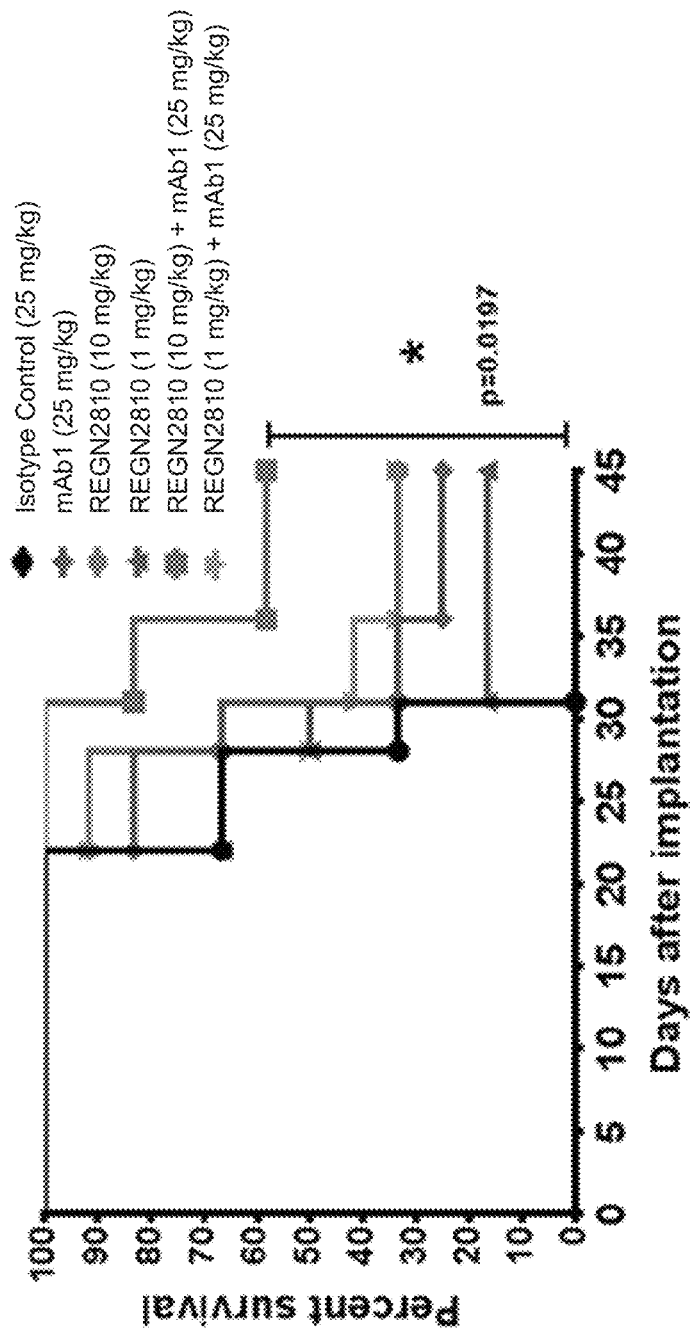

None of the tumor-free mice showed tumor recurrence for 80 days post-implantation, despite the cessation of treatment, indicating long-lasting effects of combination immunotherapy. mAb1 (25 mg/kg)+REGN2810 (10 mg/kg) treatment also resulted in a significant improvement in animal survival rate (p=0.0197), as analyzed by log-rank (Mantel-Cox) test (FIG. 7C). Also, no evidence of body weight loss was observed.

Figure 8A:
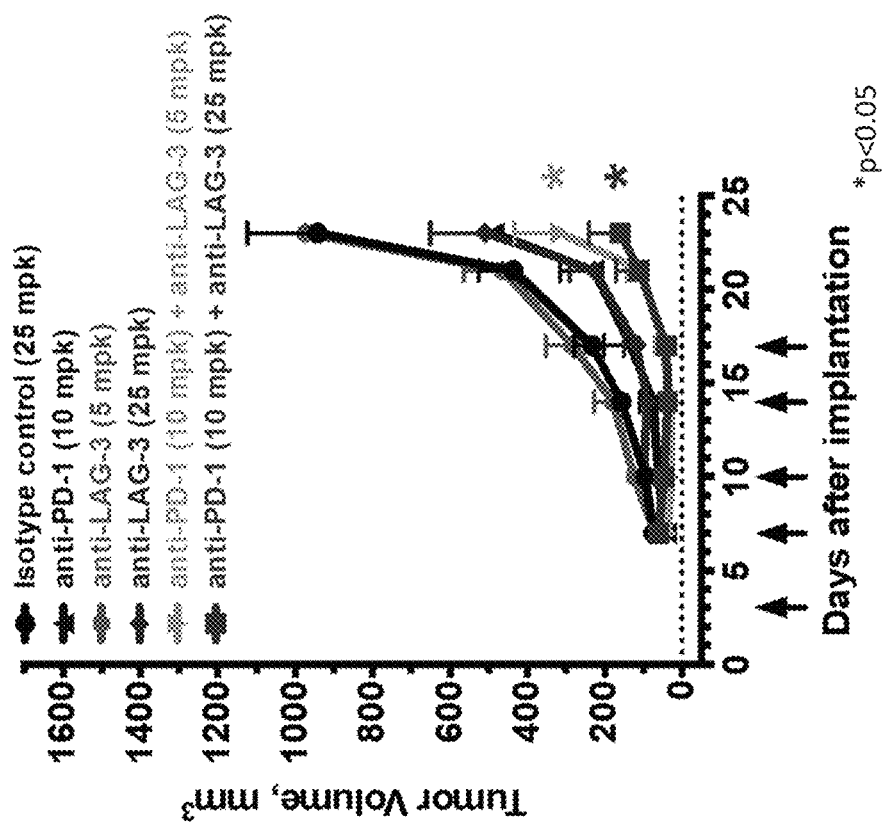
FIGS. 8A-8C summarizes the in vivo efficacy of anti-human LAG3 antibody ("mAb1") alone and in combination with anti-human PD-1 antibody (REGN2810) against MC38 tumors in a second experiment (described in Example 14).
Figure 8B:
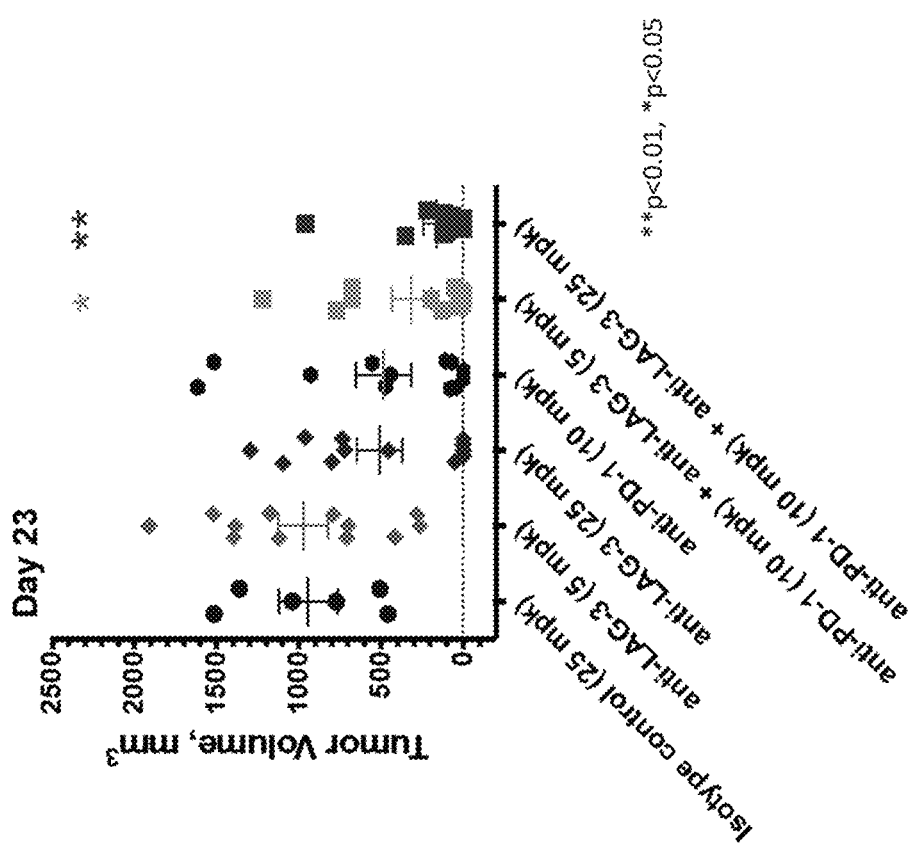
Figure 8C:
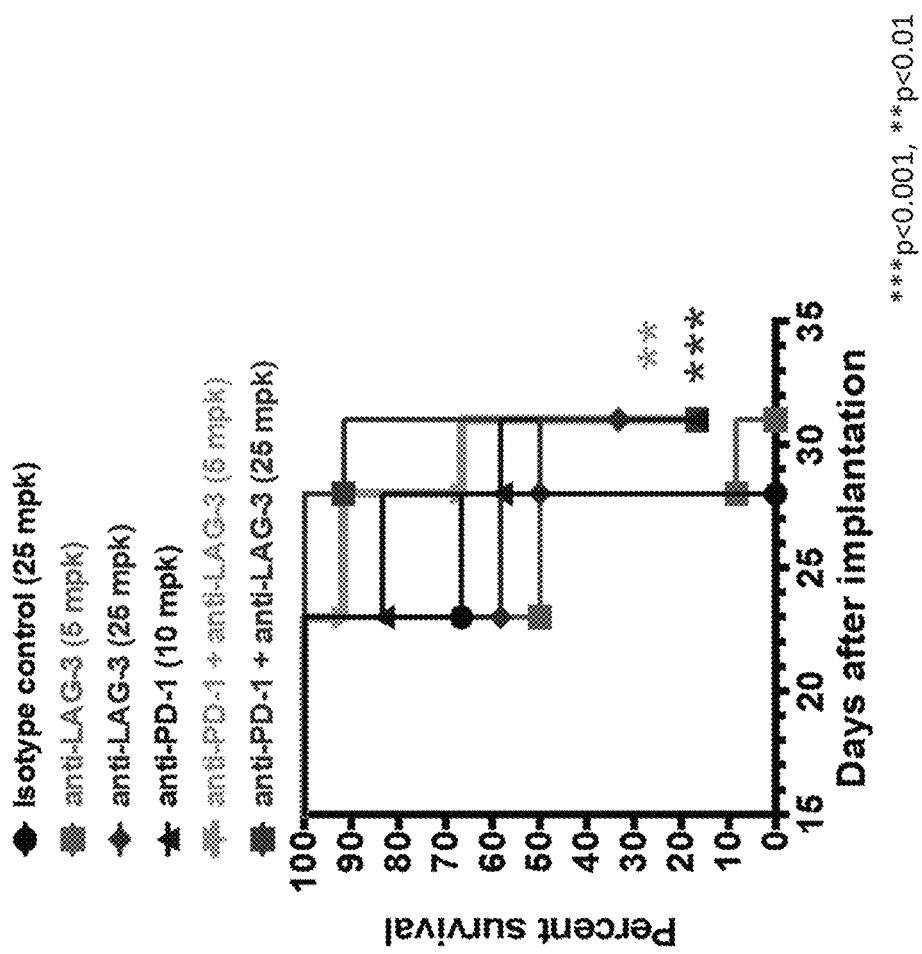

In a second experiment, mAb1 (anti-hLAG3) was titrated and tested at 25 mg/kg and 5 mg/kg dose levels, both dose groups as a single agent and in combination with REGN2810 (anti-hPD-1) (10 mg/kg). The results of both combination treatment groups were compared to mAb1 (5 mg/kg or 25 mg/kg) or REGN2810 (10 mg/kg) monotherapy to determine if an additive/synergistic anti-tumor effect is observed. Treatment with isotype control antibody (25 mg/kg) was also tested. LAG-3hum/humPD-1 hum/hum mice were inoculated with MC38.Ova cells on day 0 and randomized into six treatment groups (N=6 in the isotype control group and N=12 in mAb1, REGN2810, or REGN2810+mAb1 treatment groups). Mice were administered: mAb1 (5 mg/kg); mAb1 (25 mg/kg); REGN2810 (10 mg/kg); mAb1 (5 mg/kg)+REGN2810 (10 mg/kg); mAb1 (25 mg/kg)+REGN2810 (10 mg/kg); or isotype control (25 mg/kg), via intraperitoneal injection on days 3, 7, 10, 14 and 17. Tumor volumes were monitored for 31 days.

mAb1 monotherapy at 5 mg/kg showed minimal tumor regression similar to isotype control treatment group. The combination of mAb1 (25 mg/kg)+REGN2810 (10 mg/kg) showed the most robust tumor reduction (FIG. 8A). A potent combination effect was also demonstrated by the mAb1 (5 mg/kg)+REGN2810 (10 mg/kg) treatment group. Tumor volumes as measured on Day 23 are shown in FIG. 8B. The combination of anti-LAG-3 antibody and REGN2810 also showed a significant improvement in animal survival (p<0.001, as analyzed by log rank Mantel-Cox test) (FIG. 8C). The results show that a potent combination effect is seen even at low anti-LAG3 antibody doses. Based on the results shown herein, it may not be necessary to use high doses of anti-LAG3 antibodies in a combination with anti-PD-1 antibodies in treatment regimens against tumors.

In summary, combination of REGN2810 (anti-hPD-1) and mAb1 (anti-hLAG3) in MC38.ova tumor model in double humanized LAG3/PD-1 mice, which allows testing of clinical antibodies that do not cross to mouse receptors, demonstrated improved dose-dependent efficacy, including reduced tumor growth and improved survival, compared to REGN2810 (anti-hPD-1) and mAb1 (anti-hLAG3) monotherapies. Robust anti-tumor efficacy of REGN2810 (anti-hPD-1) and mAb1 (anti-hLAG3) combination in preclinical setting supports their clinical development as a combination cancer immunotherapy.

Example 15: In Vivo Efficacy of a Combination of Anti-Human LAG3 and Anti-Human PD-1 Antibodies Against Established MC38 Tumors In this experiment, the efficacy of mAb1 (anti-hLAG3) in combination with REGN2810 (anti-hPD-1) was examined against established MC38.Ova tumors in double-humanized LAG3$^{hum/hum}$PD-1$^{hum/hum}$ mice. Double-humanized mice are described in Example 12 herein.

The exemplary anti-LAG3 antibody used for this study is a fully human antibody that binds specifically to human LAG3 and comprises HCDR1-HCDR2-HCDR3-LCDR1-LCDR2-LCDR3 of SEQ ID NOs: 420-422-424-428-430-432 and HCVR/LCVR of SEQ ID Nos: 418/426 (also known as H4sH15482P and hereinafter "mAb1").

The anti-PD-1 antibody used in this Example is H4H7798N (as disclosed in US20150203579; also known as REGN2810). REGN2810 (Anti-hPD-1) binds with high affinity to human PD-1 and blocks PD-1 interaction with PD-L1 and PD-L2.

LAG-3$^{hum/hum}$ PD-1$^{hum/hum}$ mice were inoculated with MC38.Ova cells subcutaneously on day 0. On day 10 mice with an average tumor volume of 100 mm$^3$ were selected and randomized into four treatment groups. Mice were administered mAb1 (25 mg/kg; N=9), REGN2810 (10 mg/kg; N=10), mAb1 (25 mg/kg)+REGN2810 (10 mg/kg) combination (N=11) or isotype control antibody (25 mg/kg; N=7) by IP injection on days 10, 14, 17, 22. Tumor volumes were monitored for 28 days post tumor implantation.

Figure 9:
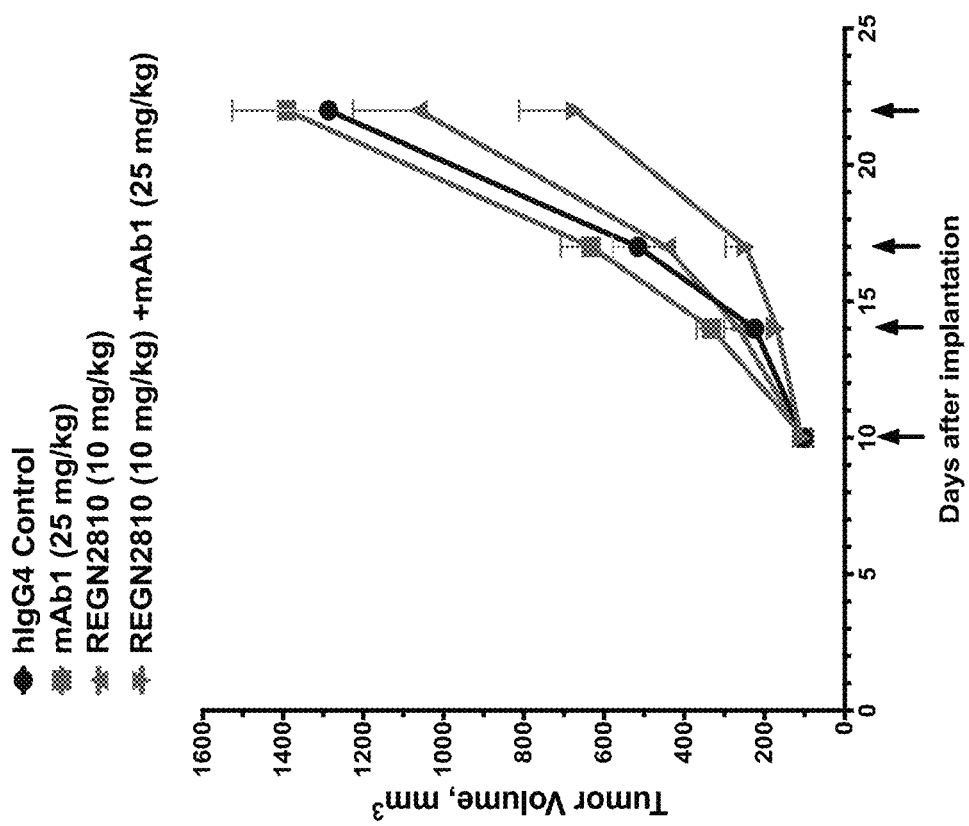
FIG. 9 shows average tumor volumes (mm³±SEM) in each treatment group at multiple time points post tumor implantation in an experiment to assess efficacy of anti-human LAG3 antibody ("mAb1") alone and in combination with anti-human PD-1 antibody (REGN2810) against established MC38 tumors (described in Example 15 herein). Treatment days are indicated by arrows.
Figure 10:
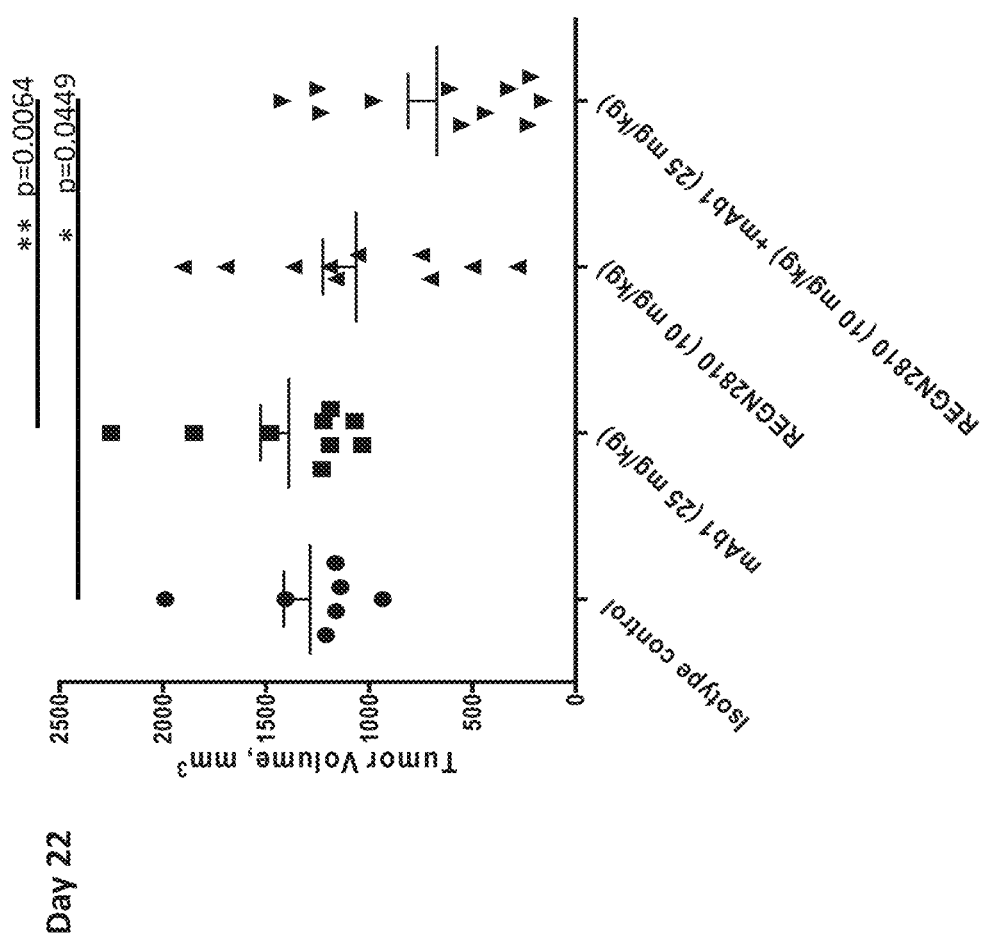
FIG. 10 shows individual tumor volumes in each treatment group as measured on day 22 post-implantation in the experiment described in Example 15. Statistical significance was determined by one-way ANOVA with Dunnett's multiple comparison test.
Figure 11:
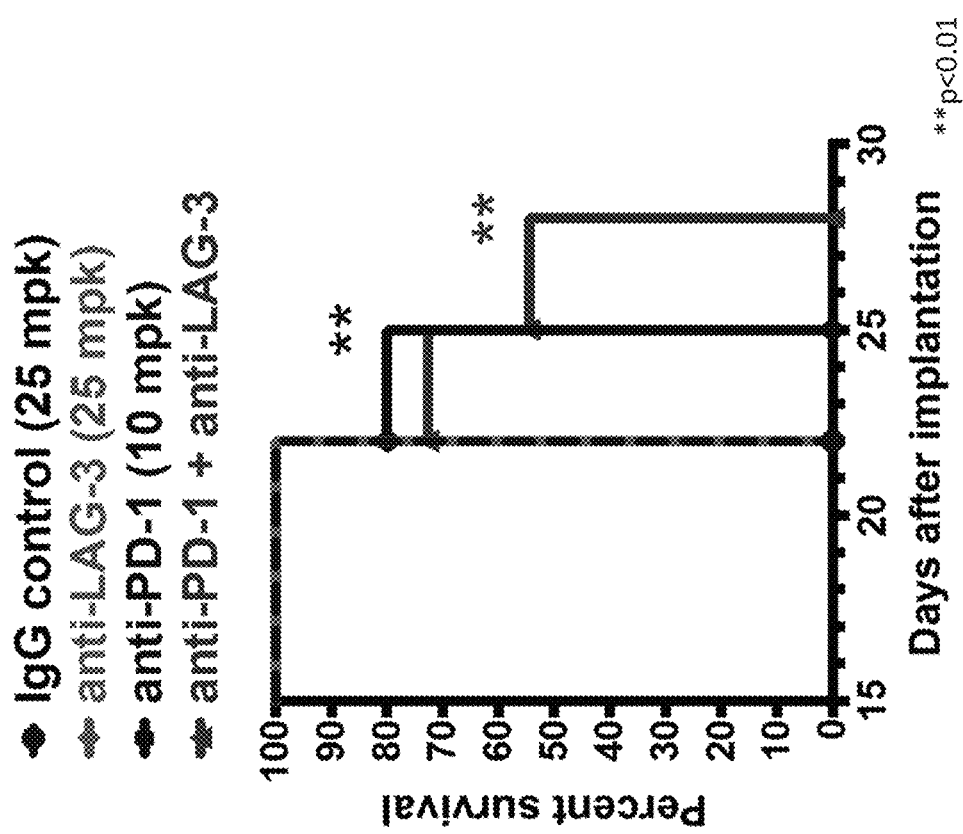
FIG. 11 shows percent tumor-free survival in treated mice in the experiment described in Example 15 herein. Statistical significance was determined by log-rank (Mantel-Cox) test, with Bonferroni adjustment for multiple comparisons (**p<0.01).

Treatment of MC38.ova tumor-bearing humanized mice with a combination of anti-hPD-1 and anti-hLAG-3 antibodies triggered activation of intratumoral and peripheral T cells. REGN2810 monotherapy resulted in partial tumor growth inhibition, while mAb1 monotherapy did not show reduction in mean tumor volume compared to isotype control treated mice (FIG. 9). By contrast, combination of mAb1 (25 mg/kg) and REGN2810 (10 mg/kg) demonstrated robust inhibition of MC38.Ova tumor growth. One-way analysis of variance (ANOVA) with Bonferroni's multiple comparison post-test revealed a significant difference in mean tumor volumes between mAb1 and REGN2810 combination group compared to mAb1 monotherapy (p<0.01) or isotype control (p<0.05) (FIG. 10). When combination therapy was compared to REGN2810 monotherapy, the overall mean tumor volumes over the course of the experiment were lower for combination therapy but this difference didn't reach statistical significance. The combination of anti-LAG-3 antibody and REGN2810 also resulted in significant increase in animal survival, as well as in duration of survival (p<0.01, as analyzed by log rank Mantel-Cox test). At day 25, 50% of mice treated with the combination therapy survived as compared to control and monotherapy (FIG. 11). Based on the results, the combination treatment exhibited an additive, dose dependent anti-tumor effect compared to the respective monotherapies.

Example 16: Pharmacokinetics of an Anti-LAG-3 Antibody in Cynomolgus Monkey

Figure 12:
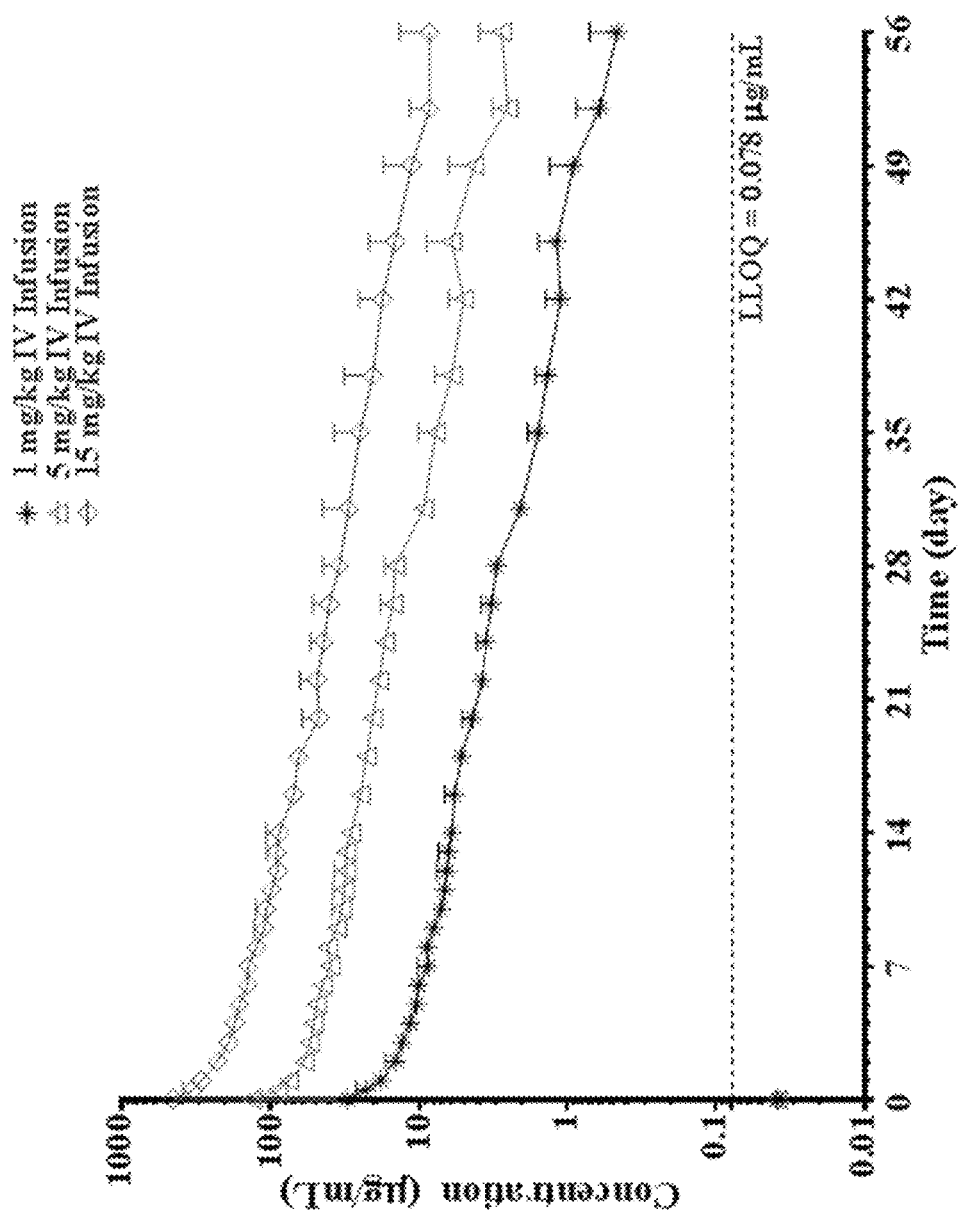
FIG. 12 shows a graph of mean (+SD) functional mAb1 concentrations in serum vs. time following a single intravenous infusion of mAb1 in female cynomolgus monkey (described in Example 16).

Pharmacokinetics (PK) of anti-LAG3 antibody mAb1 was characterized after a single intravenous (IV) dose of 1.0, 5.0, or 15.0 mg/kg to female cynomolgus monkeys (5 animals per dose group). Blood samples for the determination of functional mAb1 concentration were collected at various time points from all animals. Concentrations of functional mAb1 in serum were determined using an enzyme-linked immunosorbent assay (ELISA). Anti-mAb1 antibodies in serum were analyzed using an electrochemiluminescence-based bridging immunoassay. The PK parameters were estimated using non-compartmental analysis (NCA). Mean concentration-time profiles are characterized by an initial brief distribution phase, followed by a linear beta elimination phase (FIG. 12). No target-mediated clearance phase was observed over the 8 week study duration. Mean AUC$_{inf}$ increased in a dose-proportional manner as demonstrated by similar AUC$_{inf}$/Dose values across the tested dose levels. Consistent with this finding, the mean total body clearance (CL) values were similar for the 3 dose groups. In addition, the beta phase half-lives ($t_{1/2}$) for the 3 dose groups were comparable, ranging from 10.8 to 11.5 days. Based on the results, no-observed-adverse-effect level (NOAEL) could be established up to 50 mg/kg. These results indicated that mAb1 demonstrated linear kinetics under the conditions of this study.

Example 17: Assessment of Toxicology of Anti-LAG3 Antibody in Cynomolgus Monkeys The in vivo toxicology and toxicokinetic profiles of mAb1 were evaluated during a 4-week, repeat-dose, GLP-compliant toxicology study in male and female cynomolgus monkeys. Monkeys (5 animals/sex/group) were given 0, 2, 10, or 50 mg/kg/week mAb1 by IV infusion. Assessment of toxicity was based on mortality, moribundity, clinical observations, body weights, food consumption, ophthalmic examinations, ECG evaluations, respiration rates, pulse oximetry, body temperature, and blood pressure evaluations, and neurologic examinations. Clinical pathology parameters (hematology, coagulation, clinical chemistry, and urinalysis) and immunophenotyping were also evaluated. Gross necropsy examinations, measurement of organ weights, and histopathologic evaluations were conducted. Complete necropsies were performed at the end of the dosing period or at the end of the 8-week recovery period. Selected organs were weighed, and tissues were examined macroscopically and microscopically.

mAb1 was well tolerated at all dose levels evaluated when administered via weekly IV infusion to cynomolgus monkeys. Because mAb1 was well tolerated and there were no mAb1-related changes in any of the safety parameters evaluated, the no-observed-adverse-effect-level (NOAEL) for the study is considered to be 50 mg/kg/dose, the highest dose administered in this study.

Example 18: Hydrogen/Deuterium Exchange (H/D)-Based Epitope Mapping of Anti-LAG3 Antibody H4sH15482P Binding to the Extracellular Domain of hLAG3

Experiments were conducted to determine the amino acid residues of the human LAG3 extracellular domain (amino acids Leu23-Leu450 of human LAG3, UniProt Accession Number P18627, produced with a human IgG1 tag at the c-terminus ("hLag3.Fc") (R&D Systems, Minneapolis, Minn.) (SEQ ID NO: 587) with which the anti-LAG3 antibody H4sH15482P interacts. For this purpose, Hydrogen/Deuterium (H/D) Exchange epitope mapping with mass spectrometry (HDX-MS) was utilized. A general description of the HDX method is set forth in Ehring (1999) Analytical Biochemistry 267(2):252-259; and Engen and Smith (2001) Anal. Chem. 73:256A-265A.

Experimental Procedure

HDX-MS experiments were performed on an integrated Waters HDX/MS platform (Waters Corporation, Milford, Mass.), consisting of a Leaptec HDX PAL system for the deuterium labeling, a Waters Acquity M-Class (Auxiliary solvent manager) for the sample digestion and loading, a Waters Acquity M-Class (μBinary solvent manager) for the analytical column gradient, and a Synapt G2-Si mass spectrometer for peptic peptide mass measurement.

The labeling solution was prepared in 10 mM PBS buffer in $D_2O$ at pD 7.0. For deuterium labeling, 3.8 μL of hLAG3.Fc (5 pmol/μL) or hLAG3.Fc premixed with the anti-Lag3 antibody H4sH15482P in a 1:1 molar ratio was incubated with 56.2 μL $D_2O$ labeling solution for various time-points (e.g., undeuterated control=0 sec, deuterium labeling: 1 min and 20 min). The deuteration was quenched by transferring 50 μL of sample to 50 μL of pre-chilled quench buffer (0.2 M TCEP, 6 M guanidine chloride in 100 mM phosphate buffer, pH 2.5) and the mixture was incubated at 1.0° C. for 4 min. The quenched sample was then injected into a Waters HDX Manager for online pepsin/protease XIII digestion. The digested peptides were trapped onto an ACQUITY UPLC BEH C18 1.7-μm, 2.1×5 mm VanGuard pre-column (Waters Corporation) at 0° C. and eluted to an analytical column ACQUITY UPLC BEH C18 1.7-μm, 1.0×50 mm for a 9-minute gradient separation of 5%-40% B (mobile phase A: 0.1% formic acid in water, mobile phase B: 0.1% formic acid in acetonitrile). The mass spectrometer was set at cone voltage of 37 V, a scan time of 0.5 s, and mass/charge range of 50-1700 Thomson units (Th).

For the identification of the peptide residues of human Lag3 with which H4sH15482P interacts, LC-$MS^E$ data from the undeuterated sample were processed and searched against a database that included sequences for human LAG3, pepsin, and randomized sequences using the Waters ProteinLynx Global Server (PLGS) software. The identified peptides were imported to DynamX software and filtered by two criteria: 1) minimum products per amino acid=0.2, and 2) replication file threshold=3. DynamX software then automatically determined deuterium uptake of each peptide based on retention time and high mass accuracy (<10 ppm) across multiple time points with 3 replicates at each time.

Results

Using the online pepsin/protease XIII column coupled with $MS^E$ data acquisition, a total of 123 peptides from human LAG3 were reproducibly identified in the absence or presence of the antibody, representing 78.3% sequence coverage. Four Lag-3 peptides had significantly reduced deuteration uptake (centroid delta values >0.8 daltons with p-values <0.05) when bound to H4sH15482P. The recorded peptide mass corresponds to the average value of the centroid $MH^+$ mass from three replicates. These peptides, corresponding to amino acids 34-77 of hLAG3.Fc, (SEQ ID NO: 587), had slower deuteration rates when bound to H4sH15482P. These identified residues also correspond to residues 28-71 of human LAG3 as defined by Uniprot entry P18627 (LAG3_HUMAN, SEQ ID NO: 588), and as illustrated in Table 18.

TABLE 18

Human LAG3 Peptides with Altered Deuteration Rates upon Binding H4sH15482P

| Amino acid residues of SEQ ID NO: 588 | T = 1 min deuteration | | | T = 20 min deuteration | | |
|---|---|---|---|---|---|---|
| | hLAG3.Fc; $MH^+$ | hLAG3.Fc + H4sH15482P; $MH^+$ | Δ | hLAG3.Fc; $MH^+$ | hLAG3.Fc + H4sH15482P; $MH^+$ | Δ |
| 28-69 | 4352.30 ± 0.03 | 4350.14 ± 0.06 | −2.15 | 4352.33 ± 0.20 | 4351.43 ± 0.12 | −0.90 |
| 28-71 | 4672.54 ± 0.03 | 4670.42 ± 0.01 | −2.12 | 4672.69 ± 0.21 | 4671.57 ± 0.18 | −1.13 |

TABLE 18-continued

Human LAG3 Peptides with Altered Deuteration Rates upon Binding H4sH15482P

| Amino acid residues of SEQ ID NO: 588 | T = 1 min deuteration | | | T = 20 min deuteration | | |
|---|---|---|---|---|---|---|
| | hLAG3.Fc; MH+ | hLAG3.Fc + H4sH15482P; MH+ | Δ | hLAG3.Fc; MH+ | hLAG3.Fc + H4sH15482P; MH+ | Δ |
| 31-52 | 2198.11 ± 0.10 | 2196.49 ± 0.01 | −1.61 | 2198.97 ± 0.18 | 2197.18 ± 0.10 | −1.79 |
| 32-69 | 3853.07 ± 0.12 | 3851.37 ± 0.07 | −1.69 | 3853.23 ± 0.07 | 3852.35 ± 0.14 | −0.88 |

Example 19: Clinical Trial of Anti-LAG3 Antibody in Patients with Advanced Malignancies This Example describes a clinical trial to assess the safety, tolerability and anti-tumor activity of an anti-LAG3 antibody as monotherapy and in combination with an anti-PD-1 antibody in patients with advanced malignancies.

The exemplary anti-LAG3 antibody used for this study is a fully human antibody that binds specifically to human LAG3 and comprises HCDR1-HCDR2-HCDR3-LCDR1-LCDR2-LCDR3 of SEQ ID NOs: 420-422-424-428-430-432 and HCVR/LCVR of SEQ ID Nos: 418/426 (also known as H4sH15482P and hereinafter "mAb1").

The anti-PD-1 antibody used for this study is H4H7798N (as disclosed in US20150203579; also known as REGN2810). REGN2810 (Anti-hPD-1) binds with high affinity to human PD-1 and blocks PD-1 interaction with PD-L1 and PD-L2.

Study Objectives

The primary objectives of the study are:

In the Dose Escalation Phase:

To evaluate safety and pharmacokinetics (PK) in order to determine an phase 2 dose of mAb1 as monotherapy and in combination with REGN2810 in patients with advanced malignancies, including lymphoma. The endpoints include rate of dose limiting toxicities (DLTs), adverse events (AEs) (including immune-related), serious adverse events (SAEs), deaths, and laboratory abnormalities (grade 3 or higher per Common Terminology Criteria for Adverse Events [CT-CAE]), and pharmacokinetics.

In the Dose Expansion Phase:

To assess preliminary anti-tumor activity of mAb1 alone and in combination with REGN2810 (separately by cohort) as measured by ORR. The endpoints include overall response rate (ORR) based on Response Evaluation Criteria in Solid Tumors (RECIST) 1.1 (Eisenhauer et al 2009, Eur. J. Cancer 45: 228-247) (solid tumors) and Lugano criteria (Cheson et al 2014, J. Clin. Oncol. 32: 3059-3068) (lymphoma).

The secondary objectives are: (a) to assess preliminary anti-tumor activity of mAb1 alone and in combination with REGN2810 (separately by cohort) as measured by ORR based on immune-related Response Evaluation Criteria in Solid Tumors (irRECIST) (Wolchok et al 2009, Clin. Cancer Res. 15: 7412-7420; Nishino et al 2013, Clin. Cancer Res. 19: 3936-3943), best overall response (BOR), duration of response (DOR), disease control rate, and PFS based on RECIST, irRECIST, and Lugano criteria (Cheson et al 2014, J. Clin. Oncol. 32: 3059-3068); (b) to characterize the safety profile in each expansion cohort as determined in the dose escalation phase; (c) to characterize the PK of mAb1 as monotherapy and mAb1 and REGN2810 when given in combination; and (d) to assess immunogenicity as measured by anti-drug antibodies (ADA) for mAb1 and REGN2810

The exploratory objectives of the study are: (a) to assess tumor volume; (b) to explore the pharmacodynamic effects of REGN2810 in serum, plasma, peripheral blood mononuclear cells (PBMC), and in tumor tissue samples (including archival tumor tissue) obtained at baseline, during treatment, and at the time of progression from patients treated with mAb1 as monotherapy or in combination with REGN2810; and (c) to assess the predictive potential and correlation to clinical response for biomarkers of interest that may include, but are not limited to: (i) circulating tumor nucleic acids; (ii) PBMC subset distribution and expression of immune checkpoint molecules and other biomarkers of interest; (iii) tumor RNA expression; (iv) number and distribution of tumor infiltrating lymphocytes (CD8+ T cells, CD4+ T cells, T regulatory cells, and tissue permitting, other subtypes such as B cells, myeloid-derived cells, NK cells, etc.); (v) expression levels (messenger RNA and/or protein) of PD-1, PD-L1, LAG3, and possibly other checkpoint modulators; (vi) mutations in known oncogenes and potential tumor neo-antigens; and (vii) tumor mutational burden.

Study Design

This is a phase 1, first-in-human (FIH), open-label, multicenter, dose-escalation study of the safety, tolerability, activity and PK of mAb1 administered as monotherapy and in combination with REGN2810 in patients with advanced malignancies. Three dose levels of mAb1 (1.0, 3.0 and 10 mg/kg) are investigated as monotherapy and in combination with REGN2810 at a dose of 3.0 mg/kg.

After a screening period of up to 28 days, patients receive up to seventeen 21-day treatment cycles (for a total of up to 51 weeks of treatment), followed by a 24-week follow-up period. Each patient receives mAb1 (+/−REGN2810) every 21 days.

Treatment continues until the 51-week treatment period is complete, or until disease progression, unacceptable toxicity, withdrawal of consent, or study withdrawal criterion is met. Response assessment is every 6 weeks for the first 24 weeks, then every 9 weeks for the subsequent 27 weeks, regardless of delays in dosing of study drugs. After a minimum of 24 weeks of treatment (minimum 8 treatment cycles), patients with confirmed complete remission (CR) may elect to discontinue treatment and continue with all relevant study assessments. Similarly, after consultation with the physician, patients who have been treated for a minimum of 24 weeks with stable disease (SD) or partial response (PR) that has been maintained for 3 successive tumor evaluations may elect to discontinue treatment but continue with all relevant study assessments. For patients who experience a response and subsequently progress, a tumor biopsy at the time of progression is requested. Patients who tolerate 4 doses of mAb1 monotherapy and who have an initial tumor assessment of at least SD, but who subsequently demonstrate progressive disease (PD), have the option of adding REGN2810 3.0 mg/kg to the highest dose of mAb1 safely administered up to that point (if one is known) in an attempt to "rescue" a response by combined lymphocyte activation gene 2 (LAG-3) and programmed death 1 (PD-1) blockade. Safety evaluations are conducted at each study drug dosing visit.

Dose Escalation

Three dose escalation monotherapy and combination therapy cohorts are planned to be enrolled (1.0, 3.0 and 10 mg/kg mAb1 with or without 3 mg/kg REGN2810). The first cohort to be enrolled receives mAb1 monotherapy at 1.0 mg/kg. Subsequent enrollment of each additional cohorts may be limited by the number of dose-limiting toxicities (DLT) observed in prior cohorts. Dose de-escalation cohorts (0.3 mg/kg mAb1 with or without 3 mg/kg REGN2810) are enrolled if necessary.

Dose Escalation Rules

A modification of the traditional 3+3 design ("4+3") is used for evaluation of all dose levels for both mAb1 monotherapy and mAb1+REGN2810 cohorts. Although a minimum of 3 patients at each dose level are required to be evaluable for DLT, to maximize the efficiency of the phase 1 dose escalation while maintaining patient safety, 4 patients are enrolled at each dose level in case a patient discontinues prior to being evaluable for DLT. The DLT evaluation period is 28 days. Tolerability of a dose level is only achieved if all potentially DLT evaluable patients complete the 28-day DLT period without a DLT (0/3 or 0/4). If 3 patients complete the DLT period without experiencing a DLT, but there is a fourth patient in the DLT evaluation period, tolerability of the dose level is only achieved when the fourth patient completes the DLT evaluation period or discontinues therapy prior to being evaluable for DLT. If there is 1 DLT out of either 3 or 4 DLT-evaluable patients, then 4 or 3 more patients (respectively) are enrolled for a total of 7 patients. Similarly, 1/6 or 1/7 DLTs are considered tolerable. Two DLTs out of 2 to 7 evaluable patients will have exceeded the maximum tolerated dose (MTD). At the highest dose level tolerated, to further evaluate safety, additional 3 to 4 patients will be enrolled for a total of 6 to 10 DLT-evaluable patients. Zero to 1 out of 6 to 8, or 2 out of 9 to 10 DLTs will be considered acceptable. To further evaluate safety, 3 additional patients may be enrolled at any dose level at the discretion of the sponsor (in consultation with investigators).

If 1.0 mg/kg mAb1 (dose level 1; DL1) is deemed safe (after 3 to 7 patients), enrollment will commence at 3.0 mg/kg mAb1 (DL2). Following enrollment of 4 patients in DL2, enrollment in the first combination cohort (1.0 mg/kg mAb1+3.0 mg/kg REGN2810; DL3) may begin. Dose escalation to 10 mg/kg mAb1 (DL4) may commence once 3.0 mg/kg mAb1 (DL2) is deemed safe. The second combination cohort (3.0 mg/kg mAb1+3.0 mg/kg REGN2810; DL5) only enrolls after both DL2 and DL3 are deemed safe. The third combination cohort (10 mg/kg mAb1+3.0 mg/kg REGN2810; DL6) only enrolls after both DL4 and DL5 are deemed safe. If multiple cohorts are open simultaneously, priority is given to the lower number cohort (ie, DL2 over DL3 or DL3 over DL4).

Dose-Limiting Toxicities

The DLT observation period for determination of safety for dose escalation or initiation of new combination therapy is defined as 28 days starting with cycle 1, day 1, with the intent to monitor the safety and tolerability of the first 2 doses of study drug(s) (mAb1 with or without REGN2810 as applicable). To be evaluable for a DLT, a patient must have received at least the first 2 doses of study drug(s) (ie, day 1 and day 22) and be monitored for at least 28 days following the first administration, and at least 7 days from the second administration or experienced a DLT (defined below) prior to the completion of the DLT period. Delays in the administration of the second dose of study drug(s) beyond day 35 and/or study drug discontinuation are considered a DLT if study drug-related. The duration of the DLT observation period is therefore longer for patients whose second dose is delayed, and for patients experiencing an AE for which the duration must be assessed in order to determine if the event was a DLT.

In addition to the inability to administer (due to study drug toxicity) dose #2 within the window, a DLT in general is defined as any of the following study drug-related toxicities:

Non-Hematologic Toxicity:
Grade ≥2 uveitis
Any grade ≥3 non-hematologic toxicity (excluding clinically insignificant laboratory abnormalities such as asymptomatic elevations in amylase or lipase)

Hematologic Toxicity:
Grade 4 neutropenia lasting >7 days
Grade 4 thrombocytopenia
Grade 3 thrombocytopenia with bleeding
Grade ≥3 febrile neutropenia or grade ≥3 neutropenia with documented infection Both irAEs and non-irAEs that meet the definition of a DLT are considered to be DLTs.

Maximum Tolerated Dose

The MTD is defined as the dose level immediately below that at which dosing is stopped due to 2 or more DLTs out of 6 to 7 evaluable patients, and will be determined separately for monotherapy and combination therapy. However, due to the known occurrence of AEs due to monotherapy with REGN2810 and other PD-1/PD-L1 antibodies, for the combination cohorts the intensity, frequency and novelty of combination toxicity may be considered in the determination of MTD and the decision to add additional patients at a dose level. If dose escalation is not stopped for DLTs, it will be considered that the MTD has not been determined. An additional 3 patients will enroll in each of the monotherapy and combination cohorts deemed the highest dose levels tolerated (ie, 6 to 10 patients in each of these cohorts). If dose escalation for mAb1 monotherapy or combination therapy with REGN2810 is stopped at 1.0 mg/kg due to DLTs, a cohort is enrolled at a dose of 0.3 mg/kg. If dose escalation for mAb1 monotherapy or combination therapy is stopped due to DLTs at the 3.0 or 10 mg/kg dose level, the dose of mAb1 is reduced to the previously tested dose level for newly enrolled patients (in monotherapy or combination therapy cohorts respectively). No patients are allowed to initiate combination therapy with a dose of mAb1 that was not tolerable as monotherapy.

Recommended Phase 2 Dose

The RP2D for the expansion cohorts will be no higher than the MTD or highest dose tested and may be different for monotherapy and combination therapy cohorts. The determination of the RP2D will be based on safety and PK data.

Patients in monotherapy cohorts who tolerate 4 doses of mAb1 and who have an initial tumor assessment of at least SD, but who subsequently demonstrate PD, have the option of adding REGN2810 3.0 mg/kg to the highest dose of mAb1 safely administered up to that point (if one is known) in an attempt to "rescue" a response by combined LAG-3 and PD-1 blockade.

Expansion Cohorts

Once tolerability of mAb1 has been established alone and in combination with REGN2810, multiple expansion cohorts using monotherapy or combination therapy in select indications [non-small cell lung cancer (NSCLC), clear cell renal cancer (ccRCC), triple-negative breast cancer (TNBC), melanoma, and diffuse large B cell lymphoma (DLBCL)] are enrolled to further evaluate safety and seek preliminary evidence of anti-tumor activity in tumors where LAG3 is known to be expressed or over-expressed; anti-tumor activity of mAb1 alone or in combination with REGN2810 may occur. Enrollment in the expansion cohorts begins after dose escalation is complete. An additional 10 expansion cohorts (Table 19) utilizing the Simon 2-stage design (Simon 1989, Controlled Clinical Trials 10: 1-10) are enrolled after confirmation of the RP2D. A patient is assigned to a specific treatment cohort based on the patient's tumor type, presence or absence of prior anti-PD-1/anti-programmed death ligand 1 (PD-L1) therapy, the investigator's assessment of the appropriateness of a therapy regimen for that patient, and the availability of patient slots in the assigned treatment cohort. If safety issues develop in an individual expansion cohort during stage 1 of the Simon 2-stage design, enrollment may be paused. After a discussion between the investigators and Regeneron, enrollment may be resumed at the same or lower dose of mAb1. Safety issues triggering a pause could include early or late safety events. Patients are treated with mAb1 (dose determined by dose escalation findings) monotherapy or combination of mAb1 and REGN2810 3 mg/kg Q3W for up to 51 weeks. The enrollment of stage 2 for each expansion cohort occurs only if the minimum number of tumor responses is observed at stage 1.

TABLE 19

Expansion Cohorts Table

| Expansion Cohort | Tumor Type | Anti-PD-1/PD-L1 Naïve | Anti-PD-1/PD-L1 experienced | Treatment |
| --- | --- | --- | --- | --- |
| 1 | Non small-cell lung cancer | X | | Combination mAb1 and REGN2810 |
| 2 | Non small-cell lung cancer | | X | Combination mAb1 and REGN2810 |
| 3 | Clear cell renal cancer | X | | Combination mAb1 and REGN2810 |
| 4 | Clear cell renal cancer | | X | Combination mAb1 and REGN2810 |
| 5 | Triple negative breast cancer | X | | Combination mAb1 and REGN2810 |
| 6 | Melanoma | X | | Combination mAb1 and REGN2810 |
| 7 | Melanoma | | X | Combination mAb1 and REGN2810 |
| 8 | Diffuse large B cell lymphoma | X | | mAb1 monotherapy |
| 9 | Diffuse large B cell lymphoma | X | | Combination mAb1 and REGN2810 |
| 10 | Diffuse large B cell lymphoma | | X | Combination mAb1 and REGN2810 |

Study Population

In the Dose Escalation Phase:

Patients with advanced malignancies who have not received prior therapy with an anti-LAG3 drug and/or PD-1/PD-L1 inhibitor and who are not candidates for standard therapy, or for whom no available therapy is expected to convey clinical benefit, and patients with malignancies that are incurable and have failed to respond to or have shown tumor progression despite standard therapy.

In the Dose Expansion Cohorts:

Patients with select malignancies who have not received prior therapy with an anti-LAG-3 drug and who:

have not previously received therapy with anti-PD-1/PD-L1 but are appropriate candidates to receive anti-PD-1-based therapy (cohorts 1, 3, 5, 6, and 9) or have previously received anti-PD-1/PD-L1 based therapy and had a confirmed objective response (CR or PR) or SD for at least 3 months on anti-PD-1/PD-L1 therapy but subsequently progressed on that therapy or had SD or a PR as best response with subsequent stable response for 6 months (cohorts 2, 4, 7, and 10) or are not candidates for standard therapy, or for whom no available therapy is expected to convey clinical benefit and are appropriate for mAb1 monotherapy (cohort 8)

Inclusion Criteria:

A patient must meet the following criteria to be eligible for inclusion in the study:

1. Men and women ≥18 years of age.
2. Dose escalation cohorts: Patients with histologically or cytologically confirmed diagnosis of malignancy (including lymphoma) with demonstrated progression of a tumor for whom there is no alternative standard of care therapeutic option, or no alternative standard of care with curative potential (ie, failed to respond to or developed tumor progression despite standard therapy), AND have not been previously treated with a PD-1/PD-L1 inhibitor. These patients do not require measurable disease per RECIST 1.1 or Lugano criteria.
3. Dose expansion cohorts: Patients with histologically or cytologically confirmed diagnosis of 1 of the following tumors with measurable disease per RECIST 1.1 or Lugano criteria meeting the following criteria:
   i. Anti-PD-1/PD-L1 naïve stage IIIB or IV NSCLC either without prior therapy for metastatic disease or with disease progression/recurrence after one platinum-containing regimen (cohort 1)
   ii. Anti-PD-1/PD-L1 experienced* stage IIIB or IV NSCLC with no more than 2 prior therapies for metastatic disease (cohort 2)
   iii. Anti-PD-1/PD-L1 naïve advanced or metastatic ccRCC with a clear cell component who had received 1 to 2 previous regimens of anti-angiogenic therapy (cohort 3)
   iv. Anti-PD-1/PD-L1 experienced* advanced or metastatic ccRCC with a clear cell component who had received 1 to 2 previous regimens of anti-angiogenic therapy (cohort 4)
   v. Anti-PD-1/PD-L1 naïve metastatic TNBC (estrogen, progesterone, and human epidermal growth factor receptor 2 negative) who have received 5 or fewer prior lines of therapy (cohort 5)
   vi. Anti-PD-1/PD-L1 naïve advanced or metastatic melanoma who have received no more than 2 previous regimens for metastatic disease (cohort 6)
   vii. Anti-PD-1/PD-L1 experienced* advanced or metastatic melanoma who have received no more than 2 previous regimens for metastatic disease (cohort 7)
   viii. Anti-PD-1/PD-L1 naïve relapsed/refractory DLBCL who have either progressed after or are not candidates for autologous stem cell transplant (cohorts 8 and 9)
   ix. Anti-PD-1/PD-L1 experienced* relapsed/refractory DLBCL who have either progressed after or are not candidates for autologous stem cell transplant (cohort 10)
   NOTE: *Anti-PD-1/PD-L1 experienced is defined as having tolerated or tolerating anti-PD-1/PD-L1 therapy (ie, did not discontinue due to toxicity) and having had disease control with either:
   a. a CR/PR confirmed by repeat imaging or SD for at least 12 weeks from first dose, prior to disease progression. Disease progression must have either been on therapy with anti-PD-1/PD-L1 or within 12 weeks of the last dose.
    b. SD or a PR as best response with subsequent stable response (no greater than 70% decline from baseline) for 6 months while on anti-PD-1/PD-L1 therapy.
 4. Eastern Cooperative Oncology Group performance status of 0 or 1
 5. Life expectancy of at least 3 months
 6. Adequate organ and bone marrow function as follows: (a) Hemoglobin ≥9.0 g/dL; (b) Absolute neutrophil count ≥1.5×10$^9$/L; (c) Platelet count ≥75×10$^9$/L; (d) Serum creatinine ≤1.5× upper limit of normal (ULN) or estimated glomerular filtration rate >50 mL/min/1.73 m$^2$; (e) Total bilirubin ≤1.5×ULN; (f) Aspartate aminotransferase and alanine aminotransferase (ALT) 53×ULN or ≤5×ULN, if liver metastases; and/or (g) Alkaline phosphatase ≤2.5×ULN (or ≤5.0×ULN, if liver or bone metastases)
 7. Willing and able to comply with clinic visits and study-related procedures
 8. Provide signed informed consent.
Exclusion Criteria:
A patient who meets any of the following criteria will be excluded from the study: 1. Currently receiving treatment in another study, or has participated in a study of an investigational agent and received treatment, or used an investigational device within 4 weeks of first dose of study therapy, or received treatment with an approved systemic therapy within 3 weeks of first dose of study therapy, or has received any previous systemic therapy within 5 half-lives of first dose of study therapy (whichever is longer). For expansion cohorts 2, 4, 7, 10 (anti-PD-1/PD-L1 experienced) only, prior anti-PD-1/PD-L1 therapy cannot have been given within 3 weeks of first dose of study therapy, regardless of half-life or approval status of the drug. 2. Prior treatment with any LAG-3 targeting biologic or small molecule 3. Radiation therapy within 2 weeks prior to randomization and not recovered to baseline from any AE due to radiation 4. Expansion cohorts only: Another malignancy that is progressing or requires active treatment with the exception of non-melanomatous skin cancer that has undergone potentially curative therapy or in situ cervical carcinoma, or any other tumor that has been deemed to be effectively treated with definitive local control for at least 2 years prior to enrollment. 5. Untreated or active central nervous system metastases. Patients with previously treated central nervous system metastases may participate provided they are stable (ie, without evidence of progression by imaging for at least 6 weeks prior to the first dose of study treatment, and any neurologic symptoms have returned to baseline), and there is no evidence of new or enlarging central nervous system metastases, and the patient does not require any systemic corticosteroids for management of central nervous system metastases within 4 weeks prior to the first dose of REGN2810. 6. Encephalitis, meningitis, or uncontrolled seizures in the year prior to informed consent 7. Ongoing or recent (within 5 years) evidence of significant autoimmune disease that required treatment with systemic immunosuppressive treatments, which may suggest risk for irAEs. The following are not exclusionary: vitiligo, childhood asthma that has resolved, hypothyroidism that required only hormone replacement, type 1 diabetes or psoriasis that does not require systemic treatment. 8. Corticosteroid therapy (>10 mg prednisone/day or equivalent) within 1 week prior to the first dose of study drug. Patients who require a brief course of steroids are not excluded. 9. Known history of, or any evidence of interstitial lung disease, or active, non-infectious pneumonitis (past 5 years) 10. Uncontrolled infection with human immunodeficiency virus, hepatitis B or hepatitis C infection; or diagnosis of immunodeficiency 11. Active infection requiring systemic therapy 12. Receipt of a live vaccine within 30 days of planned start of study medication 13. Major surgical procedure, open biopsy or significant traumatic injury within 4 weeks prior to screening 14. Myocardial infarction within 9 months prior to the first dose of study therapy 15. Prior allogeneic stem cell transplant 16. Any medical condition that in the opinion of the investigator would make participation in the study not in the best interest of the patient 17. Documented allergic or acute hypersensitivity reaction attributed to antibody treatments 18. Known allergy to doxycycline or other tetracycline antibiotics 19. Known psychiatric or substance abuse disorders that would interfere with participation with the requirements of the study 20. Sexually active men or women of childbearing potential unwilling to practice contraception during the study. Women who are pregnant, breastfeeding or expecting to conceive or men planning to father a child within the projected duration of the study (screening visit through 180 days after the last dose of study drug). 21. Sexually active men or women of childbearing potential who are unwilling to practice adequate contraception prior to the start of the first treatment, during the study, and for at least 6 months after the last dose of study drug is administered.

Study Treatments

Monotherapy:

mAb1 is administered in an outpatient setting by intravenous (IV) infusion over 30 minutes every 21 days for up to 51 weeks at the following monotherapy doses:
 DL1: 1.0 mg/kg mAb1 IV infusion over 30 minutes every 21 days for 51 weeks
 DL2: 3.0 mg/kg mAb1 IV infusion over 30 minutes every 21 days for 51 weeks
 DL4: 10 mg/kg mAb1 IV infusion over 30 minutes every 21 days for 51 weeks
 DL-1m: 0.3 mg/kg mAb1 IV infusion over 30 minutes every 21 days for 51 weeks (if necessary)

Combination Therapy:

For combination therapy, the sequence of study drug administration is mAb1 first followed by REGN2810 on the same day. Study drugs are administered in an outpatient setting by IV infusion over 30 minutes each every 21 days for up to 51 weeks. Planned combination regimens to be assigned include:
 DL3: 1.0 mg/kg mAb1 and 3.0 mg/kg REGN2810 IV infusion over 30 minutes each every 21 days for 51 weeks
 DL5: 3.0 mg/kg mAb1 and 3.0 mg/kg REGN2810 IV infusion over 30 minutes each every 21 days for 51 weeks
 DL6: 10.0 mg/kg mAb1 and 3.0 mg/kg REGN2810 IV infusion over 30 minutes each every 21 days for 51 weeks
 DL-1c: 0.3 mg/kg mAb1 and 3.0 mg/kg REGN2810 IV infusion over 30 minutes each every 21 days for 51 weeks (if necessary)

Study Endpoints

Primary Endpoints

In the Dose Escalation Phase: Rate of DLTs, adverse events (AEs; including immune-related), serious adverse events (SAEs), deaths, and laboratory abnormalities (grade 3 or higher per Common Terminology Criteria for Adverse Events [CTCAE]), and PK In the Dose Expansion Phase: Objective response rate (ORR) based on RECIST 1.1 (solid tumors) and Lugano criteria (lymphoma)

Secondary Endpoints

ORR based on immune-related Response Evaluation Criteria in Solid Tumors (irRECIST); Best overall response (BOR), duration of response (DOR), disease control rate, and progression free survival (PFS) based on RECIST, irRECIST, and Lugano criteria); AEs; including immune-related, SAEs, deaths, and laboratory abnormalities (grade 3 or higher per CTCAE); PK and ADA Procedures and Assessments The safety and tolerability of mAb1 alone or in combination with REGN2810 is monitored by clinical assessment of AEs and by repeated measurements of clinical evaluation including vital signs (temperature, blood pressure, pulse, and respiration), physical examinations (complete and limited), 12-lead electrocardiograms (ECGs), and laboratory assessment including standard hematology, chemistry and urinalysis.

Blood samples for the determination of functional mAb1 and functional REGN2810 in serum and ADA (anti-mAb1 or anti-REGN2810) samples are collected. Serum and plasma samples are collected for analysis of additional biomarkers. Speculated pharmacodynamic, predictive and prognostic biomarkers related to mAb1 and REGN2810 treatment exposure, clinical activity, or underlying disease are investigated in serum, plasma, peripheral blood mononuclear cells (PBMCs), and tumor tissue. Anti-tumor activity is assessed by CT and MRI. A genomic DNA sample is collected from patients who have consented to the optional pharmacogenomics sub-study.

Results

It is expected that mAb1 administration is safe and well tolerated by patients with advanced malignancies in the study. Combination with 3 mg/kg of REGN2810 is expected to lead to tumor regression as assessed by ORR in patients with solid tumors such as non-small-cell lung cancer, melanoma, clear cell renal cancer, B-cell lymphoma or breast cancer.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A set of polynucleotide molecules comprising:
a first polynucleotide molecule comprising polynucleotide sequences encoding three heavy chain complementarity determining regions (HCDRs) (HCDR1, HCDR2, and HCDR3) within a heavy chain variable region (HCVR) of an antibody that binds specifically to human lymphocyte activation gene 3 (LAG3) protein, wherein the first polynucleotide molecule comprises a polynucleotide sequence of an HCDR1 as set forth in SEQ ID NO: 419, a polynucleotide sequence of an HCDR2 as set forth in SEQ ID NO: 421, and a polynucleotide sequence of an HCDR3 as set forth in SEQ ID NO: 423.

2. The set of claim 1, further comprising a second polynucleotide molecule, wherein the second polynucleotide molecule comprises polynucleotide sequences encoding three light chain complementarity determining regions (LCDRs) (LCDR1, LCDR2, and LCDR3) within a light chain variable region (LCVR) of an antibody that binds specifically to human lymphocyte activation gene 3 (LAG3) protein, wherein the second polynucleotide molecule comprises a polynucleotide sequence of an LCDR1 as set forth in SEQ ID NO: 427, a polynucleotide sequence of an LCDR2 as set forth in SEQ ID NO: 429, and a polynucleotide sequence of an LCDR3 as set forth in SEQ ID NO: 431.

3. The set of claim 1, wherein the first polynucleotide molecules comprises a polynucleotide sequence as set forth in SEQ ID NO: 417 or a sequence at least 95% identical thereto.

4. The set of claim 2, wherein the second polynucleotide molecule comprises a polynucleotide sequence as set forth in SEQ ID NO: 425 or a sequence at least 95% identical thereto.

5. The set of claim 3, comprising:
a polynucleotide sequence as set forth in SEQ ID NO: 417.

6. The set of claim 4, comprising:
a polynucleotide sequence as set forth in SEQ ID NO: 425.

7. A set of expression vectors comprising a first expression vector comprising the first polynucleotide molecule of claim 1.

8. The set of claim 7 further comprising a second expression vector comprising the second polynucleotide molecule of claim 2.

9. An isolated host cell comprising the set of claim 8.

10. The host cell of claim 9, wherein the host cell is a mammalian cell or a prokaryotic cell.

11. The host cell of claim 9, wherein the host cell is an *Escherichia coli* (*E. coli*) cell.

12. The host cell of claim 9, wherein the host cell is a Chinese Hamster Ovary (CHO) cell.

13. A method of producing an anti-LAG3 antibody or antigen-binding fragment thereof, comprising growing the host cell of claim 9 under conditions permitting production of the antibody or fragment, and recovering the antibody or antigen-binding fragment thereof so produced.

14. The method of claim 13, wherein the host cell is a CHO cell.

15. A set of polynucleotide molecules comprising:
a first isolated polynucleotide molecule comprising a polynucleotide sequence that encodes a heavy chain variable region (HCVR) of an antibody that binds specifically to human lymphocyte activation gene 3 (LAG3) protein, wherein the HCVR comprises: a heavy chain complementarity determining region (HCDR1) encoded by a polynucleotide sequence as set forth in SEQ ID NO: 419, a heavy chain complementarity determining region 2 (HCDR2) encoded by a polynucleotide sequence as set forth in SEQ ID NO: 421, and a heavy chain complementarity determining region 3 (HCDR3) encoded by a polynucleotide sequence as set forth in SEQ ID NO: 423.

16. The set of claim 15 further comprising:
a second isolated polynucleotide molecule comprising a polynucleotide sequence that encodes a light chain variable region (LCVR) of an antibody that binds specifically to human lymphocyte activation gene 3 (LAG3) protein, wherein the LCVR comprises: a light chain complementarity determining region (LCDR1) encoded by a polynucleotide sequence as set forth in SEQ ID NO: 427, a light chain complementarity determining region 2 (LCDR2) encoded by a polynucleotide sequence as set forth in SEQ ID NO: 429, and a light chain complementarity determining region 3 (LCDR3) encoded by a polynucleotide sequence as set forth in SEQ ID NO: 431.

17. The set of claim 15,
wherein the first polynucleotide molecule comprises a polynucleotide sequence as set forth in SEQ ID NO: 417 or a sequence at least 95% identical thereto.

18. The set of claim 16,
wherein the second polynucleotide molecule comprises a polynucleotide sequence as set forth in SEQ ID NO: 425 or a sequence at least 95% identical thereto.

19. The set of claim 17,
wherein the first polynucleotide molecule comprises a polynucleotide sequence as set forth in SEQ ID NO: 417.

20. The set of claim 18,
wherein the second polynucleotide molecule comprises a polynucleotide sequence as set forth in SEQ ID NO: 425.

21. A set of expression vectors comprising a first expression vector comprising the first polynucleotide molecule of claim 15.

22. The set of claim 21 further comprising a second expression vector comprising the second polynucleotide molecule of claim 16.

23. An isolated host cell comprising the set of claim 22.

24. The host cell of claim 23, wherein the host cell is a mammalian cell or a prokaryotic cell.

25. The host cell of claim 23, wherein the host cell is an *Escherichia coli* (*E. coli*) cell.

26. The host cell of claim 23, wherein the host cell is a Chinese Hamster Ovary (CHO) cell.

27. A method of producing an anti-LAG3 antibody or antigen-binding fragment thereof, comprising growing the host cell of claim 23 under conditions permitting production of the antibody or fragment, and recovering the antibody or antigen-binding fragment thereof so produced.

28. The method of claim 27, wherein the host cell is a CHO cell.

* * * * *

SEQUENCE LISTING

```
<160> NUMBER OF SEQ ID NOS: 589

<210> SEQ ID NO 1
<211> LENGTH: 372
<212> TYPE: DNA
<213> ORGANISM: Artificial Sequence
<220> FEATURE:
<223> OTHER INFORMATION: synthetic

<400> SEQUENCE: 1
gaggtgcagc tgttggagtc tgggggaggc ttggtacagc ctgggggtc cctgagactc     60 tcctgtgtgg cctctggatt caccttttagc acctatgcca tgagttgggt ccgccaggct    120
ccagggatgg ggctggagtg ggtctcaagt attagtggta gtggtcgtaa cacatactat    180
gcagactccg tgaagggccg gttcaccatc tccagagaca attccaagaa cacgctgttt    240
cttcaaatga acagcctgag agccgaggac acggccgttt attactgtgc gaaagagtcc    300
gtaactggaa cttcgtccta ctactacggt gtggacgtct ggggccaagg gaccacggtc    360
accgtctcct cg                                                         372

<210> SEQ ID NO 2
<211> LENGTH: 124
<212> TYPE: PRT
<213> ORGANISM: Artificial Sequence
<220> FEATURE:
<223> OTHER INFORMATION: synthetic

<400> SEQUENCE: 2

Glu Val Gln Leu Leu Glu Ser Gly Gly Gly Leu Val Gln Pro Gly Gly
 1               5                  10                  15

Ser Leu Arg Leu Ser Cys Val Ala Ser Gly Phe Thr Phe Ser Thr Tyr
            20                  25                  30

Ala Met Ser Trp Val Arg Gln Ala Pro Gly Met Gly Leu Glu Trp Val
        35                  40                  45

Ser Ser Ile Ser Gly Ser Gly Arg Asn Thr Tyr Tyr Ala Asp Ser Val
    50                  55                  60
```

```
Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Lys Glu Ser Val Thr Gly Thr Ser Ser Tyr Tyr Tyr Gly Val Asp
            100                 105                 110

Val Trp Gly Gln Gly Thr Thr Val Thr Val Ser Ser
            115                 120
```

<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3
ggattcacct ttagcaccta tgcc        24

<210> SEQ ID NO 4
<211> LENGTH: 8
<212> TYPE: PRT
<213> ORGANISM: Artificial Sequence
<220> FEATURE:
<223> OTHER INFORMATION: synthetic

<400> SEQUENCE: 4

```
Gly Phe Thr Phe Ser Thr Tyr Ala
 1               5
```

<210> SEQ ID NO 5
<211> LENGTH: 24
<212> TYPE: DNA
<213> ORGANISM: Artificial Sequence
<220> FEATURE:
<223> OTHER INFORMATION: synthetic

<400> SEQUENCE: 5
attagtggta gtggtcgtaa caca        24

<210> SEQ ID NO 6
<211> LENGTH: 8
<212> TYPE: PRT
<213> ORGANISM: Artificial Sequence
<220> FEATURE:
<223> OTHER INFORMATION: synthetic

<400> SEQUENCE: 6

```
Ile Ser Gly Ser Gly Arg Asn Thr
 1               5
```

<210> SEQ ID NO 7
<211> LENGTH: 51
<212> TYPE: DNA
<213> ORGANISM: Artificial Sequence
<220> FEATURE:
<223> OTHER INFORMATION: synthetic

<400> SEQUENCE: 7
gcgaaagagt ccgtaactgg aacttcgtcc tactactacg gtgtggacgt c        51

<210> SEQ ID NO 8
<211> LENGTH: 17
<212> TYPE: PRT
<213> ORGANISM: Artificial Sequence
<220> FEATURE:
<223> OTHER INFORMATION: synthetic

<400> SEQUENCE: 8

Ala Lys Glu Ser Val Thr Gly Thr Ser Ser Tyr Tyr Tyr Gly Val Asp
1               5                   10                  15
Val

<210> SEQ ID NO 9
<211> LENGTH: 321
<212> TYPE: DNA
<213> ORGANISM: Artificial Sequence
<220> FEATURE:
<223> OTHER INFORMATION: synthetic

<400> SEQUENCE: 9
gacatccaga tgacccagtc tccatcctcc ctgtctgcat ctgtaggaga cagagtcacc     60
atcacttgcc gggcaagtca gagcattagc agttatttaa attggtatca tcagaaacca    120
gggaaagccc caaagctcct gatctatgct gcatccagtt tgcaaaatgg ggtcccatca    180
aggttcagtg gcagtggatc tgggacagat ttcactctca ccatcagcag tctgcaacct    240
gaagattttg catcttacta ctgtcaacag agttacagaa ccccgctcac tttcggcgga    300
gggaccaagg tggagatcaa a                                              321

<210> SEQ ID NO 10
<211> LENGTH: 107
<212> TYPE: PRT
<213> ORGANISM: Artificial Sequence
<220> FEATURE:
<223> OTHER INFORMATION: synthetic

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr His Gln Lys Pro Gly Lys Ala Pro Lys Leu Leu Ile
        35                  40                  45

Tyr Ala Ala Ser Ser Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ser Tyr Tyr Cys Gln Gln Ser Tyr Arg Thr Pro Leu
                85                  90                  95

Thr Phe Gly Gly Gly Thr Lys Val Glu Ile Lys
            100                 105

<210> SEQ ID NO 11
<211> LENGTH: 18
<212> TYPE: DNA
<213> ORGANISM: Artificial Sequence
<220> FEATURE:
<223> OTHER INFORMATION: synthetic

<400> SEQUENCE: 11
cagagcatta gcagttat                                                   18

<210> SEQ ID NO 12
<211> LENGTH: 6
<212> TYPE: PRT

```
<213> ORGANISM: Artificial Sequence
<220> FEATURE:
<223> OTHER INFORMATION: synthetic

<400> SEQUENCE: 12

Gln Ser Ile Ser Ser Tyr
1               5

<210> SEQ ID NO 13
<211> LENGTH: 9
<212> TYPE: DNA
<213> ORGANISM: Artificial Sequence
<220> FEATURE:
<223> OTHER INFORMATION: synthetic

<400> SEQUENCE: 13 gctgcatcc                                                            9

<210> SEQ ID NO 14
<211> LENGTH: 3
<212> TYPE: PRT
<213> ORGANISM: Artificial Sequence
<220> FEATURE:
<223> OTHER INFORMATION: synthetic

<400> SEQUENCE: 14

Ala Ala Ser
1

<210> SEQ ID NO 15
<211> LENGTH: 27
<212> TYPE: DNA
<213> ORGANISM: Artificial Sequence
<220> FEATURE:
<223> OTHER INFORMATION: synthetic

<400> SEQUENCE: 15
caacagagtt acagaacccc gctcact                                       27

<210> SEQ ID NO 16
<211> LENGTH: 9
<212> TYPE: PRT
<213> ORGANISM: Artificial Sequence
<220> FEATURE:
<223> OTHER INFORMATION: synthetic

<400> SEQUENCE: 16

Gln Gln Ser Tyr Arg Thr Pro Leu Thr
1               5

<210> SEQ ID NO 17
<211> LENGTH: 387
<212> TYPE: DNA
<213> ORGANISM: Artificial Sequence
<220> FEATURE:
<223> OTHER INFORMATION: synthetic

<400> SEQUENCE: 17
caggtgcagc tggaggagtc tgggggaggc gtggtccagc ctggggaggtc cctgagactc      60 tcctgtgcag cgtctggatt caccttcagt tggtatggca tgcactgggt ccgccaggct     120
ccaggcaagg ggctggagtg ggtggcactt atatgggtatg atggaactaa taaaaagtat     180
ggagactccg tgaagggccg attcaccatt tccagagaca attccaagaa cacggtgtat     240
ctgcaaatga acagcctgag agccgaggac acggctgtgt attactgtgc gagagattgt     300
```
ggacatagtg gcaacgatcg ggggacttac tattactact acggtatgga cgtctggggc    360
caagggacca cggtcaccgt ctcctca    387

<210> SEQ ID NO 18
<211> LENGTH: 129
<212> TYPE: PRT
<213> ORGANISM: Artificial Sequence
<220> FEATURE:
<223> OTHER INFORMATION: synthetic

<400> SEQUENCE: 18

Gln Val Gln Leu Glu Glu Ser Gly Gly Gly Val Val Gln Pro Gly Arg
1               5                   10                  15

Ser Leu Arg Leu Ser Cys Ala Ala Ser Gly Phe Thr Phe Ser Trp Tyr
            20                  25                  30

Gly Met His Trp Val Arg Gln Ala Pro Gly Lys Gly Leu Glu Trp Val
        35                  40                  45

Ala Leu Ile Trp Tyr Asp Gly Thr Asn Lys Lys Tyr Gly Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Arg Asp Cys Gly His Ser Gly Asn Asp Arg Gly Tyr Tyr Tyr
            100                 105                 110

Tyr Tyr Gly Met Asp Val Trp Gly Gln Gly Thr Thr Val Thr Val Ser
        115                 120                 125

Ser

<210> SEQ ID NO 19
<211> LENGTH: 24
<212> TYPE: DNA
<213> ORGANISM: Artificial Sequence
<220> FEATURE:
<223> OTHER INFORMATION: synthetic

<400> SEQUENCE: 19
ggattcacct tcagttggta tggc    24

<210> SEQ ID NO 20
<211> LENGTH: 8
<212> TYPE: PRT
<213> ORGANISM: Artificial Sequence
<220> FEATURE:
<223> OTHER INFORMATION: synthetic

<400> SEQUENCE: 20

Gly Phe Thr Phe Ser Trp Tyr Gly
1               5

<210> SEQ ID NO 21
<211> LENGTH: 24
<212> TYPE: DNA
<213> ORGANISM: Artificial Sequence
<220> FEATURE:
<223> OTHER INFORMATION: synthetic

<400> SEQUENCE: 21
atatggtatg atggaactaa taaa    24

<210> SEQ ID NO 22

<210> SEQ ID NO 22
<211> LENGTH: 8
<212> TYPE: PRT
<213> ORGANISM: Artificial Sequence
<220> FEATURE:
<223> OTHER INFORMATION: synthetic

<400> SEQUENCE: 22

Ile Trp Tyr Asp Gly Thr Asn Lys
1               5

<210> SEQ ID NO 23
<211> LENGTH: 66
<212> TYPE: DNA
<213> ORGANISM: Artificial Sequence
<220> FEATURE:
<223> OTHER INFORMATION: synthetic

<400> SEQUENCE: 23
gcgagagatt gtggacatag tggcaacgat cggggggactt actattacta ctacggtatg      60
gacgtc                                                                  66

<210> SEQ ID NO 24
<211> LENGTH: 22
<212> TYPE: PRT
<213> ORGANISM: Artificial Sequence
<220> FEATURE:
<223> OTHER INFORMATION: synthetic

<400> SEQUENCE: 24

Ala Arg Asp Cys Gly His Ser Gly Asn Asp Arg Gly Thr Tyr Tyr Tyr
1               5                   10                  15

Tyr Tyr Gly Met Asp Val
            20

<210> SEQ ID NO 25
<211> LENGTH: 324
<212> TYPE: DNA
<213> ORGANISM: Artificial Sequence
<220> FEATURE:
<223> OTHER INFORMATION: synthetic

<400> SEQUENCE: 25
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcaacag agttacagta cccctccgat caccttcggc     300
caagggacac gactggagat taaa                                             324

<210> SEQ ID NO 26
<211> LENGTH: 108
<212> TYPE: PRT
<213> ORGANISM: Artificial Sequence
<220> FEATURE:
<223> OTHER INFORMATION: synthetic

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Pro
                 85                  90                  95

Ile Thr Phe Gly Gln Gly Thr Arg Leu Glu Ile Lys
            100                 105

<210> SEQ ID NO 27
<211> LENGTH: 18
<212> TYPE: DNA
<213> ORGANISM: Artificial Sequence
<220> FEATURE:
<223> OTHER INFORMATION: synthetic

<400> SEQUENCE: 27
cagagcatta gcagctat                                                   18

<210> SEQ ID NO 28
<211> LENGTH: 6
<212> TYPE: PRT
<213> ORGANISM: Artificial Sequence
<220> FEATURE:
<223> OTHER INFORMATION: synthetic

<400> SEQUENCE: 28

Gln Ser Ile Ser Ser Tyr
 1               5

<210> SEQ ID NO 29
<211> LENGTH: 9
<212> TYPE: DNA
<213> ORGANISM: Artificial Sequence
<220> FEATURE:
<223> OTHER INFORMATION: synthetic

<400> SEQUENCE: 29 gctgcatcc                                                              9

<210> SEQ ID NO 30
<211> LENGTH: 3
<212> TYPE: PRT
<213> ORGANISM: Artificial Sequence
<220> FEATURE:
<223> OTHER INFORMATION: synthetic

<400> SEQUENCE: 30

Ala Ala Ser
 1

<210> SEQ ID NO 31
<211> LENGTH: 30
<212> TYPE: DNA
<213> ORGANISM: Artificial Sequence
<220> FEATURE:
<223> OTHER INFORMATION: synthetic

<400> SEQUENCE: 31
caacagagtt acagtacccc tccgatcacc                                      30

<210> SEQ ID NO 32

<211> LENGTH: 10
<212> TYPE: PRT
<213> ORGANISM: Artificial Sequence
<220> FEATURE:
<223> OTHER INFORMATION: synthetic

<400> SEQUENCE: 32

Gln Gln Ser Tyr Ser Thr Pro Pro Ile Thr
1               5                   10

<210> SEQ ID NO 33
<211> LENGTH: 357
<212> TYPE: DNA
<213> ORGANISM: Artificial Sequence
<220> FEATURE:
<223> OTHER INFORMATION: synthetic

<400> SEQUENCE: 33
caggtgcagc tacagcagtg gggcgcagga ctgttgaagc cttcggagac cctgtccctc      60
acctgcgctg tctatggtgg gtccttcagt ggttactact ggaactggat ccgccagccc     120
ccagggaagg gctggagtg ggttggggaa atcagtcata gaggaaccac caactacaac      180
ccgtccctca gagtcgagt caccatatca ctggacacgt ccaagaacca gttctccctg      240
aaactgacct ctgtgaccgc cgcggacacg gctgtgtatt actgttcgag agacgaggaa     300
ctggaattcc gtttctttga ctactggggc cagggaaccc tggtcaccgt ctcctca       357

<210> SEQ ID NO 34
<211> LENGTH: 119
<212> TYPE: PRT
<213> ORGANISM: Artificial Sequence
<220> FEATURE:
<223> OTHER INFORMATION: synthetic

<400> SEQUENCE: 34

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Asn Trp Ile Arg Gln Pro Pro Gly Lys Gly Leu Glu Trp Val
            35                  40                  45

Gly Glu Ile Ser His Arg Gly Thr Thr Asn Tyr Asn Pro Ser Leu Lys
        50                  55                  60

Ser Arg Val Thr Ile Ser Leu Asp Thr Ser Lys Asn Gln Phe Ser Leu
65                  70                  75                  80

Lys Leu Thr Ser Val Thr Ala Ala Asp Thr Ala Val Tyr Tyr Cys Ser
                85                  90                  95

Arg Asp Glu Glu Leu Glu Phe Arg Phe Phe Asp Tyr Trp Gly Gln Gly
            100                 105                 110

Thr Leu Val Thr Val Ser Ser
        115

<210> SEQ ID NO 35
<211> LENGTH: 24
<212> TYPE: DNA
<213> ORGANISM: Artificial Sequence
<220> FEATURE:
<223> OTHER INFORMATION: synthetic

<400> SEQUENCE: 35
ggtgggtcct tcagtggtta ctac                                            24

<210> SEQ ID NO 36
<211> LENGTH: 8
<212> TYPE: PRT
<213> ORGANISM: Artificial Sequence
<220> FEATURE:
<223> OTHER INFORMATION: synthetic

<400> SEQUENCE: 36

Gly Gly Ser Phe Ser Gly Tyr Tyr
1               5

<210> SEQ ID NO 37
<211> LENGTH: 21
<212> TYPE: DNA
<213> ORGANISM: Artificial Sequence
<220> FEATURE:
<223> OTHER INFORMATION: synthetic

<400> SEQUENCE: 37
atcagtcata gaggaaccac c                                           21

<210> SEQ ID NO 38
<211> LENGTH: 7
<212> TYPE: PRT
<213> ORGANISM: Artificial Sequence
<220> FEATURE:
<223> OTHER INFORMATION: synthetic

<400> SEQUENCE: 38

Ile Ser His Arg Gly Thr Thr
1               5

<210> SEQ ID NO 39
<211> LENGTH: 39
<212> TYPE: DNA
<213> ORGANISM: Artificial Sequence
<220> FEATURE:
<223> OTHER INFORMATION: synthetic

<400> SEQUENCE: 39
tcgagagacg aggaactgga attccgtttc tttgactac                         39

<210> SEQ ID NO 40
<211> LENGTH: 13
<212> TYPE: PRT
<213> ORGANISM: Artificial Sequence
<220> FEATURE:
<223> OTHER INFORMATION: synthetic

<400> SEQUENCE: 40

Ser Arg Asp Glu Glu Leu Glu Phe Arg Phe Phe Asp Tyr
1               5                   10

<210> SEQ ID NO 41
<211> LENGTH: 321
<212> TYPE: DNA
<213> ORGANISM: Artificial Sequence
<220> FEATURE:
<223> OTHER INFORMATION: synthetic

<400> SEQUENCE: 41
gaaattgtgt tgacacagtc tccagccacc ctgtctttgt ctccagggga aagagccacc    60
ctctcctgca gggccagtca gagtgttagc agctatttag cctggtacca acaaaaacct   120
ggccaggctc ccaggctcct cgtctatggt gcatccaaca gggccactgg catcccagcc   180

```
aggttcagtg gcagtgggtc tgggacagac ttcactctca ccatcagcag cctagagcct    240
gaagattttg catttttatta ctgtcagcag cgtagcaact ggccgctcac tttcggcgga    300
gggaccaagg tggagatcaa a                                              321
```

```
<210> SEQ ID NO 42
<211> LENGTH: 107
<212> TYPE: PRT
<213> ORGANISM: Artificial Sequence
<220> FEATURE:
<223> OTHER INFORMATION: synthetic

<400> SEQUENCE: 42
```

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Val
        35                  40                  45

Tyr Gly Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Phe Tyr Tyr Cys Gln Gln Arg Ser Asn Trp Pro Leu
                85                  90                  95

Thr Phe Gly Gly Gly Thr Lys Val Glu Ile Lys
            100                 105

```
<210> SEQ ID NO 43
<211> LENGTH: 18
<212> TYPE: DNA
<213> ORGANISM: Artificial Sequence
<220> FEATURE:
<223> OTHER INFORMATION: synthetic

<400> SEQUENCE: 43
cagagtgtta gcagctat                                                   18

<210> SEQ ID NO 44
<211> LENGTH: 6
<212> TYPE: PRT
<213> ORGANISM: Artificial Sequence
<220> FEATURE:
<223> OTHER INFORMATION: synthetic

<400> SEQUENCE: 44
```

Gln Ser Val Ser Ser Tyr
1               5

```
<210> SEQ ID NO 45
<211> LENGTH: 9
<212> TYPE: DNA
<213> ORGANISM: Artificial Sequence
<220> FEATURE:
<223> OTHER INFORMATION: synthetic

<400> SEQUENCE: 45 ggtgcatcc                                                              9

<210> SEQ ID NO 46
<211> LENGTH: 3
<212> TYPE: PRT
<213> ORGANISM: Artificial Sequence
```

<220> FEATURE:
<223> OTHER INFORMATION: synthetic

<400> SEQUENCE: 46

Gly Ala Ser
1

<210> SEQ ID NO 47
<211> LENGTH: 27
<212> TYPE: DNA
<213> ORGANISM: Artificial Sequence
<220> FEATURE:
<223> OTHER INFORMATION: synthetic

<400> SEQUENCE: 47
cagcagcgta gcaactggcc gctcact                                        27

<210> SEQ ID NO 48
<211> LENGTH: 9
<212> TYPE: PRT
<213> ORGANISM: Artificial Sequence
<220> FEATURE:
<223> OTHER INFORMATION: synthetic

<400> SEQUENCE: 48

Gln Gln Arg Ser Asn Trp Pro Leu Thr
1               5

<210> SEQ ID NO 49
<211> LENGTH: 357
<212> TYPE: DNA
<213> ORGANISM: Artificial Sequence
<220> FEATURE:
<223> OTHER INFORMATION: synthetic

<400> SEQUENCE: 49
cagctgcagc tgcaggagtc gggcccagga ctggtgaagc cttcggagac cctgtccctc    60
acctgcactg tctctggtga ctccatcatc agtaatagtt attactgggg ctggatccgc   120
cagcccccag gaaggggct ggagtggatt ggcaatttct tttatactgg ggccacctac    180
tacaacccgt ccctcaagag tcgagtcacc atatccgctg acacgtccaa gaatcagttc   240
tccctgaagc tgagctctgt gaccgccgca gacacggctc tgtattattg tgcgagttat   300
aataggaatt accggttcga ccctgggggc cagggaaccc tggtcaccgt ctcctca      357

<210> SEQ ID NO 50
<211> LENGTH: 119
<212> TYPE: PRT
<213> ORGANISM: Artificial Sequence
<220> FEATURE:
<223> OTHER INFORMATION: synthetic

<400> SEQUENCE: 50

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ile Ser Asn
            20                  25                  30

Ser Tyr Tyr Trp Gly Trp Ile Arg Gln Pro Pro Gly Lys Gly Leu Glu
        35                  40                  45

Trp Ile Gly Asn Phe Phe Tyr Thr Gly Ala Thr Tyr Tyr Asn Pro Ser
    50                  55                  60

Leu Lys Ser Arg Val Thr Ile Ser Ala Asp Thr Ser Lys Asn Gln Phe
65                  70                  75                  80

Ser Leu Lys Leu Ser Ser Val Thr Ala Ala Asp Thr Ala Leu Tyr Tyr
            85                  90                  95

Cys Ala Ser Tyr Asn Arg Asn Tyr Arg Phe Asp Pro Trp Gly Gln Gly
            100                 105                 110

Thr Leu Val Thr Val Ser Ser
        115

<210> SEQ ID NO 51
<211> LENGTH: 30
<212> TYPE: DNA
<213> ORGANISM: Artificial Sequence
<220> FEATURE:
<223> OTHER INFORMATION: synthetic

<400> SEQUENCE: 51
ggtgactcca tcatcagtaa tagttattac                                        30

<210> SEQ ID NO 52
<211> LENGTH: 10
<212> TYPE: PRT
<213> ORGANISM: Artificial Sequence
<220> FEATURE:
<223> OTHER INFORMATION: synthetic

<400> SEQUENCE: 52

Gly Asp Ser Ile Ile Ser Asn Ser Tyr Tyr
1               5                   10

<210> SEQ ID NO 53
<211> LENGTH: 21
<212> TYPE: DNA
<213> ORGANISM: Artificial Sequence
<220> FEATURE:
<223> OTHER INFORMATION: synthetic

<400> SEQUENCE: 53
ttcttttata ctggggccac c                                                 21

<210> SEQ ID NO 54
<211> LENGTH: 7
<212> TYPE: PRT
<213> ORGANISM: Artificial Sequence
<220> FEATURE:
<223> OTHER INFORMATION: synthetic

<400> SEQUENCE: 54

Phe Phe Tyr Thr Gly Ala Thr
1               5

<210> SEQ ID NO 55
<211> LENGTH: 33
<212> TYPE: DNA
<213> ORGANISM: Artificial Sequence
<220> FEATURE:
<223> OTHER INFORMATION: synthetic

<400> SEQUENCE: 55
gcgagttata ataggaatta ccggttcgac ccc                                    33

<210> SEQ ID NO 56
<211> LENGTH: 11
<212> TYPE: PRT
<213> ORGANISM: Artificial Sequence
<220> FEATURE:
<223> OTHER INFORMATION: synthetic

<400> SEQUENCE: 56

Ala Ser Tyr Asn Arg Asn Tyr Arg Phe Asp Pro
1               5                   10

<210> SEQ ID NO 57
<211> LENGTH: 324
<212> TYPE: DNA
<213> ORGANISM: Artificial Sequence
<220> FEATURE:
<223> OTHER INFORMATION: synthetic

<400> SEQUENCE: 57

```
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttactt ctgtcaacag agttacagta cccctccgat caccttcggc     300
caagggacac gactggagat taaa                                            324
```

<210> SEQ ID NO 58
<211> LENGTH: 108
<212> TYPE: PRT
<213> ORGANISM: Artificial Sequence
<220> FEATURE:
<223> OTHER INFORMATION: synthetic

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 59
<211> LENGTH: 18
<212> TYPE: DNA
<213> ORGANISM: Artificial Sequence
<220> FEATURE:
<223> OTHER INFORMATION: synthetic

<400> SEQUENCE: 59
cagagcatta gcagctat                                                    18

<210> SEQ ID NO 60
<211> LENGTH: 6
<212> TYPE: PRT
<213> ORGANISM: Artificial Sequence
<220> FEATURE:
<223> OTHER INFORMATION: synthetic

<400> SEQUENCE: 60

Gln Ser Ile Ser Ser Tyr
1               5

<210> SEQ ID NO 61
<211> LENGTH: 9
<212> TYPE: DNA
<213> ORGANISM: Artificial Sequence
<220> FEATURE:
<223> OTHER INFORMATION: synthetic

<400> SEQUENCE: 61 gctgcatcc                                                                9

<210> SEQ ID NO 62
<211> LENGTH: 3
<212> TYPE: PRT
<213> ORGANISM: Artificial Sequence
<220> FEATURE:
<223> OTHER INFORMATION: synthetic

<400> SEQUENCE: 62

Ala Ala Ser
1

<210> SEQ ID NO 63
<211> LENGTH: 30
<212> TYPE: DNA
<213> ORGANISM: Artificial Sequence
<220> FEATURE:
<223> OTHER INFORMATION: synthetic

<400> SEQUENCE: 63
caacagagtt acagtacccc tccgatcacc                                        30

<210> SEQ ID NO 64
<211> LENGTH: 10
<212> TYPE: PRT
<213> ORGANISM: Artificial Sequence
<220> FEATURE:
<223> OTHER INFORMATION: synthetic

<400> SEQUENCE: 64

Gln Gln Ser Tyr Ser Thr Pro Pro Ile Thr
1               5                   10

<210> SEQ ID NO 65
<211> LENGTH: 381
<212> TYPE: DNA
<213> ORGANISM: Artificial Sequence
<220> FEATURE:
<223> OTHER INFORMATION: synthetic

<400> SEQUENCE: 65
caggtgcagc tacagcagtg gggcgcagga ctgttgaagc cttcggagac cctgtccctc        60
acctgcgctg tctatggtgg gtccttcagt acttactact ggagctggat ccgccagccc       120
ccagggaagg ggctggagtg gattggagag atcaatcata gtggaaacgc cgactacaac       180
ccgtccctca gagtcgagt ctccatatca gtggacacgt ccaagaacca gttctccctg       240
aggctgagct ctgtgaccgc cgcggacacg gctatttatt actgtgcgag agcgggctat       300
tgtagtagtc ccacctgcta ttcctactac tacttcggta tggacgtctg gggccaaggg       360
accacggtca ccgtctcctc a                                                381

<210> SEQ ID NO 66
<211> LENGTH: 127
<212> TYPE: PRT
<213> ORGANISM: Artificial Sequence
<220> FEATURE:
<223> OTHER INFORMATION: synthetic

<400> SEQUENCE: 66

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Thr Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Asn Ala Asp Tyr Asn Pro Ser Leu Lys
    50                  55                  60

Ser Arg Val Ser Ile Ser Val Asp Thr Ser Lys Asn Gln Phe Ser Leu
65                  70                  75                  80

Arg Leu Ser Ser Val Thr Ala Ala Asp Thr Ala Ile Tyr Tyr Cys Ala
                85                  90                  95

Arg Ala Gly Tyr Cys Ser Ser Pro Thr Cys Tyr Ser Tyr Tyr Tyr Phe
            100                 105                 110

Gly Met Asp Val Trp Gly Gln Gly Thr Thr Val Thr Val Ser Ser
        115                 120                 125
```

<210> SEQ ID NO 67
<211> LENGTH: 24
<212> TYPE: DNA
<213> ORGANISM: Artificial Sequence
<220> FEATURE:
<223> OTHER INFORMATION: synthetic

<400> SEQUENCE: 67
ggtgggtcct tcagtactta ctac                                          24

<210> SEQ ID NO 68
<211> LENGTH: 8
<212> TYPE: PRT
<213> ORGANISM: Artificial Sequence
<220> FEATURE:
<223> OTHER INFORMATION: synthetic

<400> SEQUENCE: 68

```
Gly Gly Ser Phe Ser Thr Tyr Tyr
1               5
```

<210> SEQ ID NO 69
<211> LENGTH: 21
<212> TYPE: DNA
<213> ORGANISM: Artificial Sequence
<220> FEATURE:
<223> OTHER INFORMATION: synthetic

<400> SEQUENCE: 69
atcaatcata gtggaaacgc c                                             21

<210> SEQ ID NO 70
<211> LENGTH: 7
<212> TYPE: PRT
<213> ORGANISM: Artificial Sequence
<220> FEATURE:
<223> OTHER INFORMATION: synthetic

<400> SEQUENCE: 70

Ile Asn His Ser Gly Asn Ala
1               5

<210> SEQ ID NO 71
<211> LENGTH: 63
<212> TYPE: DNA
<213> ORGANISM: Artificial Sequence
<220> FEATURE:
<223> OTHER INFORMATION: synthetic

<400> SEQUENCE: 71
gcgagagcgg gctattgtag tagtcccacc tgctattcct actactactt cggtatggac    60
gtc                                                                 63

<210> SEQ ID NO 72
<211> LENGTH: 21
<212> TYPE: PRT
<213> ORGANISM: Artificial Sequence
<220> FEATURE:
<223> OTHER INFORMATION: synthetic

<400> SEQUENCE: 72

Ala Arg Ala Gly Tyr Cys Ser Ser Pro Thr Cys Tyr Ser Tyr Tyr Tyr
1               5                   10                  15

Phe Gly Met Asp Val
            20

<210> SEQ ID NO 73
<211> LENGTH: 324
<212> TYPE: DNA
<213> ORGANISM: Artificial Sequence
<220> FEATURE:
<223> OTHER INFORMATION: synthetic

<400> SEQUENCE: 73
gaaattgtgt tgacgcagtc tccaggcacc ctgtctttgt ctctagggga aagagccacc    60
ctctcctgca gggccagtca gagtgttatc agcagcttct tagcctggta ccagcagaaa   120
cctggccagg ctcccaggct cctcatctat ggtgcatcca gcagggccac tggcttccca   180
gacaggttca gtggcagtgg gtctgggaca gacttcactc tcaccatccg cagactggag   240
cctgaagatt ttgcagtgta ttactgtcag cagtatggta actcaccttg gacgttcggc   300
caagggacca aggtggagat caaa                                          324

<210> SEQ ID NO 74
<211> LENGTH: 108
<212> TYPE: PRT
<213> ORGANISM: Artificial Sequence
<220> FEATURE:
<223> OTHER INFORMATION: synthetic

<400> SEQUENCE: 74

Glu Ile Val Leu Thr Gln Ser Pro Gly Thr Leu Ser Leu Ser Leu Gly
1               5                   10                  15

Glu Arg Ala Thr Leu Ser Cys Arg Ala Ser Gln Ser Val Ile Ser Ser
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Phe Pro Asp Arg Phe Ser
    50                  55                  60

Gly Ser Gly Ser Gly Thr Asp Phe Thr Leu Thr Ile Arg Arg Leu Glu
65                  70                  75                  80

Pro Glu Asp Phe Ala Val Tyr Tyr Cys Gln Gln Tyr Gly Asn Ser Pro
                85                  90                  95

Trp Thr Phe Gly Gln Gly Thr Lys Val Glu Ile Lys
            100                 105

<210> SEQ ID NO 75
<211> LENGTH: 21
<212> TYPE: DNA
<213> ORGANISM: Artificial Sequence
<220> FEATURE:
<223> OTHER INFORMATION: synthetic

<400> SEQUENCE: 75
cagagtgtta tcagcagctt c                                              21

<210> SEQ ID NO 76
<211> LENGTH: 7
<212> TYPE: PRT
<213> ORGANISM: Artificial Sequence
<220> FEATURE:
<223> OTHER INFORMATION: synthetic

<400> SEQUENCE: 76

Gln Ser Val Ile Ser Ser Phe
1               5

<210> SEQ ID NO 77
<211> LENGTH: 9
<212> TYPE: DNA
<213> ORGANISM: Artificial Sequence
<220> FEATURE:
<223> OTHER INFORMATION: synthetic

<400> SEQUENCE: 77 ggtgcatcc                                                             9

<210> SEQ ID NO 78
<211> LENGTH: 3
<212> TYPE: PRT
<213> ORGANISM: Artificial Sequence
<220> FEATURE:
<223> OTHER INFORMATION: synthetic

<400> SEQUENCE: 78

Gly Ala Ser
1

<210> SEQ ID NO 79
<211> LENGTH: 27
<212> TYPE: DNA
<213> ORGANISM: Artificial Sequence
<220> FEATURE:
<223> OTHER INFORMATION: synthetic

<400> SEQUENCE: 79
cagcagtatg gtaactcacc ttggacg                                         27

<210> SEQ ID NO 80
<211> LENGTH: 9
<212> TYPE: PRT
<213> ORGANISM: Artificial Sequence
<220> FEATURE:
<223> OTHER INFORMATION: synthetic

<400> SEQUENCE: 80

Gln Gln Tyr Gly Asn Ser Pro Trp Thr
1               5

<210> SEQ ID NO 81
<211> LENGTH: 387
<212> TYPE: DNA
<213> ORGANISM: Artificial Sequence
<220> FEATURE:
<223> OTHER INFORMATION: synthetic

<400> SEQUENCE: 81
caggtcacct tgaaggagtc tggtcctgtg ctggtgaaac ccacagagac cctcacgctg        60
acctgcaccg tctctgggtt ctcactcagc aatgctggga tgggtgtgag ctgggtccgt       120 cagcccctg ggaaggccct ggagtggctt gcacacattt tttcgaatga cgagaagtcc       180
tacagcacat ctctgaggac cagactcacc atctccaagg acacctccaa aagccaggtg      240
gtccttaccg tgaccaactt ggaccctgtg gacacagcca catatttctg tgcacggata      300
ccagagttta ccagctcgtc gtgggctctc tactacttct acggtatgga cgtctggggc      360
caagggacca cggtcaccgt ctcctca                                           387

<210> SEQ ID NO 82
<211> LENGTH: 129
<212> TYPE: PRT
<213> ORGANISM: Artificial Sequence
<220> FEATURE:
<223> OTHER INFORMATION: synthetic

<400> SEQUENCE: 82

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Gly Met Gly Val Ser Trp Val Arg Gln Pro Pro Gly Lys Ala Leu Glu
        35                  40                  45

Trp Leu Ala His Ile Phe Ser Asn Asp Glu Lys Ser Tyr Ser Thr Ser
    50                  55                  60

Leu Arg Thr Arg Leu Thr Ile Ser Lys Asp Thr Ser Lys Ser Gln Val
65                  70                  75                  80

Val Leu Thr Val Thr Asn Leu Asp Pro Val Asp Thr Ala Thr Tyr Phe
                85                  90                  95

Cys Ala Arg Ile Pro Glu Phe Thr Ser Ser Trp Ala Leu Tyr Tyr
            100                 105                 110

Phe Tyr Gly Met Asp Val Trp Gly Gln Gly Thr Thr Val Thr Val Ser
        115                 120                 125

Ser

<210> SEQ ID NO 83
<211> LENGTH: 30
<212> TYPE: DNA
<213> ORGANISM: Artificial Sequence
<220> FEATURE:
<223> OTHER INFORMATION: synthetic

<400> SEQUENCE: 83
gggttctcac tcagcaatgc tgggatgggt                                         30

<210> SEQ ID NO 84

```
<211> LENGTH: 10
<212> TYPE: PRT
<213> ORGANISM: Artificial Sequence
<220> FEATURE:
<223> OTHER INFORMATION: synthetic

<400> SEQUENCE: 84

Gly Phe Ser Leu Ser Asn Ala Gly Met Gly
1               5                   10

<210> SEQ ID NO 85
<211> LENGTH: 21
<212> TYPE: DNA
<213> ORGANISM: Artificial Sequence
<220> FEATURE:
<223> OTHER INFORMATION: synthetic

<400> SEQUENCE: 85 atttttcga atgacgagaa g                                          21

<210> SEQ ID NO 86
<211> LENGTH: 7
<212> TYPE: PRT
<213> ORGANISM: Artificial Sequence
<220> FEATURE:
<223> OTHER INFORMATION: synthetic

<400> SEQUENCE: 86

Ile Phe Ser Asn Asp Glu Lys
1               5

<210> SEQ ID NO 87
<211> LENGTH: 63
<212> TYPE: DNA
<213> ORGANISM: Artificial Sequence
<220> FEATURE:
<223> OTHER INFORMATION: synthetic

<400> SEQUENCE: 87
gcacggatac cagagtttac cagctcgtcg tgggctctct actacttcta cggtatggac    60
gtc                                                                 63

<210> SEQ ID NO 88
<211> LENGTH: 21
<212> TYPE: PRT
<213> ORGANISM: Artificial Sequence
<220> FEATURE:
<223> OTHER INFORMATION: synthetic

<400> SEQUENCE: 88

Ala Arg Ile Pro Glu Phe Thr Ser Ser Ser Trp Ala Leu Tyr Tyr Phe
1               5                   10                  15

Tyr Gly Met Asp Val
            20

<210> SEQ ID NO 89
<211> LENGTH: 324
<212> TYPE: DNA
<213> ORGANISM: Artificial Sequence
<220> FEATURE:
<223> OTHER INFORMATION: synthetic

<400> SEQUENCE: 89
gaaattgtgt tgacgcagtc tccaggcacc ctgtctttgt ctccagggga aagcgccacc    60
ctctcctgca gggccagtca gagtattacc agcacctact tcgcctggta ccagcagaaa   120
```

-continued

```
cctggccagg ctcccaggct cctcatctat gctacatcca gcagggccac tggcgtccca      180
gacaggttca gtggcagtgg gtctgggacg gacttcactc tcaccatcag cagactggag      240
cctgatgatt ttgcagtgta ttactgtcag caatatggta ggtcaccttg gacgttcggc      300
caagggacca aggtggaagt caaa                                             324
```

<210> SEQ ID NO 90
<211> LENGTH: 108
<212> TYPE: PRT
<213> ORGANISM: Artificial Sequence
<220> FEATURE:
<223> OTHER INFORMATION: synthetic

<400> SEQUENCE: 90

Glu Ile Val Leu Thr Gln Ser Pro Gly Thr Leu Ser Leu Ser Pro Gly
1               5                   10                  15

Glu Ser Ala Thr Leu Ser Cys Arg Ala Ser Gln Ser Ile Thr Ser Thr
            20                  25                  30

Tyr Phe Ala Trp Tyr Gln Gln Lys Pro Gly Gln Ala Pro Arg Leu Leu
        35                  40                  45

Ile Tyr Ala Thr Ser Ser Arg Ala Thr Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Asp Asp Phe Ala Val Tyr Tyr Cys Gln Gln Tyr Gly Arg Ser Pro
                85                  90                  95

Trp Thr Phe Gly Gln Gly Thr Lys Val Glu Val Lys
            100                 105

<210> SEQ ID NO 91
<211> LENGTH: 21
<212> TYPE: DNA
<213> ORGANISM: Artificial Sequence
<220> FEATURE:
<223> OTHER INFORMATION: synthetic

<400> SEQUENCE: 91
cagagtatta ccagcaccta c                                                21

<210> SEQ ID NO 92
<211> LENGTH: 7
<212> TYPE: PRT
<213> ORGANISM: Artificial Sequence
<220> FEATURE:
<223> OTHER INFORMATION: synthetic

<400> SEQUENCE: 92

Gln Ser Ile Thr Ser Thr Tyr
1               5

<210> SEQ ID NO 93
<211> LENGTH: 9
<212> TYPE: DNA
<213> ORGANISM: Artificial Sequence
<220> FEATURE:
<223> OTHER INFORMATION: synthetic

<400> SEQUENCE: 93 gctacatcc                                                              9

<210> SEQ ID NO 94

<210> SEQ ID NO 94
<211> LENGTH: 3
<212> TYPE: PRT
<213> ORGANISM: Artificial Sequence
<220> FEATURE:
<223> OTHER INFORMATION: synthetic

<400> SEQUENCE: 94

Ala Thr Ser
1

<210> SEQ ID NO 95
<211> LENGTH: 27
<212> TYPE: DNA
<213> ORGANISM: Artificial Sequence
<220> FEATURE:
<223> OTHER INFORMATION: synthetic

<400> SEQUENCE: 95
cagcaatatg gtaggtcacc ttggacg                                        27

<210> SEQ ID NO 96
<211> LENGTH: 9
<212> TYPE: PRT
<213> ORGANISM: Artificial Sequence
<220> FEATURE:
<223> OTHER INFORMATION: synthetic

<400> SEQUENCE: 96

Gln Gln Tyr Gly Arg Ser Pro Trp Thr
1               5

<210> SEQ ID NO 97
<211> LENGTH: 363
<212> TYPE: DNA
<213> ORGANISM: Artificial Sequence
<220> FEATURE:
<223> OTHER INFORMATION: synthetic

<400> SEQUENCE: 97
caggttcagc tggtgcagtc tggagctgag gtgaagaagc ctggggcctc agtgaaggtc    60
tcctgcaagg cttctggtta ccctttacc agttatggta tcagctgggt gcgacaggcc    120
cctggacaag ggcttgagtg gatgggatgg atcagcgctt acaatgataa cacaaactat   180
gcacagaagc tccagggcag agtcaccatg accgcagaca catccacgaa tacagcctac   240
atggagctaa ggagcctgag atctgacgac acggccattt attactgtgt gcgatggaat   300
tggggttccg tctactggta cttcgatctc tggggccgtg gcaccctggt cactgtctcc   360
tca                                                                 363

<210> SEQ ID NO 98
<211> LENGTH: 121
<212> TYPE: PRT
<213> ORGANISM: Artificial Sequence
<220> FEATURE:
<223> OTHER INFORMATION: synthetic

<400> SEQUENCE: 98

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Asp Asn Thr Asn Tyr Ala Gln Lys Leu
            50                  55                  60

Gln Gly Arg Val Thr Met Thr Ala Asp Thr Ser Thr Asn Thr Ala Tyr
 65                  70                  75                  80

Met Glu Leu Arg Ser Leu Arg Ser Asp Asp Thr Ala Ile Tyr Tyr Cys
                 85                  90                  95

Val Arg Trp Asn Trp Gly Ser Val Tyr Trp Tyr Phe Asp Leu Trp Gly
            100                 105                 110

Arg Gly Thr Leu Val Thr Val Ser Ser
        115                 120

<210> SEQ ID NO 99
<211> LENGTH: 24
<212> TYPE: DNA
<213> ORGANISM: Artificial Sequence
<220> FEATURE:
<223> OTHER INFORMATION: synthetic

<400> SEQUENCE: 99
ggttacacct ttaccagtta tggt                                           24

<210> SEQ ID NO 100
<211> LENGTH: 8
<212> TYPE: PRT
<213> ORGANISM: Artificial Sequence
<220> FEATURE:
<223> OTHER INFORMATION: synthetic

<400> SEQUENCE: 100

Gly Tyr Thr Phe Thr Ser Tyr Gly
 1               5

<210> SEQ ID NO 101
<211> LENGTH: 24
<212> TYPE: DNA
<213> ORGANISM: Artificial Sequence
<220> FEATURE:
<223> OTHER INFORMATION: synthetic

<400> SEQUENCE: 101
atcagcgctt acaatgataa caca                                           24

<210> SEQ ID NO 102
<211> LENGTH: 8
<212> TYPE: PRT
<213> ORGANISM: Artificial Sequence
<220> FEATURE:
<223> OTHER INFORMATION: synthetic

<400> SEQUENCE: 102

Ile Ser Ala Tyr Asn Asp Asn Thr
 1               5

<210> SEQ ID NO 103
<211> LENGTH: 42
<212> TYPE: DNA
<213> ORGANISM: Artificial Sequence
<220> FEATURE:
<223> OTHER INFORMATION: synthetic

<400> SEQUENCE: 103
gtgcgatgga attggggttc cgtctactgg tacttcgatc tc                       42

<210> SEQ ID NO 104

<211> LENGTH: 14
<212> TYPE: PRT
<213> ORGANISM: Artificial Sequence
<220> FEATURE:
<223> OTHER INFORMATION: synthetic

<400> SEQUENCE: 104

Val Arg Trp Asn Trp Gly Ser Val Tyr Trp Tyr Phe Asp Leu
1               5                   10

<210> SEQ ID NO 105
<211> LENGTH: 324
<212> TYPE: DNA
<213> ORGANISM: Artificial Sequence
<220> FEATURE:
<223> OTHER INFORMATION: synthetic

<400> SEQUENCE: 105
gaaattgtgt tgacgcagtc tccaggcacc ctgtctttgt ctccagggga aagagccacc      60
ctctcctgca gggccagtca gattattagc agcagctact tgcctggta ccagcagaaa     120 cctggccagg ctcccaggct cctcatctat ggtgcgtcca gcagggccac tggcatccca    180
gacaggttca gtggcagtgt gtctgggaca gacttcactc tcaccatcag cagactggag    240
cctgaagatt ttgcaatgta tttctgtcag cagtatggta actcaccttg gacgttcggc    300
caagggacca aggtggaaat caaa                                            324

<210> SEQ ID NO 106
<211> LENGTH: 108
<212> TYPE: PRT
<213> ORGANISM: Artificial Sequence
<220> FEATURE:
<223> OTHER INFORMATION: synthetic

<400> SEQUENCE: 106

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ile Ile Ser Ser Ser
                20                  25                  30

Tyr Phe Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Val Ser Gly Thr Asp Phe Thr Leu Thr Ile Ser Arg Leu Glu
65                  70                  75                  80

Pro Glu Asp Phe Ala Met Tyr Phe Cys Gln Gln Tyr Gly Asn Ser Pro
                85                  90                  95

Trp Thr Phe Gly Gln Gly Thr Lys Val Glu Ile Lys
            100                 105

<210> SEQ ID NO 107
<211> LENGTH: 21
<212> TYPE: DNA
<213> ORGANISM: Artificial Sequence
<220> FEATURE:
<223> OTHER INFORMATION: synthetic

<400> SEQUENCE: 107
cagattatta gcagcagcta c                                               21

<210> SEQ ID NO 108
<211> LENGTH: 7

<212> TYPE: PRT
<213> ORGANISM: Artificial Sequence
<220> FEATURE:
<223> OTHER INFORMATION: synthetic

<400> SEQUENCE: 108

Gln Ile Ile Ser Ser Ser Tyr
1               5

<210> SEQ ID NO 109
<211> LENGTH: 9
<212> TYPE: DNA
<213> ORGANISM: Artificial Sequence
<220> FEATURE:
<223> OTHER INFORMATION: synthetic

<400> SEQUENCE: 109 ggtgcgtcc                                                                9

<210> SEQ ID NO 110
<211> LENGTH: 3
<212> TYPE: PRT
<213> ORGANISM: Artificial Sequence
<220> FEATURE:
<223> OTHER INFORMATION: synthetic

<400> SEQUENCE: 110

Gly Ala Ser
1

<210> SEQ ID NO 111
<211> LENGTH: 27
<212> TYPE: DNA
<213> ORGANISM: Artificial Sequence
<220> FEATURE:
<223> OTHER INFORMATION: synthetic

<400> SEQUENCE: 111
cagcagtatg gtaactcacc ttggacg                                           27

<210> SEQ ID NO 112
<211> LENGTH: 9
<212> TYPE: PRT
<213> ORGANISM: Artificial Sequence
<220> FEATURE:
<223> OTHER INFORMATION: synthetic

<400> SEQUENCE: 112

Gln Gln Tyr Gly Asn Ser Pro Trp Thr
1               5

<210> SEQ ID NO 113
<211> LENGTH: 351
<212> TYPE: DNA
<213> ORGANISM: Artificial Sequence
<220> FEATURE:
<223> OTHER INFORMATION: synthetic

<400> SEQUENCE: 113
cagatcacct tgaaggagtc tggtcctacg ctggtgaaac ccacacagac cctcacgctg        60
acttgcacct tctctgggtt ctcactcaac actcatagag tgggtgtagg ctggatccgg      120
cagcccccag gaaaggccct ggagtggctt gcactcattt atgggaatga tgttaagaac      180 tacagccat ctctggagac caggctcacc atcgccaagg acacctccaa aaaccaggtg       240
gtccttacaa tgaccaacat ggaccctgtg gacacagcca catatttctg ttcgtacata      300

```
acgggggaag gaatgtactg gggccaggga accctggtca ccgtctcctc a         351
```

<210> SEQ ID NO 114
<211> LENGTH: 117
<212> TYPE: PRT
<213> ORGANISM: Artificial Sequence
<220> FEATURE:
<223> OTHER INFORMATION: synthetic

<400> SEQUENCE: 114

```
Gln Ile Thr Leu Lys Glu Ser Gly Pro Thr Leu Val Lys Pro Thr Gln
1               5                   10                  15
Thr Leu Thr Leu Thr Cys Thr Phe Ser Gly Phe Ser Leu Asn Thr His
            20                  25                  30
Arg Val Gly Val Gly Trp Ile Arg Gln Pro Pro Gly Lys Ala Leu Glu
        35                  40                  45
Trp Leu Ala Leu Ile Tyr Gly Asn Asp Val Lys Asn Tyr Ser Pro Ser
    50                  55                  60
Leu Glu Thr Arg Leu Thr Ile Ala Lys Asp Thr Ser Lys Asn Gln Val
65                  70                  75                  80
Val Leu Thr Met Thr Asn Met Asp Pro Val Asp Thr Ala Thr Tyr Phe
                85                  90                  95
Cys Ser Tyr Ile Thr Gly Glu Gly Met Tyr Trp Gly Gln Gly Thr Leu
            100                 105                 110
Val Thr Val Ser Ser
        115
```

<210> SEQ ID NO 115
<211> LENGTH: 30
<212> TYPE: DNA
<213> ORGANISM: Artificial Sequence
<220> FEATURE:
<223> OTHER INFORMATION: synthetic

<400> SEQUENCE: 115

```
gggttctcac tcaacactca tagagtgggt                                30
```

<210> SEQ ID NO 116
<211> LENGTH: 10
<212> TYPE: PRT
<213> ORGANISM: Artificial Sequence
<220> FEATURE:
<223> OTHER INFORMATION: synthetic

<400> SEQUENCE: 116

```
Gly Phe Ser Leu Asn Thr His Arg Val Gly
1               5                   10
```

<210> SEQ ID NO 117
<211> LENGTH: 21
<212> TYPE: DNA
<213> ORGANISM: Artificial Sequence
<220> FEATURE:
<223> OTHER INFORMATION: synthetic

<400> SEQUENCE: 117

```
atttatggga atgatgttaa g                                         21
```

<210> SEQ ID NO 118
<211> LENGTH: 7
<212> TYPE: PRT
<213> ORGANISM: Artificial Sequence
<220> FEATURE:
<223> OTHER INFORMATION: synthetic

<400> SEQUENCE: 118

Ile Tyr Gly Asn Asp Val Lys
1               5

<210> SEQ ID NO 119
<211> LENGTH: 27
<212> TYPE: DNA
<213> ORGANISM: Artificial Sequence
<220> FEATURE:
<223> OTHER INFORMATION: synthetic

<400> SEQUENCE: 119
tcgtacataa cggggggaagg aatgtac                                         27

<210> SEQ ID NO 120
<211> LENGTH: 9
<212> TYPE: PRT
<213> ORGANISM: Artificial Sequence
<220> FEATURE:
<223> OTHER INFORMATION: synthetic

<400> SEQUENCE: 120

Ser Tyr Ile Thr Gly Glu Gly Met Tyr
1               5

<210> SEQ ID NO 121
<211> LENGTH: 333
<212> TYPE: DNA
<213> ORGANISM: Artificial Sequence
<220> FEATURE:
<223> OTHER INFORMATION: synthetic

<400> SEQUENCE: 121
gatgttgtga tgactcagtc tccactctcc ctgtccgtca cccttggaca gccggcctcc      60
atttcctgta ggtctagtca aaacctcatg tacagtgatg gaaacaccta cttgaattgg     120
tttcaccaga ggccaggcca atctccaagg cgtctaattt ataaggtttc taaccgggac     180
tctggggtcc cagacagatt cagcggcagt gggtcaggca ctgatttcac actgaaaatc     240
agcagggtgg aggctgagga tgttgggggtt tattactgca tgcaaggtac acactggtac     300
acatttggcc aggggaccaa gctggagatc aaa                                  333

<210> SEQ ID NO 122
<211> LENGTH: 111
<212> TYPE: PRT
<213> ORGANISM: Artificial Sequence
<220> FEATURE:
<223> OTHER INFORMATION: synthetic

<400> SEQUENCE: 122

Asp Val Val Met Thr Gln Ser Pro Leu Ser Leu Ser Val Thr Leu Gly
1               5                   10                  15

Gln Pro Ala Ser Ile Ser Cys Arg Ser Ser Gln Asn Leu Met Tyr Ser
            20                  25                  30

Asp Gly Asn Thr Tyr Leu Asn Trp Phe His Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
            85                  90                  95

Thr His Trp Tyr Thr Phe Gly Gln Gly Thr Lys Leu Glu Ile Lys
            100                 105                 110

<210> SEQ ID NO 123
<211> LENGTH: 33
<212> TYPE: DNA
<213> ORGANISM: Artificial Sequence
<220> FEATURE:
<223> OTHER INFORMATION: synthetic

<400> SEQUENCE: 123
caaaacctca tgtacagtga tggaaacacc tac                                   33

<210> SEQ ID NO 124
<211> LENGTH: 11
<212> TYPE: PRT
<213> ORGANISM: Artificial Sequence
<220> FEATURE:
<223> OTHER INFORMATION: synthetic

<400> SEQUENCE: 124

Gln Asn Leu Met Tyr Ser Asp Gly Asn Thr Tyr
1               5                   10

<210> SEQ ID NO 125
<211> LENGTH: 9
<212> TYPE: DNA
<213> ORGANISM: Artificial Sequence
<220> FEATURE:
<223> OTHER INFORMATION: synthetic

<400> SEQUENCE: 125 aaggtttct                                                              9

<210> SEQ ID NO 126
<211> LENGTH: 3
<212> TYPE: PRT
<213> ORGANISM: Artificial Sequence
<220> FEATURE:
<223> OTHER INFORMATION: synthetic

<400> SEQUENCE: 126

Lys Val Ser
1

<210> SEQ ID NO 127
<211> LENGTH: 24
<212> TYPE: DNA
<213> ORGANISM: Artificial Sequence
<220> FEATURE:
<223> OTHER INFORMATION: synthetic

<400> SEQUENCE: 127
atgcaaggta cacactggta caca                                             24

<210> SEQ ID NO 128
<211> LENGTH: 8
<212> TYPE: PRT
<213> ORGANISM: Artificial Sequence
<220> FEATURE:
<223> OTHER INFORMATION: synthetic

<400> SEQUENCE: 128

Met Gln Gly Thr His Trp Tyr Thr
1               5

<210> SEQ ID NO 129
<211> LENGTH: 357
<212> TYPE: DNA
<213> ORGANISM: Artificial Sequence
<220> FEATURE:
<223> OTHER INFORMATION: synthetic

<400> SEQUENCE: 129

```
caggtgcagc tgcagcagtg gggcgcagga ctattgaagc cttcggagac cctgtccctc      60
acctgcgctg tctatggtgg gtctttcagt ggttattact ggagctggat ccgccagccc     120
ccagggaagg gtctggaatg gattggggaa atcaatcata gaggaaacac caactacaac     180
ccgtccctca gagtcgagt caccatatca ctcgacacgt ccaagaaaca gttctccctg      240
aacctgagtt ctgtgaccgc cgcggacacg gctatgtatt actgtacgag agacgaagaa     300
caggaactac gtttccttga ctactggggc cagggaaccc tggtcaccgt ctcctca       357
```

<210> SEQ ID NO 130
<211> LENGTH: 119
<212> TYPE: PRT
<213> ORGANISM: Artificial Sequence
<220> FEATURE:
<223> OTHER INFORMATION: synthetic

<400> SEQUENCE: 130

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Asn Thr Asn Tyr Asn Pro Ser Leu Lys
    50                  55                  60

Ser Arg Val Thr Ile Ser Leu Asp Thr Ser Lys Lys Gln Phe Ser Leu
65                  70                  75                  80

Asn Leu Ser Ser Val Thr Ala Ala Asp Thr Ala Met Tyr Tyr Cys Thr
                85                  90                  95

Arg Asp Glu Glu Gln Glu Leu Arg Phe Leu Asp Tyr Trp Gly Gln Gly
            100                 105                 110

Thr Leu Val Thr Val Ser Ser
        115

<210> SEQ ID NO 131
<211> LENGTH: 24
<212> TYPE: DNA
<213> ORGANISM: Artificial Sequence
<220> FEATURE:
<223> OTHER INFORMATION: synthetic

<400> SEQUENCE: 131

```
ggtgggtctt tcagtggtta ttac                                             24
```

<210> SEQ ID NO 132
<211> LENGTH: 8
<212> TYPE: PRT
<213> ORGANISM: Artificial Sequence
<220> FEATURE:
<223> OTHER INFORMATION: synthetic

<400> SEQUENCE: 132

Gly Gly Ser Phe Ser Gly Tyr Tyr
1               5

<210> SEQ ID NO 133
<211> LENGTH: 21
<212> TYPE: DNA
<213> ORGANISM: Artificial Sequence
<220> FEATURE:
<223> OTHER INFORMATION: synthetic

<400> SEQUENCE: 133
atcaatcata gaggaaacac c                                      21

<210> SEQ ID NO 134
<211> LENGTH: 7
<212> TYPE: PRT
<213> ORGANISM: Artificial Sequence
<220> FEATURE:
<223> OTHER INFORMATION: synthetic

<400> SEQUENCE: 134

Ile Asn His Arg Gly Asn Thr
1               5

<210> SEQ ID NO 135
<211> LENGTH: 39
<212> TYPE: DNA
<213> ORGANISM: Artificial Sequence
<220> FEATURE:
<223> OTHER INFORMATION: synthetic

<400> SEQUENCE: 135
acgagagacg aagaacagga actacgtttc cttgactac                   39

<210> SEQ ID NO 136
<211> LENGTH: 13
<212> TYPE: PRT
<213> ORGANISM: Artificial Sequence
<220> FEATURE:
<223> OTHER INFORMATION: synthetic

<400> SEQUENCE: 136

Thr Arg Asp Glu Glu Gln Glu Leu Arg Phe Leu Asp Tyr
1               5                   10

<210> SEQ ID NO 137
<211> LENGTH: 321
<212> TYPE: DNA
<213> ORGANISM: Artificial Sequence
<220> FEATURE:
<223> OTHER INFORMATION: synthetic

<400> SEQUENCE: 137
gagattgtgt tgacacagtc tccagccacc ctgtctttgt ctccagggga aagagccacc    60
ctctcctgca gggccagtca ggatattagc acctacttag cctggtacca acagagagct   120
ggccaggctc ccaggctcct catctatggt gcttccaaca gggccactgg catcccagcc   180
aggttcagtg gcagtgggtc tgggacagac ttcactctca ccatcagcag cctagagcct   240
gaagattttg catttttatta ctgtcaacag cgcagcaact ggccgctcac tttcggcgga   300
gggaccgagg tggagatcaa a                                             321

<210> SEQ ID NO 138

<211> LENGTH: 107
<212> TYPE: PRT
<213> ORGANISM: Artificial Sequence
<220> FEATURE:
<223> OTHER INFORMATION: synthetic

<400> SEQUENCE: 138

```
Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Asp Ile Ser Thr Tyr
            20                  25                  30
Leu Ala Trp Tyr Gln Gln Arg Ala Gly Gln Ala Pro Arg Leu Leu Ile
        35                  40                  45
Tyr Gly Ala Ser Asn Arg Ala Thr Gly Ile Pro Ala Arg Phe Ser Gly
50                  55                  60
Ser Gly Ser Gly Thr Asp Phe Thr Leu Thr Ile Ser Ser Leu Glu Pro
65                  70                  75                  80
Glu Asp Phe Ala Phe Tyr Tyr Cys Gln Gln Arg Ser Asn Trp Pro Leu
                85                  90                  95
Thr Phe Gly Gly Gly Thr Glu Val Glu Ile Lys
            100                 105
```

<210> SEQ ID NO 139
<211> LENGTH: 18
<212> TYPE: DNA
<213> ORGANISM: Artificial Sequence
<220> FEATURE:
<223> OTHER INFORMATION: synthetic

<400> SEQUENCE: 139
caggatatta gcacctac                                                    18

<210> SEQ ID NO 140
<211> LENGTH: 6
<212> TYPE: PRT
<213> ORGANISM: Artificial Sequence
<220> FEATURE:
<223> OTHER INFORMATION: synthetic

<400> SEQUENCE: 140

```
Gln Asp Ile Ser Thr Tyr
1               5
```

<210> SEQ ID NO 141
<211> LENGTH: 9
<212> TYPE: DNA
<213> ORGANISM: Artificial Sequence
<220> FEATURE:
<223> OTHER INFORMATION: synthetic

<400> SEQUENCE: 141 ggtgcttcc                                                               9

<210> SEQ ID NO 142
<211> LENGTH: 3
<212> TYPE: PRT
<213> ORGANISM: Artificial Sequence
<220> FEATURE:
<223> OTHER INFORMATION: synthetic

<400> SEQUENCE: 142

```
Gly Ala Ser
1
```

<210> SEQ ID NO 143
<211> LENGTH: 27
<212> TYPE: DNA
<213> ORGANISM: Artificial Sequence
<220> FEATURE:
<223> OTHER INFORMATION: synthetic

<400> SEQUENCE: 143
caacagcgca gcaactggcc gctcact                                          27

<210> SEQ ID NO 144
<211> LENGTH: 9
<212> TYPE: PRT
<213> ORGANISM: Artificial Sequence
<220> FEATURE:
<223> OTHER INFORMATION: synthetic

<400> SEQUENCE: 144

Gln Gln Arg Ser Asn Trp Pro Leu Thr
1               5

<210> SEQ ID NO 145
<211> LENGTH: 366
<212> TYPE: DNA
<213> ORGANISM: Artificial Sequence
<220> FEATURE:
<223> OTHER INFORMATION: synthetic

<400> SEQUENCE: 145
caggtgcagc tacagcagtg gggcgcagga ctgttgaagc cttcggagac cctgtccctc      60
acctgcgttg tccatggtgg gtccttcagt ggttactact ggaactggat ccgccagccc     120
ccagggaagg gctggagtg gattggggaa atcaatcata gaggaaacac caactacaac      180
ccgtccctca agagtcgagt caccgtatca gaagacacgt ccaagaacca gttctccctg     240
aagctgagct ctttgaccgc cgcggacacg gctgtgtatt actgtgtgag aggagaggat     300
tacgattttt ggagtgatta ttataatgac tactggggcc agggaaccct ggtcaccgtc     360
tcctca                                                                366

<210> SEQ ID NO 146
<211> LENGTH: 122
<212> TYPE: PRT
<213> ORGANISM: Artificial Sequence
<220> FEATURE:
<223> OTHER INFORMATION: synthetic

<400> SEQUENCE: 146

Gln Val Gln Leu Gln Gln Trp Gly Ala Gly Leu Leu Lys Pro Ser Glu
1               5                   10                  15

Thr Leu Ser Leu Thr Cys Val Val His Gly Gly Ser Phe Ser Gly Tyr
            20                  25                  30

Tyr Trp Asn Trp Ile Arg Gln Pro Pro Gly Lys Gly Leu Glu Trp Ile
        35                  40                  45

Gly Glu Ile Asn His Arg Gly Asn Thr Asn Tyr Asn Pro Ser Leu Lys
    50                  55                  60

Ser Arg Val Thr Val Ser Glu Asp Thr Ser Lys Asn Gln Phe Ser Leu
65                  70                  75                  80

Lys Leu Ser Ser Leu Thr Ala Ala Asp Thr Ala Val Tyr Tyr Cys Val
                85                  90                  95

Arg Gly Glu Asp Tyr Asp Phe Trp Ser Asp Tyr Tyr Asn Asp Tyr Trp
            100                 105                 110

Gly Gln Gly Thr Leu Val Thr Val Ser Ser
        115                 120

<210> SEQ ID NO 147
<211> LENGTH: 24
<212> TYPE: DNA
<213> ORGANISM: Artificial Sequence
<220> FEATURE:
<223> OTHER INFORMATION: synthetic

<400> SEQUENCE: 147
ggtgggtcct tcagtggtta ctac                                              24

<210> SEQ ID NO 148
<211> LENGTH: 8
<212> TYPE: PRT
<213> ORGANISM: Artificial Sequence
<220> FEATURE:
<223> OTHER INFORMATION: synthetic

<400> SEQUENCE: 148

Gly Gly Ser Phe Ser Gly Tyr Tyr
1               5

<210> SEQ ID NO 149
<211> LENGTH: 21
<212> TYPE: DNA
<213> ORGANISM: Artificial Sequence
<220> FEATURE:
<223> OTHER INFORMATION: synthetic

<400> SEQUENCE: 149
atcaatcata gaggaaacac c                                                 21

<210> SEQ ID NO 150
<211> LENGTH: 7
<212> TYPE: PRT
<213> ORGANISM: Artificial Sequence
<220> FEATURE:
<223> OTHER INFORMATION: synthetic

<400> SEQUENCE: 150

Ile Asn His Arg Gly Asn Thr
1               5

<210> SEQ ID NO 151
<211> LENGTH: 48
<212> TYPE: DNA
<213> ORGANISM: Artificial Sequence
<220> FEATURE:
<223> OTHER INFORMATION: synthetic

<400> SEQUENCE: 151
gtgagaggag aggattacga tttttggagt gattattata atgactac                    48

<210> SEQ ID NO 152
<211> LENGTH: 16
<212> TYPE: PRT
<213> ORGANISM: Artificial Sequence
<220> FEATURE:
<223> OTHER INFORMATION: synthetic

<400> SEQUENCE: 152

Val Arg Gly Glu Asp Tyr Asp Phe Trp Ser Asp Tyr Tyr Asn Asp Tyr
1               5                   10                  15

-continued

```
<210> SEQ ID NO 153
<211> LENGTH: 321
<212> TYPE: DNA
<213> ORGANISM: Artificial Sequence
<220> FEATURE:
<223> OTHER INFORMATION: synthetic

<400> SEQUENCE: 153
gaaattgtgt tgacacagtc tccagccacc ctgtctttgt ctccagggga aagagccacc    60
ctctcctgca gggccagtca gactattagc agctacttag cctggcacca acagaaacct   120
ggccaggctc ccaggctcct catctatgat gcatccaaaa gggccacggg catcccagcc   180
aggttcagtg gcagtgggtc tgggacagac ttcactctca ccatcaccag cctagagcct   240
gaagattttg cagtttatta ctgtcagcag cgtagcaact ggcctctcac tttcggcgga   300
gggaccaagg tggagatcaa a                                             321

<210> SEQ ID NO 154
<211> LENGTH: 107
<212> TYPE: PRT
<213> ORGANISM: Artificial Sequence
<220> FEATURE:
<223> OTHER INFORMATION: synthetic

<400> SEQUENCE: 154

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Thr Ile Ser Ser Tyr
            20                  25                  30

Leu Ala Trp His Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Thr Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 155
<211> LENGTH: 18
<212> TYPE: DNA
<213> ORGANISM: Artificial Sequence
<220> FEATURE:
<223> OTHER INFORMATION: synthetic

<400> SEQUENCE: 155
cagactatta gcagctac                                                  18

<210> SEQ ID NO 156
<211> LENGTH: 6
<212> TYPE: PRT
<213> ORGANISM: Artificial Sequence
<220> FEATURE:
<223> OTHER INFORMATION: synthetic

<400> SEQUENCE: 156

Gln Thr Ile Ser Ser Tyr
1               5
```

<210> SEQ ID NO 157
<211> LENGTH: 9
<212> TYPE: DNA
<213> ORGANISM: Artificial Sequence
<220> FEATURE:
<223> OTHER INFORMATION: synthetic

<400> SEQUENCE: 157 gatgcatcc                                                                9

<210> SEQ ID NO 158
<211> LENGTH: 3
<212> TYPE: PRT
<213> ORGANISM: Artificial Sequence
<220> FEATURE:
<223> OTHER INFORMATION: synthetic

<400> SEQUENCE: 158

Asp Ala Ser
1

<210> SEQ ID NO 159
<211> LENGTH: 27
<212> TYPE: DNA
<213> ORGANISM: Artificial Sequence
<220> FEATURE:
<223> OTHER INFORMATION: synthetic

<400> SEQUENCE: 159
cagcagcgta gcaactggcc tctcact                                            27

<210> SEQ ID NO 160
<211> LENGTH: 9
<212> TYPE: PRT
<213> ORGANISM: Artificial Sequence
<220> FEATURE:
<223> OTHER INFORMATION: synthetic

<400> SEQUENCE: 160

Gln Gln Arg Ser Asn Trp Pro Leu Thr
1               5

<210> SEQ ID NO 161
<211> LENGTH: 372
<212> TYPE: DNA
<213> ORGANISM: Artificial Sequence
<220> FEATURE:
<223> OTHER INFORMATION: synthetic

<400> SEQUENCE: 161
caggtgcagc tacagcagtg gggcgcagga ctgttgccgc cttcggagac cctgtccctc        60
atctgcgctg tctatggtgg gtccttcagt ggttactact ggagctggat ccgccagccc       120
ccagggaagg ggctggagtg gattgggaa atcaatcata gaggaagcac caactacaac        180
ccgtccctca agagtcgagc caccatatca gttgacacgt ccaagaacca gttctccctg      240
aagctgagct ctgtgaccgc cgcggacacg gctgtgtatt actgttcgag aggcgaggat       300
tactatgata gtagtggtta ctcgtactac tttgactact ggggccaggg aaccctggtc       360
accgtctcct ca                                                          372

<210> SEQ ID NO 162
<211> LENGTH: 124
<212> TYPE: PRT
<213> ORGANISM: Artificial Sequence
<220> FEATURE:

<223> OTHER INFORMATION: synthetic

<400> SEQUENCE: 162

Gln Val Gln Leu Gln Gln Trp Gly Ala Gly Leu Leu Pro Pro Ser Glu
1               5                   10                  15

Thr Leu Ser Leu Ile Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Thr Asn Tyr Asn Pro Ser Leu Lys
    50                  55                  60

Ser Arg Ala Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ser
                85                  90                  95

Arg Gly Glu Asp Tyr Tyr Asp Ser Ser Gly Tyr Ser Tyr Tyr Phe Asp
            100                 105                 110

Tyr Trp Gly Gln Gly Thr Leu Val Thr Val Ser Ser
        115                 120

<210> SEQ ID NO 163
<211> LENGTH: 24
<212> TYPE: DNA
<213> ORGANISM: Artificial Sequence
<220> FEATURE:
<223> OTHER INFORMATION: synthetic

<400> SEQUENCE: 163
ggtgggtcct tcagtggtta ctac                                          24

<210> SEQ ID NO 164
<211> LENGTH: 8
<212> TYPE: PRT
<213> ORGANISM: Artificial Sequence
<220> FEATURE:
<223> OTHER INFORMATION: synthetic

<400> SEQUENCE: 164

Gly Gly Ser Phe Ser Gly Tyr Tyr
1               5

<210> SEQ ID NO 165
<211> LENGTH: 21
<212> TYPE: DNA
<213> ORGANISM: Artificial Sequence
<220> FEATURE:
<223> OTHER INFORMATION: synthetic

<400> SEQUENCE: 165
atcaatcata gaggaagcac c                                             21

<210> SEQ ID NO 166
<211> LENGTH: 7
<212> TYPE: PRT
<213> ORGANISM: Artificial Sequence
<220> FEATURE:
<223> OTHER INFORMATION: synthetic

<400> SEQUENCE: 166

Ile Asn His Arg Gly Ser Thr
1               5

<210> SEQ ID NO 167
<211> LENGTH: 54
<212> TYPE: DNA
<213> ORGANISM: Artificial Sequence
<220> FEATURE:
<223> OTHER INFORMATION: synthetic

<400> SEQUENCE: 167

```
tcgagaggcg aggattacta tgatagtagt ggttactcgt actactttga ctac        54
```

<210> SEQ ID NO 168
<211> LENGTH: 18
<212> TYPE: PRT
<213> ORGANISM: Artificial Sequence
<220> FEATURE:
<223> OTHER INFORMATION: synthetic

<400> SEQUENCE: 168

Ser Arg Gly Glu Asp Tyr Tyr Asp Ser Ser Gly Tyr Ser Tyr Phe
1               5                   10                  15

Asp Tyr

<210> SEQ ID NO 169
<211> LENGTH: 321
<212> TYPE: DNA
<213> ORGANISM: Artificial Sequence
<220> FEATURE:
<223> OTHER INFORMATION: synthetic

<400> SEQUENCE: 169

```
gaaattgtgt tgacacagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggccgctcac tttcggcgga   300
gggaccaagg tggagatcaa a                                             321
```

<210> SEQ ID NO 170
<211> LENGTH: 107
<212> TYPE: PRT
<213> ORGANISM: Artificial Sequence
<220> FEATURE:
<223> OTHER INFORMATION: synthetic

<400> SEQUENCE: 170

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 171
<211> LENGTH: 18
<212> TYPE: DNA
<213> ORGANISM: Artificial Sequence
<220> FEATURE:
<223> OTHER INFORMATION: synthetic

<400> SEQUENCE: 171
cagagtgtta gcagctac                                               18

<210> SEQ ID NO 172
<211> LENGTH: 6
<212> TYPE: PRT
<213> ORGANISM: Artificial Sequence
<220> FEATURE:
<223> OTHER INFORMATION: synthetic

<400> SEQUENCE: 172

Gln Ser Val Ser Ser Tyr
1               5

<210> SEQ ID NO 173
<211> LENGTH: 9
<212> TYPE: DNA
<213> ORGANISM: Artificial Sequence
<220> FEATURE:
<223> OTHER INFORMATION: synthetic

<400> SEQUENCE: 173 gatgcatcc                                                          9

<210> SEQ ID NO 174
<211> LENGTH: 3
<212> TYPE: PRT
<213> ORGANISM: Artificial Sequence
<220> FEATURE:
<223> OTHER INFORMATION: synthetic

<400> SEQUENCE: 174

Asp Ala Ser
1

<210> SEQ ID NO 175
<211> LENGTH: 27
<212> TYPE: DNA
<213> ORGANISM: Artificial Sequence
<220> FEATURE:
<223> OTHER INFORMATION: synthetic

<400> SEQUENCE: 175
cagcagcgta gcaactggcc gctcact                                     27

<210> SEQ ID NO 176
<211> LENGTH: 9
<212> TYPE: PRT
<213> ORGANISM: Artificial Sequence
<220> FEATURE:
<223> OTHER INFORMATION: synthetic

<400> SEQUENCE: 176

Gln Gln Arg Ser Asn Trp Pro Leu Thr
1               5

<210> SEQ ID NO 177
<211> LENGTH: 366
<212> TYPE: DNA

<213> ORGANISM: Artificial Sequence
<220> FEATURE:
<223> OTHER INFORMATION: synthetic

<400> SEQUENCE: 177

```
caggtgcagc tacagcagtg gggcgcagga ctgttgaggc cttcggagac cctgtccctc    60
acctgcgctg tctatggtgg gtccttcagt ggttactact ggaattggat ccgccagtcc   120
ccagggacgg ggctggagtg gattggggaa atcaatcata gagggaacat caacttcaac   180
ccgtccctca agagtcgagt caccatatca gaggacacgt ccaaaaacca attctccctg   240
aggctgaact ctgtgaccgc cgcggacacg gctgtgtatt actgtgcgag aggagaggat   300
tacgatattt ggagtggtta ttatagggag tactggggcc agggaaccct ggtcaccgtc   360
tcctca                                                              366
```

<210> SEQ ID NO 178
<211> LENGTH: 122
<212> TYPE: PRT
<213> ORGANISM: Artificial Sequence
<220> FEATURE:
<223> OTHER INFORMATION: synthetic

<400> SEQUENCE: 178

Gln Val Gln Leu Gln Gln Trp Gly Ala Gly Leu Leu Arg Pro Ser Glu
1               5                   10                  15

Thr Leu Ser Leu Thr Cys Ala Val Tyr Gly Gly Ser Phe Ser Gly Tyr
            20                  25                  30

Tyr Trp Asn Trp Ile Arg Gln Ser Pro Gly Thr Gly Leu Glu Trp Ile
        35                  40                  45

Gly Glu Ile Asn His Arg Gly Asn Ile Asn Phe Asn Pro Ser Leu Lys
    50                  55                  60

Ser Arg Val Thr Ile Ser Glu Asp Thr Ser Lys Asn Gln Phe Ser Leu
65                  70                  75                  80

Arg Leu Asn Ser Val Thr Ala Ala Asp Thr Ala Val Tyr Tyr Cys Ala
                85                  90                  95

Arg Gly Glu Asp Tyr Asp Ile Trp Ser Gly Tyr Tyr Arg Glu Tyr Trp
            100                 105                 110

Gly Gln Gly Thr Leu Val Thr Val Ser Ser
        115                 120

<210> SEQ ID NO 179
<211> LENGTH: 24
<212> TYPE: DNA
<213> ORGANISM: Artificial Sequence
<220> FEATURE:
<223> OTHER INFORMATION: synthetic

<400> SEQUENCE: 179

```
ggtgggtcct tcagtggtta ctac                                           24
```

<210> SEQ ID NO 180
<211> LENGTH: 8
<212> TYPE: PRT
<213> ORGANISM: Artificial Sequence
<220> FEATURE:
<223> OTHER INFORMATION: synthetic

<400> SEQUENCE: 180

Gly Gly Ser Phe Ser Gly Tyr Tyr
1               5

<210> SEQ ID NO 181
<211> LENGTH: 21
<212> TYPE: DNA
<213> ORGANISM: Artificial Sequence
<220> FEATURE:
<223> OTHER INFORMATION: synthetic

<400> SEQUENCE: 181
atcaatcata gagggaacat c                                              21

<210> SEQ ID NO 182
<211> LENGTH: 7
<212> TYPE: PRT
<213> ORGANISM: Artificial Sequence
<220> FEATURE:
<223> OTHER INFORMATION: synthetic

<400> SEQUENCE: 182

Ile Asn His Arg Gly Asn Ile
1               5

<210> SEQ ID NO 183
<211> LENGTH: 48
<212> TYPE: DNA
<213> ORGANISM: Artificial Sequence
<220> FEATURE:
<223> OTHER INFORMATION: synthetic

<400> SEQUENCE: 183
gcgagaggag aggattacga tatttggagt ggttattata gggagtac                 48

<210> SEQ ID NO 184
<211> LENGTH: 16
<212> TYPE: PRT
<213> ORGANISM: Artificial Sequence
<220> FEATURE:
<223> OTHER INFORMATION: synthetic

<400> SEQUENCE: 184

Ala Arg Gly Glu Asp Tyr Asp Ile Trp Ser Gly Tyr Tyr Arg Glu Tyr
1               5                   10                  15

<210> SEQ ID NO 185
<211> LENGTH: 321
<212> TYPE: DNA
<213> ORGANISM: Artificial Sequence
<220> FEATURE:
<223> OTHER INFORMATION: synthetic

<400> SEQUENCE: 185
gaaattgtgt tgacacagtc tccagccacc ctgtctttgt ctccagggga aagagccact    60
ctctcctgca gggccagtca gagtgttagc agctacttag cctggtacca gcagaaacct   120
ggccaggctc ccaggctcct catctatgat gcatccaaga gggccactgg catcccagcc   180
aggttcagtg gcagtgggtc tgggacagac ttcactctca ccatcagcag cctagagcct   240
gaagattttg ctgtttatta ctgtcagcag cgtagcaact ggcctctcgc tttcggcgga   300
gggaccaagg tggagatcaa a                                             321

<210> SEQ ID NO 186
<211> LENGTH: 107
<212> TYPE: PRT
<213> ORGANISM: Artificial Sequence
<220> FEATURE:
<223> OTHER INFORMATION: synthetic

<400> SEQUENCE: 186

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Ala Phe Gly Gly Gly Thr Lys Val Glu Ile Lys
            100                 105

<210> SEQ ID NO 187
<211> LENGTH: 18
<212> TYPE: DNA
<213> ORGANISM: Artificial Sequence
<220> FEATURE:
<223> OTHER INFORMATION: synthetic

<400> SEQUENCE: 187
cagagtgtta gcagctac                                                 18

<210> SEQ ID NO 188
<211> LENGTH: 6
<212> TYPE: PRT
<213> ORGANISM: Artificial Sequence
<220> FEATURE:
<223> OTHER INFORMATION: synthetic

<400> SEQUENCE: 188

Gln Ser Val Ser Ser Tyr
1               5

<210> SEQ ID NO 189
<211> LENGTH: 9
<212> TYPE: DNA
<213> ORGANISM: Artificial Sequence
<220> FEATURE:
<223> OTHER INFORMATION: synthetic

<400> SEQUENCE: 189 gatgcatcc                                                            9

<210> SEQ ID NO 190
<211> LENGTH: 3
<212> TYPE: PRT
<213> ORGANISM: Artificial Sequence
<220> FEATURE:
<223> OTHER INFORMATION: synthetic

<400> SEQUENCE: 190

Asp Ala Ser
1

<210> SEQ ID NO 191
<211> LENGTH: 27
<212> TYPE: DNA
<213> ORGANISM: Artificial Sequence
<220> FEATURE:
<223> OTHER INFORMATION: synthetic

<400> SEQUENCE: 191
cagcagcgta gcaactggcc tctcgct                                            27

<210> SEQ ID NO 192
<211> LENGTH: 9
<212> TYPE: PRT
<213> ORGANISM: Artificial Sequence
<220> FEATURE:
<223> OTHER INFORMATION: synthetic

<400> SEQUENCE: 192

Gln Gln Arg Ser Asn Trp Pro Leu Ala
1               5

<210> SEQ ID NO 193
<211> LENGTH: 357
<212> TYPE: DNA
<213> ORGANISM: Artificial Sequence
<220> FEATURE:
<223> OTHER INFORMATION: synthetic

<400> SEQUENCE: 193
caggtgcagc tacagcagtg gggcgcagga ctgttgaagc cttcggagac cctgtccctc        60
acctgcgctg tctatggtgg gtccttcagt gagttctact ggaactggat ccgccagccc       120
ccagagaagg gcctggagtg gattggggaa atcaatcatc gtggaaacac caactacaac       180
ccgtccctca agagtcgagt caccatatca gtagacatgt ccaagaacca gttctccctg       240
cagctgaact ctgtgaccgt cgcggacacg gctctgtatt actgtgcgtt tggctacgat       300
tttcggagtt cttatgagga cgtctggggc caagggacca cggtcaccgt ctcctca         357

<210> SEQ ID NO 194
<211> LENGTH: 119
<212> TYPE: PRT
<213> ORGANISM: Artificial Sequence
<220> FEATURE:
<223> OTHER INFORMATION: synthetic

<400> SEQUENCE: 194

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Glu Phe
            20                  25                  30

Tyr Trp Asn Trp Ile Arg Gln Pro Pro Glu Lys Gly Leu Glu Trp Ile
        35                  40                  45

Gly Glu Ile Asn His Arg Gly Asn Thr Asn Tyr Asn Pro Ser Leu Lys
    50                  55                  60

Ser Arg Val Thr Ile Ser Val Asp Met Ser Lys Asn Gln Phe Ser Leu
65                  70                  75                  80

Gln Leu Asn Ser Val Thr Val Ala Asp Thr Ala Leu Tyr Tyr Cys Ala
                85                  90                  95

Phe Gly Tyr Asp Phe Arg Ser Ser Tyr Glu Asp Val Trp Gly Gln Gly
            100                 105                 110

Thr Thr Val Thr Val Ser Ser
        115

<210> SEQ ID NO 195
<211> LENGTH: 24

```
<212> TYPE: DNA
<213> ORGANISM: Artificial Sequence
<220> FEATURE:
<223> OTHER INFORMATION: synthetic

<400> SEQUENCE: 195
ggtgggtcct tcagtgagtt ctac                                          24

<210> SEQ ID NO 196
<211> LENGTH: 8
<212> TYPE: PRT
<213> ORGANISM: Artificial Sequence
<220> FEATURE:
<223> OTHER INFORMATION: synthetic

<400> SEQUENCE: 196

Gly Gly Ser Phe Ser Glu Phe Tyr
1               5

<210> SEQ ID NO 197
<211> LENGTH: 21
<212> TYPE: DNA
<213> ORGANISM: Artificial Sequence
<220> FEATURE:
<223> OTHER INFORMATION: synthetic

<400> SEQUENCE: 197
atcaatcatc gtggaaacac c                                             21

<210> SEQ ID NO 198
<211> LENGTH: 7
<212> TYPE: PRT
<213> ORGANISM: Artificial Sequence
<220> FEATURE:
<223> OTHER INFORMATION: synthetic

<400> SEQUENCE: 198

Ile Asn His Arg Gly Asn Thr
1               5

<210> SEQ ID NO 199
<211> LENGTH: 39
<212> TYPE: DNA
<213> ORGANISM: Artificial Sequence
<220> FEATURE:
<223> OTHER INFORMATION: synthetic

<400> SEQUENCE: 199
gcgtttggct acgattttcg gagttcttat gaggacgtc                          39

<210> SEQ ID NO 200
<211> LENGTH: 13
<212> TYPE: PRT
<213> ORGANISM: Artificial Sequence
<220> FEATURE:
<223> OTHER INFORMATION: synthetic

<400> SEQUENCE: 200

Ala Phe Gly Tyr Asp Phe Arg Ser Ser Tyr Glu Asp Val
1               5                   10

<210> SEQ ID NO 201
<211> LENGTH: 321
<212> TYPE: DNA
<213> ORGANISM: Artificial Sequence
<220> FEATURE:
<223> OTHER INFORMATION: synthetic
```

<400> SEQUENCE: 201

```
gaaattgtgt tgacacagtc tccagccacc ctgtctttgt ctccagggga aagagccacc    60
ctctcctgca gggccagtca ggatattagc acctacttag cctggcacca acagaaacct   120
ggccagcctc ccaggctcct catctatggt tcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggcctctcac tttcggcgga   300
gggaccaagg tggagatcaa a                                             321
```

<210> SEQ ID NO 202
<211> LENGTH: 107
<212> TYPE: PRT
<213> ORGANISM: Artificial Sequence
<220> FEATURE:
<223> OTHER INFORMATION: synthetic

<400> SEQUENCE: 202

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Thr Tyr
            20                  25                  30

Leu Ala Trp His Gln Gln Lys Pro Gly Gln Pro Pro Arg Leu Leu Ile
        35                  40                  45

Tyr Gly Ser Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105
```

<210> SEQ ID NO 203
<211> LENGTH: 18
<212> TYPE: DNA
<213> ORGANISM: Artificial Sequence
<220> FEATURE:
<223> OTHER INFORMATION: synthetic

<400> SEQUENCE: 203

```
caggatatta gcacctac                                                  18
```

<210> SEQ ID NO 204
<211> LENGTH: 6
<212> TYPE: PRT
<213> ORGANISM: Artificial Sequence
<220> FEATURE:
<223> OTHER INFORMATION: synthetic

<400> SEQUENCE: 204

```
Gln Asp Ile Ser Thr Tyr
1               5
```

<210> SEQ ID NO 205
<211> LENGTH: 9
<212> TYPE: DNA
<213> ORGANISM: Artificial Sequence
<220> FEATURE:
<223> OTHER INFORMATION: synthetic

<400> SEQUENCE: 205 ggttcatcc                                                                                        9

<210> SEQ ID NO 206
<211> LENGTH: 3
<212> TYPE: PRT
<213> ORGANISM: Artificial Sequence
<220> FEATURE:
<223> OTHER INFORMATION: synthetic

<400> SEQUENCE: 206

Gly Ser Ser
1

<210> SEQ ID NO 207
<211> LENGTH: 27
<212> TYPE: DNA
<213> ORGANISM: Artificial Sequence
<220> FEATURE:
<223> OTHER INFORMATION: synthetic

<400> SEQUENCE: 207
cagcagcgta gcaactggcc tctcact                                                                   27

<210> SEQ ID NO 208
<211> LENGTH: 9
<212> TYPE: PRT
<213> ORGANISM: Artificial Sequence
<220> FEATURE:
<223> OTHER INFORMATION: synthetic

<400> SEQUENCE: 208

Gln Gln Arg Ser Asn Trp Pro Leu Thr
1               5

<210> SEQ ID NO 209
<211> LENGTH: 372
<212> TYPE: DNA
<213> ORGANISM: Artificial Sequence
<220> FEATURE:
<223> OTHER INFORMATION: synthetic

<400> SEQUENCE: 209
gaggtgcagc tgttggagtc tgggggaggc ttggtacagc cggggggtc cctgagactc        60 tcctgtgcag cctctggatt caccttcaga agctatgcca tgagttgggt ccgccaggct      120
ccagggaagg gctggagtg gtctcagtt attagtggtg gtggtggtag dacatactac       180
acagactccg tgaagggccg gttcaccatc tccagagaca attccaagag catgctgtat      240
ctgcaaatga acagcctgag agccgaggac acggccattt attactgtgc gaaagagagg      300
gtaactggaa tagaccacta ctactacggt gtggacgtct ggggccaagg gaccacggtc      360
accgtctcct ca                                                          372

<210> SEQ ID NO 210
<211> LENGTH: 124
<212> TYPE: PRT
<213> ORGANISM: Artificial Sequence
<220> FEATURE:
<223> OTHER INFORMATION: synthetic

<400> SEQUENCE: 210

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Arg Ser Tyr
         20                  25                  30

Ala Met Ser Trp Val Arg Gln Ala Pro Gly Lys Gly Leu Glu Trp Val
         35                  40                  45

Ser Val Ile Ser Gly Gly Gly Arg Thr Tyr Tyr Thr Asp Ser Val
 50                  55                  60

Lys Gly Arg Phe Thr Ile Ser Arg Asp Asn Ser Lys Ser Met Leu Tyr
 65                  70                  75                  80

Leu Gln Met Asn Ser Leu Arg Ala Glu Asp Thr Ala Ile Tyr Tyr Cys
                 85                  90                  95

Ala Lys Glu Arg Val Thr Gly Ile Asp His Tyr Tyr Tyr Gly Val Asp
             100                 105                 110

Val Trp Gly Gln Gly Thr Thr Val Thr Val Ser Ser
        115                 120
```

<210> SEQ ID NO 211
<211> LENGTH: 24
<212> TYPE: DNA
<213> ORGANISM: Artificial Sequence
<220> FEATURE:
<223> OTHER INFORMATION: synthetic

<400> SEQUENCE: 211
ggattcacct tcagaagcta tgcc                                    24

<210> SEQ ID NO 212
<211> LENGTH: 8
<212> TYPE: PRT
<213> ORGANISM: Artificial Sequence
<220> FEATURE:
<223> OTHER INFORMATION: synthetic

<400> SEQUENCE: 212

```
Gly Phe Thr Phe Arg Ser Tyr Ala
 1               5
```

<210> SEQ ID NO 213
<211> LENGTH: 24
<212> TYPE: DNA
<213> ORGANISM: Artificial Sequence
<220> FEATURE:
<223> OTHER INFORMATION: synthetic

<400> SEQUENCE: 213
attagtggtg gtggtggtag gaca                                    24

<210> SEQ ID NO 214
<211> LENGTH: 8
<212> TYPE: PRT
<213> ORGANISM: Artificial Sequence
<220> FEATURE:
<223> OTHER INFORMATION: synthetic

<400> SEQUENCE: 214

```
Ile Ser Gly Gly Gly Gly Arg Thr
 1               5
```

<210> SEQ ID NO 215
<211> LENGTH: 51
<212> TYPE: DNA
<213> ORGANISM: Artificial Sequence
<220> FEATURE:
<223> OTHER INFORMATION: synthetic

<400> SEQUENCE: 215

```
gcgaaagaga gggtaactgg aatagaccac tactactacg gtgtggacgt c          51
```

<210> SEQ ID NO 216
<211> LENGTH: 17
<212> TYPE: PRT
<213> ORGANISM: Artificial Sequence
<220> FEATURE:
<223> OTHER INFORMATION: synthetic

<400> SEQUENCE: 216

```
Ala Lys Glu Arg Val Thr Gly Ile Asp His Tyr Tyr Tyr Gly Val Asp
1               5                   10                  15
Val
```

<210> SEQ ID NO 217
<211> LENGTH: 321
<212> TYPE: DNA
<213> ORGANISM: Artificial Sequence
<220> FEATURE:
<223> OTHER INFORMATION: synthetic

<400> SEQUENCE: 217

```
gacatccaga tgacccagtc tccatcctcc ctgtctgcat ctgtaggaga cagagtcacc    60
atcacttgcc gggcaagtca gagcattagt agctatttaa attggtatca gcagaaacca   120
gggaaagccc ctaagctcct gatctatgct acatccagtt tgcaaagtgg ggtcccatca   180
cggttcagtg gcagtgcatc tggaacagat ttcactctcg ccatcagcag tctgcaacct   240
gaagattttg caacttacta ctgtcaacag agttacacta ccccccctcac tttcggcgga   300 gggaccaagg tggagatcaa a                                            321
```

<210> SEQ ID NO 218
<211> LENGTH: 107
<212> TYPE: PRT
<213> ORGANISM: Artificial Sequence
<220> FEATURE:
<223> OTHER INFORMATION: synthetic

<400> SEQUENCE: 218

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Thr Ser Ser Leu Gln Ser Gly Val Pro Ser Arg Phe Ser Gly
        50                  55                  60

Ser Ala Ser Gly Thr Asp Phe Thr Leu Ala Ile Ser Ser Leu Gln Pro
65                  70                  75                  80

Glu Asp Phe Ala Thr Tyr Tyr Cys Gln Gln Ser Tyr Thr Thr Pro Leu
                85                  90                  95

Thr Phe Gly Gly Gly Thr Lys Val Glu Ile Lys
            100                 105
```

<210> SEQ ID NO 219
<211> LENGTH: 18
<212> TYPE: DNA
<213> ORGANISM: Artificial Sequence
<220> FEATURE:
<223> OTHER INFORMATION: synthetic

```
<400> SEQUENCE: 219
cagagcatta gtagctat                                                        18

<210> SEQ ID NO 220
<211> LENGTH: 6
<212> TYPE: PRT
<213> ORGANISM: Artificial Sequence
<220> FEATURE:
<223> OTHER INFORMATION: synthetic

<400> SEQUENCE: 220

Gln Ser Ile Ser Ser Tyr
1               5

<210> SEQ ID NO 221
<211> LENGTH: 9
<212> TYPE: DNA
<213> ORGANISM: Artificial Sequence
<220> FEATURE:
<223> OTHER INFORMATION: synthetic

<400> SEQUENCE: 221 gctacatcc                                                                   9

<210> SEQ ID NO 222
<211> LENGTH: 3
<212> TYPE: PRT
<213> ORGANISM: Artificial Sequence
<220> FEATURE:
<223> OTHER INFORMATION: synthetic

<400> SEQUENCE: 222

Ala Thr Ser
1

<210> SEQ ID NO 223
<211> LENGTH: 27
<212> TYPE: DNA
<213> ORGANISM: Artificial Sequence
<220> FEATURE:
<223> OTHER INFORMATION: synthetic

<400> SEQUENCE: 223
caacagagtt acactacccc cctcact                                              27

<210> SEQ ID NO 224
<211> LENGTH: 9
<212> TYPE: PRT
<213> ORGANISM: Artificial Sequence
<220> FEATURE:
<223> OTHER INFORMATION: synthetic

<400> SEQUENCE: 224

Gln Gln Ser Tyr Thr Thr Pro Leu Thr
1               5

<210> SEQ ID NO 225
<211> LENGTH: 390
<212> TYPE: DNA
<213> ORGANISM: Artificial Sequence
<220> FEATURE:
<223> OTHER INFORMATION: synthetic

<400> SEQUENCE: 225
gaggtgcagc tggtggagtc tgggggaggc ttggtacaac ctggagggtc cctgagactt          60
```

```
tcctgtgcag cctctggatt tacattcagc agttatgaaa tgaactgggt ccgccaggct      120
ccagggaagg ggctggagtg ggtttcatat atcagtagta gtggtaatac caaagactac      180
gcaggctctg tgaagggccg agtcaccatc tccagagaca acgccaagaa cttactgtat      240
ctgcaaatga acagcctgag agccgaggac acggctgttt atcactgtgc gagagatgga      300
gggcattacg atattttgac tggttccatg tcctactact actacgcttt ggacgtctgg      360
ggccaaggga ccacggtcac cgtctcctca                                       390
```

```
<210> SEQ ID NO 226
<211> LENGTH: 130
<212> TYPE: PRT
<213> ORGANISM: Artificial Sequence
<220> FEATURE:
<223> OTHER INFORMATION: synthetic

<400> SEQUENCE: 226
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Asn Thr Lys Asp Tyr Ala Gly Ser Val
    50                  55                  60

Lys Gly Arg Val Thr Ile Ser Arg Asp Asn Ala Lys Asn Leu Leu Tyr
65                  70                  75                  80

Leu Gln Met Asn Ser Leu Arg Ala Glu Asp Thr Ala Val Tyr His Cys
                85                  90                  95

Ala Arg Asp Gly Gly His Tyr Asp Ile Leu Thr Gly Ser Met Ser Tyr
            100                 105                 110

Tyr Tyr Tyr Ala Leu Asp Val Trp Gly Gln Gly Thr Thr Val Thr Val
        115                 120                 125

Ser Ser
    130

```
<210> SEQ ID NO 227
<211> LENGTH: 24
<212> TYPE: DNA
<213> ORGANISM: Artificial Sequence
<220> FEATURE:
<223> OTHER INFORMATION: synthetic

<400> SEQUENCE: 227
ggatttacat tcagcagtta tgaa                                              24
```

```
<210> SEQ ID NO 228
<211> LENGTH: 8
<212> TYPE: PRT
<213> ORGANISM: Artificial Sequence
<220> FEATURE:
<223> OTHER INFORMATION: synthetic

<400> SEQUENCE: 228
```

Gly Phe Thr Phe Ser Ser Tyr Glu
1               5

```
<210> SEQ ID NO 229
<211> LENGTH: 24
<212> TYPE: DNA
```

```
<213> ORGANISM: Artificial Sequence
<220> FEATURE:
<223> OTHER INFORMATION: synthetic

<400> SEQUENCE: 229
atcagtagta gtggtaatac caaa                                          24

<210> SEQ ID NO 230
<211> LENGTH: 8
<212> TYPE: PRT
<213> ORGANISM: Artificial Sequence
<220> FEATURE:
<223> OTHER INFORMATION: synthetic

<400> SEQUENCE: 230

Ile Ser Ser Ser Gly Asn Thr Lys
1               5

<210> SEQ ID NO 231
<211> LENGTH: 69
<212> TYPE: DNA
<213> ORGANISM: Artificial Sequence
<220> FEATURE:
<223> OTHER INFORMATION: synthetic

<400> SEQUENCE: 231
gcgagagatg gagggcatta cgatattttg actggttcca tgtcctacta ctactacgct   60
ttggacgtc                                                           69

<210> SEQ ID NO 232
<211> LENGTH: 23
<212> TYPE: PRT
<213> ORGANISM: Artificial Sequence
<220> FEATURE:
<223> OTHER INFORMATION: synthetic

<400> SEQUENCE: 232

Ala Arg Asp Gly Gly His Tyr Asp Ile Leu Thr Gly Ser Met Ser Tyr
1               5                   10                  15

Tyr Tyr Tyr Ala Leu Asp Val
            20

<210> SEQ ID NO 233
<211> LENGTH: 324
<212> TYPE: DNA
<213> ORGANISM: Artificial Sequence
<220> FEATURE:
<223> OTHER INFORMATION: synthetic

<400> SEQUENCE: 233
gacatccaga tgacccagtc tccatcctcc ctgtctgcat ctgtaggaga cagagtcacc   60
atcacttgcc gggcaagtca gagcattagc agctatttaa attggtatca gcagaaacca  120
gggaaagccc ctaagctcct gatctatgct gcatccagtt tgcaaagtgg ggtcccgtca  180
aggttcagtg gcagtggatc tgggacagat ttcactctca ccatcagcag tctgcaacct  240
gaagattttg caacttacta ctgtcaacag agttacagta cccctccgat caccttcggc  300
caagggacac gactggagat taaa                                         324

<210> SEQ ID NO 234
<211> LENGTH: 108
<212> TYPE: PRT
<213> ORGANISM: Artificial Sequence
<220> FEATURE:
```

<223> OTHER INFORMATION: synthetic

<400> SEQUENCE: 234

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 235
<211> LENGTH: 18
<212> TYPE: DNA
<213> ORGANISM: Artificial Sequence
<220> FEATURE:
<223> OTHER INFORMATION: synthetic

<400> SEQUENCE: 235
cagagcatta gcagctat                                                 18

<210> SEQ ID NO 236
<211> LENGTH: 6
<212> TYPE: PRT
<213> ORGANISM: Artificial Sequence
<220> FEATURE:
<223> OTHER INFORMATION: synthetic

<400> SEQUENCE: 236

Gln Ser Ile Ser Ser Tyr
1               5

<210> SEQ ID NO 237
<211> LENGTH: 9
<212> TYPE: DNA
<213> ORGANISM: Artificial Sequence
<220> FEATURE:
<223> OTHER INFORMATION: synthetic

<400> SEQUENCE: 237 gctgcatcc                                                            9

<210> SEQ ID NO 238
<211> LENGTH: 3
<212> TYPE: PRT
<213> ORGANISM: Artificial Sequence
<220> FEATURE:
<223> OTHER INFORMATION: synthetic

<400> SEQUENCE: 238

Ala Ala Ser
1

<210> SEQ ID NO 239
<211> LENGTH: 30
<212> TYPE: DNA

<213> ORGANISM: Artificial Sequence
<220> FEATURE:
<223> OTHER INFORMATION: synthetic

<400> SEQUENCE: 239

```
caacagagtt acagtacccc tccgatcacc                                30
```

<210> SEQ ID NO 240
<211> LENGTH: 10
<212> TYPE: PRT
<213> ORGANISM: Artificial Sequence
<220> FEATURE:
<223> OTHER INFORMATION: synthetic

<400> SEQUENCE: 240

```
Gln Gln Ser Tyr Ser Thr Pro Pro Ile Thr
1               5                   10
```

<210> SEQ ID NO 241
<211> LENGTH: 363
<212> TYPE: DNA
<213> ORGANISM: Artificial Sequence
<220> FEATURE:
<223> OTHER INFORMATION: synthetic

<400> SEQUENCE: 241

```
gaggtgcagc tggtggagtc tgggggaggc ttggtacagc ctggggggtc cctgagactc     60
tcctgtgcag cctctggatt cacctttaaa acctatgcca tgagctgggt ccgccaggct    120
ccagggaggg ggctggagtg ggtctcaggt attagtggta gtggtagtac ctcatactac    180
gcagactccg tgaagggccg gttcaccatc tccagagaca attacaagaa gacgctgtct    240
ctgcaaatga acagtctgag agccgaggac acggccgttt attactgtgc gctggatata    300
atggcaacgg taggaggtct ctttaacaac tggggccagg gaaccctggt caccgtctcc    360
tca                                                                  363
```

<210> SEQ ID NO 242
<211> LENGTH: 121
<212> TYPE: PRT
<213> ORGANISM: Artificial Sequence
<220> FEATURE:
<223> OTHER INFORMATION: synthetic

<400> SEQUENCE: 242

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Lys Thr Tyr
            20                  25                  30

Ala Met Ser Trp Val Arg Gln Ala Pro Gly Arg Gly Leu Glu Trp Val
        35                  40                  45

Ser Gly Ile Ser Gly Ser Gly Ser Thr Ser Tyr Tyr Ala Asp Ser Val
    50                  55                  60

Lys Gly Arg Phe Thr Ile Ser Arg Asp Asn Lys Lys Thr Leu Ser
65                  70                  75                  80

Leu Gln Met Asn Ser Leu Arg Ala Glu Asp Thr Ala Val Tyr Tyr Cys
            85                  90                  95

Ala Leu Asp Ile Met Ala Thr Val Gly Gly Leu Phe Asn Asn Trp Gly
        100                 105                 110

Gln Gly Thr Leu Val Thr Val Ser Ser
    115                 120
```

<210> SEQ ID NO 243
<211> LENGTH: 24
<212> TYPE: DNA
<213> ORGANISM: Artificial Sequence
<220> FEATURE:
<223> OTHER INFORMATION: synthetic

<400> SEQUENCE: 243
ggattcacct ttaaaaccta tgcc                                            24

<210> SEQ ID NO 244
<211> LENGTH: 8
<212> TYPE: PRT
<213> ORGANISM: Artificial Sequence
<220> FEATURE:
<223> OTHER INFORMATION: synthetic

<400> SEQUENCE: 244

Gly Phe Thr Phe Lys Thr Tyr Ala
1               5

<210> SEQ ID NO 245
<211> LENGTH: 24
<212> TYPE: DNA
<213> ORGANISM: Artificial Sequence
<220> FEATURE:
<223> OTHER INFORMATION: synthetic

<400> SEQUENCE: 245
attagtggta gtggtagtac ctca                                            24

<210> SEQ ID NO 246
<211> LENGTH: 8
<212> TYPE: PRT
<213> ORGANISM: Artificial Sequence
<220> FEATURE:
<223> OTHER INFORMATION: synthetic

<400> SEQUENCE: 246

Ile Ser Gly Ser Gly Ser Thr Ser
1               5

<210> SEQ ID NO 247
<211> LENGTH: 42
<212> TYPE: DNA
<213> ORGANISM: Artificial Sequence
<220> FEATURE:
<223> OTHER INFORMATION: synthetic

<400> SEQUENCE: 247
gcgctggata taatggcaac ggtaggaggt ctctttaaca ac                        42

<210> SEQ ID NO 248
<211> LENGTH: 14
<212> TYPE: PRT
<213> ORGANISM: Artificial Sequence
<220> FEATURE:
<223> OTHER INFORMATION: synthetic

<400> SEQUENCE: 248

Ala Leu Asp Ile Met Ala Thr Val Gly Gly Leu Phe Asn Asn
1               5                   10

<210> SEQ ID NO 249
<211> LENGTH: 324
<212> TYPE: DNA

<213> ORGANISM: Artificial Sequence
<220> FEATURE:
<223> OTHER INFORMATION: synthetic

<400> SEQUENCE: 249

```
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcaccttg gacgttcggc   300
caagggacca aggtggaaat caaa                                           324
```

<210> SEQ ID NO 250
<211> LENGTH: 108
<212> TYPE: PRT
<213> ORGANISM: Artificial Sequence
<220> FEATURE:
<223> OTHER INFORMATION: synthetic

<400> SEQUENCE: 250

```
Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Ser
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Ser Ser Pro
                85                  90                  95
Trp Thr Phe Gly Gln Gly Thr Lys Val Glu Ile Lys
            100                 105
```

<210> SEQ ID NO 251
<211> LENGTH: 21
<212> TYPE: DNA
<213> ORGANISM: Artificial Sequence
<220> FEATURE:
<223> OTHER INFORMATION: synthetic

<400> SEQUENCE: 251

```
cagagtgtta gcagcagcta c                                              21
```

<210> SEQ ID NO 252
<211> LENGTH: 7
<212> TYPE: PRT
<213> ORGANISM: Artificial Sequence
<220> FEATURE:
<223> OTHER INFORMATION: synthetic

<400> SEQUENCE: 252

```
Gln Ser Val Ser Ser Ser Tyr
1               5
```

<210> SEQ ID NO 253
<211> LENGTH: 9
<212> TYPE: DNA
<213> ORGANISM: Artificial Sequence
<220> FEATURE:
<223> OTHER INFORMATION: synthetic

<400> SEQUENCE: 253 ggtgcatcc                                                                     9

<210> SEQ ID NO 254
<211> LENGTH: 3
<212> TYPE: PRT
<213> ORGANISM: Artificial Sequence
<220> FEATURE:
<223> OTHER INFORMATION: synthetic

<400> SEQUENCE: 254

Gly Ala Ser
1

<210> SEQ ID NO 255
<211> LENGTH: 27
<212> TYPE: DNA
<213> ORGANISM: Artificial Sequence
<220> FEATURE:
<223> OTHER INFORMATION: synthetic

<400> SEQUENCE: 255
cagcagtatg gtagctcacc ttggacg                                                27

<210> SEQ ID NO 256
<211> LENGTH: 9
<212> TYPE: PRT
<213> ORGANISM: Artificial Sequence
<220> FEATURE:
<223> OTHER INFORMATION: synthetic

<400> SEQUENCE: 256

Gln Gln Tyr Gly Ser Ser Pro Trp Thr
1               5

<210> SEQ ID NO 257
<211> LENGTH: 360
<212> TYPE: DNA
<213> ORGANISM: Artificial Sequence
<220> FEATURE:
<223> OTHER INFORMATION: synthetic

<400> SEQUENCE: 257
caggtgcagc tggtgcagtc tggggctgag gtgaagaagc ctgggtcctc ggtgaaggtc             60
tcctgcaagg cttctggagg caccttcagc agacatacta tcagctgggt gcgacaggcc           120
cctggacaag gcttgagtg gatgggaggg atcatccta tctttggtac agcaaactac            180
gcacacaagt tccagggcag agtcacgatt accacggacg aatccacgag cacagcctac          240
atggagctga gcagcctgag atctgaggac acggccgtat attattgtgc gagagcccct          300 tatcccgac aggggtactt cgatctctgg ggccgtggca ccctggtcac cgtctcctca           360

<210> SEQ ID NO 258
<211> LENGTH: 120
<212> TYPE: PRT
<213> ORGANISM: Artificial Sequence
<220> FEATURE:
<223> OTHER INFORMATION: synthetic

<400> SEQUENCE: 258

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Arg His
            20                  25                  30

Thr Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala His Lys Phe
 50                  55                  60

Gln Gly Arg Val Thr Ile Thr Thr Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Pro Tyr Thr Arg Gln Gly Tyr Phe Asp Leu Trp Gly Arg
            100                 105                 110

Gly Thr Leu Val Thr Val Ser Ser
        115                 120

<210> SEQ ID NO 259
<211> LENGTH: 24
<212> TYPE: DNA
<213> ORGANISM: Artificial Sequence
<220> FEATURE:
<223> OTHER INFORMATION: synthetic

<400> SEQUENCE: 259
ggaggcacct tcagcagaca tact                                          24

<210> SEQ ID NO 260
<211> LENGTH: 8
<212> TYPE: PRT
<213> ORGANISM: Artificial Sequence
<220> FEATURE:
<223> OTHER INFORMATION: synthetic

<400> SEQUENCE: 260

Gly Gly Thr Phe Ser Arg His Thr
1               5

<210> SEQ ID NO 261
<211> LENGTH: 24
<212> TYPE: DNA
<213> ORGANISM: Artificial Sequence
<220> FEATURE:
<223> OTHER INFORMATION: synthetic

<400> SEQUENCE: 261
atcatcccta tctttggtac agca                                          24

<210> SEQ ID NO 262
<211> LENGTH: 8
<212> TYPE: PRT
<213> ORGANISM: Artificial Sequence
<220> FEATURE:
<223> OTHER INFORMATION: synthetic

<400> SEQUENCE: 262

Ile Ile Pro Ile Phe Gly Thr Ala
1               5

<210> SEQ ID NO 263
<211> LENGTH: 39
<212> TYPE: DNA
<213> ORGANISM: Artificial Sequence
<220> FEATURE:
<223> OTHER INFORMATION: synthetic

<400> SEQUENCE: 263
gcgagagccc cttatacccg acaggggtac ttcgatctc                                39

<210> SEQ ID NO 264
<211> LENGTH: 13
<212> TYPE: PRT
<213> ORGANISM: Artificial Sequence
<220> FEATURE:
<223> OTHER INFORMATION: synthetic

<400> SEQUENCE: 264

Ala Arg Ala Pro Tyr Thr Arg Gln Gly Tyr Phe Asp Leu
1               5                   10

<210> SEQ ID NO 265
<211> LENGTH: 339
<212> TYPE: DNA
<213> ORGANISM: Artificial Sequence
<220> FEATURE:
<223> OTHER INFORMATION: synthetic

<400> SEQUENCE: 265
gacatcgtga tgacccagtc tccagactcc ctggctgtgt ctctgggcga gagggccacc      60
atcaactgca gtccagccag agtgttttta tacagctcca acaataagaa ctacttagct     120
tggtaccagc agaaaccagg acagcctcct aagctactac tttactgggc atctacccgg     180
gaatccgggg tccctgaccg attcagtggc agcgggtctg ggacagattt cactctcacc     240
atcagcagcc tgcaggctga agatgtggca gtttattact gtcagcaaga ttatagtact     300
ccgtggacgt tcggccaagg gaccaaggtg gaaatcaaa                            339

<210> SEQ ID NO 266
<211> LENGTH: 113
<212> TYPE: PRT
<213> ORGANISM: Artificial Sequence
<220> FEATURE:
<223> OTHER INFORMATION: synthetic

<400> SEQUENCE: 266

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Asp Tyr Ser Thr Pro Trp Thr Phe Gly Gln Gly Thr Lys Val Glu Ile
            100                 105                 110

Lys

<210> SEQ ID NO 267
<211> LENGTH: 36
<212> TYPE: DNA
<213> ORGANISM: Artificial Sequence
<220> FEATURE:

<223> OTHER INFORMATION: synthetic

<400> SEQUENCE: 267
cagagtgttt tatacagctc caacaataag aactac    36

<210> SEQ ID NO 268
<211> LENGTH: 12
<212> TYPE: PRT
<213> ORGANISM: Artificial Sequence
<220> FEATURE:
<223> OTHER INFORMATION: synthetic

<400> SEQUENCE: 268

Gln Ser Val Leu Tyr Ser Ser Asn Asn Lys Asn Tyr
1               5                   10

<210> SEQ ID NO 269
<211> LENGTH: 9
<212> TYPE: DNA
<213> ORGANISM: Artificial Sequence
<220> FEATURE:
<223> OTHER INFORMATION: synthetic

<400> SEQUENCE: 269 tgggcatct    9

<210> SEQ ID NO 270
<211> LENGTH: 3
<212> TYPE: PRT
<213> ORGANISM: Artificial Sequence
<220> FEATURE:
<223> OTHER INFORMATION: synthetic

<400> SEQUENCE: 270

Trp Ala Ser
1

<210> SEQ ID NO 271
<211> LENGTH: 27
<212> TYPE: DNA
<213> ORGANISM: Artificial Sequence
<220> FEATURE:
<223> OTHER INFORMATION: synthetic

<400> SEQUENCE: 271
cagcaagatt atagtactcc gtggacg    27

<210> SEQ ID NO 272
<211> LENGTH: 9
<212> TYPE: PRT
<213> ORGANISM: Artificial Sequence
<220> FEATURE:
<223> OTHER INFORMATION: synthetic

<400> SEQUENCE: 272

Gln Gln Asp Tyr Ser Thr Pro Trp Thr
1               5

<210> SEQ ID NO 273
<211> LENGTH: 354
<212> TYPE: DNA
<213> ORGANISM: Artificial Sequence
<220> FEATURE:
<223> OTHER INFORMATION: synthetic

<400> SEQUENCE: 273

```
caggtgcagc tggtgcagtc tggggctgag gtgaagaagc ctggggcctc agtgaaggtt    60
tcctgcaagg catctggata caccttcacc aactactata tacactgggt gcgacaggcc   120
cctggacaag ggcttgactg gatgggaatt atcaaccctg gtggtggtaa cacaaactac   180
gcacagaagt tcctgggcag agtcaccatg accagggaca cgtccacgac acagtctac    240 atggagctga gcagcctgag atctgaggac acggccatat attactgtgc gagagaaaac   300
tggaactctt actttgacaa ctggggccag ggaaccctgg tcaccgtctc ctca         354
```

<210> SEQ ID NO 274
<211> LENGTH: 118
<212> TYPE: PRT
<213> ORGANISM: Artificial Sequence
<220> FEATURE:
<223> OTHER INFORMATION: synthetic

<400> SEQUENCE: 274

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Asp Trp Met
        35                  40                  45

Gly Ile Ile Asn Pro Gly Gly Gly Asn Thr Asn Tyr Ala Gln Lys Phe
    50                  55                  60

Leu Gly Arg Val Thr Met Thr Arg Asp Thr Ser Thr Thr Thr Val Tyr
65                  70                  75                  80

Met Glu Leu Ser Ser Leu Arg Ser Glu Asp Thr Ala Ile Tyr Tyr Cys
                85                  90                  95

Ala Arg Glu Asn Trp Asn Ser Tyr Phe Asp Asn Trp Gly Gln Gly Thr
            100                 105                 110

Leu Val Thr Val Ser Ser
        115
```

<210> SEQ ID NO 275
<211> LENGTH: 24
<212> TYPE: DNA
<213> ORGANISM: Artificial Sequence
<220> FEATURE:
<223> OTHER INFORMATION: synthetic

<400> SEQUENCE: 275

```
ggatacacct tcaccaacta ctat                                           24
```

<210> SEQ ID NO 276
<211> LENGTH: 8
<212> TYPE: PRT
<213> ORGANISM: Artificial Sequence
<220> FEATURE:
<223> OTHER INFORMATION: synthetic

<400> SEQUENCE: 276

```
Gly Tyr Thr Phe Thr Asn Tyr Tyr
1               5
```

<210> SEQ ID NO 277
<211> LENGTH: 24
<212> TYPE: DNA
<213> ORGANISM: Artificial Sequence
<220> FEATURE:
<223> OTHER INFORMATION: synthetic

<400> SEQUENCE: 277
atcaaccctg gtggtggtaa caca                                                  24

<210> SEQ ID NO 278
<211> LENGTH: 8
<212> TYPE: PRT
<213> ORGANISM: Artificial Sequence
<220> FEATURE:
<223> OTHER INFORMATION: synthetic

<400> SEQUENCE: 278

Ile Asn Pro Gly Gly Gly Asn Thr
1               5

<210> SEQ ID NO 279
<211> LENGTH: 33
<212> TYPE: DNA
<213> ORGANISM: Artificial Sequence
<220> FEATURE:
<223> OTHER INFORMATION: synthetic

<400> SEQUENCE: 279
gcgagagaaa actggaactc ttactttgac aac                                        33

<210> SEQ ID NO 280
<211> LENGTH: 11
<212> TYPE: PRT
<213> ORGANISM: Artificial Sequence
<220> FEATURE:
<223> OTHER INFORMATION: synthetic

<400> SEQUENCE: 280

Ala Arg Glu Asn Trp Asn Ser Tyr Phe Asp Asn
1               5                   10

<210> SEQ ID NO 281
<211> LENGTH: 339
<212> TYPE: DNA
<213> ORGANISM: Artificial Sequence
<220> FEATURE:
<223> OTHER INFORMATION: synthetic

<400> SEQUENCE: 281
gacatcgtga tgacccagtc tccagactcc ctggctgtgt ctctgggcga gagggccacc           60
atcaactgca agtccagcca gagtgtttta tacagctcca acaataagaa cttcttagct          120
tggtaccagc agaaaccagg acagcctcct aagctgctca tttactgggc atctacccgg          180
gaatccgggg tccctgaccg attcagtggc agcgggtctg ggacagattt cactctcacc          240
atcagcagcc tgcaggctga agatgtggca ctttattact gtcagcaata ttatggtgct          300
ccgtggacgt tcggccaagg gaccaaggtg gaaatcaaa                                 339

<210> SEQ ID NO 282
<211> LENGTH: 113
<212> TYPE: PRT
<213> ORGANISM: Artificial Sequence
<220> FEATURE:
<223> OTHER INFORMATION: synthetic

<400> SEQUENCE: 282

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

```
Ser Asn Asn Lys Asn Phe Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Leu Tyr Tyr Cys Gln Gln
                85                  90                  95

Tyr Tyr Gly Ala Pro Trp Thr Phe Gly Gln Gly Thr Lys Val Glu Ile
            100                 105                 110

Lys

<210> SEQ ID NO 283
<211> LENGTH: 36
<212> TYPE: DNA
<213> ORGANISM: Artificial Sequence
<220> FEATURE:
<223> OTHER INFORMATION: synthetic

<400> SEQUENCE: 283
cagagtgttt tatacagctc caacaataag aacttc                            36

<210> SEQ ID NO 284
<211> LENGTH: 12
<212> TYPE: PRT
<213> ORGANISM: Artificial Sequence
<220> FEATURE:
<223> OTHER INFORMATION: synthetic

<400> SEQUENCE: 284

Gln Ser Val Leu Tyr Ser Ser Asn Asn Lys Asn Phe
1               5                   10

<210> SEQ ID NO 285
<211> LENGTH: 9
<212> TYPE: DNA
<213> ORGANISM: Artificial Sequence
<220> FEATURE:
<223> OTHER INFORMATION: synthetic

<400> SEQUENCE: 285 tgggcatct                                                          9

<210> SEQ ID NO 286
<211> LENGTH: 3
<212> TYPE: PRT
<213> ORGANISM: Artificial Sequence
<220> FEATURE:
<223> OTHER INFORMATION: synthetic

<400> SEQUENCE: 286

Trp Ala Ser
1

<210> SEQ ID NO 287
<211> LENGTH: 27
<212> TYPE: DNA
<213> ORGANISM: Artificial Sequence
<220> FEATURE:
<223> OTHER INFORMATION: synthetic

<400> SEQUENCE: 287
cagcaatatt atggtgctcc gtggacg                                      27
```

<210> SEQ ID NO 288
<211> LENGTH: 9
<212> TYPE: PRT
<213> ORGANISM: Artificial Sequence
<220> FEATURE:
<223> OTHER INFORMATION: synthetic

<400> SEQUENCE: 288

Gln Gln Tyr Tyr Gly Ala Pro Trp Thr
1               5

<210> SEQ ID NO 289
<211> LENGTH: 357
<212> TYPE: DNA
<213> ORGANISM: Artificial Sequence
<220> FEATURE:
<223> OTHER INFORMATION: synthetic

<400> SEQUENCE: 289

```
caggtccagc tggtgcagtc tggggctgag gtgaagaagc ctgggtcctc ggtgaaggtc      60
tcctgcaagg cttctggagg caccttcagc agctatacta tcaactgggt gcgacaggcc     120
cctggacaag gcttgagtg gatgggaggg atcatcccta tctttggtat agcaaactac     180
gcacagaagt tccagggcag agtcacgatt accacggacg aatccacgaa cacagcctac     240
atggagctga gcagcctgag atctgaggac acggccattt attactgtgc gagagcgaga     300
tatggttcgg ggagttatga ctactggggc cagggaaccc tggtcaccgt ctcctca        357
```

<210> SEQ ID NO 290
<211> LENGTH: 119
<212> TYPE: PRT
<213> ORGANISM: Artificial Sequence
<220> FEATURE:
<223> OTHER INFORMATION: synthetic

<400> SEQUENCE: 290

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Asn Trp Val Arg Gln Ala Pro Gly Gln Gly Leu Glu Trp Met
        35                  40                  45

Gly Gly Ile Ile Pro Ile Phe Gly Ile Ala Asn Tyr Ala Gln Lys Phe
    50                  55                  60

Gln Gly Arg Val Thr Ile Thr Thr Asp Glu Ser Thr Asn Thr Ala Tyr
65                  70                  75                  80

Met Glu Leu Ser Ser Leu Arg Ser Glu Asp Thr Ala Ile Tyr Tyr Cys
                85                  90                  95

Ala Arg Ala Arg Tyr Gly Ser Gly Ser Tyr Asp Tyr Trp Gly Gln Gly
            100                 105                 110

Thr Leu Val Thr Val Ser Ser
        115

<210> SEQ ID NO 291
<211> LENGTH: 24
<212> TYPE: DNA
<213> ORGANISM: Artificial Sequence
<220> FEATURE:
<223> OTHER INFORMATION: synthetic

<400> SEQUENCE: 291
ggaggcacct tcagcagcta tact                                            24

<210> SEQ ID NO 292
<211> LENGTH: 8
<212> TYPE: PRT
<213> ORGANISM: Artificial Sequence
<220> FEATURE:
<223> OTHER INFORMATION: synthetic

<400> SEQUENCE: 292

Gly Gly Thr Phe Ser Ser Tyr Thr
1               5

<210> SEQ ID NO 293
<211> LENGTH: 24
<212> TYPE: DNA
<213> ORGANISM: Artificial Sequence
<220> FEATURE:
<223> OTHER INFORMATION: synthetic

<400> SEQUENCE: 293
atcatcccta tctttggtat agca                                            24

<210> SEQ ID NO 294
<211> LENGTH: 8
<212> TYPE: PRT
<213> ORGANISM: Artificial Sequence
<220> FEATURE:
<223> OTHER INFORMATION: synthetic

<400> SEQUENCE: 294

Ile Ile Pro Ile Phe Gly Ile Ala
1               5

<210> SEQ ID NO 295
<211> LENGTH: 36
<212> TYPE: DNA
<213> ORGANISM: Artificial Sequence
<220> FEATURE:
<223> OTHER INFORMATION: synthetic

<400> SEQUENCE: 295
gcgagagcga gatatggttc ggggagttat gactac                               36

<210> SEQ ID NO 296
<211> LENGTH: 12
<212> TYPE: PRT
<213> ORGANISM: Artificial Sequence
<220> FEATURE:
<223> OTHER INFORMATION: synthetic

<400> SEQUENCE: 296

Ala Arg Ala Arg Tyr Gly Ser Gly Ser Tyr Asp Tyr
1               5                   10

<210> SEQ ID NO 297
<211> LENGTH: 339
<212> TYPE: DNA
<213> ORGANISM: Artificial Sequence
<220> FEATURE:
<223> OTHER INFORMATION: synthetic

<400> SEQUENCE: 297
gacatcgtga tgacccagtc tccagactcc ctggctgtgt ctctgggcga gagggccacc     60
atcaactgca agtccagcca gagtgtttta tacacctcca acaataagaa ctacttagct    120

```
tggtaccagc agaaaccagg acagcctcct aagctgctca tttactgggc atctacccgg    180
gaatccgggg tccctgaccg attcagtggc agcgggtctg ggacagattt cactctcacc    240
atcagcagcc tgcaggctga agatgtggca gtttattact gtcagcaata ttataatact    300
ccatggacgt tcggccaagg gaccaaggtg gaaatcaaa                            339
```

<210> SEQ ID NO 298
<211> LENGTH: 113
<212> TYPE: PRT
<213> ORGANISM: Artificial Sequence
<220> FEATURE:
<223> OTHER INFORMATION: synthetic

<400> SEQUENCE: 298

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Thr
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Asn Thr Pro Trp Thr Phe Gly Gln Gly Thr Lys Val Glu Ile
            100                 105                 110

Lys
```

<210> SEQ ID NO 299
<211> LENGTH: 36
<212> TYPE: DNA
<213> ORGANISM: Artificial Sequence
<220> FEATURE:
<223> OTHER INFORMATION: synthetic

<400> SEQUENCE: 299

```
cagagtgttt tatacacctc caacaataag aactac                               36
```

<210> SEQ ID NO 300
<211> LENGTH: 12
<212> TYPE: PRT
<213> ORGANISM: Artificial Sequence
<220> FEATURE:
<223> OTHER INFORMATION: synthetic

<400> SEQUENCE: 300

```
Gln Ser Val Leu Tyr Thr Ser Asn Asn Lys Asn Tyr
1               5                   10
```

<210> SEQ ID NO 301
<211> LENGTH: 9
<212> TYPE: DNA
<213> ORGANISM: Artificial Sequence
<220> FEATURE:
<223> OTHER INFORMATION: synthetic

<400> SEQUENCE: 301

```
tgggcatct                                                             9
```

<210> SEQ ID NO 302
<211> LENGTH: 3
<212> TYPE: PRT
<213> ORGANISM: Artificial Sequence
<220> FEATURE:
<223> OTHER INFORMATION: synthetic

<400> SEQUENCE: 302

Trp Ala Ser
1

<210> SEQ ID NO 303
<211> LENGTH: 27
<212> TYPE: DNA
<213> ORGANISM: Artificial Sequence
<220> FEATURE:
<223> OTHER INFORMATION: synthetic

<400> SEQUENCE: 303
cagcaatatt ataatactcc atggacg                                          27

<210> SEQ ID NO 304
<211> LENGTH: 9
<212> TYPE: PRT
<213> ORGANISM: Artificial Sequence
<220> FEATURE:
<223> OTHER INFORMATION: synthetic

<400> SEQUENCE: 304

Gln Gln Tyr Tyr Asn Thr Pro Trp Thr
1               5

<210> SEQ ID NO 305
<211> LENGTH: 360
<212> TYPE: DNA
<213> ORGANISM: Artificial Sequence
<220> FEATURE:
<223> OTHER INFORMATION: synthetic

<400> SEQUENCE: 305
cagatcacct tgaaggagtc tggtcctacg ctggtgaaac ccacacagac cctcacgctg      60
acctgcacct tctctgggtt ctcactcagc actaatggag tgggtgtggg ctggatccgt     120
cagcccccag gaaaggccct ggagtggctt ggaatcattt attggaatga tgataagcgc     180
tacagcccat ctctgaggag cagactcacc atcaccaagg acacctccaa aaaccaggtg     240
gtccttacaa tgaccaacat ggaccctgtg gacacagcca catattactg tgcacacaga     300
ggcctcttcg gaggttggtt cgacccctgg ggccagggaa ccctggtcac cgtctcctca     360

<210> SEQ ID NO 306
<211> LENGTH: 120
<212> TYPE: PRT
<213> ORGANISM: Artificial Sequence
<220> FEATURE:
<223> OTHER INFORMATION: synthetic

<400> SEQUENCE: 306

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Asn
            20                  25                  30

Gly Val Gly Val Gly Trp Ile Arg Gln Pro Pro Gly Lys Ala Leu Glu
        35                  40                  45

Trp Leu Gly Ile Ile Tyr Trp Asn Asp Asp Lys Arg Tyr Ser Pro Ser
    50                  55                  60

Leu Arg Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg Gly Leu Phe Gly Gly Trp Phe Asp Pro Trp Gly Gln
            100                 105                 110

Gly Thr Leu Val Thr Val Ser Ser
        115                 120

<210> SEQ ID NO 307
<211> LENGTH: 30
<212> TYPE: DNA
<213> ORGANISM: Artificial Sequence
<220> FEATURE:
<223> OTHER INFORMATION: synthetic

<400> SEQUENCE: 307
gggttctcac tcagcactaa tggagtgggt                                30

<210> SEQ ID NO 308
<211> LENGTH: 10
<212> TYPE: PRT
<213> ORGANISM: Artificial Sequence
<220> FEATURE:
<223> OTHER INFORMATION: synthetic

<400> SEQUENCE: 308

Gly Phe Ser Leu Ser Thr Asn Gly Val Gly
1               5                   10

<210> SEQ ID NO 309
<211> LENGTH: 21
<212> TYPE: DNA
<213> ORGANISM: Artificial Sequence
<220> FEATURE:
<223> OTHER INFORMATION: synthetic

<400> SEQUENCE: 309
atttattgga atgatgataa g                                         21

<210> SEQ ID NO 310
<211> LENGTH: 7
<212> TYPE: PRT
<213> ORGANISM: Artificial Sequence
<220> FEATURE:
<223> OTHER INFORMATION: synthetic

<400> SEQUENCE: 310

Ile Tyr Trp Asn Asp Asp Lys
1               5

<210> SEQ ID NO 311
<211> LENGTH: 36
<212> TYPE: DNA
<213> ORGANISM: Artificial Sequence
<220> FEATURE:
<223> OTHER INFORMATION: synthetic

<400> SEQUENCE: 311
gcacacagag gcctcttcgg aggttggttc gacccc                         36

<210> SEQ ID NO 312

<210> SEQ ID NO 312
<211> LENGTH: 12
<212> TYPE: PRT
<213> ORGANISM: Artificial Sequence
<220> FEATURE:
<223> OTHER INFORMATION: synthetic

<400> SEQUENCE: 312

```
Ala His Arg Gly Leu Phe Gly Gly Trp Phe Asp Pro
1               5                   10
```

<210> SEQ ID NO 313
<211> LENGTH: 321
<212> TYPE: DNA
<213> ORGANISM: Artificial Sequence
<220> FEATURE:
<223> OTHER INFORMATION: synthetic

<400> SEQUENCE: 313

```
gacatccaga tgacccagtc tccatcctcc ctgtctgcat ctgtaggaga cagagtcacc    60
atcacttgcc gggcaagtca gagcattagc aggtatttaa attggtatca gcagaaacca   120
gggaaagccc ctaacctcct gatctttgct gcatccagtt tgcaaagtgg ggtcccatca   180
aggttcagtg gcagtggatc tgggacagat ttcactctca ccatcagcag tctgcaacct   240
gaagattttg caacttactt ctgtcaacag agttacaata ccccgctcac tttcggcgga   300
gggaccaagg tggagatcaa a                                             321
```

<210> SEQ ID NO 314
<211> LENGTH: 107
<212> TYPE: PRT
<213> ORGANISM: Artificial Sequence
<220> FEATURE:
<223> OTHER INFORMATION: synthetic

<400> SEQUENCE: 314

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Arg Tyr
            20                  25                  30
Leu Asn Trp Tyr Gln Gln Lys Pro Gly Lys Ala Pro Asn Leu Leu Ile
        35                  40                  45
Phe Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Phe Cys Gln Gln Ser Tyr Asn Thr Pro Leu
                85                  90                  95
Thr Phe Gly Gly Gly Thr Lys Val Glu Ile Lys
            100                 105
```

<210> SEQ ID NO 315
<211> LENGTH: 18
<212> TYPE: DNA
<213> ORGANISM: Artificial Sequence
<220> FEATURE:
<223> OTHER INFORMATION: synthetic

<400> SEQUENCE: 315

```
cagagcatta gcaggtat                                                  18
```

<210> SEQ ID NO 316
<211> LENGTH: 6

```
<212> TYPE: PRT
<213> ORGANISM: Artificial Sequence
<220> FEATURE:
<223> OTHER INFORMATION: synthetic

<400> SEQUENCE: 316

Gln Ser Ile Ser Arg Tyr
1               5

<210> SEQ ID NO 317
<211> LENGTH: 9
<212> TYPE: DNA
<213> ORGANISM: Artificial Sequence
<220> FEATURE:
<223> OTHER INFORMATION: synthetic

<400> SEQUENCE: 317 gctgcatcc                                                                  9

<210> SEQ ID NO 318
<211> LENGTH: 3
<212> TYPE: PRT
<213> ORGANISM: Artificial Sequence
<220> FEATURE:
<223> OTHER INFORMATION: synthetic

<400> SEQUENCE: 318

Ala Ala Ser
1

<210> SEQ ID NO 319
<211> LENGTH: 27
<212> TYPE: DNA
<213> ORGANISM: Artificial Sequence
<220> FEATURE:
<223> OTHER INFORMATION: synthetic

<400> SEQUENCE: 319
caacagagtt acaataccccc gctcact                                            27

<210> SEQ ID NO 320
<211> LENGTH: 9
<212> TYPE: PRT
<213> ORGANISM: Artificial Sequence
<220> FEATURE:
<223> OTHER INFORMATION: synthetic

<400> SEQUENCE: 320

Gln Gln Ser Tyr Asn Thr Pro Leu Thr
1               5

<210> SEQ ID NO 321
<211> LENGTH: 366
<212> TYPE: DNA
<213> ORGANISM: Artificial Sequence
<220> FEATURE:
<223> OTHER INFORMATION: synthetic

<400> SEQUENCE: 321
gaggtgcagc tggtggagtc tgggggaggc ttggtacagc cggggggtc  cctgagactc         60 tcctgtgcaa tctctggatt cacctttagg agttatgcca tgacctgggt ccgccaggct        120
ccagggaagg cgctggagtg ggtctcagtt attagtggta gcggtggtaa cacatactac        180
gcagactccg tgaagggccg gttcaccgtc tccagagaca attccaggaa cacgctgtat        240
ctgcaaatga acagcctgag agccgaggac acggccgtat atttctgttc gaaagttgca        300
```

```
gcagctaata attactatta cgctttggac gtctggggcc aagggaccac ggtcaccgtc      360
tcctca                                                                 366
```

<210> SEQ ID NO 322
<211> LENGTH: 122
<212> TYPE: PRT
<213> ORGANISM: Artificial Sequence
<220> FEATURE:
<223> OTHER INFORMATION: synthetic

<400> SEQUENCE: 322

```
Glu Val Gln Leu Val Glu Ser Gly Gly Gly Leu Val Gln Pro Gly Gly
1               5                   10                  15

Ser Leu Arg Leu Ser Cys Ala Ile Ser Gly Phe Thr Phe Arg Ser Tyr
            20                  25                  30

Ala Met Thr Trp Val Arg Gln Ala Pro Gly Lys Ala Leu Glu Trp Val
        35                  40                  45

Ser Val Ile Ser Gly Ser Gly Asn Thr Tyr Tyr Ala Asp Ser Val
    50                  55                  60

Lys Gly Arg Phe Thr Val Ser Arg Asp Asn Ser Arg Asn Thr Leu Tyr
65                  70                  75                  80

Leu Gln Met Asn Ser Leu Arg Ala Glu Asp Thr Ala Val Tyr Phe Cys
                85                  90                  95

Ser Lys Val Ala Ala Asn Asn Tyr Tyr Tyr Ala Leu Asp Val Trp
            100                 105                 110

Gly Gln Gly Thr Thr Val Thr Val Ser Ser
        115                 120
```

<210> SEQ ID NO 323
<211> LENGTH: 24
<212> TYPE: DNA
<213> ORGANISM: Artificial Sequence
<220> FEATURE:
<223> OTHER INFORMATION: synthetic

<400> SEQUENCE: 323

```
ggattcacct ttaggagtta tgcc                                              24
```

<210> SEQ ID NO 324
<211> LENGTH: 8
<212> TYPE: PRT
<213> ORGANISM: Artificial Sequence
<220> FEATURE:
<223> OTHER INFORMATION: synthetic

<400> SEQUENCE: 324

```
Gly Phe Thr Phe Arg Ser Tyr Ala
1               5
```

<210> SEQ ID NO 325
<211> LENGTH: 24
<212> TYPE: DNA
<213> ORGANISM: Artificial Sequence
<220> FEATURE:
<223> OTHER INFORMATION: synthetic

<400> SEQUENCE: 325

```
attagtggta gcggtggtaa caca                                              24
```

<210> SEQ ID NO 326
<211> LENGTH: 8

```
<212> TYPE: PRT
<213> ORGANISM: Artificial Sequence
<220> FEATURE:
<223> OTHER INFORMATION: synthetic

<400> SEQUENCE: 326

Ile Ser Gly Ser Gly Gly Asn Thr
1               5

<210> SEQ ID NO 327
<211> LENGTH: 45
<212> TYPE: DNA
<213> ORGANISM: Artificial Sequence
<220> FEATURE:
<223> OTHER INFORMATION: synthetic

<400> SEQUENCE: 327
tcgaaagttg cagcagctaa taattactat tacgctttgg acgtc                45

<210> SEQ ID NO 328
<211> LENGTH: 15
<212> TYPE: PRT
<213> ORGANISM: Artificial Sequence
<220> FEATURE:
<223> OTHER INFORMATION: synthetic

<400> SEQUENCE: 328

Ser Lys Val Ala Ala Ala Asn Asn Tyr Tyr Tyr Ala Leu Asp Val
1               5                   10                  15

<210> SEQ ID NO 329
<211> LENGTH: 336
<212> TYPE: DNA
<213> ORGANISM: Artificial Sequence
<220> FEATURE:
<223> OTHER INFORMATION: synthetic

<400> SEQUENCE: 329
gatattgtga tgactcagtc tccactctcc ctgcccgtca cccctggaga gccggcctcc      60
atctcctgca ggtctagtca gagcctcctg catagtaatg gatacaagta tttggattgg    120
tacctgcaga agccagggca gtctccacaa ctcctgatct atttggtttc taatcgggcc    180
tccggggtcc ctgacaggtt cagtggcagt ggatcaggca cagattttac actgaaaatc    240
agcagagtgg aggctgagga tgttggggtt tattattgca tgcaagctct acaaactccg    300
tacacttttg gccaggggac caagctggag atcaaa                              336

<210> SEQ ID NO 330
<211> LENGTH: 112
<212> TYPE: PRT
<213> ORGANISM: Artificial Sequence
<220> FEATURE:
<223> OTHER INFORMATION: synthetic

<400> SEQUENCE: 330

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Lys Tyr Leu Asp Trp Tyr Leu Gln Lys Pro Gly Gln Ser
        35                  40                  45

Pro Gln Leu Leu Ile Tyr Leu Val Ser Asn Arg Ala Ser Gly Val Pro
    50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Tyr Thr Phe Gly Gln Gly Thr Lys Leu Glu Ile Lys
            100                 105                 110
```

<210> SEQ ID NO 331
<211> LENGTH: 33
<212> TYPE: DNA
<213> ORGANISM: Artificial Sequence
<220> FEATURE:
<223> OTHER INFORMATION: synthetic

<400> SEQUENCE: 331
cagagcctcc tgcatagtaa tggatacaag tat                                33

<210> SEQ ID NO 332
<211> LENGTH: 11
<212> TYPE: PRT
<213> ORGANISM: Artificial Sequence
<220> FEATURE:
<223> OTHER INFORMATION: synthetic

<400> SEQUENCE: 332

```
Gln Ser Leu Leu His Ser Asn Gly Tyr Lys Tyr
  1               5                  10
```

<210> SEQ ID NO 333
<211> LENGTH: 9
<212> TYPE: DNA
<213> ORGANISM: Artificial Sequence
<220> FEATURE:
<223> OTHER INFORMATION: synthetic

<400> SEQUENCE: 333 ttggtttct                                                           9

<210> SEQ ID NO 334
<211> LENGTH: 3
<212> TYPE: PRT
<213> ORGANISM: Artificial Sequence
<220> FEATURE:
<223> OTHER INFORMATION: synthetic

<400> SEQUENCE: 334

```
Leu Val Ser
  1
```

<210> SEQ ID NO 335
<211> LENGTH: 27
<212> TYPE: DNA
<213> ORGANISM: Artificial Sequence
<220> FEATURE:
<223> OTHER INFORMATION: synthetic

<400> SEQUENCE: 335
atgcaagctc tacaaactcc gtacact                                       27

<210> SEQ ID NO 336
<211> LENGTH: 9
<212> TYPE: PRT
<213> ORGANISM: Artificial Sequence
<220> FEATURE:
<223> OTHER INFORMATION: synthetic

<400> SEQUENCE: 336

Met Gln Ala Leu Gln Thr Pro Tyr Thr
1               5

<210> SEQ ID NO 337
<211> LENGTH: 381
<212> TYPE: DNA
<213> ORGANISM: Artificial Sequence
<220> FEATURE:
<223> OTHER INFORMATION: synthetic

<400> SEQUENCE: 337
caggtgcagc tggtggagtc tgggggaggc gtggtccagc ctgggaggtc cctgagactc    60
tcctgtgtag cgtctggatt caccttcagt aactatggca tgcactgggt ccgccaggct   120
ccaggcaagg gctggagtg gtggcagtt atatggaatg atggaagtaa taaatactat    180
gcagactccg tgaagggccg attcaccatc tccagagaca attccaagaa cacgctgtat   240
ctccaagtga gcagcctgag agccgatgac acggctgtat attactgtgc gagggacgga   300
gaggtcgaat atagcagctc gaattacaac tactacggtc tggatgtctg gggccaaggg   360
accacggtca ccgtctcctc a                                             381

<210> SEQ ID NO 338
<211> LENGTH: 127
<212> TYPE: PRT
<213> ORGANISM: Artificial Sequence
<220> FEATURE:
<223> OTHER INFORMATION: synthetic

<400> SEQUENCE: 338

Gln Val Gln Leu Val Glu Ser Gly Gly Gly Val Val Gln Pro Gly Arg
1               5                   10                  15
Ser Leu Arg Leu Ser Cys Val Ala Ser Gly Phe Thr Phe Ser Asn Tyr
            20                  25                  30
Gly Met His Trp Val Arg Gln Ala Pro Gly Lys Gly Leu Glu Trp Val
        35                  40                  45
Ala Val Ile Trp Asn Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Val Ser Ser Leu Arg Ala Asp Asp Thr Ala Val Tyr Tyr Cys
                85                  90                  95
Ala Arg Asp Gly Glu Val Glu Tyr Ser Ser Ser Asn Tyr Asn Tyr Tyr
            100                 105                 110
Gly Leu Asp Val Trp Gly Gln Gly Thr Thr Val Thr Val Ser Ser
        115                 120                 125

<210> SEQ ID NO 339
<211> LENGTH: 24
<212> TYPE: DNA
<213> ORGANISM: Artificial Sequence
<220> FEATURE:
<223> OTHER INFORMATION: synthetic

<400> SEQUENCE: 339
ggattcacct tcagtaacta tggc                                           24

<210> SEQ ID NO 340
<211> LENGTH: 8
<212> TYPE: PRT

```
<213> ORGANISM: Artificial Sequence
<220> FEATURE:
<223> OTHER INFORMATION: synthetic

<400> SEQUENCE: 340

Gly Phe Thr Phe Ser Asn Tyr Gly
1               5

<210> SEQ ID NO 341
<211> LENGTH: 24
<212> TYPE: DNA
<213> ORGANISM: Artificial Sequence
<220> FEATURE:
<223> OTHER INFORMATION: synthetic

<400> SEQUENCE: 341
atatggaatg atggaagtaa taaa                                          24

<210> SEQ ID NO 342
<211> LENGTH: 8
<212> TYPE: PRT
<213> ORGANISM: Artificial Sequence
<220> FEATURE:
<223> OTHER INFORMATION: synthetic

<400> SEQUENCE: 342

Ile Trp Asn Asp Gly Ser Asn Lys
1               5

<210> SEQ ID NO 343
<211> LENGTH: 60
<212> TYPE: DNA
<213> ORGANISM: Artificial Sequence
<220> FEATURE:
<223> OTHER INFORMATION: synthetic

<400> SEQUENCE: 343
gcgagggacg gagaggtcga atatagcagc tcgaattaca actactacgg tctggatgtc    60

<210> SEQ ID NO 344
<211> LENGTH: 20
<212> TYPE: PRT
<213> ORGANISM: Artificial Sequence
<220> FEATURE:
<223> OTHER INFORMATION: synthetic

<400> SEQUENCE: 344

Ala Arg Asp Gly Glu Val Glu Tyr Ser Ser Ser Asn Tyr Asn Tyr Tyr
1               5                   10                  15

Gly Leu Asp Val
            20

<210> SEQ ID NO 345
<211> LENGTH: 321
<212> TYPE: DNA
<213> ORGANISM: Artificial Sequence
<220> FEATURE:
<223> OTHER INFORMATION: synthetic

<400> SEQUENCE: 345
gacatccaga tgacccagtc tccatcctcc ctgtctgcat ctgtaggaga cagagtcacc    60
atcacttgcc aggcgagtca ggacattagc aactatttaa attggtatca gcagaaacca   120
gggaaagccc ctaaactcct gatctacgat gcatccaatt tggaaacagg ggtcccatca   180
aggttcagtg gaagtggatc tgggacagat tttactttca ccatcagcag cctgcagcct   240
```

```
gaagatattg taacatatta ctgtcaacag tatgatgatc tcccgatcac cttcggccaa    300
gggacacgac tggagattaa a                                              321
```

<210> SEQ ID NO 346
<211> LENGTH: 107
<212> TYPE: PRT
<213> ORGANISM: Artificial Sequence
<220> FEATURE:
<223> OTHER INFORMATION: synthetic

<400> SEQUENCE: 346

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Val Thr Tyr Tyr Cys Gln Gln Tyr Asp Asp Leu Pro Ile
                85                  90                  95

Thr Phe Gly Gln Gly Thr Arg Leu Glu Ile Lys
            100                 105

<210> SEQ ID NO 347
<211> LENGTH: 18
<212> TYPE: DNA
<213> ORGANISM: Artificial Sequence
<220> FEATURE:
<223> OTHER INFORMATION: synthetic

<400> SEQUENCE: 347
caggacatta gcaactat                                                  18

<210> SEQ ID NO 348
<211> LENGTH: 6
<212> TYPE: PRT
<213> ORGANISM: Artificial Sequence
<220> FEATURE:
<223> OTHER INFORMATION: synthetic

<400> SEQUENCE: 348

Gln Asp Ile Ser Asn Tyr
1               5

<210> SEQ ID NO 349
<211> LENGTH: 9
<212> TYPE: DNA
<213> ORGANISM: Artificial Sequence
<220> FEATURE:
<223> OTHER INFORMATION: synthetic

<400> SEQUENCE: 349 gatgcatcc                                                            9

<210> SEQ ID NO 350
<211> LENGTH: 3
<212> TYPE: PRT
<213> ORGANISM: Artificial Sequence
<220> FEATURE:

<223> OTHER INFORMATION: synthetic

<400> SEQUENCE: 350

Asp Ala Ser
1

<210> SEQ ID NO 351
<211> LENGTH: 27
<212> TYPE: DNA
<213> ORGANISM: Artificial Sequence
<220> FEATURE:
<223> OTHER INFORMATION: synthetic

<400> SEQUENCE: 351
caacagtatg atgatctccc gatcacc         27

<210> SEQ ID NO 352
<211> LENGTH: 9
<212> TYPE: PRT
<213> ORGANISM: Artificial Sequence
<220> FEATURE:
<223> OTHER INFORMATION: synthetic

<400> SEQUENCE: 352

Gln Gln Tyr Asp Asp Leu Pro Ile Thr
1               5

<210> SEQ ID NO 353
<211> LENGTH: 375
<212> TYPE: DNA
<213> ORGANISM: Artificial Sequence
<220> FEATURE:
<223> OTHER INFORMATION: synthetic

<400> SEQUENCE: 353
gaggtgcagc tggtggagtc tgggggaggc ttggtacagc ctggggggtc cctgagactc         60
tcctgtgcag cctctggatt ctcctttcat aattttgcca tgaactgggt ccgccaggct        120
ccagggaagg ggctggagtg ggtctcagtt attactggta gtggtactag cacacactac        180
gcagactccg tgaagggccg gttcaccatc tccagagaca attccaagaa aacgctatat        240
ctgcaaatga atagcctgag agccgaggac acggccgtat attactgtgc gaaagatcgg        300
ggctatgatt atagtggttc ttactacaac tggttcgacc cctggggcca gggaaccctg        360
gtcaccgtct cctca                                                          375

<210> SEQ ID NO 354
<211> LENGTH: 125
<212> TYPE: PRT
<213> ORGANISM: Artificial Sequence
<220> FEATURE:
<223> OTHER INFORMATION: synthetic

<400> SEQUENCE: 354

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe His Asn Phe
            20                  25                  30

Ala Met Asn Trp Val Arg Gln Ala Pro Gly Lys Gly Leu Glu Trp Val
        35                  40                  45

Ser Val Ile Thr Gly Ser Gly Thr Ser Thr His Tyr Ala Asp Ser Val
    50                  55                  60

Lys Gly Arg Phe Thr Ile Ser Arg Asp Asn Ser Lys Lys Thr Leu Tyr

|   |   |   |   | 65 |   |   |   | 70 |   |   |   | 75 |   |   |   | 80 |
|---|---|---|---|---|---|---|---|---|---|---|---|---|---|---|---|---|

Leu Gln Met Asn Ser Leu Arg Ala Glu Asp Thr Ala Val Tyr Tyr Cys
                85                      90                      95

Ala Lys Asp Arg Gly Tyr Asp Tyr Ser Gly Ser Tyr Tyr Asn Trp Phe
                100                     105                     110

Asp Pro Trp Gly Gln Gly Thr Leu Val Thr Val Ser Ser
                115                     120                     125

<210> SEQ ID NO 355
<211> LENGTH: 24
<212> TYPE: DNA
<213> ORGANISM: Artificial Sequence
<220> FEATURE:
<223> OTHER INFORMATION: synthetic

<400> SEQUENCE: 355
ggattctcct ttcataattt tgcc                                       24

<210> SEQ ID NO 356
<211> LENGTH: 8
<212> TYPE: PRT
<213> ORGANISM: Artificial Sequence
<220> FEATURE:
<223> OTHER INFORMATION: synthetic

<400> SEQUENCE: 356

Gly Phe Ser Phe His Asn Phe Ala
1               5

<210> SEQ ID NO 357
<211> LENGTH: 24
<212> TYPE: DNA
<213> ORGANISM: Artificial Sequence
<220> FEATURE:
<223> OTHER INFORMATION: synthetic

<400> SEQUENCE: 357
attactggta gtggtactag caca                                       24

<210> SEQ ID NO 358
<211> LENGTH: 8
<212> TYPE: PRT
<213> ORGANISM: Artificial Sequence
<220> FEATURE:
<223> OTHER INFORMATION: synthetic

<400> SEQUENCE: 358

Ile Thr Gly Ser Gly Thr Ser Thr
1               5

<210> SEQ ID NO 359
<211> LENGTH: 54
<212> TYPE: DNA
<213> ORGANISM: Artificial Sequence
<220> FEATURE:
<223> OTHER INFORMATION: synthetic

<400> SEQUENCE: 359
gcgaaagatc ggggctatga ttatagtggt tcttactaca actggttcga cccc       54

<210> SEQ ID NO 360
<211> LENGTH: 18
<212> TYPE: PRT
<213> ORGANISM: Artificial Sequence
<220> FEATURE:

<223> OTHER INFORMATION: synthetic

<400> SEQUENCE: 360

Ala Lys Asp Arg Gly Tyr Asp Tyr Ser Gly Ser Tyr Tyr Asn Trp Phe
1               5                   10                  15

Asp Pro

<210> SEQ ID NO 361
<211> LENGTH: 327
<212> TYPE: DNA
<213> ORGANISM: Artificial Sequence
<220> FEATURE:
<223> OTHER INFORMATION: synthetic

<400> SEQUENCE: 361

```
gacatccaga tgacccagtc tccatcctcc ctgtctgcat ctgtaggaga cagaatcacc    60
atcacttgcc gggcaagtca gagtattagc agctatttaa attggtatca gcagaaacca   120
gggaaagccc ctaaactcct gatctttgct gcatcaaatt tgcaaagtgg ggtcccatca   180
aggttcagtg gcagtggatc tgggacagat ttcactctca ccatcagtag tctgcaacct   240
gaagattttg caacttacta ctgtcaacag agttacagta ccccatcctt attcactttc   300
ggccctggga ccaaagtgga tatcaaa                                       327
```

<210> SEQ ID NO 362
<211> LENGTH: 109
<212> TYPE: PRT
<213> ORGANISM: Artificial Sequence
<220> FEATURE:
<223> OTHER INFORMATION: synthetic

<400> SEQUENCE: 362

Asp Ile Gln Met Thr Gln Ser Pro Ser Ser Leu Ser Ala Ser Val Gly
1               5                   10                  15

Asp Arg Ile Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Phe Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ser
                85                  90                  95

Leu Phe Thr Phe Gly Pro Gly Thr Lys Val Asp Ile Lys
            100                 105

<210> SEQ ID NO 363
<211> LENGTH: 18
<212> TYPE: DNA
<213> ORGANISM: Artificial Sequence
<220> FEATURE:
<223> OTHER INFORMATION: synthetic

<400> SEQUENCE: 363
cagagtatta gcagctat                                                  18

<210> SEQ ID NO 364
<211> LENGTH: 6
<212> TYPE: PRT
<213> ORGANISM: Artificial Sequence

```
<220> FEATURE:
<223> OTHER INFORMATION: synthetic

<400> SEQUENCE: 364

Gln Ser Ile Ser Ser Tyr
1               5

<210> SEQ ID NO 365
<211> LENGTH: 9
<212> TYPE: DNA
<213> ORGANISM: Artificial Sequence
<220> FEATURE:
<223> OTHER INFORMATION: synthetic

<400> SEQUENCE: 365 gctgcatca                                                                 9

<210> SEQ ID NO 366
<211> LENGTH: 3
<212> TYPE: PRT
<213> ORGANISM: Artificial Sequence
<220> FEATURE:
<223> OTHER INFORMATION: synthetic

<400> SEQUENCE: 366

Ala Ala Ser
1

<210> SEQ ID NO 367
<211> LENGTH: 33
<212> TYPE: DNA
<213> ORGANISM: Artificial Sequence
<220> FEATURE:
<223> OTHER INFORMATION: synthetic

<400> SEQUENCE: 367
caacagagtt acagtacccc atccttattc act                                     33

<210> SEQ ID NO 368
<211> LENGTH: 11
<212> TYPE: PRT
<213> ORGANISM: Artificial Sequence
<220> FEATURE:
<223> OTHER INFORMATION: synthetic

<400> SEQUENCE: 368

Gln Gln Ser Tyr Ser Thr Pro Ser Leu Phe Thr
1               5                   10

<210> SEQ ID NO 369
<211> LENGTH: 384
<212> TYPE: DNA
<213> ORGANISM: Artificial Sequence
<220> FEATURE:
<223> OTHER INFORMATION: synthetic

<400> SEQUENCE: 369
gaggtgcagc tggtggagtc tgggggaggc ttggtacagc ctggagggtc cctgagactc        60
tcctgtgcag tctctggatt caccttcagt agttacgaga tgaactgggt ccgccaggct       120
ccagggaagg ggctggaatg ggtttcacac attagtagta gtggaagtac catatactac       180
gcagactctg tgaagggccg attcaccatg tccagagaca acgccaagaa ctcactgtat       240
ctgcaaatga acagcctgag agccgaggac acggctgttt attactgtgc gagagatggg       300
aatatctgga gtggttatta tgccgcctac tacttctacg gtatggacgt ctggggccaa       360
```
gggaccacgg tcaccgtctc ctca                                          384

<210> SEQ ID NO 370
<211> LENGTH: 128
<212> TYPE: PRT
<213> ORGANISM: Artificial Sequence
<220> FEATURE:
<223> OTHER INFORMATION: synthetic

<400> SEQUENCE: 370

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser His Ile Ser Ser Ser Gly Ser Thr Ile Tyr Tyr Ala Asp Ser Val
    50                  55                  60

Lys Gly Arg Phe Thr Met Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Asn Ile Trp Ser Gly Tyr Tyr Ala Ala Tyr Tyr Phe
            100                 105                 110

Tyr Gly Met Asp Val Trp Gly Gln Gly Thr Thr Val Thr Val Ser Ser
        115                 120                 125

<210> SEQ ID NO 371
<211> LENGTH: 24
<212> TYPE: DNA
<213> ORGANISM: Artificial Sequence
<220> FEATURE:
<223> OTHER INFORMATION: synthetic

<400> SEQUENCE: 371
ggattcacct tcagtagtta cgag                                          24

<210> SEQ ID NO 372
<211> LENGTH: 8
<212> TYPE: PRT
<213> ORGANISM: Artificial Sequence
<220> FEATURE:
<223> OTHER INFORMATION: synthetic

<400> SEQUENCE: 372

Gly Phe Thr Phe Ser Ser Tyr Glu
1               5

<210> SEQ ID NO 373
<211> LENGTH: 24
<212> TYPE: DNA
<213> ORGANISM: Artificial Sequence
<220> FEATURE:
<223> OTHER INFORMATION: synthetic

<400> SEQUENCE: 373
attagtagta gtggaagtac cata                                          24

<210> SEQ ID NO 374
<211> LENGTH: 8
<212> TYPE: PRT
<213> ORGANISM: Artificial Sequence
<220> FEATURE:
<223> OTHER INFORMATION: synthetic

<400> SEQUENCE: 374

Ile Ser Ser Ser Gly Ser Thr Ile
1               5

<210> SEQ ID NO 375
<211> LENGTH: 63
<212> TYPE: DNA
<213> ORGANISM: Artificial Sequence
<220> FEATURE:
<223> OTHER INFORMATION: synthetic

<400> SEQUENCE: 375
gcgagagatg ggaatatctg gagtggttat tatgccgcct actacttcta cggtatggac    60
gtc                                                                  63

<210> SEQ ID NO 376
<211> LENGTH: 21
<212> TYPE: PRT
<213> ORGANISM: Artificial Sequence
<220> FEATURE:
<223> OTHER INFORMATION: synthetic

<400> SEQUENCE: 376

Ala Arg Asp Gly Asn Ile Trp Ser Gly Tyr Tyr Ala Ala Tyr Tyr Phe
1               5                   10                  15

Tyr Gly Met Asp Val
            20

<210> SEQ ID NO 377
<211> LENGTH: 336
<212> TYPE: DNA
<213> ORGANISM: Artificial Sequence
<220> FEATURE:
<223> OTHER INFORMATION: synthetic

<400> SEQUENCE: 377
gatattgtga tgacccagac tccactctcc tcacctgtca cccttggaca gccggcctcc    60
atctcctgca ggtctagtca aagcctcgta cacagtgatg gaaaaaccta cttgagttgg   120
cttcagcaga ggccaggcca gcctccaaga ctcctaattt ataagatttc taaccggttc   180
tctggggtcc cagacagaat cagtggcagt ggggcaggga cagatttcac actgaaaatc   240
agcagggtgg aagctgagga tgtcggggtt tattactgca tgcaagctgt acaatttcct   300
cggacgttcg gccaagggac caaggtggaa atcaaa                             336

<210> SEQ ID NO 378
<211> LENGTH: 112
<212> TYPE: PRT
<213> ORGANISM: Artificial Sequence
<220> FEATURE:
<223> OTHER INFORMATION: synthetic

<400> SEQUENCE: 378

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
                20                  25                  30

Asp Gly Lys Thr Tyr Leu Ser Trp Leu Gln Gln Arg Pro Gly Gln Pro
            35                  40                  45

```
Pro Arg Leu Leu Ile Tyr Lys Ile Ser Asn Arg Phe Ser Gly Val Pro
        50                  55                  60
Asp Arg Ile Ser Gly Ser Gly Ala Gly Thr Asp Phe Thr Leu Lys Ile
 65                  70                  75                  80
Ser Arg Val Glu Ala Glu Asp Val Gly Val Tyr Tyr Cys Met Gln Ala
                 85                  90                  95
Val Gln Phe Pro Arg Thr Phe Gly Gln Gly Thr Lys Val Glu Ile Lys
            100                 105                 110
```

<210> SEQ ID NO 379
<211> LENGTH: 33
<212> TYPE: DNA
<213> ORGANISM: Artificial Sequence
<220> FEATURE:
<223> OTHER INFORMATION: synthetic

<400> SEQUENCE: 379
caaagcctcg tacacagtga tggaaaaacc tac                33

<210> SEQ ID NO 380
<211> LENGTH: 11
<212> TYPE: PRT
<213> ORGANISM: Artificial Sequence
<220> FEATURE:
<223> OTHER INFORMATION: synthetic

<400> SEQUENCE: 380

```
Gln Ser Leu Val His Ser Asp Gly Lys Thr Tyr
 1               5                  10
```

<210> SEQ ID NO 381
<211> LENGTH: 9
<212> TYPE: DNA
<213> ORGANISM: Artificial Sequence
<220> FEATURE:
<223> OTHER INFORMATION: synthetic

<400> SEQUENCE: 381 aagatttct                9

<210> SEQ ID NO 382
<211> LENGTH: 3
<212> TYPE: PRT
<213> ORGANISM: Artificial Sequence
<220> FEATURE:
<223> OTHER INFORMATION: synthetic

<400> SEQUENCE: 382

```
Lys Ile Ser
 1
```

<210> SEQ ID NO 383
<211> LENGTH: 27
<212> TYPE: DNA
<213> ORGANISM: Artificial Sequence
<220> FEATURE:
<223> OTHER INFORMATION: synthetic

<400> SEQUENCE: 383
atgcaagctg tacaatttcc tcggacg              27

<210> SEQ ID NO 384
<211> LENGTH: 9
<212> TYPE: PRT
<213> ORGANISM: Artificial Sequence

```
<220> FEATURE:
<223> OTHER INFORMATION: synthetic

<400> SEQUENCE: 384

Met Gln Ala Val Gln Phe Pro Arg Thr
1               5

<210> SEQ ID NO 385
<211> LENGTH: 366
<212> TYPE: DNA
<213> ORGANISM: Artificial Sequence
<220> FEATURE:
<223> OTHER INFORMATION: synthetic

<400> SEQUENCE: 385
caggtgcagc tacagcagtg gggcgcagga ctgttgaacc cttcggagac cctgtccctc      60
acctgcgctg tctatggtgg ggccttcagt gattactact ggaattggat ccgccagccc     120
ccagggaagg gactggagtg gattggggaa atcaatcatc gcggaagcac caactacaac     180
ccgtccctca gagtcgtgt caccatttca gttgacacgt ccaagaacca gttctccctg      240
aggatgagct ctgtgaccgc cgcggacgcg gctgtgtatt actgtgcgag aggagaggat     300
tacgatattt ggaatggtta ttatcaggaa aaatggggcc agggaaccct ggtcaccgtc     360
tcctca                                                               366

<210> SEQ ID NO 386
<211> LENGTH: 122
<212> TYPE: PRT
<213> ORGANISM: Artificial Sequence
<220> FEATURE:
<223> OTHER INFORMATION: synthetic

<400> SEQUENCE: 386

Gln Val Gln Leu Gln Gln Trp Gly Ala Gly Leu Leu Asn Pro Ser Glu
1               5                   10                  15

Thr Leu Ser Leu Thr Cys Ala Val Tyr Gly Gly Ala Phe Ser Asp Tyr
            20                  25                  30

Tyr Trp Asn Trp Ile Arg Gln Pro Pro Gly Lys Gly Leu Glu Trp Ile
        35                  40                  45

Gly Glu Ile Asn His Arg Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Arg Met Ser Ser Val Thr Ala Ala Asp Ala Ala Val Tyr Tyr Cys Ala
                85                  90                  95

Arg Gly Glu Asp Tyr Asp Ile Trp Asn Gly Tyr Tyr Gln Glu Lys Trp
            100                 105                 110

Gly Gln Gly Thr Leu Val Thr Val Ser Ser
        115                 120

<210> SEQ ID NO 387
<211> LENGTH: 24
<212> TYPE: DNA
<213> ORGANISM: Artificial Sequence
<220> FEATURE:
<223> OTHER INFORMATION: synthetic

<400> SEQUENCE: 387
ggtggggcct tcagtgatta ctac                                            24
```

-continued

<210> SEQ ID NO 388
<211> LENGTH: 8
<212> TYPE: PRT
<213> ORGANISM: Artificial Sequence
<220> FEATURE:
<223> OTHER INFORMATION: synthetic

<400> SEQUENCE: 388

Gly Gly Ala Phe Ser Asp Tyr Tyr
1               5

<210> SEQ ID NO 389
<211> LENGTH: 21
<212> TYPE: DNA
<213> ORGANISM: Artificial Sequence
<220> FEATURE:
<223> OTHER INFORMATION: synthetic

<400> SEQUENCE: 389
atcaatcatc gcggaagcac c                                           21

<210> SEQ ID NO 390
<211> LENGTH: 7
<212> TYPE: PRT
<213> ORGANISM: Artificial Sequence
<220> FEATURE:
<223> OTHER INFORMATION: synthetic

<400> SEQUENCE: 390

Ile Asn His Arg Gly Ser Thr
1               5

<210> SEQ ID NO 391
<211> LENGTH: 48
<212> TYPE: DNA
<213> ORGANISM: Artificial Sequence
<220> FEATURE:
<223> OTHER INFORMATION: synthetic

<400> SEQUENCE: 391
gcgagaggag aggattacga tatttggaat ggttattatc aggaaaaa              48

<210> SEQ ID NO 392
<211> LENGTH: 16
<212> TYPE: PRT
<213> ORGANISM: Artificial Sequence
<220> FEATURE:
<223> OTHER INFORMATION: synthetic

<400> SEQUENCE: 392

Ala Arg Gly Glu Asp Tyr Asp Ile Trp Asn Gly Tyr Tyr Gln Glu Lys
1               5                   10                  15

<210> SEQ ID NO 393
<211> LENGTH: 321
<212> TYPE: DNA
<213> ORGANISM: Artificial Sequence
<220> FEATURE:
<223> OTHER INFORMATION: synthetic

<400> SEQUENCE: 393
gaaattgtgt tgacacagtc tccagccacc ctgtctttgt ctccagggga aagagccacc   60
ctctcctgca gggccagtca gagtattagc acctacttag cctggtacca acagaagcct  120
ggccaggctc ccaggctcct catctatgat gcatccaaga gggccactgg catcccagcc  180
aggttcagtg gcagtgggtc tgggacagac ttcactctca ccatcagcag cctagagcct  240

```
gaagattttg tagtttatta ctgtcaccag cgtagcaact ggcctctcac tttcggcgga      300
gggaccaagg tggagatcaa a                                                321
```

<210> SEQ ID NO 394
<211> LENGTH: 107
<212> TYPE: PRT
<213> ORGANISM: Artificial Sequence
<220> FEATURE:
<223> OTHER INFORMATION: synthetic

<400> SEQUENCE: 394

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Thr Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Val Val Tyr Tyr Cys His Gln Arg Ser Asn Trp Pro Leu
                85                  90                  95

Thr Phe Gly Gly Gly Thr Lys Val Glu Ile Lys
            100                 105
```

<210> SEQ ID NO 395
<211> LENGTH: 18
<212> TYPE: DNA
<213> ORGANISM: Artificial Sequence
<220> FEATURE:
<223> OTHER INFORMATION: synthetic

<400> SEQUENCE: 395

```
cagagtatta gcacctac                                                    18
```

<210> SEQ ID NO 396
<211> LENGTH: 6
<212> TYPE: PRT
<213> ORGANISM: Artificial Sequence
<220> FEATURE:
<223> OTHER INFORMATION: synthetic

<400> SEQUENCE: 396

```
Gln Ser Ile Ser Thr Tyr
1               5
```

<210> SEQ ID NO 397
<211> LENGTH: 9
<212> TYPE: DNA
<213> ORGANISM: Artificial Sequence
<220> FEATURE:
<223> OTHER INFORMATION: synthetic

<400> SEQUENCE: 397

```
gatgcatcc                                                              9
```

<210> SEQ ID NO 398
<211> LENGTH: 3
<212> TYPE: PRT
<213> ORGANISM: Artificial Sequence
<220> FEATURE:

<223> OTHER INFORMATION: synthetic

<400> SEQUENCE: 398

Asp Ala Ser
1

<210> SEQ ID NO 399
<211> LENGTH: 27
<212> TYPE: DNA
<213> ORGANISM: Artificial Sequence
<220> FEATURE:
<223> OTHER INFORMATION: synthetic

<400> SEQUENCE: 399
caccagcgta gcaactggcc tctcact                                         27

<210> SEQ ID NO 400
<211> LENGTH: 9
<212> TYPE: PRT
<213> ORGANISM: Artificial Sequence
<220> FEATURE:
<223> OTHER INFORMATION: synthetic

<400> SEQUENCE: 400

His Gln Arg Ser Asn Trp Pro Leu Thr
1               5

<210> SEQ ID NO 401
<211> LENGTH: 351
<212> TYPE: DNA
<213> ORGANISM: Artificial Sequence
<220> FEATURE:
<223> OTHER INFORMATION: synthetic

<400> SEQUENCE: 401
caggtgcagc tgcaggagtc gggggccagga ctggtgaagc cttcggagac cctgtccctc     60
acctgcactg tctctggtgg ttccttcagt agttactact ggagttggct ccggcagccc    120
ccaggaaagg gctggagtg gattggatat atcttttaca gtgggagtac cgactacaac     180
ccctccctca agagtcgagt caccatttca gtagacacgt ccaagaagca gttctccctg    240
aagctgacct ctgtgaccgc tgcggacacg gccgtctatt actgtgcgcg aacaataagt    300
acgtggtggt tcgcccccctg gggccaggga accctggtca ccgtctcctc a             351

<210> SEQ ID NO 402
<211> LENGTH: 117
<212> TYPE: PRT
<213> ORGANISM: Artificial Sequence
<220> FEATURE:
<223> OTHER INFORMATION: synthetic

<400> SEQUENCE: 402

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Phe Ser Ser Tyr
                20                  25                  30

Tyr Trp Ser Trp Leu Arg Gln Pro Pro Gly Lys Gly Leu Glu Trp Ile
            35                  40                  45

Gly Tyr Ile Phe Tyr Ser Gly Ser Thr Asp Tyr Asn Pro Ser Leu Lys
        50                  55                  60

Ser Arg Val Thr Ile Ser Val Asp Thr Ser Lys Lys Gln Phe Ser Leu
65                  70                  75                  80

Lys Leu Thr Ser Val Thr Ala Ala Asp Thr Ala Val Tyr Tyr Cys Ala
            85                  90                  95

Arg Thr Ile Ser Thr Trp Trp Phe Ala Pro Trp Gly Gln Gly Thr Leu
            100                 105                 110

Val Thr Val Ser Ser
        115

<210> SEQ ID NO 403
<211> LENGTH: 24
<212> TYPE: DNA
<213> ORGANISM: Artificial Sequence
<220> FEATURE:
<223> OTHER INFORMATION: synthetic

<400> SEQUENCE: 403
ggtggttcct tcagtagtta ctac            24

<210> SEQ ID NO 404
<211> LENGTH: 8
<212> TYPE: PRT
<213> ORGANISM: Artificial Sequence
<220> FEATURE:
<223> OTHER INFORMATION: synthetic

<400> SEQUENCE: 404

Gly Gly Ser Phe Ser Ser Tyr Tyr
1               5

<210> SEQ ID NO 405
<211> LENGTH: 21
<212> TYPE: DNA
<213> ORGANISM: Artificial Sequence
<220> FEATURE:
<223> OTHER INFORMATION: synthetic

<400> SEQUENCE: 405
atcttttaca gtgggagtac c            21

<210> SEQ ID NO 406
<211> LENGTH: 7
<212> TYPE: PRT
<213> ORGANISM: Artificial Sequence
<220> FEATURE:
<223> OTHER INFORMATION: synthetic

<400> SEQUENCE: 406

Ile Phe Tyr Ser Gly Ser Thr
1               5

<210> SEQ ID NO 407
<211> LENGTH: 33
<212> TYPE: DNA
<213> ORGANISM: Artificial Sequence
<220> FEATURE:
<223> OTHER INFORMATION: synthetic

<400> SEQUENCE: 407
gcgcgaacaa taagtacgtg gtggttcgcc ccc            33

<210> SEQ ID NO 408
<211> LENGTH: 11
<212> TYPE: PRT
<213> ORGANISM: Artificial Sequence
<220> FEATURE:
<223> OTHER INFORMATION: synthetic -continued

<400> SEQUENCE: 408

Ala Arg Thr Ile Ser Thr Trp Trp Phe Ala Pro
1               5                   10

<210> SEQ ID NO 409
<211> LENGTH: 318
<212> TYPE: DNA
<213> ORGANISM: Artificial Sequence
<220> FEATURE:
<223> OTHER INFORMATION: synthetic

<400> SEQUENCE: 409

```
gaaatagtga tgacacagtc tccagccacc ctgtctgtgt ctccagggg aagagccacc    60
ctctcctgca gggccagtca gagtgttagc aacaacgtag cctggtacca gcagaaacct   120
ggccaggctc ccaggctcct catctatggt gcatccacca gggccactgg tatcccaggc   180
aggttcagtg gcagtgggtc tgggacagag ttcactctca ccatcagcag cctgcagtct   240
gaagattttg cagtttattc ctgtcagcag tataataact ggctcacttt cggcggaggg   300
accaaggtgg agatcaaa                                                318
```

<210> SEQ ID NO 410
<211> LENGTH: 106
<212> TYPE: PRT
<213> ORGANISM: Artificial Sequence
<220> FEATURE:
<223> OTHER INFORMATION: synthetic

<400> SEQUENCE: 410

Glu Ile Val Met Thr Gln Ser Pro Ala Thr Leu Ser Val Ser Pro Gly
1               5                   10                  15
Gly Arg Ala Thr Leu Ser Cys Arg Ala Ser Gln Ser Val Ser Asn Asn
            20                  25                  30
Val Ala Trp Tyr Gln Gln Lys Pro Gly Gln Ala Pro Arg Leu Leu Ile
        35                  40                  45
Tyr Gly Ala Ser Thr Arg Ala Thr Gly Ile Pro Gly Arg Phe Ser Gly
    50                  55                  60
Ser Gly Ser Gly Thr Glu Phe Thr Leu Thr Ile Ser Ser Leu Gln Ser
65                  70                  75                  80
Glu Asp Phe Ala Val Tyr Ser Cys Gln Gln Tyr Asn Asn Trp Leu Thr
                85                  90                  95
Phe Gly Gly Gly Thr Lys Val Glu Ile Lys
            100                 105

<210> SEQ ID NO 411
<211> LENGTH: 18
<212> TYPE: DNA
<213> ORGANISM: Artificial Sequence
<220> FEATURE:
<223> OTHER INFORMATION: synthetic

<400> SEQUENCE: 411
cagagtgtta gcaacaac                                                 18

<210> SEQ ID NO 412
<211> LENGTH: 6
<212> TYPE: PRT
<213> ORGANISM: Artificial Sequence
<220> FEATURE:
<223> OTHER INFORMATION: synthetic

<400> SEQUENCE: 412

Gln Ser Val Ser Asn Asn
1               5

<210> SEQ ID NO 413
<211> LENGTH: 9
<212> TYPE: DNA
<213> ORGANISM: Artificial Sequence
<220> FEATURE:
<223> OTHER INFORMATION: synthetic

<400> SEQUENCE: 413 ggtgcatcc                                                                9

<210> SEQ ID NO 414
<211> LENGTH: 3
<212> TYPE: PRT
<213> ORGANISM: Artificial Sequence
<220> FEATURE:
<223> OTHER INFORMATION: synthetic

<400> SEQUENCE: 414

Gly Ala Ser
1

<210> SEQ ID NO 415
<211> LENGTH: 24
<212> TYPE: DNA
<213> ORGANISM: Artificial Sequence
<220> FEATURE:
<223> OTHER INFORMATION: synthetic

<400> SEQUENCE: 415
cagcagtata ataactggct cact                                              24

<210> SEQ ID NO 416
<211> LENGTH: 8
<212> TYPE: PRT
<213> ORGANISM: Artificial Sequence
<220> FEATURE:
<223> OTHER INFORMATION: synthetic

<400> SEQUENCE: 416

Gln Gln Tyr Asn Asn Trp Leu Thr
1               5

<210> SEQ ID NO 417
<211> LENGTH: 369
<212> TYPE: DNA
<213> ORGANISM: Artificial Sequence
<220> FEATURE:
<223> OTHER INFORMATION: synthetic

<400> SEQUENCE: 417
caggtgcagc tggtggagtc tgggggaggc gtggtccagc ctggggaggtc cctgagactc      60 tcctgtgtag cgtctggatt cactttcagt agttatggca tgcactgggt ccgccaggct     120
ccaggcaagg ggctggagtg ggtggcaatt atatggtatg atggaagtaa taaatactat     180
gcagactccg tgaagggccg attcaccata tccagagaca attccaagaa cacacagtat     240
ctgcaaatga acagcctgag agccgaggac acggctgtgt attactgtgc gtcagtagct     300
acgtctgggg acttcgacta ctacggtatg gacgtctggg gccaagggac cacggtcacc     360
gtctcctca                                                              369

```
<210> SEQ ID NO 418
<211> LENGTH: 123
<212> TYPE: PRT
<213> ORGANISM: Artificial Sequence
<220> FEATURE:
<223> OTHER INFORMATION: synthetic

<400> SEQUENCE: 418
```

Gln Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Gln Tyr
65                  70                  75                  80

Leu Gln Met Asn Ser Leu Arg Ala Glu Asp Thr Ala Val Tyr Tyr Cys
                85                  90                  95

Ala Ser Val Ala Thr Ser Gly Asp Phe Asp Tyr Tyr Gly Met Asp Val
            100                 105                 110

Trp Gly Gln Gly Thr Thr Val Thr Val Ser Ser
        115                 120

```
<210> SEQ ID NO 419
<211> LENGTH: 24
<212> TYPE: DNA
<213> ORGANISM: Artificial Sequence
<220> FEATURE:
<223> OTHER INFORMATION: synthetic

<400> SEQUENCE: 419
```
ggattcactt tcagtagtta tggc                                          24

```
<210> SEQ ID NO 420
<211> LENGTH: 8
<212> TYPE: PRT
<213> ORGANISM: Artificial Sequence
<220> FEATURE:
<223> OTHER INFORMATION: synthetic

<400> SEQUENCE: 420
```

Gly Phe Thr Phe Ser Ser Tyr Gly
1               5

```
<210> SEQ ID NO 421
<211> LENGTH: 24
<212> TYPE: DNA
<213> ORGANISM: Artificial Sequence
<220> FEATURE:
<223> OTHER INFORMATION: synthetic

<400> SEQUENCE: 421
```
atatggtatg atggaagtaa taaa                                          24

```
<210> SEQ ID NO 422
<211> LENGTH: 8
<212> TYPE: PRT
<213> ORGANISM: Artificial Sequence
<220> FEATURE:
<223> OTHER INFORMATION: synthetic

<400> SEQUENCE: 422
```

```
Ile Trp Tyr Asp Gly Ser Asn Lys
1               5
```

<210> SEQ ID NO 423
<211> LENGTH: 48
<212> TYPE: DNA
<213> ORGANISM: Artificial Sequence
<220> FEATURE:
<223> OTHER INFORMATION: synthetic

<400> SEQUENCE: 423

```
gcgtcagtag ctacgtctgg ggacttcgac tactacggta tggacgtc                48
```

<210> SEQ ID NO 424
<211> LENGTH: 16
<212> TYPE: PRT
<213> ORGANISM: Artificial Sequence
<220> FEATURE:
<223> OTHER INFORMATION: synthetic

<400> SEQUENCE: 424

```
Ala Ser Val Ala Thr Ser Gly Asp Phe Asp Tyr Tyr Gly Met Asp Val
1               5                   10                  15
```

<210> SEQ ID NO 425
<211> LENGTH: 321
<212> TYPE: DNA
<213> ORGANISM: Artificial Sequence
<220> FEATURE:
<223> OTHER INFORMATION: synthetic

<400> SEQUENCE: 425

```
gaaattgtgt tgacacagtc tccagccacc ctgtctttgt ctccagggga aagaaccacc     60
ctctcctgca gggccagtca gagaattagc acctacttag cctggtatca acagaaacct    120
ggccaggctc ccaggctcct catctatgat gcatccaaaa gggccactgg catcccagcc    180
aggttcagtg gtagtgggtc tgggacaggc ttcactctca ccatcagcag cctagagcct    240
gaagattttg cagtttatta ctgtcagcag cgtagtaact ggcctctcac tttcggcgga    300
gggaccaagg tggagatcaa a                                              321
```

<210> SEQ ID NO 426
<211> LENGTH: 107
<212> TYPE: PRT
<213> ORGANISM: Artificial Sequence
<220> FEATURE:
<223> OTHER INFORMATION: synthetic

<400> SEQUENCE: 426

```
Glu Ile Val Leu Thr Gln Ser Pro Ala Thr Leu Ser Leu Ser Pro Gly
1               5                   10                  15

Glu Arg Thr Thr Leu Ser Cys Arg Ala Ser Gln Arg Ile Ser Thr Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Gly Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95
```

Thr Phe Gly Gly Gly Thr Lys Val Glu Ile Lys
            100                 105

<210> SEQ ID NO 427
<211> LENGTH: 18
<212> TYPE: DNA
<213> ORGANISM: Artificial Sequence
<220> FEATURE:
<223> OTHER INFORMATION: synthetic

<400> SEQUENCE: 427
cagagaatta gcacctac                                                 18

<210> SEQ ID NO 428
<211> LENGTH: 6
<212> TYPE: PRT
<213> ORGANISM: Artificial Sequence
<220> FEATURE:
<223> OTHER INFORMATION: synthetic

<400> SEQUENCE: 428

Gln Arg Ile Ser Thr Tyr
1               5

<210> SEQ ID NO 429
<211> LENGTH: 9
<212> TYPE: DNA
<213> ORGANISM: Artificial Sequence
<220> FEATURE:
<223> OTHER INFORMATION: synthetic

<400> SEQUENCE: 429 gatgcatcc                                                            9

<210> SEQ ID NO 430
<211> LENGTH: 3
<212> TYPE: PRT
<213> ORGANISM: Artificial Sequence
<220> FEATURE:
<223> OTHER INFORMATION: synthetic

<400> SEQUENCE: 430

Asp Ala Ser
1

<210> SEQ ID NO 431
<211> LENGTH: 27
<212> TYPE: DNA
<213> ORGANISM: Artificial Sequence
<220> FEATURE:
<223> OTHER INFORMATION: synthetic

<400> SEQUENCE: 431
cagcagcgta gtaactggcc tctcact                                       27

<210> SEQ ID NO 432
<211> LENGTH: 9
<212> TYPE: PRT
<213> ORGANISM: Artificial Sequence
<220> FEATURE:
<223> OTHER INFORMATION: synthetic

<400> SEQUENCE: 432

Gln Gln Arg Ser Asn Trp Pro Leu Thr
1               5

<210> SEQ ID NO 433
<211> LENGTH: 357
<212> TYPE: DNA
<213> ORGANISM: Artificial Sequence
<220> FEATURE:
<223> OTHER INFORMATION: synthetic

<400> SEQUENCE: 433

```
gaggtgcagc tggtgcagtc tggagcagag gtgagaaagc ccggggagtc tctgaagatc      60
tcctgtaagg gttctggata cagctttact aactactgga tcgtctgggt gcgccagatg     120
cccgggaaag gcctggagtg gatggggatc atctatcctg gtgactctga taccagatac     180
agcccgtcct ccaaggcca ggtcaccatc tcagccgaca gtccatcag caccgcctac      240
ctgcagtgga gcagcctgaa ggcctcggac accgccatgt attactgtgc gagacgggat     300
acgatttttcc cttcctatcc cctctggggc cagggaaccc tggtcaccgt ctcctca      357
```

<210> SEQ ID NO 434
<211> LENGTH: 119
<212> TYPE: PRT
<213> ORGANISM: Artificial Sequence
<220> FEATURE:
<223> OTHER INFORMATION: synthetic

<400> SEQUENCE: 434

Glu Val Gln Leu Val Gln Ser Gly Ala Glu Val Arg Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Val Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Asp Thr Ile Phe Pro Ser Tyr Pro Leu Trp Gly Gln Gly
            100                 105                 110

Thr Leu Val Thr Val Ser Ser
        115

<210> SEQ ID NO 435
<211> LENGTH: 24
<212> TYPE: DNA
<213> ORGANISM: Artificial Sequence
<220> FEATURE:
<223> OTHER INFORMATION: synthetic

<400> SEQUENCE: 435

```
ggatacagct ttactaacta ctgg                                              24
```

<210> SEQ ID NO 436
<211> LENGTH: 8
<212> TYPE: PRT
<213> ORGANISM: Artificial Sequence
<220> FEATURE:
<223> OTHER INFORMATION: synthetic

<400> SEQUENCE: 436

Gly Tyr Ser Phe Thr Asn Tyr Trp
1               5

<210> SEQ ID NO 437
<211> LENGTH: 24
<212> TYPE: DNA
<213> ORGANISM: Artificial Sequence
<220> FEATURE:
<223> OTHER INFORMATION: synthetic

<400> SEQUENCE: 437
atctatcctg gtgactctga tacc                                           24

<210> SEQ ID NO 438
<211> LENGTH: 8
<212> TYPE: PRT
<213> ORGANISM: Artificial Sequence
<220> FEATURE:
<223> OTHER INFORMATION: synthetic

<400> SEQUENCE: 438

Ile Tyr Pro Gly Asp Ser Asp Thr
1               5

<210> SEQ ID NO 439
<211> LENGTH: 36
<212> TYPE: DNA
<213> ORGANISM: Artificial Sequence
<220> FEATURE:
<223> OTHER INFORMATION: synthetic

<400> SEQUENCE: 439
gcgagacggg atacgatttt cccttcctat cccctc                              36

<210> SEQ ID NO 440
<211> LENGTH: 12
<212> TYPE: PRT
<213> ORGANISM: Artificial Sequence
<220> FEATURE:
<223> OTHER INFORMATION: synthetic

<400> SEQUENCE: 440

Ala Arg Arg Asp Thr Ile Phe Pro Ser Tyr Pro Leu
1               5                   10

<210> SEQ ID NO 441
<211> LENGTH: 336
<212> TYPE: DNA
<213> ORGANISM: Artificial Sequence
<220> FEATURE:
<223> OTHER INFORMATION: synthetic

<400> SEQUENCE: 441
gatattgtga tgactcagtc tcctctctcc ctgcccgtca cccctggaga gccggcctcc    60
atctcctgca ggtctagtca gagcctcctg aatagtaatg gatacaactt tttggattgg   120
tacctgcaga agccagggca gtctccacaa ctcctgatct atttggtttc taatcgggcc   180
tccggggtcc ctgacaggtt cagtggcagt ggatcaggca cagatttac actgaaaatc    240 agcagagtgg aggctgagga tattggggtt tattactgca tgcaagctct ccaaactccg   300
atcaccttcg gccaagggac acgactggag attaaa                             336

<210> SEQ ID NO 442
<211> LENGTH: 112
<212> TYPE: PRT
<213> ORGANISM: Artificial Sequence
<220> FEATURE:

<223> OTHER INFORMATION: synthetic

<400> SEQUENCE: 442

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Asn Ser
            20                  25                  30

Asn Gly Tyr Asn Phe Leu Asp Trp Tyr Leu Gln Lys Pro Gly Gln Ser
        35                  40                  45

Pro Gln Leu Leu Ile Tyr Leu Val Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Ile Gly Val Tyr Tyr Cys Met Gln Ala
                85                  90                  95

Leu Gln Thr Pro Ile Thr Phe Gly Gln Gly Thr Arg Leu Glu Ile Lys
            100                 105                 110

<210> SEQ ID NO 443
<211> LENGTH: 33
<212> TYPE: DNA
<213> ORGANISM: Artificial Sequence
<220> FEATURE:
<223> OTHER INFORMATION: synthetic

<400> SEQUENCE: 443
cagagcctcc tgaatagtaa tggatacaac ttt                                   33

<210> SEQ ID NO 444
<211> LENGTH: 11
<212> TYPE: PRT
<213> ORGANISM: Artificial Sequence
<220> FEATURE:
<223> OTHER INFORMATION: synthetic

<400> SEQUENCE: 444

Gln Ser Leu Leu Asn Ser Asn Gly Tyr Asn Phe
1               5                   10

<210> SEQ ID NO 445
<211> LENGTH: 9
<212> TYPE: DNA
<213> ORGANISM: Artificial Sequence
<220> FEATURE:
<223> OTHER INFORMATION: synthetic

<400> SEQUENCE: 445 ttggtttct                                                              9

<210> SEQ ID NO 446
<211> LENGTH: 3
<212> TYPE: PRT
<213> ORGANISM: Artificial Sequence
<220> FEATURE:
<223> OTHER INFORMATION: synthetic

<400> SEQUENCE: 446

Leu Val Ser
1

<210> SEQ ID NO 447
<211> LENGTH: 27
<212> TYPE: DNA

<213> ORGANISM: Artificial Sequence
<220> FEATURE:
<223> OTHER INFORMATION: synthetic

<400> SEQUENCE: 447
atgcaagctc tccaaactcc gatcacc                                27

<210> SEQ ID NO 448
<211> LENGTH: 9
<212> TYPE: PRT
<213> ORGANISM: Artificial Sequence
<220> FEATURE:
<223> OTHER INFORMATION: synthetic

<400> SEQUENCE: 448

Met Gln Ala Leu Gln Thr Pro Ile Thr
1               5

<210> SEQ ID NO 449
<211> LENGTH: 360
<212> TYPE: DNA
<213> ORGANISM: Artificial Sequence
<220> FEATURE:
<223> OTHER INFORMATION: synthetic

<400> SEQUENCE: 449
cagatcacct tgaaggagtc tggtcctacg ctggtgaaac ccacacagac cctcacgctg     60
acctgcacct tctctgggtt ctcactcagc actaatggag tgggtgtggg ctggatccgt    120
cagcccccag gaaaggccct ggagtggctt acactcattt attggaatga aaataagcac    180
tacagcccat ctctgaaaaa caggatcacc atcaccaagg acacctccaa aaaccaggtg    240
gtccttacaa tgaccaactt ggaccctgtg gacacagcca cttattactg tgtacacagg    300
ggatggttgg gagcaatctt tgcctactgg ggccaggaa ccctggtcac cgtctcctca     360

<210> SEQ ID NO 450
<211> LENGTH: 120
<212> TYPE: PRT
<213> ORGANISM: Artificial Sequence
<220> FEATURE:
<223> OTHER INFORMATION: synthetic

<400> SEQUENCE: 450

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Asn
            20                  25                  30

Gly Val Gly Val Gly Trp Ile Arg Gln Pro Pro Gly Lys Ala Leu Glu
        35                  40                  45

Trp Leu Thr Leu Ile Tyr Trp Asn Glu Asn Lys His Tyr Ser Pro Ser
    50                  55                  60

Leu Lys Asn Arg Ile Thr Ile Thr Lys Asp Thr Ser Lys Asn Gln Val
65                  70                  75                  80

Val Leu Thr Met Thr Asn Leu Asp Pro Val Asp Thr Ala Thr Tyr Tyr
                85                  90                  95

Cys Val His Arg Gly Trp Leu Gly Ala Ile Phe Ala Tyr Trp Gly Gln
            100                 105                 110

Gly Thr Leu Val Thr Val Ser Ser
        115                 120

<210> SEQ ID NO 451

```
<211> LENGTH: 30
<212> TYPE: DNA
<213> ORGANISM: Artificial Sequence
<220> FEATURE:
<223> OTHER INFORMATION: synthetic

<400> SEQUENCE: 451
gggttctcac tcagcactaa tggagtgggt                                    30

<210> SEQ ID NO 452
<211> LENGTH: 10
<212> TYPE: PRT
<213> ORGANISM: Artificial Sequence
<220> FEATURE:
<223> OTHER INFORMATION: synthetic

<400> SEQUENCE: 452

Gly Phe Ser Leu Ser Thr Asn Gly Val Gly
1               5                   10

<210> SEQ ID NO 453
<211> LENGTH: 21
<212> TYPE: DNA
<213> ORGANISM: Artificial Sequence
<220> FEATURE:
<223> OTHER INFORMATION: synthetic

<400> SEQUENCE: 453
atttattgga atgaaaataa g                                             21

<210> SEQ ID NO 454
<211> LENGTH: 7
<212> TYPE: PRT
<213> ORGANISM: Artificial Sequence
<220> FEATURE:
<223> OTHER INFORMATION: synthetic

<400> SEQUENCE: 454

Ile Tyr Trp Asn Glu Asn Lys
1               5

<210> SEQ ID NO 455
<211> LENGTH: 36
<212> TYPE: DNA
<213> ORGANISM: Artificial Sequence
<220> FEATURE:
<223> OTHER INFORMATION: synthetic

<400> SEQUENCE: 455
gtacacaggg gatggttggg agcaatcttt gcctac                             36

<210> SEQ ID NO 456
<211> LENGTH: 12
<212> TYPE: PRT
<213> ORGANISM: Artificial Sequence
<220> FEATURE:
<223> OTHER INFORMATION: synthetic

<400> SEQUENCE: 456

Val His Arg Gly Trp Leu Gly Ala Ile Phe Ala Tyr
1               5                   10

<210> SEQ ID NO 457
<211> LENGTH: 378
<212> TYPE: DNA
<213> ORGANISM: Artificial Sequence
<220> FEATURE:
```

<223> OTHER INFORMATION: synthetic

<400> SEQUENCE: 457

```
gaggtgcagc tggtggagtc tgggggaggc ttggtacagc ctgggggtc cctgagactc    60
tcctgtgcag cctctggatt cacctttact agttatgcca tgacctgggt ccgccaggct   120
ccagggaagg ggctggagtg ggtctcagat attagtggta gtggtggtag aacatattac   180
gcagactccg tgaagggccg gttcaccatc tccagagaca attccaagaa tatgctgtat   240
ctgcaaatga acatcctgag agccgaagac acggccgtat atcattgtgc gaagggaaca   300
ggccagcagg tggaccttta caactactac tatgctttgg acgtctgggg ccaagggacc   360
acggtcaccg tctcctca                                                 378
```

<210> SEQ ID NO 458
<211> LENGTH: 126
<212> TYPE: PRT
<213> ORGANISM: Artificial Sequence
<220> FEATURE:
<223> OTHER INFORMATION: synthetic

<400> SEQUENCE: 458

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Ala Met Thr Trp Val Arg Gln Ala Pro Gly Lys Gly Leu Glu Trp Val
        35                  40                  45

Ser Asp Ile Ser Gly Ser Gly Gly Arg Thr Tyr Tyr Ala Asp Ser Val
    50                  55                  60

Lys Gly Arg Phe Thr Ile Ser Arg Asp Asn Ser Lys Asn Met Leu Tyr
65                  70                  75                  80

Leu Gln Met Asn Ile Leu Arg Ala Glu Asp Thr Ala Val Tyr His Cys
                85                  90                  95

Ala Lys Gly Thr Gly Gln Gln Val Asp Leu Tyr Asn Tyr Tyr Tyr Ala
            100                 105                 110

Leu Asp Val Trp Gly Gln Gly Thr Thr Val Thr Val Ser Ser
        115                 120                 125
```

<210> SEQ ID NO 459
<211> LENGTH: 24
<212> TYPE: DNA
<213> ORGANISM: Artificial Sequence
<220> FEATURE:
<223> OTHER INFORMATION: synthetic

<400> SEQUENCE: 459

```
ggattcacct ttactagtta tgcc                                           24
```

<210> SEQ ID NO 460
<211> LENGTH: 8
<212> TYPE: PRT
<213> ORGANISM: Artificial Sequence
<220> FEATURE:
<223> OTHER INFORMATION: synthetic

<400> SEQUENCE: 460

```
Gly Phe Thr Phe Thr Ser Tyr Ala
1               5
```

<210> SEQ ID NO 461

```
<211> LENGTH: 24
<212> TYPE: DNA
<213> ORGANISM: Artificial Sequence
<220> FEATURE:
<223> OTHER INFORMATION: synthetic

<400> SEQUENCE: 461
attagtggta gtggtggtag aaca                                          24

<210> SEQ ID NO 462
<211> LENGTH: 8
<212> TYPE: PRT
<213> ORGANISM: Artificial Sequence
<220> FEATURE:
<223> OTHER INFORMATION: synthetic

<400> SEQUENCE: 462

Ile Ser Gly Ser Gly Gly Arg Thr
1               5

<210> SEQ ID NO 463
<211> LENGTH: 57
<212> TYPE: DNA
<213> ORGANISM: Artificial Sequence
<220> FEATURE:
<223> OTHER INFORMATION: synthetic

<400> SEQUENCE: 463
gcgaagggaa caggccagca ggtggacctt tacaactact actatgcttt ggacgtc      57

<210> SEQ ID NO 464
<211> LENGTH: 19
<212> TYPE: PRT
<213> ORGANISM: Artificial Sequence
<220> FEATURE:
<223> OTHER INFORMATION: synthetic

<400> SEQUENCE: 464

Ala Lys Gly Thr Gly Gln Gln Val Asp Leu Tyr Asn Tyr Tyr Tyr Ala
1               5                   10                  15

Leu Asp Val

<210> SEQ ID NO 465
<211> LENGTH: 387
<212> TYPE: DNA
<213> ORGANISM: Artificial Sequence
<220> FEATURE:
<223> OTHER INFORMATION: synthetic

<400> SEQUENCE: 465
caggtgcagc tggtggagtc tgggggaggc gtggtccagc ctgggaggtc cctgagactc    60
tcctgtgcag cgtctggatt caccttcagt tactatggca tgcactgggt ccgccaggct   120
ccaggcaagg ggctggagtg ggtggcagtt atatggtatg atggaagtaa taaacactat   180
gcagactccg tgaagggccg attcaccatc tccagagaca attccaagaa cacgctgtat   240
ctgcaaatga acagcctgag agccgacgac acggctgtct attactgtgc gagagataag   300
ggtataagtg gaattaaggg gggttcttac tactactact atgccatgga cgtctggggc   360
caagggacca cggtcaccgt ctcctca                                      387

<210> SEQ ID NO 466
<211> LENGTH: 129
<212> TYPE: PRT
<213> ORGANISM: Artificial Sequence
```

-continued

```
<220> FEATURE:
<223> OTHER INFORMATION: synthetic

<400> SEQUENCE: 466

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Tyr Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Ala Arg Asp Lys Gly Ile Ser Gly Ile Lys Gly Gly Ser Tyr Tyr Tyr
            100                 105                 110

Tyr Tyr Ala Met Asp Val Trp Gly Gln Gly Thr Thr Val Thr Val Ser
        115                 120                 125

Ser

<210> SEQ ID NO 467
<211> LENGTH: 24
<212> TYPE: DNA
<213> ORGANISM: Artificial Sequence
<220> FEATURE:
<223> OTHER INFORMATION: synthetic

<400> SEQUENCE: 467
ggattcacct tcagttacta tggc                                          24

<210> SEQ ID NO 468
<211> LENGTH: 8
<212> TYPE: PRT
<213> ORGANISM: Artificial Sequence
<220> FEATURE:
<223> OTHER INFORMATION: synthetic

<400> SEQUENCE: 468

Gly Phe Thr Phe Ser Tyr Tyr Gly
1               5

<210> SEQ ID NO 469
<211> LENGTH: 24
<212> TYPE: DNA
<213> ORGANISM: Artificial Sequence
<220> FEATURE:
<223> OTHER INFORMATION: synthetic

<400> SEQUENCE: 469
atatggtatg atggaagtaa taaa                                          24

<210> SEQ ID NO 470
<211> LENGTH: 8
<212> TYPE: PRT
<213> ORGANISM: Artificial Sequence
<220> FEATURE:
<223> OTHER INFORMATION: synthetic

<400> SEQUENCE: 470

Ile Trp Tyr Asp Gly Ser Asn Lys
```

```
<210> SEQ ID NO 471
<211> LENGTH: 66
<212> TYPE: DNA
<213> ORGANISM: Artificial Sequence
<220> FEATURE:
<223> OTHER INFORMATION: synthetic

<400> SEQUENCE: 471
gcgagagata agggtataag tggaattaag gggggttctt actactacta ctatgccatg    60
gacgtc                                                               66

<210> SEQ ID NO 472
<211> LENGTH: 22
<212> TYPE: PRT
<213> ORGANISM: Artificial Sequence
<220> FEATURE:
<223> OTHER INFORMATION: synthetic

<400> SEQUENCE: 472

Ala Arg Asp Lys Gly Ile Ser Gly Ile Lys Gly Gly Ser Tyr Tyr Tyr
1               5                   10                  15

Tyr Tyr Ala Met Asp Val
            20

<210> SEQ ID NO 473
<211> LENGTH: 360
<212> TYPE: DNA
<213> ORGANISM: Artificial Sequence
<220> FEATURE:
<223> OTHER INFORMATION: synthetic

<400> SEQUENCE: 473
gaggtgcagc tggtggagtc tgggggaggc ttggtaaagc ctggggggtc ccttagactc    60
tcctgtgcag cctctggatt cactttcagt aacgcctgga tgacctgggt ccgccaggct   120
ccagggaagg ggctggagtg ggttggccgt attaaaaaca aaattgatgg tgggacaaca   180
gactacgctg cacccgtgaa aggcagattc accatctcaa gagatgattc aaaaaacacg   240
gtttatctgc aaatgaacag cctgaaaacc gaggacacag ccgtttatta ctgttccacg   300
gtggactaca attggtactt cgatttctgg ggccgtggca ccctggtcac tgtctcctca   360

<210> SEQ ID NO 474
<211> LENGTH: 120
<212> TYPE: PRT
<213> ORGANISM: Artificial Sequence
<220> FEATURE:
<223> OTHER INFORMATION: synthetic

<400> SEQUENCE: 474

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Thr Trp Val Arg Gln Ala Pro Gly Lys Gly Leu Glu Trp Val
        35                  40                  45

Gly Arg Ile Lys Asn Lys Ile Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80
```

```
Val Tyr Leu Gln Met Asn Ser Leu Lys Thr Glu Asp Thr Ala Val Tyr
             85                  90                  95

Tyr Cys Ser Thr Val Asp Tyr Asn Trp Tyr Phe Asp Phe Trp Gly Arg
            100                 105                 110

Gly Thr Leu Val Thr Val Ser Ser
        115                 120
```

<210> SEQ ID NO 475
<211> LENGTH: 24
<212> TYPE: DNA
<213> ORGANISM: Artificial Sequence
<220> FEATURE:
<223> OTHER INFORMATION: synthetic

<400> SEQUENCE: 475
ggattcactt tcagtaacgc ctgg                                          24

<210> SEQ ID NO 476
<211> LENGTH: 8
<212> TYPE: PRT
<213> ORGANISM: Artificial Sequence
<220> FEATURE:
<223> OTHER INFORMATION: synthetic

<400> SEQUENCE: 476

```
Gly Phe Thr Phe Ser Asn Ala Trp
1               5
```

<210> SEQ ID NO 477
<211> LENGTH: 30
<212> TYPE: DNA
<213> ORGANISM: Artificial Sequence
<220> FEATURE:
<223> OTHER INFORMATION: synthetic

<400> SEQUENCE: 477
attaaaaaca aaattgatgg tgggacaaca                                    30

<210> SEQ ID NO 478
<211> LENGTH: 10
<212> TYPE: PRT
<213> ORGANISM: Artificial Sequence
<220> FEATURE:
<223> OTHER INFORMATION: synthetic

<400> SEQUENCE: 478

```
Ile Lys Asn Lys Ile Asp Gly Gly Thr Thr
1               5                  10
```

<210> SEQ ID NO 479
<211> LENGTH: 33
<212> TYPE: DNA
<213> ORGANISM: Artificial Sequence
<220> FEATURE:
<223> OTHER INFORMATION: synthetic

<400> SEQUENCE: 479
tccacggtgg actacaattg gtacttcgat ttc                                33

<210> SEQ ID NO 480
<211> LENGTH: 11
<212> TYPE: PRT
<213> ORGANISM: Artificial Sequence
<220> FEATURE:
<223> OTHER INFORMATION: synthetic

<400> SEQUENCE: 480

Ser Thr Val Asp Tyr Asn Trp Tyr Phe Asp Phe
1               5                   10

<210> SEQ ID NO 481
<211> LENGTH: 387
<212> TYPE: DNA
<213> ORGANISM: Artificial Sequence
<220> FEATURE:
<223> OTHER INFORMATION: synthetic

<400> SEQUENCE: 481
caggtgcagc tggtggagtc tgggggaggc gtggtccagc ctgggaggtc cctgagactc      60
tcctgtgcag cgtctggatt caccttcagt ttctttggca tgcactgggt ccgccaggct     120
ccaggcaagg ggctggagtg gtggcactt atatggtatg atggaactaa tgaaaactat      180
gcagactccg tgaagggccg attcaccatc tccagagaca attccaagtc cacgctgtat     240
ctgcaaatga acagtctgag agccgaggac acggctgttt actactgtgc gagagatagg    300
ggagtggcga catttacgag ggggaattac tactacaact acggtatgga cgtctggggc    360
caagggacca cggtcaccgt ctcctca                                         387

<210> SEQ ID NO 482
<211> LENGTH: 129
<212> TYPE: PRT
<213> ORGANISM: Artificial Sequence
<220> FEATURE:
<223> OTHER INFORMATION: synthetic

<400> SEQUENCE: 482

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Phe Phe
            20                  25                  30

Gly Met His Trp Val Arg Gln Ala Pro Gly Lys Gly Leu Glu Trp Val
        35                  40                  45

Ala Leu Ile Trp Tyr Asp Gly Thr Asn Glu Asn Tyr Ala Asp Ser Val
    50                  55                  60

Lys Gly Arg Phe Thr Ile Ser Arg Asp Asn Ser Lys Ser Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Ala Thr Phe Thr Arg Gly Asn Tyr Tyr Tyr
            100                 105                 110

Asn Tyr Gly Met Asp Val Trp Gly Gln Gly Thr Thr Val Thr Val Ser
        115                 120                 125

Ser

<210> SEQ ID NO 483
<211> LENGTH: 24
<212> TYPE: DNA
<213> ORGANISM: Artificial Sequence
<220> FEATURE:
<223> OTHER INFORMATION: synthetic

<400> SEQUENCE: 483
ggattcacct tcagtttctt tggc                                            24

<210> SEQ ID NO 484

```
<211> LENGTH: 8
<212> TYPE: PRT
<213> ORGANISM: Artificial Sequence
<220> FEATURE:
<223> OTHER INFORMATION: synthetic

<400> SEQUENCE: 484

Gly Phe Thr Phe Ser Phe Phe Gly
1               5

<210> SEQ ID NO 485
<211> LENGTH: 24
<212> TYPE: DNA
<213> ORGANISM: Artificial Sequence
<220> FEATURE:
<223> OTHER INFORMATION: synthetic

<400> SEQUENCE: 485
atatggtatg atggaactaa tgaa                                          24

<210> SEQ ID NO 486
<211> LENGTH: 8
<212> TYPE: PRT
<213> ORGANISM: Artificial Sequence
<220> FEATURE:
<223> OTHER INFORMATION: synthetic

<400> SEQUENCE: 486

Ile Trp Tyr Asp Gly Thr Asn Glu
1               5

<210> SEQ ID NO 487
<211> LENGTH: 66
<212> TYPE: DNA
<213> ORGANISM: Artificial Sequence
<220> FEATURE:
<223> OTHER INFORMATION: synthetic

<400> SEQUENCE: 487
gcgagagata ggggagtggc gacatttacg agggggaatt actactacaa ctacggtatg   60
gacgtc                                                              66

<210> SEQ ID NO 488
<211> LENGTH: 22
<212> TYPE: PRT
<213> ORGANISM: Artificial Sequence
<220> FEATURE:
<223> OTHER INFORMATION: synthetic

<400> SEQUENCE: 488

Ala Arg Asp Arg Gly Val Ala Thr Phe Thr Arg Gly Asn Tyr Tyr Tyr
1               5                   10                  15

Asn Tyr Gly Met Asp Val
            20

<210> SEQ ID NO 489
<211> LENGTH: 387
<212> TYPE: DNA
<213> ORGANISM: Artificial Sequence
<220> FEATURE:
<223> OTHER INFORMATION: synthetic

<400> SEQUENCE: 489
caggtgcagc tggtggagtc tgggggaggc gtggtccagc ctggggaggtc cctgagactc   60 tcctgtgcag cgtctggatt caccttcagt ttctatggca tgcactgggt ccgccaggct  120
```

```
ccaggcaagg ggctggaggg ggtggcagtt atatggtatg atggaagtaa taaatactat    180
gcagactccg tgaagggccg attcaccata tccagagaca attccaagaa catgctgtat    240
ctacaaatga ccagcctgag agccgaggac acggctgtgt attactgtgc gagagattcg    300
ggtaaaactg gaactgggat aactgggtac tcctactact acggtatgga cgtctggggc    360
caagggacca cggtcaccgt ctcctca                                         387
```

<210> SEQ ID NO 490
<211> LENGTH: 129
<212> TYPE: PRT
<213> ORGANISM: Artificial Sequence
<220> FEATURE:
<223> OTHER INFORMATION: synthetic

<400> SEQUENCE: 490

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Phe Tyr
            20                  25                  30

Gly Met His Trp Val Arg Gln Ala Pro Gly Lys Gly Leu Glu Gly Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Met Leu Tyr
65                  70                  75                  80

Leu Gln Met Thr Ser Leu Arg Ala Glu Asp Thr Ala Val Tyr Tyr Cys
                85                  90                  95

Ala Arg Asp Ser Gly Lys Thr Gly Thr Gly Ile Thr Gly Tyr Ser Tyr
            100                 105                 110

Tyr Tyr Gly Met Asp Val Trp Gly Gln Gly Thr Thr Val Thr Val Ser
        115                 120                 125

Ser

<210> SEQ ID NO 491
<211> LENGTH: 24
<212> TYPE: DNA
<213> ORGANISM: Artificial Sequence
<220> FEATURE:
<223> OTHER INFORMATION: synthetic

<400> SEQUENCE: 491
ggattcacct tcagtttcta tggc                                            24

<210> SEQ ID NO 492
<211> LENGTH: 8
<212> TYPE: PRT
<213> ORGANISM: Artificial Sequence
<220> FEATURE:
<223> OTHER INFORMATION: synthetic

<400> SEQUENCE: 492

Gly Phe Thr Phe Ser Phe Tyr Gly
1               5

<210> SEQ ID NO 493
<211> LENGTH: 24
<212> TYPE: DNA
<213> ORGANISM: Artificial Sequence
<220> FEATURE:
<223> OTHER INFORMATION: synthetic

<400> SEQUENCE: 493
atatggtatg atggaagtaa taaa                                              24

<210> SEQ ID NO 494
<211> LENGTH: 8
<212> TYPE: PRT
<213> ORGANISM: Artificial Sequence
<220> FEATURE:
<223> OTHER INFORMATION: synthetic

<400> SEQUENCE: 494

Ile Trp Tyr Asp Gly Ser Asn Lys
1               5

<210> SEQ ID NO 495
<211> LENGTH: 66
<212> TYPE: DNA
<213> ORGANISM: Artificial Sequence
<220> FEATURE:
<223> OTHER INFORMATION: synthetic

<400> SEQUENCE: 495
gcgagagatt cgggtaaaac tggaactggg ataactgggt actcctacta ctacggtatg       60
gacgtc                                                                  66

<210> SEQ ID NO 496
<211> LENGTH: 22
<212> TYPE: PRT
<213> ORGANISM: Artificial Sequence
<220> FEATURE:
<223> OTHER INFORMATION: synthetic

<400> SEQUENCE: 496

Ala Arg Asp Ser Gly Lys Thr Gly Thr Gly Ile Thr Gly Tyr Ser Tyr
1               5                   10                  15

Tyr Tyr Gly Met Asp Val
            20

<210> SEQ ID NO 497
<211> LENGTH: 354
<212> TYPE: DNA
<213> ORGANISM: Artificial Sequence
<220> FEATURE:
<223> OTHER INFORMATION: synthetic

<400> SEQUENCE: 497
cagctgcagc tgcaggagtc gggcccagga ctggtgaagc cttcggagac cctgtccctc       60
acctgcactg tctctggtgg ctccatcatc actaatagtt attactgggg ctggatccgc      120
cagcccccag ggaagggtct ggagtggatt ggtagtatct attatagtgg gaggacctac      180
tacaacccgt ccctcgagag tcgagtcacc atatccgtgg acacgtccaa gaaccagttc      240
tccctgaagt tgacctctgt gaccgccgca gacacggcta tatattactg tgcgagggaa      300
ggggatccgt cgctcgaccc ctggggccag ggaaccctgg tcaccgtctc ctca            354

<210> SEQ ID NO 498
<211> LENGTH: 118
<212> TYPE: PRT
<213> ORGANISM: Artificial Sequence
<220> FEATURE:
<223> OTHER INFORMATION: synthetic

<400> SEQUENCE: 498

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ile Thr Asn
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Arg Thr Tyr Tyr Asn Pro Ser
    50                  55                  60

Leu Glu Ser Arg Val Thr Ile Ser Val Asp Thr Ser Lys Asn Gln Phe
65                  70                  75                  80

Ser Leu Lys Leu Thr Ser Val Thr Ala Ala Asp Thr Ala Ile Tyr Tyr
                85                  90                  95

Cys Ala Arg Glu Gly Asp Pro Ser Leu Asp Pro Trp Gly Gln Gly Thr
            100                 105                 110

Leu Val Thr Val Ser Ser
            115
```

<210> SEQ ID NO 499
<211> LENGTH: 30
<212> TYPE: DNA
<213> ORGANISM: Artificial Sequence
<220> FEATURE:
<223> OTHER INFORMATION: synthetic

<400> SEQUENCE: 499
ggtggctcca tcatcactaa tagttattac                                    30

<210> SEQ ID NO 500
<211> LENGTH: 10
<212> TYPE: PRT
<213> ORGANISM: Artificial Sequence
<220> FEATURE:
<223> OTHER INFORMATION: synthetic

<400> SEQUENCE: 500

```
Gly Gly Ser Ile Ile Thr Asn Ser Tyr Tyr
1               5                   10
```

<210> SEQ ID NO 501
<211> LENGTH: 21
<212> TYPE: DNA
<213> ORGANISM: Artificial Sequence
<220> FEATURE:
<223> OTHER INFORMATION: synthetic

<400> SEQUENCE: 501
atctattata gtgggaggac c                                             21

<210> SEQ ID NO 502
<211> LENGTH: 7
<212> TYPE: PRT
<213> ORGANISM: Artificial Sequence
<220> FEATURE:
<223> OTHER INFORMATION: synthetic

<400> SEQUENCE: 502

```
Ile Tyr Tyr Ser Gly Arg Thr
1               5
```

<210> SEQ ID NO 503
<211> LENGTH: 30
<212> TYPE: DNA

<213> ORGANISM: Artificial Sequence
<220> FEATURE:
<223> OTHER INFORMATION: synthetic

<400> SEQUENCE: 503

```
gcgagggaag gggatccgtc gctcgacccc                                      30
```

<210> SEQ ID NO 504
<211> LENGTH: 10
<212> TYPE: PRT
<213> ORGANISM: Artificial Sequence
<220> FEATURE:
<223> OTHER INFORMATION: synthetic

<400> SEQUENCE: 504

```
Ala Arg Glu Gly Asp Pro Ser Leu Asp Pro
1               5                   10
```

<210> SEQ ID NO 505
<211> LENGTH: 363
<212> TYPE: DNA
<213> ORGANISM: Artificial Sequence
<220> FEATURE:
<223> OTHER INFORMATION: synthetic

<400> SEQUENCE: 505

```
gaggtgcagc tggtggagtc tgggggagac ttggtacagc ctgggggtc cctgagactc      60 tcctgtgcag cctctggatt cacctttagc acctatgcca tgaactgggt ccgccaggct    120
ccagggaagg gctggagtg gtctcacat attagtggta gtggtggtaa ttcatactcc      180
gcagactccg tgaagggccg gttcaccatc tccagagaca attccaagaa cacgctatat    240
ctgcaaatga acagcctgcg agccgaggac acggccatat attactgttc gctggatata    300
atggctacag taggcggtct ctttgcctac tggggccagg gaaccctggt caccgtctcc    360
tca                                                                  363
```

<210> SEQ ID NO 506
<211> LENGTH: 121
<212> TYPE: PRT
<213> ORGANISM: Artificial Sequence
<220> FEATURE:
<223> OTHER INFORMATION: synthetic

<400> SEQUENCE: 506

```
Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser His Ile Ser Gly Ser Gly Gly Asn Ser Tyr Ser Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ser Leu Asp Ile Met Ala Thr Val Gly Gly Leu Phe Ala Tyr Trp Gly
            100                 105                 110

Gln Gly Thr Leu Val Thr Val Ser Ser
        115                 120
```

<210> SEQ ID NO 507
<211> LENGTH: 24
<212> TYPE: DNA
<213> ORGANISM: Artificial Sequence
<220> FEATURE:
<223> OTHER INFORMATION: synthetic

<400> SEQUENCE: 507
ggattcacct ttagcaccta tgcc                                          24

<210> SEQ ID NO 508
<211> LENGTH: 8
<212> TYPE: PRT
<213> ORGANISM: Artificial Sequence
<220> FEATURE:
<223> OTHER INFORMATION: synthetic

<400> SEQUENCE: 508

Gly Phe Thr Phe Ser Thr Tyr Ala
1               5

<210> SEQ ID NO 509
<211> LENGTH: 24
<212> TYPE: DNA
<213> ORGANISM: Artificial Sequence
<220> FEATURE:
<223> OTHER INFORMATION: synthetic

<400> SEQUENCE: 509
attagtggta gtggtggtaa ttca                                          24

<210> SEQ ID NO 510
<211> LENGTH: 8
<212> TYPE: PRT
<213> ORGANISM: Artificial Sequence
<220> FEATURE:
<223> OTHER INFORMATION: synthetic

<400> SEQUENCE: 510

Ile Ser Gly Ser Gly Gly Asn Ser
1               5

<210> SEQ ID NO 511
<211> LENGTH: 42
<212> TYPE: DNA
<213> ORGANISM: Artificial Sequence
<220> FEATURE:
<223> OTHER INFORMATION: synthetic

<400> SEQUENCE: 511
tcgctggata taatggctac agtaggcggt ctctttgcct ac                      42

<210> SEQ ID NO 512
<211> LENGTH: 14
<212> TYPE: PRT
<213> ORGANISM: Artificial Sequence
<220> FEATURE:
<223> OTHER INFORMATION: synthetic

<400> SEQUENCE: 512

Ser Leu Asp Ile Met Ala Thr Val Gly Gly Leu Phe Ala Tyr
1               5                   10

<210> SEQ ID NO 513
<211> LENGTH: 393
<212> TYPE: DNA

<213> ORGANISM: Artificial Sequence
<220> FEATURE:
<223> OTHER INFORMATION: synthetic

<400> SEQUENCE: 513

```
caggtgcagc tggtggagtc tgggggaggc gtggtccagc ctgggaggtc cctgagactc      60
tcctgtgtag cgtctggatt catcttcagt ttctatggca tgcactgggt ccgccaggct     120
ccagacaagg gctggagtg gtggcagtt atatggtatg atggaagtaa tgaatactat       180
gcagactccg tgaagggccg attcaccatc tccagagaca attccaagaa cacgctgtat     240
ctgcaaatga acagcctgag agccgaggac acggctgtgt attactgtgg gagagatcaa     300
ggtatttcgt attacgatat tttgactggt aattataact attactacgg tgtggacgtc     360
tggggccaag ggaccacggt caccgtctcc tca                                  393
```

<210> SEQ ID NO 514
<211> LENGTH: 131
<212> TYPE: PRT
<213> ORGANISM: Artificial Sequence
<220> FEATURE:
<223> OTHER INFORMATION: synthetic

<400> SEQUENCE: 514

```
Gln Val Gln Leu Val Glu Ser Gly Gly Gly Val Val Gln Pro Gly Arg
1               5                   10                  15

Ser Leu Arg Leu Ser Cys Val Ala Ser Gly Phe Ile Phe Ser Phe Tyr
            20                  25                  30

Gly Met His Trp Val Arg Gln Ala Pro Asp Lys Gly Leu Glu Trp Val
        35                  40                  45

Ala Val Ile Trp Tyr Asp Gly Ser Asn Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Arg Asp Gln Gly Ile Ser Tyr Tyr Asp Ile Leu Thr Gly Asn Tyr
            100                 105                 110

Asn Tyr Tyr Tyr Gly Val Asp Val Trp Gly Gln Gly Thr Thr Val Thr
        115                 120                 125

Val Ser Ser
    130
```

<210> SEQ ID NO 515
<211> LENGTH: 24
<212> TYPE: DNA
<213> ORGANISM: Artificial Sequence
<220> FEATURE:
<223> OTHER INFORMATION: synthetic

<400> SEQUENCE: 515

```
ggattcatct tcagtttcta tggc                                             24
```

<210> SEQ ID NO 516
<211> LENGTH: 8
<212> TYPE: PRT
<213> ORGANISM: Artificial Sequence
<220> FEATURE:
<223> OTHER INFORMATION: synthetic

<400> SEQUENCE: 516

Gly Phe Ile Phe Ser Phe Tyr Gly
1               5

<210> SEQ ID NO 517
<211> LENGTH: 24
<212> TYPE: DNA
<213> ORGANISM: Artificial Sequence
<220> FEATURE:
<223> OTHER INFORMATION: synthetic

<400> SEQUENCE: 517
atatggtatg atggaagtaa tgaa                                           24

<210> SEQ ID NO 518
<211> LENGTH: 8
<212> TYPE: PRT
<213> ORGANISM: Artificial Sequence
<220> FEATURE:
<223> OTHER INFORMATION: synthetic

<400> SEQUENCE: 518

Ile Trp Tyr Asp Gly Ser Asn Glu
1               5

<210> SEQ ID NO 519
<211> LENGTH: 72
<212> TYPE: DNA
<213> ORGANISM: Artificial Sequence
<220> FEATURE:
<223> OTHER INFORMATION: synthetic

<400> SEQUENCE: 519
gggagagatc aaggtatttc gtattacgat attttgactg gtaattataa ctattactac    60
ggtgtggacg tc                                                        72

<210> SEQ ID NO 520
<211> LENGTH: 24
<212> TYPE: PRT
<213> ORGANISM: Artificial Sequence
<220> FEATURE:
<223> OTHER INFORMATION: synthetic

<400> SEQUENCE: 520

Gly Arg Asp Gln Gly Ile Ser Tyr Tyr Asp Ile Leu Thr Gly Asn Tyr
1               5                   10                  15

Asn Tyr Tyr Tyr Gly Val Asp Val
            20

<210> SEQ ID NO 521
<211> LENGTH: 324
<212> TYPE: DNA
<213> ORGANISM: Artificial Sequence
<220> FEATURE:
<223> OTHER INFORMATION: synthetic

<400> SEQUENCE: 521
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccgtca   180
aggttcagtg gcagtggatc tgggacagat ttcactctca ccatcagcag tctgcaacct   240
gaagattttg caacttacta ctgtcaacag agttacagta cccctccgat caccttcggc   300
caagggacac gactggagat taaa                                          324

<210> SEQ ID NO 522
<211> LENGTH: 108
<212> TYPE: PRT
<213> ORGANISM: Artificial Sequence
<220> FEATURE:
<223> OTHER INFORMATION: synthetic

<400> SEQUENCE: 522

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 523
<211> LENGTH: 18
<212> TYPE: DNA
<213> ORGANISM: Artificial Sequence
<220> FEATURE:
<223> OTHER INFORMATION: synthetic

<400> SEQUENCE: 523
cagagcatta gcagctat                                                       18

<210> SEQ ID NO 524
<211> LENGTH: 6
<212> TYPE: PRT
<213> ORGANISM: Artificial Sequence
<220> FEATURE:
<223> OTHER INFORMATION: synthetic

<400> SEQUENCE: 524

Gln Ser Ile Ser Ser Tyr
1               5

<210> SEQ ID NO 525
<211> LENGTH: 9
<212> TYPE: DNA
<213> ORGANISM: Artificial Sequence
<220> FEATURE:
<223> OTHER INFORMATION: synthetic

<400> SEQUENCE: 525 gctgcatcc                                                                  9

<210> SEQ ID NO 526
<211> LENGTH: 3
<212> TYPE: PRT
<213> ORGANISM: Artificial Sequence
<220> FEATURE:
<223> OTHER INFORMATION: synthetic

<400> SEQUENCE: 526

```
<210> SEQ ID NO 527
<211> LENGTH: 30
<212> TYPE: DNA
<213> ORGANISM: Artificial Sequence
<220> FEATURE:
<223> OTHER INFORMATION: synthetic

<400> SEQUENCE: 527
caacagagtt acagtacccc tccgatcacc                                       30

<210> SEQ ID NO 528
<211> LENGTH: 10
<212> TYPE: PRT
<213> ORGANISM: Artificial Sequence
<220> FEATURE:
<223> OTHER INFORMATION: synthetic

<400> SEQUENCE: 528
```

Gln Gln Ser Tyr Ser Thr Pro Pro Ile Thr
1               5                   10

```
<210> SEQ ID NO 529
<211> LENGTH: 324
<212> TYPE: DNA
<213> ORGANISM: Artificial Sequence
<220> FEATURE:
<223> OTHER INFORMATION: synthetic

<400> SEQUENCE: 529
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcaccttg gacgttcggc     300
caagggacca aggtggaaat caaa                                            324

<210> SEQ ID NO 530
<211> LENGTH: 108
<212> TYPE: PRT
<213> ORGANISM: Artificial Sequence
<220> FEATURE:
<223> OTHER INFORMATION: synthetic

<400> SEQUENCE: 530
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys

<210> SEQ ID NO 531
<211> LENGTH: 21
<212> TYPE: DNA
<213> ORGANISM: Artificial Sequence
<220> FEATURE:
<223> OTHER INFORMATION: synthetic

<400> SEQUENCE: 531
cagagtgtta gcagcagcta c                                              21

<210> SEQ ID NO 532
<211> LENGTH: 7
<212> TYPE: PRT
<213> ORGANISM: Artificial Sequence
<220> FEATURE:
<223> OTHER INFORMATION: synthetic

<400> SEQUENCE: 532

Gln Ser Val Ser Ser Ser Tyr
1               5

<210> SEQ ID NO 533
<211> LENGTH: 9
<212> TYPE: DNA
<213> ORGANISM: Artificial Sequence
<220> FEATURE:
<223> OTHER INFORMATION: synthetic

<400> SEQUENCE: 533 ggtgcatcc                                                             9

<210> SEQ ID NO 534
<211> LENGTH: 3
<212> TYPE: PRT
<213> ORGANISM: Artificial Sequence
<220> FEATURE:
<223> OTHER INFORMATION: synthetic

<400> SEQUENCE: 534

Gly Ala Ser
1

<210> SEQ ID NO 535
<211> LENGTH: 27
<212> TYPE: DNA
<213> ORGANISM: Artificial Sequence
<220> FEATURE:
<223> OTHER INFORMATION: synthetic

<400> SEQUENCE: 535
cagcagtatg gtagctcacc ttggacg                                        27

<210> SEQ ID NO 536
<211> LENGTH: 9
<212> TYPE: PRT
<213> ORGANISM: Artificial Sequence
<220> FEATURE:
<223> OTHER INFORMATION: synthetic

<400> SEQUENCE: 536

Gln Gln Tyr Gly Ser Ser Pro Trp Thr
1               5

<210> SEQ ID NO 537

<211> LENGTH: 357
<212> TYPE: DNA
<213> ORGANISM: Artificial Sequence
<220> FEATURE:
<223> OTHER INFORMATION: synthetic

<400> SEQUENCE: 537

```
caggtgcagc tacagcagtg gggcgcagga ctgttgaagc cttcggagac cctgtccctc    60
acctgcgctg tctatggtgg gtccttcagt ggttactact ggaactggat ccgccagccc   120
ccagggaagg ggctggagtg ggttggggaa atcagtcata gaggaagcac caactacaac   180
ccgtccctca agagtcgagt caccatatca ctggacacgt ccaagaacca gttctccctg   240
aagctgacct ctgtgaccgc cgcggacacg gctgtgtatt actgttcgag agacgaggaa   300
ctggaattcc gtttctttga ctactggggc cagggaaccc tggtcaccgt ctcctca      357
```

<210> SEQ ID NO 538
<211> LENGTH: 119
<212> TYPE: PRT
<213> ORGANISM: Artificial Sequence
<220> FEATURE:
<223> OTHER INFORMATION: synthetic

<400> SEQUENCE: 538

```
Gln Val Gln Leu Gln Gln Trp Gly Ala Gly Leu Leu Lys Pro Ser Glu
1               5                   10                  15
Thr Leu Ser Leu Thr Cys Ala Val Tyr Gly Gly Ser Phe Ser Gly Tyr
            20                  25                  30
Tyr Trp Asn Trp Ile Arg Gln Pro Pro Gly Lys Gly Leu Glu Trp Val
        35                  40                  45
Gly Glu Ile Ser His Arg Gly Ser Thr Asn Tyr Asn Pro Ser Leu Lys
    50                  55                  60
Ser Arg Val Thr Ile Ser Leu Asp Thr Ser Lys Asn Gln Phe Ser Leu
65                  70                  75                  80
Lys Leu Thr Ser Val Thr Ala Ala Asp Thr Ala Val Tyr Tyr Cys Ser
                85                  90                  95
Arg Asp Glu Glu Leu Glu Phe Arg Phe Phe Asp Tyr Trp Gly Gln Gly
            100                 105                 110
Thr Leu Val Thr Val Ser Ser
        115
```

<210> SEQ ID NO 539
<211> LENGTH: 24
<212> TYPE: DNA
<213> ORGANISM: Artificial Sequence
<220> FEATURE:
<223> OTHER INFORMATION: synthetic

<400> SEQUENCE: 539

```
ggtgggtcct tcagtggtta ctac                                           24
```

<210> SEQ ID NO 540
<211> LENGTH: 8
<212> TYPE: PRT
<213> ORGANISM: Artificial Sequence
<220> FEATURE:
<223> OTHER INFORMATION: synthetic

<400> SEQUENCE: 540

```
Gly Gly Ser Phe Ser Gly Tyr Tyr
1               5
```

<210> SEQ ID NO 541
<211> LENGTH: 21
<212> TYPE: DNA
<213> ORGANISM: Artificial Sequence
<220> FEATURE:
<223> OTHER INFORMATION: synthetic

<400> SEQUENCE: 541
atcagtcata gaggaagcac c                                      21

<210> SEQ ID NO 542
<211> LENGTH: 7
<212> TYPE: PRT
<213> ORGANISM: Artificial Sequence
<220> FEATURE:
<223> OTHER INFORMATION: synthetic

<400> SEQUENCE: 542

Ile Ser His Arg Gly Ser Thr
1               5

<210> SEQ ID NO 543
<211> LENGTH: 39
<212> TYPE: DNA
<213> ORGANISM: Artificial Sequence
<220> FEATURE:
<223> OTHER INFORMATION: synthetic

<400> SEQUENCE: 543
tcgagagacg aggaactgga attccgtttc tttgactac                    39

<210> SEQ ID NO 544
<211> LENGTH: 13
<212> TYPE: PRT
<213> ORGANISM: Artificial Sequence
<220> FEATURE:
<223> OTHER INFORMATION: synthetic

<400> SEQUENCE: 544

Ser Arg Asp Glu Glu Leu Glu Phe Arg Phe Phe Asp Tyr
1               5                   10

<210> SEQ ID NO 545
<211> LENGTH: 321
<212> TYPE: DNA
<213> ORGANISM: Artificial Sequence
<220> FEATURE:
<223> OTHER INFORMATION: synthetic

<400> SEQUENCE: 545
gaaattgtgt tgacacagtc tccagccacc ctgtctttgt ctccagggga aagagccacc    60
ctctcctgca gggccagtca gagtgttagc agctatttag cctggtacca acaaaaacct   120
ggccaggctc ccaggctcct cgtctatggt gcatccaaca gggccactgg catcccagcc   180
aggttcagtg gcagtgggtc tgggacagac ttcactctca ccatcagcag cctagagcct   240
gaagattttg catttttatta ctgtcagcag cgtagcaact ggccgctcac tttcggcgga   300
gggaccaagg tggagatcaa a                                            321

<210> SEQ ID NO 546
<211> LENGTH: 107
<212> TYPE: PRT
<213> ORGANISM: Artificial Sequence
<220> FEATURE:
<223> OTHER INFORMATION: synthetic -continued

<400> SEQUENCE: 546

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Val
        35                  40                  45

Tyr Gly Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Phe Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 547
<211> LENGTH: 18
<212> TYPE: DNA
<213> ORGANISM: Artificial Sequence
<220> FEATURE:
<223> OTHER INFORMATION: synthetic

<400> SEQUENCE: 547
cagagtgtta gcagctat                                                18

<210> SEQ ID NO 548
<211> LENGTH: 6
<212> TYPE: PRT
<213> ORGANISM: Artificial Sequence
<220> FEATURE:
<223> OTHER INFORMATION: synthetic

<400> SEQUENCE: 548

Gln Ser Val Ser Ser Tyr
1               5

<210> SEQ ID NO 549
<211> LENGTH: 9
<212> TYPE: DNA
<213> ORGANISM: Artificial Sequence
<220> FEATURE:
<223> OTHER INFORMATION: synthetic

<400> SEQUENCE: 549 ggtgcatcc                                                           9

<210> SEQ ID NO 550
<211> LENGTH: 3
<212> TYPE: PRT
<213> ORGANISM: Artificial Sequence
<220> FEATURE:
<223> OTHER INFORMATION: synthetic

<400> SEQUENCE: 550

Gly Ala Ser
1

<210> SEQ ID NO 551
<211> LENGTH: 27
<212> TYPE: DNA
<213> ORGANISM: Artificial Sequence

```
<220> FEATURE:
<223> OTHER INFORMATION: synthetic

<400> SEQUENCE: 551
cagcagcgta gcaactggcc gctcact                                           27

<210> SEQ ID NO 552
<211> LENGTH: 9
<212> TYPE: PRT
<213> ORGANISM: Artificial Sequence
<220> FEATURE:
<223> OTHER INFORMATION: synthetic

<400> SEQUENCE: 552

Gln Gln Arg Ser Asn Trp Pro Leu Thr
1               5

<210> SEQ ID NO 553
<211> LENGTH: 372
<212> TYPE: DNA
<213> ORGANISM: Artificial Sequence
<220> FEATURE:
<223> OTHER INFORMATION: synthetic

<400> SEQUENCE: 553
gaggtgcagc tggtggagtc tgggggaggc ttggtacagc ctgggggtc cctgagactc         60 tcctgtgtag cctctggatt cacctttagc ctctatgcca tgacctgggt ccgccaggtt       120
ccagggaagg gctggaatg gtctcaact attagtggta gtggtggtgg cacatactac         180
acagactccg ttaagggccg gttcaccatc tccagagaca attccaagaa cacactgtat       240
ctgcaaatga acagcctgag agccgacgac acggccgttt tttactgtac gaaagagagt       300
acaactggaa cttactccta cttctacggt atggacgtct ggggccaagg gaccacggtc       360
accgtctcct ca                                                          372

<210> SEQ ID NO 554
<211> LENGTH: 124
<212> TYPE: PRT
<213> ORGANISM: Artificial Sequence
<220> FEATURE:
<223> OTHER INFORMATION: synthetic

<400> SEQUENCE: 554

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Leu Tyr
            20                  25                  30

Ala Met Thr Trp Val Arg Gln Val Pro Gly Lys Gly Leu Glu Trp Val
        35                  40                  45

Ser Thr Ile Ser Gly Ser Gly Gly Gly Thr Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Val Phe Tyr Cys
                85                  90                  95

Thr Lys Glu Ser Thr Thr Gly Thr Tyr Ser Tyr Phe Tyr Gly Met Asp
            100                 105                 110

Val Trp Gly Gln Gly Thr Thr Val Thr Val Ser Ser
        115                 120
```

```
<210> SEQ ID NO 555
<211> LENGTH: 24
<212> TYPE: DNA
<213> ORGANISM: Artificial Sequence
<220> FEATURE:
<223> OTHER INFORMATION: synthetic

<400> SEQUENCE: 555
ggattcacct ttagcctcta tgcc                                               24

<210> SEQ ID NO 556
<211> LENGTH: 8
<212> TYPE: PRT
<213> ORGANISM: Artificial Sequence
<220> FEATURE:
<223> OTHER INFORMATION: synthetic

<400> SEQUENCE: 556

Gly Phe Thr Phe Ser Leu Tyr Ala
1               5

<210> SEQ ID NO 557
<211> LENGTH: 24
<212> TYPE: DNA
<213> ORGANISM: Artificial Sequence
<220> FEATURE:
<223> OTHER INFORMATION: synthetic

<400> SEQUENCE: 557
attagtggta gtggtggtgg caca                                               24

<210> SEQ ID NO 558
<211> LENGTH: 8
<212> TYPE: PRT
<213> ORGANISM: Artificial Sequence
<220> FEATURE:
<223> OTHER INFORMATION: synthetic

<400> SEQUENCE: 558

Ile Ser Gly Ser Gly Gly Gly Thr
1               5

<210> SEQ ID NO 559
<211> LENGTH: 51
<212> TYPE: DNA
<213> ORGANISM: Artificial Sequence
<220> FEATURE:
<223> OTHER INFORMATION: synthetic

<400> SEQUENCE: 559
acgaaagaga gtacaactgg aacttactcc tacttctacg gtatggacgt c                 51

<210> SEQ ID NO 560
<211> LENGTH: 17
<212> TYPE: PRT
<213> ORGANISM: Artificial Sequence
<220> FEATURE:
<223> OTHER INFORMATION: synthetic

<400> SEQUENCE: 560

Thr Lys Glu Ser Thr Thr Gly Thr Tyr Ser Tyr Phe Tyr Gly Met Asp
1               5                   10                  15

Val

<210> SEQ ID NO 561
<211> LENGTH: 321
```

<212> TYPE: DNA
<213> ORGANISM: Artificial Sequence
<220> FEATURE:
<223> OTHER INFORMATION: synthetic

<400> SEQUENCE: 561

```
gacatccaga tgacccagtc tccatcctcc ctgtctgcat ctgtaggaga cagagtcacc    60
atcacttgcc gggcaagtca gaccattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccctcagcgg tctccaacct   240
gaagattttg caacttacta ctgtcaacag agttacagta ccccgctcac tttcggcgga   300
gggaccaagg tggagatcaa a                                             321
```

<210> SEQ ID NO 562
<211> LENGTH: 107
<212> TYPE: PRT
<213> ORGANISM: Artificial Sequence
<220> FEATURE:
<223> OTHER INFORMATION: synthetic

<400> SEQUENCE: 562

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Leu Ser Gly Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105
```

<210> SEQ ID NO 563
<211> LENGTH: 18
<212> TYPE: DNA
<213> ORGANISM: Artificial Sequence
<220> FEATURE:
<223> OTHER INFORMATION: synthetic

<400> SEQUENCE: 563

```
cagaccatta gcagctat                                                  18
```

<210> SEQ ID NO 564
<211> LENGTH: 6
<212> TYPE: PRT
<213> ORGANISM: Artificial Sequence
<220> FEATURE:
<223> OTHER INFORMATION: synthetic

<400> SEQUENCE: 564

```
Gln Thr Ile Ser Ser Tyr
1               5
```

<210> SEQ ID NO 565
<211> LENGTH: 9
<212> TYPE: DNA

<213> ORGANISM: Artificial Sequence
<220> FEATURE:
<223> OTHER INFORMATION: synthetic

<400> SEQUENCE: 565 gctgcatcc          9

<210> SEQ ID NO 566
<211> LENGTH: 3
<212> TYPE: PRT
<213> ORGANISM: Artificial Sequence
<220> FEATURE:
<223> OTHER INFORMATION: synthetic

<400> SEQUENCE: 566

Ala Ala Ser
1

<210> SEQ ID NO 567
<211> LENGTH: 27
<212> TYPE: DNA
<213> ORGANISM: Artificial Sequence
<220> FEATURE:
<223> OTHER INFORMATION: synthetic

<400> SEQUENCE: 567
caacagagtt acagtacccc gctcact          27

<210> SEQ ID NO 568
<211> LENGTH: 9
<212> TYPE: PRT
<213> ORGANISM: Artificial Sequence
<220> FEATURE:
<223> OTHER INFORMATION: synthetic

<400> SEQUENCE: 568

Gln Gln Ser Tyr Ser Thr Pro Leu Thr
1               5

<210> SEQ ID NO 569
<211> LENGTH: 327
<212> TYPE: PRT
<213> ORGANISM: Artificial Sequence
<220> FEATURE:
<223> OTHER INFORMATION: synthetic

<400> SEQUENCE: 569

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

```
Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 570
<211> LENGTH: 326
<212> TYPE: PRT
<213> ORGANISM: Artificial Sequence
<220> FEATURE:
<223> OTHER INFORMATION: synthetic

<400> SEQUENCE: 570

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160
```

Val Glu Val His Asn Ala Lys Thr Lys Pro Arg Glu Glu Gln Phe Asn
            165                 170                 175

Ser Thr Tyr Arg Val Val Ser Val Leu Thr Val Leu His Gln Asp Trp
        180                 185                 190

Leu Asn Gly Lys Glu Tyr Lys Cys Lys Val Ser Asn Lys Gly Leu Pro
    195                 200                 205

Ser Ser Ile Glu Lys Thr Ile Ser Lys Ala Lys Gly Gln Pro Arg Glu
210                 215                 220

Pro Gln Val Tyr Thr Leu Pro Pro Ser Gln Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
        260                 265                 270

Thr Pro Pro Val Leu Asp Ser Asp Gly Ser Phe Phe Leu Tyr Ser Arg
    275                 280                 285

Leu Thr Val Asp Lys Ser Arg Trp Gln Glu Gly Asn Val Phe Ser Cys
290                 295                 300

Ser Val Met His Glu Ala Leu His Asn His Tyr Thr Gln Lys Ser Leu
305                 310                 315                 320

Ser Leu Ser Leu Gly Lys
            325

<210> SEQ ID NO 571
<211> LENGTH: 326
<212> TYPE: PRT
<213> ORGANISM: Artificial Sequence
<220> FEATURE:
<223> OTHER INFORMATION: synthetic

<400> SEQUENCE: 571

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
            165                 170                 175

Ser Thr Tyr Arg Val Val Ser Val Leu Thr Val Leu His Gln Asp Trp
        180                 185                 190

```
Leu Asn Gly Lys Glu Tyr Lys Cys Lys Val Ser Asn Lys Gly Leu Pro
            195                 200                 205

Ser Ser Ile Glu Lys Thr Ile Ser Lys Ala Lys Gly Gln Pro Arg Glu
210                 215                 220

Pro Gln Val Tyr Thr Leu Pro Pro Ser Gln Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
            275                 280                 285

Leu Thr Val Asp Lys Ser Arg Trp Gln Glu Gly Asn Val Phe Ser Cys
        290                 295                 300

Ser Val Met His Glu Ala Leu His Asn Arg Phe Thr Gln Lys Ser Leu
305                 310                 315                 320

Ser Leu Ser Pro Gly Lys
                325

<210> SEQ ID NO 572
<211> LENGTH: 326
<212> TYPE: PRT
<213> ORGANISM: Artificial Sequence
<220> FEATURE:
<223> OTHER INFORMATION: synthetic

<400> SEQUENCE: 572

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Gly Gly Gly Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220
```

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
        260                 265                 270

Thr Pro Pro Val Leu Asp Ser Asp Gly Ser Phe Phe Leu Tyr Ser Arg
    275                 280                 285

Leu Thr Val Asp Lys Ser Arg Trp Gln Glu Gly Asn Val Phe Ser Cys
290                 295                 300

Ser Val Met His Glu Ala Leu His Asn His Tyr Thr Gln Lys Ser Leu
305                 310                 315                 320

Ser Leu Ser Leu Gly Lys
                325

<210> SEQ ID NO 573
<211> LENGTH: 326
<212> TYPE: PRT
<213> ORGANISM: Artificial Sequence
<220> FEATURE:
<223> OTHER INFORMATION: synthetic

<400> SEQUENCE: 573

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Gly Gly Gly Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
                260                 265                 270

Thr Pro Pro Val Leu Asp Ser Asp Gly Ser Phe Phe Leu Tyr Ser Arg
            275                 280                 285

Leu Thr Val Asp Lys Ser Arg Trp Gln Glu Gly Asn Val Phe Ser Cys
        290                 295                 300

Ser Val Met His Glu Ala Leu His Asn Arg Phe Thr Gln Lys Ser Leu
305                 310                 315                 320

Ser Leu Ser Pro Gly Lys
                325

<210> SEQ ID NO 574
<211> LENGTH: 450
<212> TYPE: PRT
<213> ORGANISM: Artificial Sequence
<220> FEATURE:
<223> OTHER INFORMATION: aa 1-478: Human Lag3 (aa 29 through 450 of
      NP_002277.4)
      aa 451-478: myc-myc-hexahistidine tag

<400> SEQUENCE: 574

Val Pro Val Val Trp Ala Gln Glu Gly Ala Pro Ala Gln Leu Pro Cys
1               5                   10                  15

Ser Pro Thr Ile Pro Leu Gln Asp Leu Ser Leu Leu Arg Arg Ala Gly
            20                  25                  30

Val Thr Trp Gln His Gln Pro Asp Ser Gly Pro Pro Ala Ala Ala Pro
        35                  40                  45

Gly His Pro Leu Ala Pro Gly Pro His Pro Ala Ala Pro Ser Ser Trp
    50                  55                  60

Gly Pro Arg Pro Arg Arg Tyr Thr Val Leu Ser Val Gly Pro Gly Gly
65                  70                  75                  80

Leu Arg Ser Gly Arg Leu Pro Leu Gln Pro Arg Val Gln Leu Asp Glu
                85                  90                  95

Arg Gly Arg Gln Arg Gly Asp Phe Ser Leu Trp Leu Arg Pro Ala Arg
            100                 105                 110

Arg Ala Asp Ala Gly Glu Tyr Arg Ala Ala Val His Leu Arg Asp Arg
        115                 120                 125

Ala Leu Ser Cys Arg Leu Arg Leu Arg Leu Gly Gln Ala Ser Met Thr
    130                 135                 140

Ala Ser Pro Pro Gly Ser Leu Arg Ala Ser Asp Trp Val Ile Leu Asn
145                 150                 155                 160

Cys Ser Phe Ser Arg Pro Asp Arg Pro Ala Ser Val His Trp Phe Arg
                165                 170                 175

Asn Arg Gly Gln Gly Arg Val Pro Val Arg Glu Ser Pro His His His
            180                 185                 190

Leu Ala Glu Ser Phe Leu Phe Leu Pro Gln Val Ser Pro Met Asp Ser
        195                 200                 205

Gly Pro Trp Gly Cys Ile Leu Thr Tyr Arg Asp Gly Phe Asn Val Ser
    210                 215                 220

Ile Met Tyr Asn Leu Thr Val Leu Gly Leu Glu Pro Pro Thr Pro Leu
225                 230                 235                 240

Thr Val Tyr Ala Gly Ala Gly Ser Arg Val Gly Leu Pro Cys Arg Leu
                245                 250                 255

Pro Ala Gly Val Gly Thr Arg Ser Phe Leu Thr Ala Lys Trp Thr Pro
            260                 265                 270

-continued

Pro Gly Gly Gly Pro Asp Leu Leu Val Thr Gly Asp Asn Gly Asp Phe
            275                 280                 285

Thr Leu Arg Leu Glu Asp Val Ser Gln Ala Gln Ala Gly Thr Tyr Thr
    290                 295                 300

Cys His Ile His Leu Gln Glu Gln Gln Leu Asn Ala Thr Val Thr Leu
305                 310                 315                 320

Ala Ile Ile Thr Val Thr Pro Lys Ser Phe Gly Ser Pro Gly Ser Leu
                325                 330                 335

Gly Lys Leu Leu Cys Glu Val Thr Pro Val Ser Gly Gln Glu Arg Phe
            340                 345                 350

Val Trp Ser Ser Leu Asp Thr Pro Ser Gln Arg Ser Phe Ser Gly Pro
        355                 360                 365

Trp Leu Glu Ala Gln Glu Ala Gln Leu Leu Ser Gln Pro Trp Gln Cys
    370                 375                 380

Gln Leu Tyr Gln Gly Glu Arg Leu Leu Gly Ala Ala Val Tyr Phe Thr
385                 390                 395                 400

Glu Leu Ser Ser Pro Gly Ala Gln Arg Ser Gly Arg Ala Pro Gly Ala
                405                 410                 415

Leu Pro Ala Gly His Leu Glu Gln Lys Leu Ile Ser Glu Glu Asp Leu
            420                 425                 430

Gly Gly Glu Gln Lys Leu Ile Ser Glu Glu Asp Leu His His His His
        435                 440                 445

His His
    450

<210> SEQ ID NO 575
<211> LENGTH: 655
<212> TYPE: PRT
<213> ORGANISM: Artificial Sequence
<220> FEATURE:
<223> OTHER INFORMATION: aa 1-683: Human Lag3 (aa 29 through 450 of
    NP_002277.4)
    aa 451-683: mIgG2aFc

<400> SEQUENCE: 575

Val Pro Val Val Trp Ala Gln Glu Gly Ala Pro Ala Gln Leu Pro Cys
1               5                   10                  15

Ser Pro Thr Ile Pro Leu Gln Asp Leu Ser Leu Leu Arg Arg Ala Gly
            20                  25                  30

Val Thr Trp Gln His Gln Pro Asp Ser Gly Pro Pro Ala Ala Ala Pro
        35                  40                  45

Gly His Pro Leu Ala Pro Gly Pro His Pro Ala Ala Pro Ser Ser Trp
    50                  55                  60

Gly Pro Arg Pro Arg Arg Tyr Thr Val Leu Ser Val Gly Pro Gly Gly
65                  70                  75                  80

Leu Arg Ser Gly Arg Leu Pro Leu Gln Pro Arg Val Gln Leu Asp Glu
                85                  90                  95

Arg Gly Arg Gln Arg Gly Asp Phe Ser Leu Trp Leu Arg Pro Ala Arg
            100                 105                 110

Arg Ala Asp Ala Gly Glu Tyr Arg Ala Ala Val His Leu Arg Asp Arg
        115                 120                 125

Ala Leu Ser Cys Arg Leu Arg Leu Arg Leu Gly Gln Ala Ser Met Thr
    130                 135                 140

Ala Ser Pro Pro Gly Ser Leu Arg Ala Ser Asp Trp Val Ile Leu Asn
145                 150                 155                 160

Cys Ser Phe Ser Arg Pro Asp Arg Pro Ala Ser Val His Trp Phe Arg

```
                165                 170                 175
Asn Arg Gly Gln Gly Arg Val Pro Val Arg Glu Ser Pro His His His
            180                 185                 190

Leu Ala Glu Ser Phe Leu Phe Leu Pro Gln Val Ser Pro Met Asp Ser
            195                 200                 205

Gly Pro Trp Gly Cys Ile Leu Thr Tyr Arg Asp Gly Phe Asn Val Ser
            210                 215                 220

Ile Met Tyr Asn Leu Thr Val Leu Gly Leu Glu Pro Pro Thr Pro Leu
225                 230                 235                 240

Thr Val Tyr Ala Gly Ala Gly Ser Arg Val Gly Leu Pro Cys Arg Leu
                245                 250                 255

Pro Ala Gly Val Gly Thr Arg Ser Phe Leu Thr Ala Lys Trp Thr Pro
                260                 265                 270

Pro Gly Gly Gly Pro Asp Leu Leu Val Thr Gly Asp Asn Gly Asp Phe
                275                 280                 285

Thr Leu Arg Leu Glu Asp Val Ser Gln Ala Gln Ala Gly Thr Tyr Thr
            290                 295                 300

Cys His Ile His Leu Gln Glu Gln Gln Leu Asn Ala Thr Val Thr Leu
305                 310                 315                 320

Ala Ile Ile Thr Val Thr Pro Lys Ser Phe Gly Ser Pro Gly Ser Leu
                325                 330                 335

Gly Lys Leu Leu Cys Glu Val Thr Pro Val Ser Gly Gln Glu Arg Phe
            340                 345                 350

Val Trp Ser Ser Leu Asp Thr Pro Ser Gln Arg Ser Phe Ser Gly Pro
            355                 360                 365

Trp Leu Glu Ala Gln Glu Ala Gln Leu Leu Ser Gln Pro Trp Gln Cys
            370                 375                 380

Gln Leu Tyr Gln Gly Glu Arg Leu Leu Gly Ala Ala Val Tyr Phe Thr
385                 390                 395                 400

Glu Leu Ser Ser Pro Gly Ala Gln Arg Ser Gly Arg Ala Pro Gly Ala
                405                 410                 415

Leu Pro Ala Gly His Leu Glu Pro Arg Gly Pro Thr Ile Lys Pro Cys
                420                 425                 430

Pro Pro Cys Lys Cys Pro Ala Pro Asn Leu Leu Gly Gly Pro Ser Val
            435                 440                 445

Phe Ile Phe Pro Pro Lys Ile Lys Asp Val Leu Met Ile Ser Leu Ser
450                 455                 460

Pro Ile Val Thr Cys Val Val Asp Val Ser Glu Asp Asp Pro Asp
465                 470                 475                 480

Val Gln Ile Ser Trp Phe Val Asn Asn Val Glu Val His Thr Ala Gln
                485                 490                 495

Thr Gln Thr His Arg Glu Asp Tyr Asn Ser Thr Leu Arg Val Val Ser
            500                 505                 510

Ala Leu Pro Ile Gln His Gln Asp Trp Met Ser Gly Lys Glu Phe Lys
            515                 520                 525

Cys Lys Val Asn Asn Lys Asp Leu Pro Ala Pro Ile Glu Arg Thr Ile
            530                 535                 540

Ser Lys Pro Lys Gly Ser Val Arg Ala Pro Gln Val Tyr Val Leu Pro
545                 550                 555                 560

Pro Pro Glu Glu Glu Met Thr Lys Lys Gln Val Thr Leu Thr Cys Met
                565                 570                 575

Val Thr Asp Phe Met Pro Glu Asp Ile Tyr Val Glu Trp Thr Asn Asn
            580                 585                 590
```

```
Gly Lys Thr Glu Leu Asn Tyr Lys Asn Thr Glu Pro Val Leu Asp Ser
            595                 600                 605

Asp Gly Ser Tyr Phe Met Tyr Ser Lys Leu Arg Val Glu Lys Lys Asn
            610                 615                 620

Trp Val Glu Arg Asn Ser Tyr Ser Cys Ser Val Val His Glu Gly Leu
625                 630                 635                 640

His Asn His His Thr Thr Lys Ser Phe Ser Arg Thr Pro Gly Lys
            645                 650                 655

<210> SEQ ID NO 576
<211> LENGTH: 516
<212> TYPE: PRT
<213> ORGANISM: Artificial Sequence
<220> FEATURE:
<223> OTHER INFORMATION: aa 1-533 (aa 18 through 533 of cynomolgus
      XP_005570011.1 modified to replace amino acid  at
      position 74 with a P based on Rhesus macaque
      XP_001108923.1

<400> SEQUENCE: 576

Ala Pro Val Lys Pro Pro Gln Pro Gly Ala Glu Ile Ser Val Val Trp
1               5                   10                  15

Ala Gln Glu Gly Ala Pro Ala Gln Leu Pro Cys Ser Pro Thr Ile Pro
            20                  25                  30

Leu Gln Asp Leu Ser Leu Leu Arg Arg Ala Gly Val Thr Trp Gln His
        35                  40                  45

Gln Pro Asp Ser Gly Pro Pro Ala Pro Ala Pro Gly His Pro Pro Val
    50                  55                  60

Pro Gly His Arg Pro Ala Ala Pro Tyr Ser Trp Gly Pro Arg Pro Arg
65                  70                  75                  80

Arg Tyr Thr Val Leu Ser Val Gly Pro Gly Gly Leu Arg Ser Gly Arg
                85                  90                  95

Leu Pro Leu Gln Pro Arg Val Gln Leu Asp Glu Arg Gly Arg Gln Arg
            100                 105                 110

Gly Asp Phe Ser Leu Trp Leu Arg Pro Ala Arg Arg Ala Asp Ala Gly
        115                 120                 125

Glu Tyr Arg Ala Thr Val His Leu Arg Asp Arg Ala Leu Ser Cys Arg
    130                 135                 140

Leu Arg Leu Arg Val Gly Gln Ala Ser Met Thr Ala Ser Pro Pro Gly
145                 150                 155                 160

Ser Leu Arg Thr Ser Asp Trp Val Ile Leu Asn Cys Ser Phe Ser Arg
                165                 170                 175

Pro Asp Arg Pro Ala Ser Val His Trp Phe Arg Ser Arg Gly Gln Gly
            180                 185                 190

Arg Val Pro Val Gln Gly Ser Pro His His Leu Ala Glu Ser Phe
        195                 200                 205

Leu Phe Leu Pro His Val Gly Pro Met Asp Ser Gly Leu Trp Gly Cys
    210                 215                 220

Ile Leu Thr Tyr Arg Asp Gly Phe Asn Val Ser Ile Met Tyr Asn Leu
225                 230                 235                 240

Thr Val Leu Gly Leu Glu Pro Ala Thr Pro Leu Thr Val Tyr Ala Gly
                245                 250                 255

Ala Gly Ser Arg Val Glu Leu Pro Cys Arg Leu Pro Pro Ala Val Gly
            260                 265                 270

Thr Gln Ser Phe Leu Thr Ala Lys Trp Ala Pro Pro Gly Gly Gly Pro
        275                 280                 285
```

```
Asp Leu Leu Val Ala Gly Asp Asn Gly Asp Phe Thr Leu Arg Leu Glu
        290                 295                 300

Asp Val Ser Gln Ala Gln Ala Gly Thr Tyr Ile Cys His Ile Arg Leu
305                 310                 315                 320

Gln Gly Gln Gln Leu Asn Ala Thr Val Thr Leu Ala Ile Ile Thr Val
                325                 330                 335

Thr Pro Lys Ser Phe Gly Ser Pro Gly Ser Leu Gly Lys Leu Leu Cys
            340                 345                 350

Glu Val Thr Pro Ala Ser Gly Gln Glu His Phe Val Trp Ser Pro Leu
        355                 360                 365

Asn Thr Pro Ser Gln Arg Ser Phe Ser Gly Pro Trp Leu Glu Ala Gln
    370                 375                 380

Glu Ala Gln Leu Leu Ser Gln Pro Trp Gln Cys Gln Leu His Gln Gly
385                 390                 395                 400

Glu Arg Leu Leu Gly Ala Ala Val Tyr Phe Thr Glu Leu Ser Ser Pro
                405                 410                 415

Gly Ala Gln Arg Ser Gly Arg Ala Pro Gly Ala Leu Arg Ala Gly His
            420                 425                 430

Leu Pro Leu Phe Leu Ile Leu Gly Val Leu Phe Leu Leu Leu Leu Val
        435                 440                 445

Thr Gly Ala Phe Gly Phe His Leu Trp Arg Arg Gln Trp Arg Pro Arg
    450                 455                 460

Arg Phe Ser Ala Leu Glu Gln Gly Ile His Pro Pro Gln Ala Gln Ser
465                 470                 475                 480

Lys Ile Glu Glu Leu Glu Gln Glu Pro Glu Leu Glu Pro Glu Pro Glu
                485                 490                 495

Leu Glu Arg Glu Leu Gly Pro Glu Pro Glu Pro Gly Pro Glu Pro Glu
            500                 505                 510

Pro Glu Gln Leu
    515

<210> SEQ ID NO 577
<211> LENGTH: 449
<212> TYPE: PRT
<213> ORGANISM: Artificial Sequence
<220> FEATURE:
<223> OTHER INFORMATION: synthetic

<400> SEQUENCE: 577

Gln Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Gln Tyr
65                  70                  75                  80

Leu Gln Met Asn Ser Leu Arg Ala Glu Asp Thr Ala Val Tyr Tyr Cys
                85                  90                  95

Ala Ser Val Ala Thr Ser Gly Asp Phe Asp Tyr Tyr Gly Met Asp Val
            100                 105                 110

Trp Gly Gln Gly Thr Thr Val Thr Val Ser Ser Ala Ser Thr Lys Gly
        115                 120                 125
```

```
Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 578
<211> LENGTH: 214
<212> TYPE: PRT
<213> ORGANISM: Artificial Sequence
<220> FEATURE:
<223> OTHER INFORMATION: synthetic

<400> SEQUENCE: 578

Glu Ile Val Leu Thr Gln Ser Pro Ala Thr Leu Ser Leu Ser Pro Gly
1               5                   10                  15

Glu Arg Thr Leu Ser Cys Arg Ala Ser Gln Arg Ile Ser Thr Tyr
            20                  25                  30
```

-continued

Leu Ala Trp Tyr Gln Gln Lys Pro Gly Gln Ala Pro Arg Leu Leu Ile
    35                  40                  45

Tyr Asp Ala Ser Lys Arg Ala Thr Gly Ile Pro Ala Arg Phe Ser Gly
 50                  55                  60

Ser Gly Ser Gly Thr Gly Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 579
<211> LENGTH: 450
<212> TYPE: PRT
<213> ORGANISM: Artificial Sequence
<220> FEATURE:
<223> OTHER INFORMATION: synthetic

<400> SEQUENCE: 579

Gln Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Gln Tyr
65                  70                  75                  80

Leu Gln Met Asn Ser Leu Arg Ala Glu Asp Thr Ala Val Tyr Tyr Cys
                85                  90                  95

Ala Ser Val Ala Thr Ser Gly Asp Phe Asp Tyr Tyr Gly Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

```
Pro Ala Val Leu Gln Ser Ser Gly Leu Tyr Ser Leu Ser Ser Val Val
            180                 185                 190
Thr Val Pro Ser Ser Leu Gly Thr Lys Thr Tyr Thr Cys Asn Val
        195                 200                 205
Asp His Lys Pro Ser Asn Thr Lys Val Asp Lys Arg Val Glu Ser Lys
    210                 215                 220
Tyr Gly Pro Pro Cys Pro Pro Cys Pro Ala Pro Glu Phe Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser Gln Glu
            260                 265                 270
Asp Pro Glu Val Gln Phe Asn Trp Tyr Val Asp Gly Val Glu Val His
        275                 280                 285
Asn Ala Lys Thr Lys Pro Arg Glu Glu Gln Phe Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Gly Leu Pro Ser Ser Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Gln Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Arg Leu Thr Val Asp
                405                 410                 415
Lys Ser Arg Trp Gln Glu Gly Asn Val Phe Ser Cys Ser Val Met His
            420                 425                 430
Glu Ala Leu His Asn His Tyr Thr Gln Lys Ser Leu Ser Leu Ser Leu
        435                 440                 445
Gly Lys
    450

<210> SEQ ID NO 580
<211> LENGTH: 445
<212> TYPE: PRT
<213> ORGANISM: Artificial Sequence
<220> FEATURE:
<223> OTHER INFORMATION: synthetic

<400> SEQUENCE: 580

Gln Val Gln Leu Gln Gln Trp Gly Ala Gly Leu Leu Lys Pro Ser Glu
1               5                   10                  15
Thr Leu Ser Leu Thr Cys Ala Val Tyr Gly Gly Ser Phe Ser Gly Tyr
            20                  25                  30
Tyr Trp Asn Trp Ile Arg Gln Pro Pro Gly Lys Gly Leu Glu Trp Val
        35                  40                  45
Gly Glu Ile Ser His Arg Gly Ser Thr Asn Tyr Asn Pro Ser Leu Lys
    50                  55                  60
Ser Arg Val Thr Ile Ser Leu Asp Thr Ser Lys Asn Gln Phe Ser Leu
65                  70                  75                  80
```

Lys Leu Thr Ser Val Thr Ala Ala Asp Thr Ala Val Tyr Tyr Cys Ser
                85                  90                  95

Arg Asp Glu Glu Leu Glu Phe Arg Phe Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 581
<211> LENGTH: 214
<212> TYPE: PRT
<213> ORGANISM: Artificial Sequence
<220> FEATURE:
<223> OTHER INFORMATION: synthetic

<400> SEQUENCE: 581

-continued

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Val
            35                  40                  45

Tyr Gly Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Phe Tyr Tyr Cys Gln Gln Arg Ser Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 582
<211> LENGTH: 525
<212> TYPE: PRT
<213> ORGANISM: Artificial Sequence
<220> FEATURE:
<223> OTHER INFORMATION: synthetic

<400> SEQUENCE: 582

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
            35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
            115                 120                 125

Arg Gly Asp Phe Ser Leu Trp Leu Arg Pro Ala Arg Arg Ala Asp Ala
            130                 135                 140

-continued

```
Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
            165                 170                 175

Gly Ser Leu Arg Ala Ser Asp Trp Val Ile Leu Asn Cys Ser Phe Ser
        180                 185                 190

Arg Pro Asp Arg Pro Ala Ser Val His Trp Phe Arg Asn Arg Gly Gln
    195                 200                 205

Gly Arg Val Pro Val Arg Glu Ser Pro His His Leu Ala Glu Ser
210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
            245                 250                 255

Leu Thr Val Leu Gly Leu Glu Pro Pro Thr Pro Leu Thr Val Tyr Ala
        260                 265                 270

Gly Ala Gly Ser Arg Val Gly Leu Pro Cys Arg Leu Pro Ala Gly Val
    275                 280                 285

Gly Thr Arg Ser Phe Leu Thr Ala Lys Trp Thr Pro Pro Gly Gly Gly
290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
            325                 330                 335

Leu Gln Glu Gln Gln Leu Asn Ala Thr Val Thr Leu Ala Ile Ile Thr
        340                 345                 350

Val Thr Pro Lys Ser Phe Gly Ser Pro Gly Ser Leu Gly Lys Leu Leu
    355                 360                 365

Cys Glu Val Thr Pro Val Ser Gly Gln Glu Arg Phe Val Trp Ser Ser
370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
            405                 410                 415

Gly Glu Arg Leu Leu Gly Ala Ala Val Tyr Phe Thr Glu Leu Ser Ser
        420                 425                 430

Pro Gly Ala Gln Arg Ser Gly Arg Ala Pro Gly Ala Leu Pro Ala Gly
    435                 440                 445

His Leu Leu Leu Phe Leu Ile Leu Gly Val Leu Ser Leu Leu Leu Leu
450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
            485                 490                 495

Ser Lys Ile Glu Glu Leu Glu Gln Glu Pro Glu Pro Glu Pro Glu Pro
        500                 505                 510

Glu Pro Glu Pro Glu Pro Glu Pro Glu Gln Leu
    515                 520                 525
```

<210> SEQ ID NO 583
<211> LENGTH: 15
<212> TYPE: PRT
<213> ORGANISM: Artificial Sequence
<220> FEATURE:
<223> OTHER INFORMATION: synthetic -continued

<400> SEQUENCE: 583

Glu Asn Pro Val Val His Phe Phe Lys Asn Ile Val Thr Pro Arg
1               5                   10                  15

<210> SEQ ID NO 584
<211> LENGTH: 17
<212> TYPE: DNA
<213> ORGANISM: Artificial Sequence
<220> FEATURE:
<223> OTHER INFORMATION: synthetic

<400> SEQUENCE: 584
agcagctctg ccctcat                                                    17

<210> SEQ ID NO 585
<211> LENGTH: 22
<212> TYPE: DNA
<213> ORGANISM: Artificial Sequence
<220> FEATURE:
<223> OTHER INFORMATION: synthetic

<400> SEQUENCE: 585
gctctggctg gtcttcagta tg                                              22

<210> SEQ ID NO 586
<211> LENGTH: 22
<212> TYPE: DNA
<213> ORGANISM: Artificial Sequence
<220> FEATURE:
<223> OTHER INFORMATION: synthetic

<400> SEQUENCE: 586
ttgccgtatg gttggtttga ac                                              22

<210> SEQ ID NO 587
<211> LENGTH: 665
<212> TYPE: PRT
<213> ORGANISM: Artificial Sequence
<220> FEATURE:
<223> OTHER INFORMATION: hLAG3.Fc

<400> SEQUENCE: 587

Leu Gln Pro Gly Ala Glu Val Pro Val Val Trp Ala Gln Glu Gly Ala
1               5                   10                  15

Pro Ala Gln Leu Pro Cys Ser Pro Thr Ile Pro Leu Gln Asp Leu Ser
            20                  25                  30

Leu Leu Arg Arg Ala Gly Val Thr Trp Gln His Gln Pro Asp Ser Gly
        35                  40                  45

Pro Pro Ala Ala Ala Pro Gly His Pro Leu Ala Pro Gly Pro His Pro
    50                  55                  60

Ala Ala Pro Ser Ser Trp Gly Pro Arg Pro Arg Arg Tyr Thr Val Leu
65                  70                  75                  80

Ser Val Gly Pro Gly Gly Leu Arg Ser Gly Arg Leu Pro Leu Gln Pro
                85                  90                  95

Arg Val Gln Leu Asp Glu Arg Gly Arg Gln Arg Gly Asp Phe Ser Leu
            100                 105                 110

Trp Leu Arg Pro Ala Arg Arg Ala Asp Ala Gly Glu Tyr Arg Ala Ala
        115                 120                 125

Val His Leu Arg Asp Arg Ala Leu Ser Cys Arg Leu Arg Leu Arg Leu
    130                 135                 140

-continued

```
Gly Gln Ala Ser Met Thr Ala Ser Pro Pro Gly Ser Leu Arg Ala Ser
145                 150                 155                 160

Asp Trp Val Ile Leu Asn Cys Ser Phe Ser Arg Pro Asp Arg Pro Ala
                165                 170                 175

Ser Val His Trp Phe Arg Asn Arg Gly Gln Gly Arg Val Pro Val Arg
            180                 185                 190

Glu Ser Pro His His His Leu Ala Glu Ser Phe Leu Phe Leu Pro Gln
        195                 200                 205

Val Ser Pro Met Asp Ser Gly Pro Trp Gly Cys Ile Leu Thr Tyr Arg
    210                 215                 220

Asp Gly Phe Asn Val Ser Ile Met Tyr Asn Leu Thr Val Leu Gly Leu
225                 230                 235                 240

Glu Pro Pro Thr Pro Leu Thr Val Tyr Ala Gly Ala Gly Ser Arg Val
                245                 250                 255

Gly Leu Pro Cys Arg Leu Pro Ala Gly Val Gly Thr Arg Ser Phe Leu
            260                 265                 270

Thr Ala Lys Trp Thr Pro Pro Gly Gly Gly Pro Asp Leu Leu Val Thr
        275                 280                 285

Gly Asp Asn Gly Asp Phe Thr Leu Arg Leu Glu Asp Val Ser Gln Ala
    290                 295                 300

Gln Ala Gly Thr Tyr Thr Cys His Ile His Leu Gln Glu Gln Gln Leu
305                 310                 315                 320

Asn Ala Thr Val Thr Leu Ala Ile Ile Thr Val Thr Pro Lys Ser Phe
                325                 330                 335

Gly Ser Pro Gly Ser Leu Gly Lys Leu Leu Cys Glu Val Thr Pro Val
            340                 345                 350

Ser Gly Gln Glu Arg Phe Val Trp Ser Ser Leu Asp Thr Pro Ser Gln
        355                 360                 365

Arg Ser Phe Ser Gly Pro Trp Leu Glu Ala Gln Glu Ala Gln Leu Leu
    370                 375                 380

Ser Gln Pro Trp Gln Cys Gln Leu Tyr Gln Gly Glu Arg Leu Leu Gly
385                 390                 395                 400

Ala Ala Val Tyr Phe Thr Glu Leu Ser Ser Pro Gly Ala Gln Arg Ser
                405                 410                 415

Gly Arg Ala Pro Gly Ala Leu Pro Ala Gly His Leu Ile Glu Gly Arg
            420                 425                 430

Met Asp Pro Lys Ser Cys Asp Lys Thr His Thr Cys Pro Pro Cys Pro
        435                 440                 445

Ala Pro Glu Leu Leu Gly Gly Pro Ser Val Phe Leu Phe Pro Pro Lys
    450                 455                 460

Pro Lys Asp Thr Leu Met Ile Ser Arg Thr Pro Glu Val Thr Cys Val
465                 470                 475                 480

Val Val Asp Val Ser His Glu Asp Pro Glu Val Lys Phe Asn Trp Tyr
                485                 490                 495

Val Asp Gly Val Glu Val His Asn Ala Lys Thr Lys Pro Arg Glu Glu
            500                 505                 510

Gln Tyr Asn Ser Thr Tyr Arg Val Val Ser Val Leu Thr Val Leu His
        515                 520                 525

Gln Asp Trp Leu Asn Gly Lys Glu Tyr Lys Cys Lys Val Ser Asn Lys
    530                 535                 540

Ala Leu Pro Ala Pro Ile Glu Lys Thr Ile Ser Lys Ala Lys Gly Gln
545                 550                 555                 560

Pro Arg Glu Pro Gln Val Tyr Thr Leu Pro Pro Ser Arg Asp Glu Leu
```

Thr Lys Asn Gln Val Ser Leu Thr Cys Leu Val Lys Gly Phe Tyr Pro
565                 570                 575

Ser Asp Ile Ala Val Glu Trp Glu Ser Asn Gly Gln Pro Glu Asn Asn
    580                 585                 590

Tyr Lys Thr Thr Pro Val Leu Asp Ser Asp Gly Ser Phe Phe Leu
595                 600                 605

Tyr Ser Lys Leu Thr Val Asp Lys Ser Arg Trp Gln Gln Gly Asn Val
610                 615                 620

Phe Ser Cys Ser Val Met His Glu Ala Leu His Asn His Tyr Thr Gln
625                 630                 635                 640

Lys Ser Leu Ser Leu Ser Pro Gly Lys
    645                 650                 655

660                 665

<210> SEQ ID NO 588
<211> LENGTH: 422
<212> TYPE: PRT
<213> ORGANISM: Artificial Sequence
<220> FEATURE:
<223> OTHER INFORMATION: hLAG3 extracellular domain P18627

<400> SEQUENCE: 588

Val Pro Val Val Trp Ala Gln Glu Gly Ala Pro Ala Gln Leu Pro Cys
1               5                   10                  15

Ser Pro Thr Ile Pro Leu Gln Asp Leu Ser Leu Leu Arg Arg Ala Gly
            20                  25                  30

Val Thr Trp Gln His Gln Pro Asp Ser Gly Pro Pro Ala Ala Ala Pro
        35                  40                  45

Gly His Pro Leu Ala Pro Gly Pro His Pro Ala Ala Pro Ser Ser Trp
    50                  55                  60

Gly Pro Arg Pro Arg Arg Tyr Thr Val Leu Ser Val Gly Pro Gly Gly
65                  70                  75                  80

Leu Arg Ser Gly Arg Leu Pro Leu Gln Pro Arg Val Gln Leu Asp Glu
                85                  90                  95

Arg Gly Arg Gln Arg Gly Asp Phe Ser Leu Trp Leu Arg Pro Ala Arg
            100                 105                 110

Arg Ala Asp Ala Gly Glu Tyr Arg Ala Ala Val His Leu Arg Asp Arg
        115                 120                 125

Ala Leu Ser Cys Arg Leu Arg Leu Arg Leu Gly Gln Ala Ser Met Thr
    130                 135                 140

Ala Ser Pro Pro Gly Ser Leu Arg Ala Ser Asp Trp Val Ile Leu Asn
145                 150                 155                 160

Cys Ser Phe Ser Arg Pro Asp Arg Pro Ala Ser Val His Trp Phe Arg
                165                 170                 175

Asn Arg Gly Gln Gly Arg Val Pro Val Arg Glu Ser Pro His His His
            180                 185                 190

Leu Ala Glu Ser Phe Leu Phe Leu Pro Gln Val Ser Pro Met Asp Ser
        195                 200                 205

Gly Pro Trp Gly Cys Ile Leu Thr Tyr Arg Asp Gly Phe Asn Val Ser
    210                 215                 220

Ile Met Tyr Asn Leu Thr Val Leu Gly Leu Glu Pro Pro Thr Pro Leu
225                 230                 235                 240

Thr Val Tyr Ala Gly Ala Gly Ser Arg Val Gly Leu Pro Cys Arg Leu
                245                 250                 255

Pro Ala Gly Val Gly Thr Arg Ser Phe Leu Thr Ala Lys Trp Thr Pro

```
                    260                 265                 270
Pro Gly Gly Gly Pro Asp Leu Leu Val Thr Gly Asp Asn Gly Asp Phe
            275                 280                 285

Thr Leu Arg Leu Glu Asp Val Ser Gln Ala Gln Ala Gly Thr Tyr Thr
            290                 295                 300

Cys His Ile His Leu Gln Glu Gln Gln Leu Asn Ala Thr Val Thr Leu
305                 310                 315                 320

Ala Ile Ile Thr Val Thr Pro Lys Ser Phe Gly Ser Pro Gly Ser Leu
                325                 330                 335

Gly Lys Leu Leu Cys Glu Val Thr Pro Val Ser Gly Gln Glu Arg Phe
                340                 345                 350

Val Trp Ser Ser Leu Asp Thr Pro Ser Gln Arg Ser Phe Ser Gly Pro
            355                 360                 365

Trp Leu Glu Ala Gln Glu Ala Gln Leu Leu Ser Gln Pro Trp Gln Cys
            370                 375                 380

Gln Leu Tyr Gln Gly Glu Arg Leu Leu Gly Ala Ala Val Tyr Phe Thr
385                 390                 395                 400

Glu Leu Ser Ser Pro Gly Ala Gln Arg Ser Gly Arg Ala Pro Gly Ala
                405                 410                 415

Leu Pro Ala Gly His Leu
            420

<210> SEQ ID NO 589
<211> LENGTH: 44
<212> TYPE: PRT
<213> ORGANISM: Artificial Sequence
<220> FEATURE:
<223> OTHER INFORMATION: hLAG3 epitope

<400> SEQUENCE: 589

Leu Arg Arg Ala Gly Val Thr Trp Gln His Gln Pro Asp Ser Gly Pro
1               5                   10                  15

Pro Ala Ala Ala Pro Gly His Pro Leu Ala Pro Gly Pro His Pro Ala
            20                  25                  30

Ala Pro Ser Ser Trp Gly Pro Arg Pro Arg Arg Tyr
            35                  40
```